United States Patent
Sette et al.

(10) Patent No.: US 7,462,354 B2
(45) Date of Patent: Dec. 9, 2008

(54) METHOD AND SYSTEM FOR OPTIMIZING MINIGENES AND PEPTIDES ENCODED THEREBY

(75) Inventors: Alessandro Sette, La Jolla, CA (US); Robert Chesnut, Cardiff-by-the-Sea, CA (US); Brian D. Livingston, San Diego, CA (US); Denise Marie Baker, San Diego, CA (US); Mark J. Newman, Carlsbad, CA (US)

(73) Assignee: Pharmexa Inc., San Diego, CA (US)

( * ) Notice: Subject to any disclaimer, the term of this patent is extended or adjusted under 35 U.S.C. 154(b) by 29 days.

(21) Appl. No.: 09/894,018

(22) Filed: Jun. 27, 2001

(65) Prior Publication Data

US 2002/0119127 A1 Aug. 29, 2002

Related U.S. Application Data

(63) Continuation-in-part of application No. PCT/US00/35568, filed on Dec. 28, 2000.

(60) Provisional application No. 60/173,390, filed on Dec. 28, 1999, provisional application No. 60/284,221, filed on Apr. 16, 2001.

(51) Int. Cl.
  A61K 39/00 (2006.01)
  C07K 14/00 (2006.01)
  G06F 19/00 (2006.01)
(52) U.S. Cl. .............. 424/184.1; 424/185.1; 424/192.1; 702/19; 702/20; 530/350
(58) Field of Classification Search .................. 435/7.1; 702/19, 20; 703/11
  See application file for complete search history.

(56) References Cited

U.S. PATENT DOCUMENTS

| | | | |
|---|---|---|---|
| 4,235,877 A | 11/1980 | Fullerton | |
| 4,487,715 A | 12/1984 | Nitecki et al. | |
| 4,599,230 A | 7/1986 | Milich et al. | |
| 4,599,231 A | 7/1986 | Milich et al. | |
| 4,837,028 A | 6/1989 | Allen | |
| 5,013,548 A | 5/1991 | Haynes et al. | |
| 5,128,319 A | 7/1992 | Arlinghaus | |
| 5,200,320 A | 4/1993 | Sette et al. | |
| 5,503,829 A | 4/1996 | Ladant et al. | |
| 5,633,234 A | 5/1997 | August et al. ................ 514/44 |
| 5,662,907 A | 9/1997 | Kubo et al. | |
| 5,736,142 A | 4/1998 | Sette et al. ............... 424/185.1 |
| 5,783,567 A | 7/1998 | Hedley et al. | |
| 5,846,827 A | 12/1998 | Celis et al. | |
| 6,034,214 A | 3/2000 | Boon et al. | |
| 6,037,135 A | 3/2000 | Kubo et al. | |
| 6,413,517 B1 | 7/2002 | Sette et al. | |
| 6,413,935 B1 | 7/2002 | Sette et al. | |
| 6,419,931 B1 | 7/2002 | Vitiello et al. | |
| 6,534,482 B1 | 3/2003 | Fikes et al. | |
| 6,602,510 B1 | 8/2003 | Fikes et al. | |
| 6,689,363 B1 * | 2/2004 | Sette et al. ................ 424/189.1 |
| 2002/0098197 A1 | 7/2002 | Sette et al. | |
| 2002/0119127 A1 | 8/2002 | Sette et al. | |
| 2002/0160019 A1 | 10/2002 | Sette et al. | |
| 2002/0160960 A1 | 10/2002 | Sette et al. | |
| 2002/0168374 A1 | 11/2002 | Kubo et al. | |
| 2002/0177694 A1 | 11/2002 | Sette et al. | |
| 2003/0099634 A1 | 5/2003 | Vitiello et al. | |
| 2003/0143672 A1 | 7/2003 | Tangri et al. | |
| 2003/0152580 A1 | 8/2003 | Sette et al. | |
| 2003/0185822 A1 | 10/2003 | Grey et al. | |
| 2003/0203869 A1 | 10/2003 | Fikes et al. | |
| 2003/0216342 A1 | 11/2003 | Fikes et al. | |
| 2003/0216343 A1 | 11/2003 | Fikes et al. | |
| 2003/0220285 A1 | 11/2003 | Fikes et al. | |
| 2004/0096445 A1 | 5/2004 | Sidney et al. | |
| 2004/0157273 A1 | 8/2004 | Sidney et al. | |
| 2004/0248113 A1 | 12/2004 | Sette et al. | |
| 2005/0049197 A1 | 3/2005 | Sette et al. | |

FOREIGN PATENT DOCUMENTS

| | | |
|---|---|---|
| EP | 0 044 710 A1 | 1/1982 |
| EP | 0 226 513 A1 | 6/1987 |
| EP | 0 429 816 | 6/1991 |
| EP | 0 433 242 | 6/1991 |
| EP | 0 378 881 | 6/1993 |
| WO | WO 92/02543 A1 | 2/1992 |
| WO | WO 92/12996 A2 | 8/1992 |
| WO | WO 92/21033 A1 | 11/1992 |

(Continued)

OTHER PUBLICATIONS

Anton et al. (1997). *J Immunol* 158(6):2535-42.

(Continued)

*Primary Examiner*—Marianne P Allen
(74) *Attorney, Agent, or Firm*—Sterne, Kessler, Goldstein & Fox P.L.L.C.

(57) ABSTRACT

The invention relates to the field of biology. In particular, the invention relates to a method and system for designing optimized multi-epitope vaccines having selected combinations of amino acid insertions at the junctions of the multi-epitope constructs so as to minimize the number of junctional epitopes and provide vaccines with increased immunogenicity.

20 Claims, 41 Drawing Sheets

FOREIGN PATENT DOCUMENTS

| WO | WO 93/03764 | | 3/1993 |
|---|---|---|---|
| WO | WO 93/03764 | A1 | 3/1993 |
| WO | WO 94/03205 | A1 | 2/1994 |
| WO | WO 94/11738 | A1 | 5/1994 |
| WO | WO 94/20127 | | 9/1994 |
| WO | WO 94/20127 | A1 | 9/1994 |
| WO | WO 95/04817 | A1 | 2/1995 |
| WO | WO 95/07707 | | 3/1995 |
| WO | WO 95/22317 | A1 | 8/1995 |
| WO | WO 96/03140 | A1 | 2/1996 |
| WO | WO 96/2067 | | 7/1996 |
| WO | WO 97/03778 | | 2/1997 |
| WO | WO 97/33602 | A1 | 9/1997 |
| WO | WO 97/34617 | | 9/1997 |
| WO | WO 97/34621 | A1 | 9/1997 |
| WO | WO 97/41440 | | 11/1997 |
| WO | WO 98/32456 | A1 | 7/1998 |
| WO | WO 99/10646 | | 3/1999 |
| WO | WO 99/45954 | A1 | 9/1999 |
| WO | WO 99/58658 | A2 | 11/1999 |
| WO | WO 99/61916 | A1 | 12/1999 |
| WO | WO 99/65522 | A1 | 12/1999 |
| WO | WO 00/19774 | | 4/2000 |
| WO | WO 00/27766 | | 5/2000 |
| WO | WO 01/00225 | | 1/2001 |
| WO | WO 02/20616 | | 3/2002 |
| WO | WO 02/061435 | A2 | 8/2002 |

OTHER PUBLICATIONS

Arndt et al. (1997). *Immunol Res* 16(3):261-72.
Bergmann et al. (1994). *J Virol.* 68(8):5306-10.
Bergmann et al. (1996). *J Immunol* 157(8):3242-9.
Bertoni et al. (1997). *J Clin Invest.* 100(3):503-13.
Blum et al. (1997). *Crit Rev Immunol* 17(5-6):411-7.
Chapman, H.A. (1998). *Curr Opin Immunol* 10(1):93-102.
Chimini et al. (1989). *J Exp Med* 169(1):297-302.
Copier et al. (1996). *J. Immunol.* 157:1017-1027.
Couillin et al. (1994). *J Exp Med* 180(3):1129-34.
Del Val et al. (1991). *Cell* 66(6):1145-53.
Diminsky et al. (1997). *Vaccine* 15:637-647.
Doolan et al. (1997). *Immunity* 7(1):97-112.
Gileadi et al. (1999). *Eur J Immunol* 29(7):2213-22.
Hahn et al. (1991). *J Exp Med* 174(3):733-6.
Hahn et al. (1992). *J Exp Med* 176(5):1335-41.
Hanke et al (1998). *J Gen Virol* 79(Pt 1):83-90.
Hunt et al. (1992). *Science* 256(5065):1817-20.
Ishioka et al. (1999). *J Immunol* 162(7):3915-25.
Iwasaki et al. (1999). *Vaccine* 17(15-16):2081-8.
LeBorgne et al. (1998). *Virology* 240:304-315.
Lippolis et al. (1995). *J Virol* 69(5):3134-46.
Livingston et al. (1997). *J Immunol* 159(3):1383-92.
Mateo et al. (1999). *J Immunol* 163(7):4058-63.
Moudgil et al. (1997). *J. Immunol* 159(6):2574-9.
Nakagawa et al. (1999). *Immunity* 10(2):207-17.
Niedermann et al (1995). *Immunity* 2(3):289-99.
Ogg G.S. et al. (1998). *Curr Opin Immunol* 10(4):393-6.
Paz et al. (1999). *Immunity* 11(2):241-51.
Perkins et al (1991). *J Immunol* 146(7):2137-44.
Rammensee et al. (1995). *Immunogenetics* 41:178-228.
Restifo et al. (1995). *J Immunol* 154(9):4414-22.
Sette et al. (1989). *J Immunol* 143:1268-73.
Shastri et al. (1995). *J Immunol* 155(9):4339-46.
Theobald et al. (1998). *J Exp Med* 188(6):1017-28.
Thomson et al. (1998). *J Immunol* 160(4):1717-23.
Thomson et al. (1998). *J Virol* 72(3):2246-52.
Thomson et al. (1995). *Proc Natl Acad Sci USA* 92(13):5845-9.
Threlkeld et al. (1997). *J. Immunol.* 159(4):1648-57.
Tussey et al. (1995). *Immunity* 3(1):65-77.
Wang et al. (1992). *Cell Immunol* 143(2):284-97.
Wherry et al. (1999). *J Immunol* 163(7):3735-45.
Woodberry et al. (1999). *J Virol* 73(7):5320-5.
Yewdell et al. (1999). *Annu Rev Immunol* 17:51-88.
Alexander, J., et al., "Development of High Potency Universal DR-Restricted Helper Epitopes by Modification of High Affinity DR-Blocking Peptides," *Immunity* 1:751-761, Cell Press (1994).
Barouch, D., et al., "HLA-A2 Subtypes Are Functionally Distinct in Peptide Binding and Presentation," *J. Exp. Med.* 182:1847-1858, Rockefeller University Press (1995).
Bender, A., et al., "Improved methods for the generation of dendritic cells from nonproliferating progenitors in human blood," *J. Immunol. Methods* 196:121-135, Elsevier Science (1996).
Ben-Yedidia, T., and Arnon, R., "Design of peptide and polypeptide vaccines," *Curr. Opin. Biotechnol.* 8:442-448, Current Biology, Ltd. (1997).
Carbone, F.R., and Bevan, M.J., "Induction of Ovalbumin-Specific Cytotoxic T Cells by In Vivo Peptide Immunization," *J. Exp. Med.* 169:603-612, Rockefeller University Press (1989).
Carbone, F.R., et al., "Induction of Cytotoxic T Lymphocytes by Primary In Vitro Stimulation with Peptides," *J. Exp. Med.* 167:1767-1779, Rockefeller University Press (1988).
Cassell, D., and Forman, J., "Linked Recognition of Helper and Cytotoxic Antigenic Determinants for the Generation of Cytotoxic T Lymphocytes," Ann. N.Y. Acad. Sci.532:51-60, New York Academy Of Sciences (1991).
Deres, K., et al., "In vivo priming of virus-specific cytotoxic T lymphocytes with synthetic lipopeptide vaccine," Nature 342:561-564, Nature Publishing Group (1989).
del Guercio, M-F., et al., "Potent immunogenic short linear peptide constructs composed of B cell epitopes and Pan DR T Helper Epitopes (PADRE) for antibody responses in vivo," Vaccine 15:441-448, Elsevier Science (Mar. 1997).
DiBrino, M., et al., "Endogenous Peptides with Distinct Amino Acid Anchor Residue Motifs Bind to HLA-A1 and HLA-B8," J. Immunol. 152:620-631, American Association of Immunologists (1994).
DiBrino, M., et al., "The HLA-B14 Peptide Binding Site Can Accommodate Peptides with Different Combinations of Anchor Residues," J. Biol. Chem. 269:32426-32434, American Society for Biochemistry and Molecular Biology (1994).
Donnelly, J.J., et al., "DNA Vaccines," Annu. Rev. Immunol. 15:617-648, Annual Reviews Inc. (Apr. 1997).
Francis, M.J., et al., "Non-responsiveness to a foot-and-mouth disease virus peptide overcome by addition of foreign helper T-cell determinants," Nature 330:168-170, Nature Publication Group (1987).
Fynan, E.F., et al., "DNA vaccines: Protective immunizations by parental, mucosal, and gene-gun inoculations," Proc. Natl. Acad. Sci. USA 90:11478-11482, National Academy of Sciences (1993).
Golvano, J., et al., "Polarity of immunogens: Implications for vaccine design," Eur. J. Immunol. 20:2363-2366, VCH Verlagsgesellschaft mbH (1990).
Gulukota, K., et al., "Two Complementary Methods for Predicting Peptides Binding Major Histocompatibility Complex Molecules," J. Mol. Biol. 267:1258-1267, Academic Press Limited (Apr. 1997).
Hammer, J., et al., "Precise Prediction of Major Histocompatibility Complex Class II-Peptide Interaction Based on Peptide Side Chain Scanning," J. Exp. Med. 180:2353-2358, Rockefeller University Press (1994).
Hill, C.M., et al., "Exploration of Requirements for Peptide Binding to HLA DRB1*0101 and DRB1*0401," J. Immunol. 152:2890-2898, American Association of Immunologists (1994).
Huczko, E.L., et al., "Characteristics of Endogenous Peptides Eluted from the Class I MHC Molecule HLA-B7 Determined by Mass Spectrometry and Computer Modeling," J. Immunol. 151:2572-2587, American Association of Immunologists (1993).
Ishioka, G.Y., et al., "Class I MHC-restricted, peptide specific cytotoxic T lymphocyctes generated by peptide priming in vivo," In Vaccines90: Modern Approaches to New Vaccines Including Prevention of AIDS, Brown, F., et al., Cold Spring harbor Laboratory Press, Cold Spring Harbor, NY, pp. 7-11 (1990).
Ishioka, G.Y., et al., "Induction of Class I MHC-Restricted, Peptide-Specific Cytolytic T Lymphocytes by Peptide Priming In Vivo," J. Immunol. 143:1094-1100, American Asssociation of Immunologists (1989).

Jardetzky, T.S., et al., "Peptide binding to HLA-DR1: a peptide with most residues substituted to alanine retains MHC binding," EMBO J. 9:1797-1803, Oxford University Press (1990).

Kast, W.M., et al., "Protection against lethal Sendai virus Infection by in vivo priming of virus-specific cytotoxic T lymphocytes with a free synthetic peptide," Proc. Natl. Acad. Sci. USA 88:2283-2287, National Academy of Sciences (1991).

Kondo, A., et al., "Two distinct HLA-A*0101-specific submotifs illustrate alternative peptide binding modes," Immunogenetics 45:249-258, Springer-Verlag (Jan. 1997).

Kubitscheck, U., et al., "Peptide Binding to Class I Molecules of the Major Histocompatibility Complex on the Surface of Living Target Cells," Scand. J. Immunol. 36:341-348, Blackwell Scientific Publications (1992).

Kubo, R.T., et al., "Definition of Specific Peptide Motifs for Four Major HLA-A Alleles," *J. Immunol.* 152:3913-3924, American Association of Immunologists (1994).

Kumar, A., et al., "Universal T Helper Cell Determinants Enhance Immunogenicity of a *Plasmodium falciparum* Merozoite Surface Antigen Peptide," J. Immunol. 148:1499-1505, American Association of Immunologists (1992).

Lasarte, J-J., et al., "Induction of Cytotoxic T Lymphocytes in Mice against the Principal Neutralizing Domain of HIV-1 by Immunization with an Engineered T-Cytotoxic-T-Helper Synthetic Helper Peptide Construct," Cell. Immunol. 141:211-218, Academic Press Inc. (1992).

Madden, D.R., et al., "The structure of HLA-B27 reveals nonamer self-peptides bound in an extended conformation," Nature 353:321-325, Nature Publishing Group (1991).

Maier, R., et al., "Peptide motifs of HLA-A3, -A24, and -B7 molecules as determined by pool sequencing," Immunogenetics 40:306-308, Springer-Verlag (1994).

Martinon, F., et al., "Immunization of Mice with Lipopeptides Bypasses the Prerequisite for Adjuvant," J. Immunol. 149:3416-3422, American Association of Immunologists (1992).

Niedermann, G., et al., "The specificity of proteasomes: impact on MHC class I processing and presentation of antigens," Immunol. Rev. 172:29-48, Munksgaard (Dec. 1999).

Nikolić-Zugić, J., and Carbone, F.R., "Peptide Presentation by Class-I Major Histocompatibility Complex Molecules," Immunol. Res. 10:54-65, S. Karger AG (1991).

O'Sullivan, D., et al., "Characterization of the Specificity of Peptide Binding to Four DR Haplotypes," J. Immunol. 145:1799-1808, American Association of Immunologists (1990).

O'Sullivan, D., et al., "On the Interaction of Promiscuous Antigenic Peptides with Different DR Alleles," J. Immunol. 147:2663-2669, American Association of Immunologists (1991).

Panina-Bordignon, P., et al., "Universally immunogenic T cells eptiopes: promiscuous binding to human MHC class II and promiscuous recognition by T cells," Eur. J. Immunol. 19:2237-2242, VCH Verlagsellschaft mbH (1989).

Penna, A., et al., "Cytotoxic T Lymphocytes Recognize an HLA-A2-Restricted Epitope Within the Hepatitis B Virus Nucleocapsid Antigen," J. Exp. Med. 174:1565-1570, Rockefeller University Press (1991).

Pryjma, J., et al., "Induction and Suppression of Immunoglobulin Synthesis in Cultures of Human Lymphocytes: Effects of Pokeweed Mitogen and *Staphylococcus aureus* Cowan I," J. Immunol. 124:656-661, Williams & Wilkins Co. (1980).

Rahemtulla, A., et al., "Normal development and function of CD8+ cells but markedly decreased helper cell activity in mice lacking CD4," Nature 353:180-183, Nature Publishing Group (1991).

Rammensee, H-G., et al., "SYFPEITHI: database for MHC ligands and peptide motifs," Immunogenetics 50:213-219, Springer-Verlag (Nov. 1999).

Reitermann, A., et al., "Lipopeptide Derivatives of Bacterial Lipoprotein Constitute Potent Immune Adjuvants Combined with or Covalently Coupled to Antigen or Hapten," Biol. Chem. Hoppe Seyler 370:343-352, Walter De Gruyter (1989).

Saper, M.A., et al., "Refined Structure of the Human Histocompatibility Antigen HLA-A2 at 2.6 A Resolution," J. Mol. Biol. 219:277-319, Academic Press Ltd. (1991).

Schaeffer, E.B., et al., "Relative contribution of 'determinant selection' and 'holes in the T-cell repertoire' to T-cell responses," Proc. Natl. Acad. Sci. USA 88:4649-4653, National Academy of Sciences (1989).

Schumacher, T.N.M., et al., "Peptide selection by MHC class I molecules," Nature 350:703-706, Nature Publishing Group (1991).

Sette, A., and Sidney, J., "HLA supertypes and supermotifs: a functional perspective on HLA polymorphism," Curr. Opin. Immunol. 10:478-482, Current Biology Publications (Aug. 1998).

Sette, A., et al., "A Novel Approach to the Generation of High Affinity Class II-Binding Peptides," J. Immunol. 145:1809-1813, American Association of Immunologists (1990).

Sette, A., et al., "Peptide Binding to the Most Frequent HLA-A Class I Alleles Measured by Quantitative Molecular Binding Assays," Mol. Immunol. 31:813-822, Pergamon Press (1994).

Sidney, J., et al., "Definition of an HLA-A3-Like Supermotif Demonstrates the Overlapping Peptide-Binding Repertoires of Common HLA Molecules," Hum. Immunol. 45:79-93, Elsevier Science Inc. (1996).

Sidney, J., et al., "Practical, biochemical and evolutionary Implications of the discovery of HLA class I supermotifs," Immunol. Today 17:261-266, Elsevier Science (1996).

Sidney, J., et al., "The HLA-A*0207 Peptide Binding Repertoire is Limited to a Subset of the A*0201 Repertoire," Hum. Immunol. 58:12-20, Elsevier Science Inc. (Nov. 1997).

Sinigaglia, F., and Hammer, J., "Defining rules for the peptide-MHC class II interaction," Curr. Opin. Immunol. 6:52-56, Current Biology Ltd. (1994).

Southwood, S., et al., "Several Common HLA-DR Types Share Largely Overlapping Peptide Binding Repertoires," J. Immunol. 160:3363-3373, American Association of Immunologists (Apr. 1998).

Sprent, J., and Schaefer, M., "Properties of Purified T Cell Subsets. I. In Vitro Responses to Class I vs. Class II H-2 Alloantigens," *J. Exp. Med.* 162:2068-2088, Rockefeller University Press (1985).

Stark, J.M., et al., "Immunogenicity of lipid-conjugated antigens. I. The Influence of Chain Length and Degree of Conjugation on Induction of Antibody in Mice," Immunology 39:345-352, Blackwell Scientific Publications (1980).

Steinman, R.M., "Dendritic cells and immune-based therapies," Exp. Hematol. 24:859-862, Elsevier Science Inc. (1996).

Sudo, T., et al., "Differences in MHC Class I Self Peptide Repertoires Among HLA-A2 Subtypes," *J. Immunol.* 155:4749-4756, American Association of Immunologists (1995).

Sugawara, S., et al., "A simple method to eliminate the antigenicity of surface class I MHC molecules from the membrane of viable cells by acid treatment at pH 3," J. Immunol. Methods 100:83-90, Elsevier Science (1987).

Tam, J.P., and Lu, Y-A., "Vaccine engineering: Enhancement of immunogenicity of synthetic peptide vaccines related to hepatitis in chemically defined models consisting of T- and B-cell epitopes," Proc. Natl. Acad. Sci. USA 86:9084-9088, National Academy of Sciences (1989).

Townsend, A., and Bodmer, H., "Antigen Recognition by Class I-Restricted T Lymphocytes," Ann. Rev. Immunol. 7:601-624, Annual Reviews, Inc. (1989).

von Boehmer, H., and Haas, W., "Distinct Ir Genes for Helper and Killer Cells in the Cytotoxic Response to H-Y Antigen," J. Exp. Med. 150:1134-1142, Rockefeller University Press (1979).

Watari, E., et al., "A Synthetic Peptide Induces Long-Term Protection from Lethal Infection with Herpes Simplex Virus 2," J. Exp. Med. 165:459-470, Rockefeller University Press (1987).

Wentworth, P.A., et al., "In Vitro Induction of Primary, Antigen-Specific CTL from Human Peripheral Blood Mononuclear Cells Stimulated with Synthetic Peptides," Mol. Immunol. 32:603-612, Elsevier Science Ltd. (1995).

Widmann, C., et al., "T helper epitopes enhance the cytotoxic response of mice immunized with MHC class I-restricted malaria peptides," J. Immunol. Meth. 155:95-99, Elsevier Science Publishers B.V. (1992).

Wiesmuüller, K-H., et al., "Lipopeptide-Helper-T-Cell Epitope-CT1 Epitope Conjugate Induces Antibodies Against the CTL Epitope," Innovation Perspective Solid Phase Synthesis Collect. Papers, Int. Symp. 2nd, pp. 499-502 (1991).

Wiesmüller, K-H., et al., "Novel low-molecular-weight synthetic vaccine against foot-and mouth disease containing a potent B cell and macrophage activator," Vaccine 7:29-33, Butterworth & Co. (1989).

Zhou, X., et al., "In vivo primary induction of virus-specific CTL by immunization with 9-mer synthetic peptides," J. Immunol. Methods 153:193-200, Elsevier Science Publishers B.V. (1992).

Zinkernagel, R.M., et al., "The Lymphoreticular System in Triggering Virus Plus Self-Specific Cytotoxic T Cells: Evidence for T Help," J. Exp. Med. 147:897-911, Rockefeller University Press (1978).

Altuvia, Y. et al., "A Structure-Based Algorithm to Predict Potential Binding Peptides to MHC Molecules with Hydrophobic Binding Pockets," Human Immunol. 58:1-11, Elsevier Science Inc. (1997).

An, L-L., and Whitton, J.L., "A Multivalent Minigene Vaccine, Containing B-Cell, Cytotoxic T-Lymphocyte, and $T_h$ Epitopes from Several Microbes, Induces Appropriate Responses In Vivo and Confers Protection against More than One Pathogen," J. Virol. 71:2292-2302, American Society for Microbiology (1997).

Bergmann, C.C., et al., "Flanking Residues Alter Antigenicity and Immunogenicity of Multi-Unit CTL Epitopes," J. Immunol. 157:3242-3249, American Association of Immunologists (1996).

Hanke, T., et al., "DNA multi-CTL epitope vaccines for HIV and *Plasmodium falciparum*: immunogenicity in mice," Vaccine 16:426-435, Elsevier Science (Feb. 1998).

Hanke, T., et al., "Immunogenicities of intravenous and intramuscular administrations of modified vaccinia virus Ankara-based multi-CTL epitope vaccine for human immunodeficiency virus type 1 in mice," J. Gen. Virol. 79:83-90, Society for General Microbiology (Jan. 1998).

Iwasaki, A., et al., "Epitope-specific cytotoxic T lymphocyte induction by minigene DNA immunization," Vaccine 17:2081-2088, Elsevier Science (Apr. 1999).

Jolivet, M., et al., "Polyvalent synthetic vaccines: relationship between T epitopes and immunogenicity," Vaccine 8:35-40, Butterworth & Co. (1990).

Kuhröber, A., et al., "DNA vaccination with plasmids encoding the intracellular (HBcAg) or secreted (HBeAg) form of the core protein of hepatitis B virus primes T cell responses to two overlapping $K^b$- and $K^d$-restricted epitopes," Int. Immunol. 9:1203-1212, Oxford University Press (1997).

Oseroff, C., et al., "Pools of lipidated HTL-CTL constructs prime for multiple HBV and HCV CTL epitope responses," Vaccine 16:823-833, Elsevier (Apr. 1998).

Sobao, Y., et al., "Identification of hepatitis B virus-specific CTL epitopes presented by HLA-A*2402, the most common HLA class I allele in East Asia," J. Hepatol. 34:922-929, Elsevier (2001).

Theobald, M., et al., "The Sequence Alteration Associated with a Mutational Hotspot in p53 Protects Cells From Lysis by Cytotoxic T Lymphocytes Specific for a Flanking Peptide Epitope," J. Exp. Med. 188:1017-1028, Rockefeller University Press (Sep. 1998).

Thomson, S.A., et al., "Delivery of Multiple CD8 Cytotoxic T Cell Epitopes by DNA Vaccination," J. Immunol. 160:1717-1723, American Association of Immunologists (Feb. 1998).

Thomson, S.A., et al., "Minimal epitopes expressed in a recombinant polyepitope protein are processed and presented to CD8 cytotoxic T cells: Implications for vaccine design," Proc. Natl. Acad. Acad. Sci. USA 92:5845-5849, National Academy of Sciences (1995).

Thomson, S.A., et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design," J. Virol. 72:2246-2252, American Society for Microbiology (Mar. 1998).

Toes, R.E.M., et al., "Protective anti-tumor immunity induced by vaccination with recombinant adenoviruses encoding multiple tumor-associated cytotoxic T lymphocyte epitopes in a string-of-beads fashion," Proc. Natl. Acad. Sci. USA 94:14660-14665, National Academy of Sciences (1997).

Wang, Y., et al., "Silencing of Immunodominant Epitopes by Contiguous Sequences in Complex Synthetic Peptides," Cell. Immunol. 143:284-297, Academic Press (1992).

Whitton, J.L., et al., "A 'String-of-Beads' Vaccine, Comprising Linked Minigenes, Confers Protection from Lethal-Dose Virus Challenge," J. Virol. 67:348-352, American Society for Microbiology (1993).

Woodberry, T., et al., "Immunogenicity of a Human Immunodeficiency Virus (HIV) Polytope Vaccine Containing Multiple HLA A2 HIV CD8+ Cytotoxic T-Cell Epitopes," J. Virol. 73:5320-5325, American Society for Microbiology (Jul. 1999).

Aichele, P., et al., "Antiviral cytotoxic T cell response induced by in vivo priming with a free synthetic peptide," J. Exp. Med. 171:1815-1820, Rockefeller University Press (1990).

Alexander, J., et al., "Derivation of HLA-A11/$K^b$ Transgenic Mice. Functional CTL Repertoire and Recognition of Human A11-Restricted CTL Epitopes," J. Immunol. 159:4753-4761, The American Association of Immunologists (Nov. 1997).

Bertoni, R., et al., "Human Class I Supertypes and CTL Repertoires Extend to Chimpanzees," J. Immunol. 161:4447-4455, American Association of Immunologists (Oct. 1998).

Bjorkman, P.J., et al., "Structure of the human class I histocompatibility antigen, HLA-A2," Nature 329:506-512, Macmillan Publishers, Ltd. (1987).

Bjorkman, P.J., et al., "The foreign antigen binding site and T cell recognition regions of class I histocompatibility antigens," Nature 329:512-518, Macmillan Publishers, Ltd. (1987).

Buus, S., et al., "Autologous Peptides Constitutively Occupy the Antigen Binding Site on Ia," Science 242:1045-1047, American Association for the Advancement of Science (1988).

Carreno, B.M., et al., "HLA-B37 and HLA-A2.1 molecules bind largely nonoverlapping sets of peptides," Proc. Natl. Acad. Sci. USA 87:3420-3424, National Academy Press (1990).

Corr, M., et al., "Endogenous Peptides of a Soluble Major Histocompatibility Complex Class I Molecule, $H-2L^d_s$: Sequence Motif, Quantitative Binding, and Molecular Modeling of the Complex," J. Exp. Med. 176:1681-1692, Rockefeller University Press (Dec. 1992).

De Bruijn, M.L.H., et al., "Peptide loading of empty major histocompatibility complex molecules on RMA-S cells allows the induction of primary cytotoxic T lymphocyte responses," Eur. J. Immunol. 21:2963-2970, VCH Verlagsgesellschaft mbH (1991).

Deres, K., et al., "In vivo priming of virus-specific cytotoxic T lymphocytes with synthetic lipopeptide vaccine," Nature 342:561-564, Macmillan Publishers, Ltd. (1989).

DiBrino, M., et al., "HLA-A1 and HLA-A3 T Cell Epitopes Derived from Influenza Virus Proteins Predicted from Peptide Binding Motifs," J. Immunol. 151:5930-5935, The Association of Immunologists (Dec. 1993).

DiBrino, M., et al., "Endogenous peptides bound to HLA-A3 possess a specific combination of anchor residues that permit identification of potential antigenic peptides," Proc. Natl. Acad. Sci. USA 90:1508-1512, National Academy Press (Feb. 1993).

Ding, Y.-H., et al., "Two Human T Cell Receptors Bind in a Similar Diagonal Mode to the HLA-A2/Tax Peptide Complex Using Different TCR Amino Acids," Immunity 8:403-11, Cell Press (Apr. 1998).

Eisenlohr, L.C., et al., "Flanking Sequences Influence the Presentation of an Endogenously Synthesized Peptide to Cytotoxic T Lymphocytes," J. Exp. Med. 175:481-487, The Rockefeller University Press (Feb. 1992).

Engelhard, V.H., "Structure of peptides associated with MHC Class I molecules," Curr. Opin. Immunol. 6:13-23, Current Biology, Ltd. (Feb. 1994).

Falk, K., et al., "Allele-specific motifs revealed by sequencing of self-peptides eluted from MHC molecules," Nature 351:290-296, Macmillan Publishers, Ltd. (1991).

Falk, K., et al., "*MHC peptide motif register*. Peptide motifs of HLA-B35 and -B37 molecules," Immunogenetics 38:161-162, Springer-Verlag (Apr. 1993).

Falk, K., et al., "Allele-specific peptide ligand motifs of HLA-C molecules," Proc. Natl. Acad. Sci. USA 90:12005-12009, National Academy Press (Dec. 1993).

Falk, K., et al., "Pool sequencing of natural HLA-DR, DQ, and DP ligands reveals detailed peptide motifs, constraints of processing, and general rules," *Immunogenetics* 39:230-242, Springer-Verlag (Feb. 1994).

Falk, K., et al., "Peptide motifs of HLA-A1, -A11, -A31, and -A33 molecules," *Immunogenetics* 40:238-241, Springer-Verlag (Jul. 1994).

Foon, K.A., "Biological Response Modifiers: The New Immunotherapy," *Cancer Res.* 49:1621-1639, American Association for Cancer Research (1989).

Geysen, H.M., et al., "Cognitive Features of Continuous Antigenic Determinants," *J. Mol. Recognit.* 1:32-41, Heyden & Sons, Ltd. (1988).

Guo, H.-C., et al., "Different length peptides bind to HLA-Aw68 similarly at their ends but bulge out in the middle," *Nature* 360:364-366, Macmillan Publishers, Ltd. (Nov. 1992).

Henderson, R.A., et al., "HLA-A2.1-Associated Peptides from a Mutant Cell Line: A Second Pathway of Antigen Presentation," *Science* 255:1264-1266, American Association for the Advancement of Science (Mar. 1992).

Hill, A., et al., "Characterization of two Epstein-Barr virus epitopes restricted by HLA-B7," *Eur. J. Immunol.* 25:18-24, VCH Verlagsgesellschaft mbH (Jan. 1995).

Jameson, S.C., and Bevan, M.J., "Dissection of major histocompatibility complex (MHC) and T cell receptor contact residues in a $K^{b}$-restricted ovalbumin peptide and an assessment of the predictive power of MHC-binding motifs," *Eur. J. Immunol.* 22:2663-2667, VCH Verlagsgesellschaft mbH (Oct. 1992).

Jardetzky, T.S., et al., "Identification of self peptides bound to purified HLA-B27," *Nature* 353:326-329, Macmillan Publishers, Ltd. (1991).

Kannagi, M., et al., "Target Epitope in the Tax Protein of Human T-Cell Leukemia Virus Type I Recognized by Class I Major Histocompatibility Complex-Restricted Cells," *J. Virol.* 66:2928-2933, American Society for Microbiology (May 1992).

Kast, W.M., et al., "Protection against lethal Sendai virus infection by in vivo priming of virus-specific cytotoxic T lymphocytes with a free synthetic peptide," *Proc. Natl. Acad. Sci. USA* 88:2283-2287, National Academy Press (1991).

Kast, W.M., et al., "Strict peptide length is not required for the induction of cytotoxic T lymphocyte-mediated antiviral protection by peptide vaccination," *Eur. J. Immunol.* 23:1189-1192, VCH Verlagsgesellschaft mbH (May 1993).

Krieger, J.I., et al., "Single amino acid changes in DR and antigen define residues critical for peptide-MHC binding and T cell recognition," *J. Immunol.* 146:2331-2340, American Associaton of Immunologists (1991).

Lipford, G.B., et al., "Primary in Vivo Responses to Ovalbumin. Probing the Predictive Value of the $K^b$ Binding Motif," *J. Immunol.* 150:1212-1222, The American Association of Immunologists (Feb. 1993).

Maryanski, J.L., et al., "Synthetic peptides as antigens and competitors in recognition by H-2-restricted cytolytic T cells specific for HLA," *J. Exp. Med.* 167:1391-1405, Rockefeller University Press (1988).

Maryanski, J.L., et al., "Competitor Analogs for Defined T Cell Antigens: Peptides Incorporating a Putative Binding Motif and Polyproline or Polyglycine Spacers," *Cell* 60:63-72, Cell Press (1990).

Morrison, J., et al., "Identification of the nonamer peptide from influenza A matrix protein and the role of pockets of HLA-A2 in its recognition by cytotoxic T lymphocytes," *Eur. J. Immunol.* 22:903-907, VCH Verlagsgesellschaft mbH (Apr. 1992).

Niedermann, G., et al., "The proteolytic fragments generated by vertebrate proteosomes: Structural relationships to major histocompatibility complex class I binding peptides," *Proc. Natl. Acad. Sci. USA* 93:8572-8577, National Academy Press (Aug. 1996).

Ochoa-Garay, J., et al., "The ability of peptides to induce cytotoxic T cells in vitro does not strongly correlate with their affinity for the $H-2L^d$ molecule: implications for vaccine design and immunotherapy," *Mol. Immunol.* 34:273-281, Elsevier Science, Ltd. (Feb. 1997).

Pamer, E.G., et al., "Precise prediction of a dominant class I MHC-restricted epitome of *Listeria monocytogenes*," *Nature* 353:852-855, Macmillan Publishers, Ltd. (1991).

Parham, P., et al., "The Origins of HLA-A,B,C Polymorphism," *Immunol. Rev.* 143:141-180, Munksgaard (Feb. 1995).

Parker, K.C., et al., "Peptide Binding to HLA-A2 and HLA-B27 Isolated from *Escherichia coli*," *J. Biol. Chem.* 267:5451-5459, American Society for Biochemistry and Molecular Biology, Inc. (Mar. 1992).

Parker, K.C., et al., "Sequence motifs important for peptide binding to the human MHC class I molecule, HLA-A2," *J. Immunol.* 149:3580-3587, American Association of Immunologists (Dec. 1992).

Rammensee, H.-G., et al., "Peptides Naturally Presented by MHC Class I Molecules," *Annu. Rev. Immunol.* 11:213-244, Annual Reviews, Inc. (Jan. 1993).

Reddehase, M.J., et al., "A pentapeptide as minimal antigenic determinant for MHC class I-restricted T lymphocytes," *Nature* 337:651-653, Macmillan Publishers, Ltd. (1989).

Romero, P., et al., "$H-2K^{d-}$ restricted Antigenic Peptides Share a Simple Binding Motif," *J. Exp. Med.* 174:603-612, Rockefeller University Press (1991).

Rothbard, J.B., "Major histocompatibility complex-peptide interactions," *Curr. Opin. Immunol.* 2:99-105, Current Biology, Ltd. (1989).

Rötzschke, O., et al., "Isolation and analysis of naturally processed viral peptides as recognized by cytotoxic T cells," *Nature* 348:252-254, Macmillan Publishers, Ltd. (1990).

Rötzschke, O., et al., "Characterization of Naturally Occuring Minor Histocompatibility Peptides Including H-4 and H-Y," *Science* 249:283-287, American Association for the Advancement of Science (1990).

Rötzschke, O., and Falk, K., "Naturally-occurring peptide antigens derived from the MHC class-I-restricted processing pathway," *Immunol. Today* 12:447-455, Elsevier Science Publishers, Ltd. (1991).

Rötzschke, O., et al., "Peptide motifs of closely related HLA class I molecules encompass substantial differences," *Eur. J. Immunol.* 22:2453-2456, VCH Verlagsgesellschaft mbH (Sep. 1992).

Rötzschke, O., and Falk, K., "Origin, structure and motifs of naturally processed MHC class II ligands," *Curr. Opin. Immunol.* 6:45-51, Current Biology, Ltd. (Feb. 1994).

Rudinger, J., "Characteristics of the amino acids as components of a peptide hormone sequence," in *Peptide Hormones*, Parsons, J.A., ed., University Park Press, Baltimore, MD, pp. 1-7 (1976).

Ruppert, J., et al., "Prominent Role of Secondary Anchor Residues in Peptide Binding to HLA-A2.1 Molecules," *Cell* 74:929-937, Cell Press (Sep. 1993).

Schulz, M., et al., "Major histocompatibility complex binding and T cell recognition of a viral nonapeptide containing a minimal tetrapeptide," *Eur. J. Immunol.* 21:1181-1185, VCH Verlagsgesellschaft mbH (1991).

Sette, A., et al., "Prediction of major histocompatibility complex binding regions of protein antigens by sequence pattern analysis," *Proc. Natl. Acad. Sci. USA* 86:3296-3300, National Academy Press (1989).

Sette, A., et al., "Random association between the peptide repertoire of A2.1 class I and several different DR class II molecules," *J. Immunol.* 147:3893-3900, The American Association of Immunologists (1991).

Sette, A., et al., "The Relationship Between Class I Binding Affinity and Immunogenicity of Potential Cytotoxic T Cell Epitopes," *J. Immunol.* 153:5586-5592, The American Association of Immunologists (Dec. 1994).

Sherman, L.A., et al., "Extracellular Processing of Peptide Antigens That Bind Class I Major Histocompatibility Molecules," *J. Exp. Med.* 175:1221-1226, The Rockefeller University Press (May 1992).

Shimojo, N., et al., "Specificity of peptide binding by the HLA-A2.1 molecule," *J. Immunol.* 143:2939-3947, The American Association of Immunologists (1989).

Sidney, J., et al., "Several HLA Alleles Share Overlapping Peptide Specificities," *J. Immunol.* 154:247-259, The American Association of Immunologists (Jan. 1995).

Wentworth, P.A., et al., "Differences and similarities in the A2.1-restricted cytotoxic T cell repertoire in humans and human leukocyte antigen-transgenic mice," *Eur. J. Immunol.* 26:97-101, VCH Verlagsgesellschaft mbH (Jan. 1996).

Whitton, J.L., et al., "Molecular Analyses of a Five-Amino-Acid Cytotoxic T-Lymphocyte (CTL) Epitope: an Immunodominant Region Which Induces Nonreciprocal CTL Cross-Reactivity," *J. Virol.* 63:4303-4310, American Society for Microbiology (1989).

Yewdell, J.W., and Bennink, J.R., "Cell Biology of Antigen Processing and Presentation to Major Histocompatibility Complex Class I Molecule-Restricted T Lymphocytes," *Adv. Immunol. 52*:1-123, Academic Press (Jul. 1992).

York, I.A., and Rock, K.L., "Antigen processing and presentation by the class I major histocompatibility complex," *Annu. Rev. Immunol. 14*:369-396, Annual Reviews, Inc. (Apr. 1996).

Zhang, Q-J., et al., "An HLA-A11-specific motif in nonamer peptides derived from viral and cellular proteins," *Proc. Natl. Acad. Sci. USA 90*:2217-2221, National Academy Press (Mar. 1993).

Parker, K.C., et al., "Scheme for Ranking Potential HLA-A2 Binding Peptides Based on Independent Binding of Individual Peptide Side-Chains," *J. Immunol. 152*:163-175, The American Association of Immunologists (Jan. 1994).

An, L.-L. and Whitton, J.L., "A Multivalent Minigene Vaccine, Containing B-Cell, Cytotoxic T-Lymphocyte, and $T_h$ Epitopes from Several Microbes, Induces Appropriate Responses In Vivo and Confers Protection against More than One Pathogen," *J. Virol. 71*:2292-2302, American Society for Microbiology (1997).

Chai, S.K., et al., "Immunogenic Properties of Multiple Antigen Peptide Systems Containing Defined T and B Epitopes," *J. Immunol. 149*:2385-2390, The American Association of Immunologists (1992).

Shi, Y.P., et al., "Immunogenicity and in vitro protective efficacy of a recombinant multistage *Plasmodium falciparum* candidate vaccine," *Proc. Natl. Acad. Sci. USA 96*:1615-1620, (Feb. 1999).

\* cited by examiner

FIGURE 1

*a* : HIV-FT

*b* : HBV-specific multiepitope constructs

HBV.1

HBV.2

HBV.1X $C_i$ = either W, Y, L, K, R, C, N or G

| Sequence | Length | Code | |
|---|---|---|---|
| VLAEAMSQV (SEQ ID NO:70) | 9 | A | |
| ILKEPVHGV (SEQ ID NO:71) | 9 | B | |
| TLNFPISPI (SEQ ID NO:72) | 9 | C | |
| SLLNATDIAV (SEQ ID NO:73) | 10 | D | |
| QMAVFIHNFK (SEQ ID NO:74) | 10 | E | 202 |
| VTVYYGVPVWK (SEQ ID NO:75) | 11 | F | |
| FPVRPQVPL (SEQ ID NO:76) | 9 | G | |
| YPLASLRSLF (SEQ ID NO:77) | 10 | H | |
| VIYQYMDDLY (SEQ ID NO:78) | 10 | I | |
| IYQEPFKNL (SEQ ID NO:79) | 9 | J | |
| IWGCSGKLI (SEQ ID NO:80) | 9 | K | |

| AA | C+1 ranking | N-1 ranking |
|---|---|---|
| K | 2.20 | 0.64 |
| C | 2.00 | 1.00 |
| N | 2.00 | 0.00 |
| G | 1.80 | 1.33 |
| T | 1.50 | 0.00 |
| A | 1.33 | 1.21 |
| F | 1.33 | 1.00 |
| S | 1.33 | 0.00 |
| W | 1.20 | 0.00 |
| Q | 1.20 | 0.00 |
| R | 1.17 | 1.57 |
| M | 1.00 | 0.00 |
| Y | 1.00 | 0.75 |
| I | 0.86 | 0.50 |
| L | 0.75 | 2.20 |
| V | 0.00 | 1.19 |
| D | 0.00 | 0.00 |
| H | 0.00 | 0.00 |
| E | 0.00 | 0.00 |
| P | 0.00 | 0.00 |

Motif Specification

XXXX(FY)XX(LIMV) (SEQ ID NO:370)
XXXX(FY)XXX(LIMV) (SEQ ID NO:371)
XXXXNXXX(LIMV) (SEQ ID NO:372)
XXXXNXXXX(LIMV) (SEQ ID NO:373)
X(LM)XXXXXXV (SEQ ID NO:374)
X(LM)XXXXXXXV (SEQ ID NO:375)
X(LMVT)XXXXXX(KRY) (SEQ ID NO:376)
X(LMVT)XXXXXXX(KRY) (SEQ ID NO:377)
XPXXXXXX(LIMVF) (SEQ ID NO:378)
XPXXXXXXX(LIMVF) (SEQ ID NO:379)

FIG. 11A

MaxInsertions={enter value here}   208

OutputToScreen=yes/no   210

OutputToFile=yes/no   212

MinimumAccepted={enter value here}   214

MaxDuplicateFunctionValues={enter value here}   216

MaxSearchTime (min.)={enter value here}   218

Exhaustive=yes/no   220

NumStochasticProbes={enter value here}   222

MaxHitsPerProbe={enter value here}   224

RandomProbeStart=yes/no   226

FIGURE 11B

Junctional Analyzer run on Saturday, February 26, 2000 09:06:23 pm.

The following non-zero AA weights will be used.

| AA | N-1 ranking | C+1 ranking |
|----|-------------|-------------|
| A | 1.21 | 1.33 |
| C | 1.00 | 2.00 |
| F | 1.00 | 1.33 |
| G | 1.33 | 1.80 |
| I | 0.50 | 0.86 |
| K | 0.64 | 2.20 |
| L | 2.20 | 0.75 |
| M | 0.00 | 1.00 |
| N | 0.00 | 2.00 |
| Q | 0.00 | 1.20 |
| R | 1.57 | 1.17 |
| S | 0.00 | 1.33 |
| T | 0.00 | 1.50 |
| V | 1.19 | 0.00 |
| W | 0.00 | 1.20 |
| Y | 0.75 | 1.00 |

} 204

The following 10 motif specifications will be used to search for junctionals.

| Count | Motif Specification |
|-------|---------------------|
| 1 | XXXX(FY)XX(LIMV) (SEQ ID NO:370) |
| 2 | XXXX(FY)XXX(LIMV) (SEQ ID NO:371) |
| 3 | XXXXNXXX(LIMV) (SEQ ID NO:372) |
| 4 | XXXXNXXXX(LIMV) (SEQ ID NO:373) |
| 5 | X(LM)XXXXXXV (SEQ ID NO:374) |
| 6 | X(LM)XXXXXXV (SEQ ID NO:375) |
| 7 | X(LMVT)XXXXXX(KRY) (SEQ ID NO:376) |
| 8 | X(LMVT)XXXXXXX(KRY) (SEQ ID NO:377) |
| 9 | XPXXXXXX(LIMVF) (SEQ ID NO:378) |
| 10 | XPXXXXXXX(LIMVF) (SEQ ID NO:379) |

} 206

| Code | Peptide | Length |
|------|---------|--------|
| A | VLAEAMSQV (SEQ ID NO:70) | 9 |
| B | ILKEPVHGV (SEQ ID NO:71) | 9 |
| C | TLNFPISPI (SEQ ID NO:72) | 9 |
| D | SLLNATDIAV (SEQ ID NO:73) | 10 |
| E | QMAVFIHNFK (SEQ ID NO:74) | 10 |
| F | VTVYYGVPVWK (SEQ ID NO:75) | 11 |
| G | FPVRPQVPL (SEQ ID NO:76) | 9 |
| H | YPLASLRSLF (SEQ ID NO:77) | 10 |
| I | VIYQYMDDLY (SEQ ID NO:78) | 10 |
| J | IYQEPFKNL (SEQ ID NO:79) | 9 |
| K | IWGCSGKLI (SEQ ID NO:80) | 9 |

} 202

MaxInsertions = 4 (208)

FIG. 13A

OutputToScreen = No

OutputToFile = Yes

MinimumValueAccepted = 0

MaxDuplicateFunctionValues = 50

SearchTime = 5

NumStochasticProbes = 10

MaxHitsPerProbe = 25

RandomProbeStart = Yes

| Col. 1<br>Code 1 | Col. 2<br>I1 | Col. 3<br>I2 | Col. 4<br>I3 | Col. 5<br>I4 | Col. 6<br>Code 2 | Col. 7<br>C | Col. 8<br>N | Col. 9<br>C+N | Col. 10<br>J | Col. 11<br>MaxFunc. |
|---|---|---|---|---|---|---|---|---|---|---|
| A | C | A |   | L | B | 2.00 | 2.20 | 4.40 | 0 | 8.80 |
| A | C |   |   | L | C | 2.00 | 2.20 | 4.40 | 0 | 8.80 |
| A | C |   |   | L | D | 2.00 | 2.20 | 4.40 | 0 | 8.80 |
| A | C |   |   | L | E | 2.00 | 2.20 | 4.40 | 0 | 8.80 |
| A | C |   |   | R | F | 2.00 | 1.57 | 3.14 | 2 | 1.57 |
| A | C |   |   | R | G | 2.00 | 1.57 | 3.14 | 1 | 3.14 |
| A | C |   |   | R | H | 2.00 | 1.57 | 3.14 | 0 | 6.28 |
| A | G |   |   |   | I | 1.80 | 1.33 | 2.39 | 1 | 2.39 |
| A | C | A | A |   | J | 2.00 | 1.33 | 2.66 | 0 | 5.32 |
| A | C |   |   | R | K | 2.00 | 1.57 | 3.14 | 0 | 6.28 |
| B | C | A | A | G | A | 2.00 | 1.33 | 2.66 | 0 | 5.32 |
| B | C | A |   | R | C | 2.00 | 1.57 | 3.14 | 0 | 6.28 |
| B | C | A |   | R | D | 2.00 | 1.57 | 3.14 | 0 | 6.28 |
| B | C | A |   | R | E | 2.00 | 1.57 | 3.14 | 0 | 6.28 |
| B | C | A | A | G | F | 2.00 | 1.33 | 2.66 | 1 | 2.66 |
| B | C |   |   | R | G | 2.00 | 1.57 | 3.14 | 1 | 3.14 |
| B | C |   |   | R | H | 2.00 | 1.57 | 3.14 | 0 | 6.28 |
| B | C | A | A | G | I | 2.00 | 1.33 | 2.66 | 1 | 2.66 |
| B | C | A | A | G | J | 2.00 | 1.33 | 2.66 | 0 | 5.32 |
| B | C | A | A | G | K | 2.00 | 1.33 | 2.66 | 0 | 5.32 |
| C | C | A |   | R | A | 2.00 | 1.57 | 3.14 | 1 | 3.14 |
| C | C | A |   | R | B | 2.00 | 1.57 | 3.14 | 1 | 3.14 |
| C | C |   |   | L | D | 2.00 | 2.20 | 4.40 | 1 | 4.40 |
| C | C | A |   | R | E | 2.00 | 1.57 | 3.14 | 1 | 3.14 |
| C | C |   |   | R | F | 2.00 | 1.57 | 3.14 | 1 | 3.14 |
| C | C |   |   | R | G | 2.00 | 1.57 | 3.14 | 1 | 3.14 |
| C | C |   |   | R | H | 2.00 | 1.57 | 3.14 | 0 | 6.28 |
| C | C | A |   | R | I | 2.00 | 1.57 | 3.14 | 1 | 3.14 |
| C | C | A | A | R | J | 2.00 | 1.57 | 3.14 | 0 | 6.28 |
| C | C | A | A | R | K | 2.00 | 1.57 | 3.14 | 0 | 6.28 |

FIGURE 13B

| Code 1 | I1 | I2 | I3 | I4 | Code 2 | C | N | C+N | J | MaxFunc |
|---|---|---|---|---|---|---|---|---|---|---|
| D | C |   |   | L | A | 2.00 | 2.20 | 4.40 | 0 | 8.80 |
| D | C |   |   | L | B | 2.00 | 2.20 | 4.40 | 0 | 8.80 |
| D | C |   |   | L | C | 2.00 | 2.20 | 4.40 | 0 | 8.80 |
| D | C |   |   | L | E | 2.00 | 2.20 | 4.40 | 0 | 8.80 |
| D | G |   |   |   | F | 1.80 | 1.33 | 2.39 | 0 | 4.79 |
| D | C |   |   | R | G | 2.00 | 1.57 | 3.14 | 0 | 6.28 |
| D | C | A | A | G | H | 2.00 | 1.33 | 2.66 | 0 | 5.32 |
| D | C |   |   | L | I | 2.00 | 2.20 | 4.40 | 1 | 4.40 |
| D | C | A |   | G | J | 2.00 | 1.33 | 2.66 | 0 | 5.32 |
| D | C |   |   | R | K | 2.00 | 1.57 | 3.14 | 0 | 6.28 |
| E | C | A | A | L | A | 2.00 | 2.20 | 4.40 | 0 | 8.80 |
| E | C | A | A | L | B | 2.00 | 2.20 | 4.40 | 0 | 8.80 |
| E | C | A | A | L | C | 2.00 | 2.20 | 4.40 | 0 | 8.80 |
| E | C | A | A | L | D | 2.00 | 2.20 | 4.40 | 0 | 8.80 |
| E | C | A |   | R | F | 2.00 | 1.57 | 3.14 | 0 | 6.28 |
| E | C | A |   | R | G | 2.00 | 1.57 | 3.14 | 0 | 6.28 |
| E | C | A |   | R | H | 2.00 | 1.57 | 3.14 | 0 | 6.28 |
| E | C | A | A | L | I | 2.00 | 2.20 | 4.40 | 0 | 8.80 |
| E | C | A |   | R | J | 2.00 | 1.57 | 3.14 | 0 | 6.28 |
| E | C | A |   | R | K | 2.00 | 1.57 | 3.14 | 0 | 6.28 |
| F | K |   |   | L | A | 2.20 | 2.20 | 4.84 | 1 | 4.84 |
| F | K | A | A | G | B | 2.20 | 1.33 | 2.93 | 1 | 2.93 |
| F | K | A | A | G | C | 2.20 | 1.33 | 2.93 | 0 | 5.85 |
| F | K | A | A | G | D | 2.20 | 1.33 | 2.93 | 0 | 5.85 |
| F | K | A | A | G | E | 2.20 | 1.33 | 2.93 | 0 | 5.85 |
| F | K | A |   | G | G | 2.20 | 1.33 | 2.93 | 1 | 2.93 |
| F | K | A |   | G | H | 2.20 | 1.33 | 2.93 | 1 | 2.93 |
| F | K | A | A | G | I | 2.20 | 1.33 | 2.93 | 1 | 2.93 |
| F | K |   |   | R | J | 2.20 | 1.57 | 3.45 | 1 | 3.45 |
| F | K |   |   | R | K | 2.20 | 1.57 | 3.45 | 0 | 6.91 |
| G | C | A |   | R | A | 2.00 | 1.57 | 3.14 | 1 | 3.14 |
| G | C | A |   | R | B | 2.00 | 1.57 | 3.14 | 2 | 1.57 |
| G | C | A |   | R | C | 2.00 | 1.57 | 3.14 | 1 | 3.14 |
| G | C |   |   | L | D | 2.00 | 2.20 | 4.40 | 1 | 4.40 |
| G | C | A |   | R | E | 2.00 | 1.57 | 3.14 | 2 | 1.57 |
| G | C |   |   | L | F | 2.00 | 2.20 | 4.40 | 4 | 1.10 |
| G | C |   |   | G | H | 2.00 | 1.33 | 2.66 | 0 | 5.32 |
| G | C | A | A | R | I | 2.00 | 1.57 | 3.14 | 2 | 1.57 |
| G | C | A | A | R | J | 2.00 | 1.57 | 3.14 | 1 | 3.14 |
| G | C | A | A | R | K | 2.00 | 1.57 | 3.14 | 0 | 6.28 |
| H | C | A | A | G | A | 2.00 | 1.33 | 2.66 | 0 | 5.32 |
| H | C | A | A | G | B | 2.00 | 1.33 | 2.66 | 1 | 2.66 |
| H | C | A |   | G | C | 2.00 | 1.33 | 2.66 | 0 | 5.32 |
| H | C | A |   | G | D | 2.00 | 1.33 | 2.66 | 0 | 5.32 |
| H | C | A | A | G | E | 2.00 | 1.33 | 2.66 | 0 | 5.32 |
| H | C | A | A | G | F | 2.00 | 1.33 | 2.66 | 1 | 2.66 |
| H | C |   |   | R | G | 2.00 | 1.57 | 3.14 | 1 | 3.14 |
| H | C | A | A | G | I | 2.00 | 1.33 | 2.66 | 1 | 2.66 |
| H | C | A |   | G | J | 2.00 | 1.33 | 2.66 | 1 | 2.66 |
| H | C | A | A | G | K | 2.00 | 1.33 | 2.66 | 0 | 5.32 |

FIGURE 13C

| Code 1 | I1 | I2 | I3 | I4 | Code 2 | C | N | C+N | J | MaxFunc |
|---|---|---|---|---|---|---|---|---|---|---|
| I | K | A | A | G | A | 2.20 | 1.33 | 2.93 | 0 | 5.85 |
| I | K | A | A | G | B | 2.20 | 1.33 | 2.93 | 1 | 2.93 |
| I | K | A |   | G | C | 2.20 | 1.33 | 2.93 | 0 | 5.85 |
| I | K | A |   | G | D | 2.20 | 1.33 | 2.93 | 0 | 5.85 |
| I | K | A | A | G | E | 2.20 | 1.33 | 2.93 | 0 | 5.85 |
| I | K | A | A | G | F | 2.20 | 1.33 | 2.93 | 1 | 2.93 |
| I | K |   |   | R | G | 2.20 | 1.57 | 3.45 | 1 | 3.45 |
| I | K | A | A | G | H | 2.20 | 1.33 | 2.93 | 0 | 5.85 |
| I | K | A |   | G | J | 2.20 | 1.33 | 2.93 | 1 | 2.93 |
| I | K | A | A | G | K | 2.20 | 1.33 | 2.93 | 0 | 5.85 |
| J | K | A | A | R | A | 2.20 | 1.57 | 3.45 | 0 | 6.91 |
| J | K | A | A | R | B | 2.20 | 1.57 | 3.45 | 1 | 3.45 |
| J | K | A |   | R | C | 2.20 | 1.57 | 3.45 | 0 | 6.91 |
| J | K | A |   | R | D | 2.20 | 1.57 | 3.45 | 0 | 6.91 |
| J | K | A |   | R | E | 2.20 | 1.57 | 3.45 | 1 | 3.45 |
| J | K | A | A | R | F | 2.20 | 1.57 | 3.45 | 2 | 1.73 |
| J | K |   |   | R | G | 2.20 | 1.57 | 3.45 | 1 | 3.45 |
| J | K |   |   | R | H | 2.20 | 1.57 | 3.45 | 0 | 6.91 |
| J | K | A | A | R | I | 2.20 | 1.57 | 3.45 | 1 | 3.45 |
| J | K | A | A | R | K | 2.20 | 1.57 | 3.45 | 0 | 6.91 |
| K | K |   |   | L | A | 2.20 | 2.20 | 4.84 | 0 | 9.68 |
| K | K |   |   | L | B | 2.20 | 2.20 | 4.84 | 0 | 9.68 |
| K | K |   |   | L | C | 2.20 | 2.20 | 4.84 | 0 | 9.68 |
| K | K |   |   | L | D | 2.20 | 2.20 | 4.84 | 0 | 9.68 |
| K | K | A | A | L | E | 2.20 | 2.20 | 4.84 | 0 | 9.68 |
| K | K | A | A | R | F | 2.20 | 1.57 | 3.45 | 1 | 3.45 |
| K | G |   |   |   | G | 1.80 | 1.33 | 2.39 | 0 | 4.79 |
| K | K |   |   | R | H | 2.20 | 1.57 | 3.45 | 0 | 6.91 |
| K | K |   |   | L | I | 2.20 | 2.20 | 4.84 | 1 | 4.84 |
| K | K |   |   | R | J | 2.20 | 1.57 | 3.45 | 0 | 6.91 |

Junctional Analyzer took 142.77 seconds.

FIGURE 13D

HIV 75mer: Pol 711 | GPGP | Gag 171 | GPGP | Pol 335 | GPGP | Pol 303

**E

EP-HIV-1090 (SEQ ID NO:81)
MGMQVQIQSLFLLLLWVPGSRGKLVGKLNWAGAAILKEPVHGVNAACPKVSFEPIKIPIHYCAPA
KAKFVAAWTLKAAAKAFPVRPQVPLGAAKLTPLCVTLGAAAVLAEAMSQVKVYLAWVPAHKG
AAAAIFQSSMTKKTTLFCASDAKNIPYNPQSQGVVKHPVHAGPIANVTVYYGVPVWKKAAAQMA
VFIHNFKNAAAYPLASLRSLFNLTFGWCFKLNRILQQLLFINAKIQNFRVYYRKAAVTIKIGGQLKK
VPLQLPPLKAMTNNPPIPV

ATGGGAATGCAGGTGCAGATCCAGAGCCTGTTTCTGCTCCTCCTGTGGGTGCCCGGATCCAGA
GGAAAGCTGGTGGGCAAACTCAACTGGGCCGGAGCTGCAATCCTGAAGGAGCCCGTCCACGG
GGTGAATGCCGCTTGCCCTAAAGTCAGCTTCGAACCAATTAAGATCCCCATTCATTACTGTGC
ACCTGCCAAAGCTAAGTTTGTGGCCGCTTGGACCCTCAAGGCCGCTGCAAAAGCCTTCCCAGT
GAGGCCCCAGGTGCCTCTGGGCGCCGCTAAACTCACACCACTGTGCGTCACTCTGGGAGCCGC
TGCAGTGCTGGCAGAGGCCATGTCCCAAGTGAAGGTGTATCTGGCTTGGGTGCCCGCCCACAA
GGGGGCCGCTGCAGCCATCTTTCAGTCTAGCATGACCAAGAAAACAACTCTGTTCTGTGCCTC
CGACGCTAAGAACATCCCTTATAATCCACAGTCTCAGGGCGTGGTCAAGCATCCCGTGCACGC
CGGACCTATTGCTAACGTGACCGTGTACTATGGGGTCCCAGTGTGGAAGAAAGCCGCTGCACA
GATGGCCGTGTTTATTCACAATTTCAAAAACGCCGCTGCATACCCCCTCGCCAGCCTGAGATC
CCTCTTCAACCTGACATTCGGCTGGTGCTTTAAGCTGAACCGGATCCTGCAGCAACTGCTCTTT
ATCAATGCTAAAATCCAGAACTTCCGCGTCTACTATAGGAAGGCTGCAGTGACTATCAAAATT
GGCGGACAACTGAAGAAAGTGCCTCTCCAGCTGCCCCCTCTCAAGGCAATGACCAACAATCC
CCCTATCCCAGTCTGA (SEQ ID NO:82)

HIV-CPT (SEQ ID NO:83)
MGMQVQIQSLFLLLLWVPGSRGIPIHYCAPAKAAKIQNFRVYYRKAAVTIKIGGQLKKAKFVAAW
TLKAAAKVPLQLPPLKAIFQSSMTKKLTPLCVTLGAQMAVFIHNFKGAKVYLAWVPAHKNAIPYN
PQSQGVVKAILKEPVHGVGAAALTFGWCFKLNAVLAEAMSQVNRILQQLLFINAAACPKVSFEPI
KVTVYYGVPVWKKAAHPVHAGPIANAAAYPLASLRSLFNAAATTLFCASDAKNKLVGKLNWAN
AAAFPVRPQVPLNMTNNPPIPV

ATGGGGATGCAGGTGCAGATCCAGAGCCTGTTTCTGCTCCTCCTGTGGGTGCCCGGATCCAGA
GGAATCCCCATTCACTACTGCGCCCCTGCTAAGGCAGCCAAAATCCAGAACTTCAGGGTGTAT
TACAGAAAGGCTGCAGTCACCATTAAAATCGGCGGACAACTGAAGAAAGCCAAGTTTGTGGC
CGCTTGGACACTCAAGGCCGCTGCAAAGGTCCCACTGCAGCTCCCCCCTCTGAAGGCCATCTT
CCAGAGCTCCATGACTAAGAAACTGACCCCACTGTGTGTGACACTCGGGGCCCAGATGGCTGT
GTTCATCCATAATTTTAAAGGCGCCAAGGTCTACCTGGCTTGGGTGCCCGCACACAAGAACGC
CATTCCTTACAATCCACAGTCTCAAGGAGTGGTCAAAGCTATTCTGAAGGAGCCCGTGCACGG
GGTGGGCGCCGCTGCACTCACTTTCGGATGGTGCTTTAAACTGAACGCCGTGCTGGCTGAAGC
CATGAGCCAGGTCAATCGGATCCTGCAGCAACTGCTCTTCATTAACGCCGCTGCATGTCCTAA
GGTGTCCTTCGAGCCAATCAAAGTGACCGTGTATTACGGGGTCCCCGTGTGGAAGAAAGCCGC
TCATCCTGTCCACGCAGGCCCAATCGCCAACGCCGCTGCATATCCCCTCGCCTCTCTGCGCAG
CCTGTTTAACGCCGCTGCAACAACCCTCTTTTGCGCCTCCGACGCTAAGAATAAACTGGTGGG
AAAGCTGAACTGGGCCAACGCAGCTGCATTCCCTGTGAGGCCACAGGTCCCCCTCAATATGAC
TAACAATCCCCCTATCCCAGTGTGA (SEQ ID NO:84)

FIGURE 18A

HIV-FT (SEQ ID NO:85)
MQVQIQSLFLLLLWVPGSRGKLVGKLNWAMASDFNLPPVAIFQSSMTKVTIKIGGQLKRILQQLLF
IMAVFIHNFKIPYNPQSQGVVTTLFCASDAKILKEPVHGVQMAVFIHNFKGAAVFIHNFKRCPKVSF
EPIKIQNFRVYYRLTFGWCFKLQVPLRPMTYKMTNNPPIPVTVYYGVPVWKVLAEAMSQVIPIHY
CAPAKLTPLCVTL

ATGCAGGTGCAGATCCAGAGCCTGTTTCTGCTCCTCCTGTGGGTGCCCGGATCCAGAGGAAAG
CTGGTGGGGAAGCTGAACTGGGCCATGGCCAGCGATTTCAACCTGCCCCCCGTGGCCATCTTC
CAGAGCAGCATGACCAAGGTGACCATCAAGATCGGGGGGCAGCTGAAGAGGATCCTGCAGCA
GCTGCTGTTCATCATGGCCGTGTTCATCCACAACTTCAAGATCCCCTACAACCCCCAGAGCCA
GGGGGTGGTGACCACCCTGTTCTGCGCCAGCGATGCCAAGATCCTGAAGGAGCCCGTGCACG
GGGTGCAGATGGCCGTGTTCATCCACAACTTCAAGGGCGCCGCCGTGTTCATCCACAACTTCA
AGAGGTGCCCCAAGGTGAGCTTCGAGCCCATCAAGATCCAGAACTTCAGGGTGTACTACAGG
CTGACCTTCGGGTGGTGCTTCAAGCTGCAGGTGCCCCTGAGGCCCATGACCTACAAGATGACC
AACAACCCCCCCATCCCCGTGACCGTGTACTACGGGGTGCCCGTGTGGAAGGTGCTGGCCGAG
GCCATGAGCCAGGTGATCCCCATCCACTACTGCGCCCCGCCAAGCTGACCCCCCTGTGCGTG
ACCCTG (SEQ ID NO:86)

FIGURE 18B

HIV-TC (SEQ ID NO:87)
MGMQVQIQSLFLLLLWVPGSRGYWQATWIPEWKAIFQSSMTKKVYLAWVPAHKNAACPKVSFE
PIKHPVHAGPIANLTFGWCFKLNKMIGGIGGFIKFRDYVDRFYKAAARILQQLLFINTTLFCASDAK
NQMVHQAISPRGAKLVGKLNWAGAAAIYETYGDTWKAAQVPLRPMTYKGAAAVTVLDVGDAY
NAAARYLKDQQLLNTLNFPISPINMTNNPPIPVNAPYNTPVFAIKAAAVPLQLPPLKAAIPYNPQSQ
GVVKALLQLTVWGIGAAILKEPVHGVNAAAFPISPIETVKVWKEATTTLFKAAAVTIKIGGQLKKI
YQEPFKNLKAAAVLAEAMSQVNLVGPTPVNIGAAAEVNIVTDSQYKAAAIPIHYCAPAKAVIYQY
MDDLYKAAAQMAVFIHNFKNAATYQIYQEPFKPYNEWTLELKAKIQNFRVYYRKAFPVRPQVPL
GAAAIWGCSGKLIKVMIVWQVDRNAAKAACWWAGIKAKFVAAWTLKAAAKLTPLCVTLNAAM
ASDFNLPPVKSLLNATDIAVNVTVYYGVPVWKKAAAAIIRILQQLKRAMASDFNLNAAAYPLASL
RSLF

ATGGGGATGCAGGTGCAGATCCAGAGCCTGTTTCTGCTCCTCCTGTGGGTGCCCGGATCTAGA
GGATACTGGCAAGCTACTTGGATTCCAGAATGGAAAGCTATCTTTCAATCCTCAATGACGAAG
AAGGTATACCTGGCATGGGTCCCAGCACACAAGAACGCCGCTTGCCCAAAGGTGTCCTTTGAA
CCCATTAAACACCCAGTGCACGCAGGGCCAATAGCGAATTTGACATTCGGGTGGTGCTTCAAA
CTAAACAAAATGATCGGCGGCATTGGAGGCTTTATCAAGTTTAGAGATTACGTGGACCGATTC
TATAAAGCCGCTGCCCGTATACTCCAGCAGCTACTATTCATCAACACCACTCTCTTCTGCGCTT
CAGACGCTAAGAACCAAATGGTACACCAAGCCATAAGCCCTAGAGGAGCCAAGCTCGTAGGG
AAATTAAATTGGGCGGGTGCAGCAGCAATCTACGAGACTTACGGCGATACCTGGAAAGCAGC
CCAGGTTCCGTTACGCCCAATGACCTATAAAGGCGCAGCAGCAGTAACAGTTCTAGATGTAGG
AGACGCTTACAACGCTGCCGCAAGATACCTAAAAGATCAGCAGTTACTCAACACACTAAATTT
CCCAATTAGCCCGATAAACATGACAAATAACCCACCAATTCCCGTCAATGCTCCCTACAACAC
TCCAGTATTCGCAATCAAAGCCGCTGCTGTCCCCCTGCAGCTCCCTCCTCTGAAAGCTGCGAT
ACCTTACAACCCACAGAGCCAAGGTGTTGTCAAAGCACTGCTTCAGCTAACAGTTTGGGGAAT
TGGTGCTGCAATTCTAAAAGAGCCAGTTCATGGGGTTAACGCCGCCGCCTTCCCAATCAGTCC
TATTGAGACTGTGAAAGTATGGAAAGAAGCCACAACCACACTTTTTAAGGCAGCCGCAGTTA
CAATTAAAATAGGGGGCCAACTTAAGAAAATATACCAGGAACCTTTCAAGAATCTCAAAGCC
GCTGCAGTGCTCGCCGAGGCTATGTCACAGGTGAATTTGGTCGGACCAACACCCGTAAACATC
GGAGCCGCAGCCGAAGTGAACATAGTCACCGACTCACAGTACAAAGCCGCTGCAATACCCAT
ACATTATTGTGCTCCCGCAAAGGCCGTGATCTATCAATATATGGACGACCTGTATAAGGCCGC
CGCGCAGATGGCAGTCTTTATCCACAACTTTAAAAACGCAGCTACTTATCAGATCTACCAGGA
ACCATTCAAACCGTACAATGAGTGGACCTTGGAACTAAAGGCCAAAATTCAGAACTTCAGGG
TATATTATAGAAAAGCATTTCCAGTGAGGCCCCAGGTGCCTCTGGGTGCCGCAGCAATATGGG
GATGTTCTGGAAAACTGATCAAGGTGATGATTGTATGGCAAGTGGACAGAAATGCAGCTAAG
GCAGCCTGTTGGTGGGCAGGTATAAAAGCAAAGTTCGTGGCAGCATGGACGCTTAAAGCAGC
CGCAAAACTCACTCCTCTCTGCGTGACACTTAATGCAGCCATGGCCTCTGATTTCAACCTTCCC
CCTGTAAAATCCCTGCTTAATGCGACAGATATCGCAGTCAACGTAACAGTATATTATGGCGTG
CCAGTCTGGAAAAAAGCCGCCGCGGCCATAATTCGGATACTGCAGCAGCTGAAAAGAGCTAT
GGCGAGTGACTTCAACCTGAATGCGGCCGCCTACCCCTTGGCATCGTTAAGGTCACTATTTTG
A (SEQ ID NO:88)

FIGURE 18C

HCV.1 (SEQ ID NO:89)
MGMQVQIQSLFLLLLWVPGSRGLLFNILGGWVDLMGYIPLVYLVAYQATVILAGYGAGVRLIVFP
DLGVHMWNFISGIYLLPRRGPRLYLVTRHADVVLVGGVLAALLFLLLADAFLLLADARVWMNRL
IAFACTCGSSDLYLSAFSLHSYGVAGALVAFKLPGCSFSIFKTSERSQPRLIFCHSKKKFWAKHMW
NFIPFYGKAIRMYVGGVEHRQLFTFSPRRRLGVRATRKVGIYLLPNRAKFVAAWTLKAAA*

GAATTCGCCGCCACCATGCAGGTGCAGATCCAGAGCCTGTTTCTGCTCCTCCTGTGGGTGCCCGGATCCAGAGGACTGC
TGTTCAACATCCTGGGGGGTGGGTGGATCTGATGGGGTACATCCCCCTGGTGTACCTGGTGGCCTACCAGGCCACCGT
GATCCTGGCCGGGTACGGGGCCGGGGTGAGGCTGATCGTGTTCCCCGATCTGGGGGTGCACATGTGGAACTTCATCAGC
GGGATCTACCTGCTGCCCAGGAGAGGACCTAGACTGTACCTGGTGACTAGACACGCTGATGTGGTGCTGGTGGGAGGAG
TGCTGGCTGCTCTGCTGTTTCTGCTGCTGGCTGATGCTTTCCTGCTGCTGGCTGATGCTAGAGTGTGGATGAACAGACT
GATCGCTTTCGCTTGTACATGTGGAAGCTCCGATCTGTATCTGAGCGCTTTCAGCCTGCACAGCTACGGAGTGGCTGGA
GCTCTGGTGGCTTTTAAGCTGCCTGGATGTAGCTTTAGCATCTTTAAGACCAGCGAAAGAAGCCAGCCTAGACTGATCT
TTTGTCACAGCAAGAAGAAGTTTTGGGCTAAGCACATGTGGAATTTTATCCCTTTCTATGGAAAGGCTATCAGAATGTA
TGTGGGAGGAGTGGAACACAGACAGCTGTTTACATTTAGCCCTAGAAGGAGACTGGGAGTGAGAGCTACAAGAAAGGTG
GGAATCTATCTGCTGCCTAATAGATGAAAGCTTGGG* (SEQ ID NO:90)

HCV.2 (SEQ ID NO:91)
MGMQVQIQSLFLLLLWVPGSRGDLMGYIPLVAKFVAAWTLKAAALLFLLLADALIFCHSKKKQLF
TFSPRRYLVTRHADVYLLPRRGPRLCTCGSSDLYHMWNFISGIFWAKHMWNFAKFVAAWTLKAA
AILAGYGAGVYLVAYQATVGVAGALVAFKIPFYGKAIRMYVGGVEHRVLVGGVLAAFLLLADA
RVLPGCSFSIFAKFVAAWTLKAAAKTSERSQPRRLGVRATRKRLIVFPDLGVWMNRLIAFALSAFS
LHSYLLFNILGGWVVGIYLLPNR*

GAATTCGCCGCCACCATGGGAATGCAGGTGCAGATCCAGAGCCTGTTTCTGCTCCTCCTGTGG
GTGCCCGGATCCAGAGGAGATCTGATGGGATATATCCCTCTGGTGGCTAAGTTTGTGGCTGCT
TGGACACTGAAGGCTGCTGCTCTGCTGTTTCTGCTGCTGGCTGATGCTCTGATCTTCTGTCACA
GCAAGAAGAAGCAGCTGTTTACATTTAGCCCAAGAAGATATCTGGTGACAAGACACGCTGAT
GTGTATCTGCTGCCTAGACGCGGACCTAGACTGTGTACATGTGGAAGCTCCGATCTGTATCAC
ATGTGGAACTTTATCAGCGGAATCTTTTGGGCTAAGCACATGTGGAATTTCATCCTGGCTGGA
TATGGAGCTGGAGTGTATCTGGTGGCTTATCAGGCTACAGTGGGAGTGGCTGGAGCTCTGGTG
GCTTTCAAGATCCCATTCTATGGAAAGGCTATCAGAATGTATGTGGGAGGAGTGGAACACAG
AGTGCTGGTGGGAGGAGTGCTGGCTGCTTTCCTGCTGCTGGCTGATGCTAGAGTGCTGCCAGG
ATGTAGCTTTAGCATCTTCAAGACTTCCGAACGCTCCCAGCCTAGAAGACTGGGAGTGAGAGC
TACAAGGAAGAGACTGATCGTGTTTCCAGATCTGGGAGTGTGGATGAATAGACTGATCGCTTT
CGCTCTGAGCGCTTTCAGCCTGCACAGCTATCTGCTGTTCAACATCCTGGGAGGATGGGTGGT
GGGAATCTATCTGCTGCCAAACAGATGAAAGCTT (SEQ ID NO:92)

HCV.3s1 (SEQ ID NO:93)
MGMQVQIQSLFLLLLWVPGSRGYLVAYQATVAKFVAAWTLKAAALLFLLLADALIFCHSKKKYL
VTRHADVLGFGAYMSKCTCGSSDLYHMWNFISGIFWAKHMWNF*

GAATTCGCCGCCACCATGGGAATGCAGGTGCAGATCCAAAGCCTGTTTCTGCTCCTCCTGTGG
GTGCCCGGATCCAGAGGATACCTCGTCGCCTACCAGGCCACTGTGGCTAAATTCGTGGCAGCC
TGGACACTGAAAGCTGCAGCTCTGCTCTTCCTGCTCCTGGCCGATGCACTCATCTTCTGCCATT
CCAAGAAAAAGTATCTGGTCACCAGACATGCTGACGTGCTGGGGTTTGGCGCCTACATGAGC
AAGTGCACCTGTGGCAGCTCCGACCTGTATCACATGTGGAACTTTATTTCTGGAATCTTTTGGG
CCAAGCACATGTGGAATTTCTGAAAGCTT (SEQ ID NO:94)

FIGURE 18D

HCV.3s2 (SEQ ID NO:95)
MGMQVQIQSLFLLLLWVPGSRGVLVGGVLAAAKFVAAWTLKAAAFLLLADARVLSAFSLHSYIL
AGYGAGVWMNRLIAFAIPFYGKAIVAGALVAFKVGIYLLPNR*

GAATTCGCCGCCACCATGGGAATGCAGGTGCAGATCCAAAGCCTGTTTCTGCTCCTCCTGTGG
GTGCCCGGATCCAGAGGAGTCCTGGTGGGCGGCGTCCTGGCCGCTGCTAAGTTTGTCGCTGCT
TGGACACTGAAGGCAGCCGCTTTCCTGCTCCTGGCAGACGCCAGGGTGCTGTCTGCCTTCAGC
CTCCACTCCTACATCCTCGCAGGGTATGGCGCAGGCGTGTGGATGAATCGGCTGATCGCCTTT
GCCATTCCATTCTATGGGAAAGCCATTGTGGCTGGCGCCCTGGTGGCATTCAAGGTCGGGATC
TACCTCCTGCCTAACCGCTGAAAGCTT (SEQ ID NO:96)

HCV.3s2(-3) (SEQ ID NO:97)
MGMQVQIQSLFLLLLWVPGSRGVLVGGVLAAAKFVAAWTLKAAAFLLLADARVLSAFSLHSYIL
AGYGAGVWMNRLIAFA*

GAATTCGCCGCCACCATGGGAATGCAGGTGCAGATCCAAAGCCTGTTTCTGCTCCTCCTGTGG
GTGCCCGGATCCAGAGGAGTCCTGGTGGGCGGCGTCCTGGCCGCTGCTAAGTTTGTCGCTGCT
TGGACACTGAAGGCAGCCGCTTTCCTGCTCCTGGCAGACGCCAGGGTGCTGTCTGCCTTCAGC
CTCCACTCCTACATCCTCGCAGGGTATGGCGCAGGCGTGTGGATGAATCGGCTGATCGCCTTT
GCCTGAGGATCC (SEQ ID NO:98)

HCV.3s3 (SEQ ID NO:99)
MGMQVQIQSLFLLLLWVPGSRGDLMGYIPLVAKFVAAWTLKAAARLGVRATRKLLFNILGGWV
RMYVGGVEHRRLIVFPDLGVGVAGALVAFKLPGCSFSIFKTSERSQPRQLFTFSPRRYLLPRRGPRL

GAATTCGCCGCCACCATGGGAATGCAGGTGCAGATCCAAAGCCTGTTTCTGCTCCTCCTGTGG
GTGCCCGGATCCAGAGGAGACCTGATGGGCTACATCCCTCTCGTGGCCAAGTTTGTGGCAGCT
TGGACCCTGAAGGCCGCTGCCAGACTGGGAGTGCGCGCTACACGGAAACTCCTGTTTAACATC
CTGGGAGGGTGGGTGCGGATGTACGTCGGAGGCGTCGAGCACAGAAGGCTCATTGTCTTTCC
AGATCTCGGCGTGGGCGTCGCAGGCGCACTCGTGGCCTTCAAACTGCCAGGGTGCAGCTTCAG
CATTTTCAAGACCTCCGAACGCTCCCAACCCAGACAGCTGTTCACTTTCTCTCCTCGGAGGTAT
CTGCTGCCCAGACGCGGACCCAGGCTGTGAAAGCTT (SEQ ID NO:100)

HCV.PC3 (SEQ ID NO:101)
MGMQVQIQSLFLLLLWVPGSRGLLFNILGGWVKAKFVAAWTLKAAALADGGCSGGAYRLIVFPD
LGVKFWAKHMWNFIGVAGALVAFKKQLFTFSPRR*

GAATTCGCCGCCACCATGGGAATGCAGGTGCAGATCCAAAGCCTGTTTCTGCTCCTCCTGTGG
GTGCCCGGATCCAGAGGACTGCTCTTCAACATCCTGGGCGGATGGGTGAAGGCCAAGTTCGTG
GCTGCCTGGACCCTGAAGGCTGCCGCTCTGGCCGACGGGGGATGCAGCGGCGGAGCTTACAG
GCTCATTGTCTTTCCCGATCTCGGAGTCAAATTTTGGGCAAAGCACATGTGGAATTTCATCGG
GGTGGCCGGAGCCCTGGTCGCTTTTAAAAAGCAGCTCTTCACCTTCTCCCCAAGACGGTGAGG
TACC (SEQ ID NO:102)

FIGURE 18E

HCV.PC4 (SEQ ID NO:103)
MGMQVQIQSLFLLLLWVPGSRGRLGVRATRKKAKFVAAWTLKAAAKTSERSQPRNLPGCSFSIFN
DLMGYIPLVKYLLPRRGPRLNTLCGFADLMGYRMYVGGVEHR*

```
GAATTCGCCGCCACCATGGGAATGCAGGTGCAGATCCAAAGCCTGTTTCTGCTCCTCCTGTGG
GTGCCCGGATCCAGAGGAAGGCTGGGCGTGAGAGCCACCCGGAAGAAGGCCAAGTTCGTGGC
TGCCTGGACCCTGAAGGCTGCCGCTAAAACAAGCGAGCGCTCCCAGCCCAGGAACCTGCCTG
GATGCTCTTTCAGCATCTTTAATGACCTCATGGGGTACATTCCACTGGTGAAGTATCTGCTCCC
CAGACGGGGCCCTCGCCTGAAGACTCTCTGTGGATTTGCTGATCTGATGGGGTACAGGATGTA
TGTCGGCGGAGTCGAACACAGATGAGGTACC    (SEQ ID NO:104)
```

HCV.2431(1P)  (SEQ ID NO:105)
MGMQVQIQSLFLLLLWVPGSRGVLVGGVLAAAFLLLADARVLSAFSLHSYILAGYGAGVWMNRL
IAFAGAAARLGVRATRKKAAAKTSERSQPRNLPGCSFSIFNDLMGYIPLVKYLLPRRGPRLNTLCG
FADLMGYRMYVGGVEHRKLLFNILGGWVKAAALADGGCSGGAYRLIVFPDLGVKFWAKHMWN
FIGVAGALVAFKKQLFTFSPRRNGYLVAYQATVAAALLFLLLADALIFCHSKKKYLVTRHADVLG
FGAYMSKCTCGSSDLYHMWNFISGIFWAKHMWNFKAAAAKFVAAWTLKAAA

```
GAATTCGCCGCCACCATGGGAATGCAGGTGCAGATCCAAAGCCTGTTTCTGCTCCTCCTGTGG
GTGCCCGGCTCCAGAGGAGTCCTGGTGGGCGGCGTCCTGGCAGCCGCTTTCCTGCTCCTGGCA
GACGCCAGGGTGCTGTCTGCCTTCAGCCTCCACTCCTACATCCTCGCAGGGTATGGCGCAGGC
GTGTGGATGAATCGGCTGATCGCCTTTGCCGGCGCTGCCGCAAGGCTGGGCGTGAGAGCCACC
CGGAAGAAGGCTGCCGCTAAAACAAGCGAGCGCTCCCAGCCCAGGAACCTGCCTGGATGCTC
TTTCAGCATCTTTAATGACCTCATGGGGTACATTCCACTGGTGAAGTATCTGCTCCCCAGACGG
GGCCCTCGCCTGAACACTCTCTGTGGATTTGCTGATCTGATGGGGTACAGGATGTATGTCGGC
GGAGTCGAACACAGAAAACTGCTCTTCAACATCCTGGGCGGATGGGTGAAGGCTGCCGCTCT
GGCCGACGGGGATGCAGCGGCGGAGCTTACAGGCTCATTGTCTTTCCCGATCTCGGAGTCAA
ATTTTGGGCAAAGCACATGTGGAATTTCATCGGGGTGGCCGGAGCCCTGGTCGCTTTTAAAAA
GCAGCTCTTCACCTTCTCCCCAAGACGGAACGGATACCTCGTCGCCTACCAGGCCACTGTGGC
TGCAGCTCTGCTCTTCCTGCTCCTGGCCGATGCACTCATCTTCTGCCATTCCAAGAAAAAGTAT
CTGGTCACCAGACATGCTGACGTGCTGGGGTTTGGCGCCTACATGAGCAAGTGCACCTGTGGC
AGCTCCGACCTGTATCACATGTGGAACTTTATTTCTGGAATCTTTTGGGCCAAGCACATGTGG
AATTTTAAGGCCGCAGCAGCTAAATTCGTGGCAGCCTGGACACTGAAAGCAGCTGCATGAGG
ATCC    (SEQ ID NO:106)
```

FIGURE 18F

HCV.4312(1P) (SEQ ID NO:107)
MGMQVQIQSLFLLLLWVPGSRGRLGVRATRKKAAAKTSERSQPRNLPGCSFSIFNDLMGYIPLVK
YLLPRRGPRLNTLCGFADLMGYRMYVGGVEHRKLLFNILGGWVKAAALADGGCSGGAYRLIVFP
DLGVKFWAKHMWNFIGVAGALVAFKKQLFTFSPRRNGYLVAYQATVAAALLFLLLADALIFCHS
KKKYLVTRHADVLGFGAYMSKCTCGSSDLYHMWNFISGIFWAKHMWNFKKAAAVLVGGVLAA
AFLLLADARVLSAFSLHSYILAGYGAGVWMNRLIAFANAAAKFVAAWTLKAAA*

GAATTCGCCGCCACCATGGGAATGCAGGTGCAGATCCAAAGCCTGTTTCTGCTCCTCCTGTGG
GTGCCCGGCTCCAGAGGAAGGCTGGGCGTGAGAGCCACCCGGAAGAAGGCTGCCGCTAAAAC
AAGCGAGCGCTCCCAGCCCAGGAACCTGCCTGGATGCTCTTTCAGCATCTTTAATGACCTCAT
GGGGTACATTCCACTGGTGAAGTATCTGCTCCCCAGACGGGGCCCTCGCCTGAACACTCTCTG
TGGATTTGCTGATCTGATGGGGTACAGGATGTATGTCGGCGGAGTCGAACACAGAAAACTGCT
CTTCAACATCCTGGGCGGATGGGTGAAGGCTGCCGCTCTGGCCGACGGGGATGCAGCGGCG
GAGCTTACAGGCTCATTGTCTTTCCCGATCTCGGAGTCAAATTTTGGGCAAAGCACATGTGGA
ATTTCATCGGGGTGGCCGGAGCCCTGGTCGCTTTTAAAAAGCAGCTCTTCACCTTCTCCCCAA
GACGGAACGGATACCTCGTCGCCTACCAGGCCACTGTGGCTGCAGCTCTGCTCTTCCTGCTCC
TGGCCGATGCACTCATCTTCTGCCATTCCAAGAAAAAGTATCTGGTCACCAGACATGCTGACG
TGCTGGGGTTTGGCGCCTACATGAGCAAGTGCACCTGTGGCAGCTCCGACCTGTATCACATGT
GGAACTTTATTTCTGGAATCTTTTGGGCCAAGCACATGTGGAATTTTAAGAAAGCCGCTGCAG
TCCTGGTGGGCGGCGTCCTGGCAGCCGCTTTCCTGCTCCTGGCAGACGCCAGGGTGCTGTCTG
CCTTCAGCCTCCACTCCTACATCCTCGCAGGGTATGGCGCAGGCGTGTGGATGAATCGGCTGA
TCGCCTTTGCCAATGCTGCAGCTAAATTCGTGGCAGCCTGGACACTGAAAGCAGCTGCATGAG
GATCC (SEQ ID NO:108)

AOSI.K (SEQ ID NO:109)
MGMQVQIQSLFLLLLWVPGSRGHTLWKAGILYKAKFVAAWTLKAAAFLPSDFFPSVKFLLSLGIH
LYMDDVVLGVGLSRYVARLFLLTRILTISTLPETTVVRRQAFTFSPTYKWLSLLVPFV

ATGGGAATGCAGGTGCAGATCCAGAGCCTGTTTCTGCTCCTCCTGTGGGTGCCCGGGTCCAGA
GGACACACCCTGTGGAAGGCCGGAATCCTGTATAAGGCCAAGTTCGTGGCTGCCTGGACCCTG
AAGGCTGCCGCTTTCCTGCCTAGCGATTTCTTTCCTAGCGTGAAGTTCCTGCTGTCCCTGGGAA
TCCACCTGTATATGGATGACGTGGTGCTGGGAGTGGGACTGTCCAGGTACGTGGCTAGGCTGT
TCCTGCTGACCAGAATCCTGACCATCTCCACCCTGCCAGAGACCACCGTGGTGAGGAGGCAGG
CCTTCACCTTTAGCCCTACCTATAAGTGGCTGAGCCTGCTGGTGCCCTTTGTGTGA (SEQ ID NO:110)

HBV.1 (SEQ ID NO:111)
MGMQVQIQSLFLLLLWVPGSRGHTLWKAGILYKAKFVAAWTLKAAAFLPSDFFPSVFLLSLGIHL
YMDDVVLGVGLSRYVARLFLLTRILTISTLPETTVVRRQAFTFSPTYKWLSLLVPFVIPIPSSWAFTP
ARVTGGVFKVGNFTGLYLPSDFFPSVTLWKAGILYKNVSIPWTHKLVVDFSQFSRSAICSVVRRAL
MPLYACI

ATGGGAATGCAGGTGCAGATCCAGAGCCTGTTTCTGCTCCTCCTGTGGGTGCCCGGGTCCAGA
GGACACACCCTGTGGAAGGCCGGAATCCTGTATAAGGCCAAGTTCGTGGCTGCCTGGACCCTG
AAGGCTGCCGCTTTCCTGCCTAGCGATTTCTTTCCTAGCGTGTTCCTGCTGTCCCTGGGAATCC
ACCTGTATATGGATGACGTGGTGCTGGGAGTGGGACTGTCCAGGTACGTGGCTAGGCTGTTCC
TGCTGACCAGAATCCTGACCATCTCCACCCTGCCAGAGACCACCGTGGTGAGGAGGCAGGCCT
TCACCTTTAGCCCTACCTATAAGTGGCTGAGCCTGCTGGTGCCCTTTGTGATCCCTATCCCTAG
CTCCTGGGCTTTCACCCCAGCCAGGGTGACCGGAGGAGTGTTTAAGGTGGGAAACTTCACCGG
CCTGTATCTGCCCAGCGATTTCTTTCCTAGCGTGACCCTGTGGAAGGCCGGGATCCTGTACAA
GAATGTGTCCATCCCTTGGACCCACAAGCTGGTGGTGGACTTTTCCCAGTTCAGCAGATCCGC
TATCTGCTCCGTGGTGAGGAGAGCTCTGATGCCACTGTATGCCTGTATCTGA (SEQ ID NO:112)

FIGURE 18G

HBV.2 (SEQ ID NO:113)
MGMQVQIQSLFLLLLWVPGSRGHTLWKAGILYKAKFVAAWTLKAAAFLPSDFFPSVNFLLSLGIH
LYMDDVVLGVGLSRYVARLFLLTRILTISTLPETTVVRRQAFTFSPTYKGAAAWLSLLVPFVNTPIP
SSWAFKTPARVTGGVFKVGNFTGLYNLPSDFFPSVKTLWKAGILYKNVSIPWTHKGAALVVDFSQ
FSRNSAICSVVRRALMPLYACI

ATGGGAATGCAGGTGCAGATCCAGAGCCTGTTTCTGCTCCTCCTGTGGGTGCCCGGGTCCAGA
GGACACACCCTGTGGAAGGCCGGAATCCTGTATAAGGCCAAGTTCGTGGCTGCCTGGACCCTG
AAGGCTGCCGCTTTCCTGCCTAGCGATTTCTTTCCTAGCGTGAACTTCCTGCTGTCCCTGGGAA
TCCACCTGTATATGGATGACGTGGTGCTGGGAGTGGGACTGTCCAGGTACGTGGCTAGGCTGT
TCCTGCTGACCAGAATCCTGACCATCTCCACCCTGCCAGAGACCACCGTGGTGAGGAGGCAGG
CCTTCACCTTTAGCCCTACCTATAAGGGAGCCGCTGCCTGGCTGAGCCTGCTGGTGCCCTTTGT
GAATATCCCTATCCCTAGCTCCTGGGCTTTCAAGACCCCAGCCAGGGTGACCGGAGGAGTGTT
TAAGGTGGGAAACTTCACCGGCCTGTATAACCTGCCCAGCGATTTCTTTCCTAGCGTGAAGAC
CCTGTGGAAGGCCGGAATCCTGTACAAGAATGTGTCCATCCCTTGGACCCACAAGGGAGCCG
CTCTGGTGGTGGACTTTTCCCAGTTCAGCAGAAATTCCGCTATCTGCTCCGTGGTGAGGAGAG
CTCTGATGCCACTGTATGCCTGTATCTGA    (SEQ ID NO:114)

PfCTL.1 (SEQ ID NO:115)
MQVQIQSLFLLLLWVPGSRGILSVSSFLFVNAAAQTNFKSLLRNLPSENERGYKAAALLACAGLAY
KKAAAAKFVAAWTLKAAAKAFMKAVCVEVNAAASFLFVEALFNATPYAGEPAPFKAAAKYKLA
TSVLKAGVSENIFLKNAAAYFILVNLLIKAGLLGVVSTV

ATGGGAATGCAGGTGCAGATCCAGAGCCTGTTTCTGCTCCTCCTGTGGGTGCCCGGATCCAGA
GGAATCCTGAGCGTGTCCTCTTTCCTGTTTGTCAACGCCGCTGCACAGACCAATTTCAAGAGC
CTCCTGAGGAACCTCCCCTCCGAGAACGAAAGAGGCTACAAAGCCGCTGCACTGCTCGCCTGC
GCTGGACTGGCCTATAAGAAAGCCGCTGCAGCCAAGTTCGTGGCCGCTTGGACACTGAAGGC
CGCTGCAAAAGCCTTTATGAAGGCTGTCTGTGTGGAGGTCAATGCCGCTGCATCTTTCCTGTTT
GTGGAGGCCCTCTTTAACGCTACTCCTTACGCAGGGGAACCAGCCCCCTTCAAGGCCGCTGCA
AAATATAAGCTGGCAACCAGCGTGCTGAAGGCTGGCGTGTCCGAGAATATTTTTCTGAAAAAC
GCCGCTGCATACTTCATCCTGGTGAATCTGCTCATTAAGGCCGGACTCCTGGGGGTGGTCTCT
ACAGTGTGA   (SEQ ID NO:116)

PfCTL.2 (SEQ ID NO:117)
MQVQIQSLFLLLLWVPGSRGFVEALFQEYNAAAKYLVTVFLINALACAGLAYKKFYFILVNLLKA
ALFFIIFNKNAAAKFVAAWTLKAAAKFILVNLLIFHNFQDEENIGIYKLPYGRTNLKAAAVLLGGV
GLVLNFLIFFDLFLVKAVLAGLLGVV

ATGGGAATGCAGGTGCAGATCCAGAGCCTGTTTCTGCTCCTCCTGTGGGTGCCCGGATCCAGA
GGATTCGTGGAGGCCCTGTTTCAGGAATACAACGCCGCTGCAAAGTATCTCGTCATCGTGTTC
CTGATCAATGCTCTGGCATGCGCCGGCCTCGCTTACAAAAAGTTTTACTTCATTCTGGTCAACC
TGCTCAAGGCCGCTCTGTTCTTTATCATTTTCAATAAAAACGCCGCAGCTAAGTTTGTGGCCGC
ATGGACCCTGAAGGCCGCTGCAAAATTCATCCTCGTGAATCTGCTCATTTTTCACAACTTCCAA
GACGAGGAAAATATCGGAATTTATAAGCTGCCCTACGGGAGGACAAACCTGAAAGCCGCTGC
AGTCCTGCTCGGCGGAGTGGGGCTGGTGCTCAATTTTCTGATCTTCTTTGATCTGTTCCTGGTG
AAGGCCGTCCTGGCCGGCCTGCTCGGAGTCGTGTGA   (SEQ ID NO:118)

FIGURE 18H

PfCTL.3 (SEQ ID NO:119)
MQVQIQSLFLLLLWVPGSRGVFLIFFDLFLNAAAPSDGKCNLYKAAAVTCGNGIQVRKLFHIFDGD
NEIKAHVLSHNSYEKNYYGKQENWYSLKKILSVFFLANAAAKFIKSLFHIFKAAALYISFYFIKAKF
VAAWTLKAAAKAAAYYIPHQSSLKAAAGLIMVLSFL

ATGGGAATGCAGGTGCAGATCCAGAGCCTGTTTCTGCTCCTCCTGTGGGTGCCCGGATCCAGA
GGAGTGTTCCTGATCTTCTTTGACCTGTTCCTGAACGCCGCTGCACCCAGCGATGGCAAGTGC
AATCTCTACAAGGCCGCTGCAGTGACCTGTGGAAACGGGATTCAGGTCAGGAAACTCTTTCAC
ATCTTCGACGGCGATAACGAGATCAAGGCCCATGTGCTGTCCCACAATTCTTATGAAAAAAAC
TACTATGGAAAGCAAGAGAATTGGTACAGCCTGAAGAAAATTCTGTCCGTGTTCTTTCTCGCC
AACGCCGCTGCAAAGTTTATCAAGTCTCTGTTCCATATTTTCAAGGCCGCTGCACTCTACATCA
GCTTCTATTTTATTAAAGCCAAATTTGTGGCCGCTTGGACACTGAAGGCCGCTGCAAAAGCCG
CTGCATACTATATCCCTCACCAGAGCTCCCTGAAGGCCGCTGCAGGGCTGATCATGGTGCTCT
CTTTCCTGTGA (SEQ ID NO:120)

PfCTL/HTL(N) (SEQ ID NO:121)
MQVQIQSLFLLLLWVPGSRGSSVFNVVNSSIGLIMVLSFLGPGPGLYISFYFILVNLLIFHINGKIIKN
SEGPGPGPDSIQDSLKESRKLSGPGPGVLAGLLGVVSTVLLGGVGLVLGPGPGLPSENERGYYIPHQ
SSLGPGPGQTNFKSLLRNLGVSENIFLKGPGPGFQDEENIGIYGPGPGKYLVIVFLIFFDLFLVGPGP
GKFIKSLFHIFDGDNEIGPGPGKSKYKLATSVLAGLLGPGPGLPYGKTNLGPGPGRHNWVNHAVPL
AMKLIGPGPGMRKLAILSVSSFLFVEALFQEYGPGPGVTCGNGIQVRGPGPGMNYYGKQENWYSL
KKGPGPGPSDGKCNLYADSAWENVKNVIGPFMKAVCVEVGPGPGKILSVFFLALFFIIFNKGPGPG
HVLSHNSYEKGPGPGKYKIAGGIAGGLALLACAGLAYKFVVPGAATPYAGEPAPF

ATGGGAATGCAGGTGCAGATCCAGAGCCTGTTTCTGCTCCTCCTGTGGGTGCCCGGATCCAGA
GGAAGTAGTGTGTTCAATGTTGTGAACTCATCAATTGGTCTGATCATGGTGCTGAGCTTTCTCG
GGCCAGGGCCAGGATTATATATTTCTTTCTACTTCATCCTTGTCAACCTGTTAATATTCCACAT
TAACGGCAAAATAATAAAGAACAGTGAAGGCCCTGGGCCTGGGCCTGACTCGATCCAGGATT
CTCTAAAAGAATCGAGGAAGCTCTCCGGACCAGGCCCTGGTGTACTCGCCGGGTTGCTGGGA
GTAGTTAGCACAGTGCTGTTAGGAGGCGTCGGCCTCGTCTTAGGACCTGGACCAGGTCTGCCG
TCCGAAAACGAAAGAGGATACTACATACCTCACCAGAGCAGCCTCGGCCCAGGCCCCGGACA
AACCAATTTCAAATCCCTCTTGCGAAATCTAGGAGTGAGCGAGAACATATTTCTTAAAGGACC
CGGTCCCGGCTTTCAGGACGAGGAGAATATAGGTATTTACGGTCCAGGACCTGGAAAATACCT
AGTGATCGTATTCCTAATTTTTTTTGACCTATTTCTGGTGGGCCCAGGTCCCGGAAAGTTCATT
AAATCACTCTTCCACATTTTTGACGGAGATAACGAGATAGGACCCGGTCCCGGGAAATCAAA
GTACAAACTAGCCACTTCAGTGCTGGCCGGCCTTCTAGGGCCGGGCCCAGGGCTCCCCTATGG
AAAGACAAATCTTGGCCCCGGTCCAGGACGGCACAACTGGGTGAATCATGCGGTTCCATTGG
CCATGAAACTAATCGGGCCCGGTCCAGGCATGCGCAAACTTGCAATTCTAAGCGTAAGTTCAT
TTCTGTTCGTAGAGGCACTGTTTCAAGAATATGGCCCAGGACCTGGCGTCACATGTGGGAATG
GGATCCAGGTGAGAGGACCGGGACCTGGTATGAACTATTACGGTAAACAGGAAAATTGGTAC
TCCCTGAAAAAGGGTCCAGGCCCCGGCCCCTCAGATGGTAAGTGCAACCTGTATGCTGACTCA
GCATGGGAGAACGTAAAAAATGTAATAGGCCCATTCATGAAGGCAGTTTGTGTCGAAGTCGG
ACCAGGCCCAGGAAAAATACTTTCTGTCTTCTTCCTAGCTCTCTTCTTCATCATCTTCAACAAG
GGACCAGGGCCAGGTCACGTGTTATCCCATAACTCTTATGAAAAAGGGCCAGGACCTGGGAA
ATACAAAATCGCAGGAGGGATCGCCGGCGGGCTAGCGCTCCTTGCCTGCGCAGGCTTGGCTTA
CAAATTCGTTGTACCAGGAGCTGCAACACCCTATGCAGGAGAACCTGCCCCATTTTGAAGATC
TGC (SEQ ID NO:122)

FIGURE 18I

Pf33 (SEQ ID NO:123)
MGMQVQIQSLFLLLLWVPGSRGFMKAVCVEVNVTCGNGIQVRKGLIMVLSFLNAALFHIFDGDN
EIKAALLACAGLAYKKSFLFVEALFNAAPSDGKCNLYKAAQTNFKSLLRNLPSENERGYKAAGVS
ENIFLKNAAAYFILVNLLIKAAAILSVSSFLFVNTPYAGEPAPFKAAAKYKLATSVLKAAVFLIFFDL
FLNYYIPHQSSLKAAGLLGNVSTVGAVLLGGVGLVLNLACAGLAYKKAKFIKSLFHIFKAAFYFIL
VNLLKAFLIFFDLFLVKALFFIIFNKNYYGKQENWYSLKFVEALFQEYNAAAKFVAAWTLKAAAK
ILSVFFLANAVLAGLLGNVNFQDEENIGIYKAAALYISFYFIKAFILVNLLIFHNAALPYGRTNLKAA
HVLSHNSYEKNAAAKYLVIVFLI

GCCGCCACCATGGGAATGCAGGTGCAGATCCAGAGCCTGTTTCTGCTCCTCCTGTGGGTGCCC
GGATCCAGAGGATTTATGAAAGCTGTCTGTGTAGAGGTGAATGTAACATGCGGTAACGGAAT
TCAGGTGAGAAAGGGACTCATCATGGTACTCAGCTTTCTGAACGCAGCCCTGTTCCACATCTT
TGACGGAGACAATGAAATCAAAGCCGCATTGCTCGCCTGTGCCGGACTAGCCTATAAAAAGA
GTTTCCTTTTCGTTGAAGCACTATTTAACGCAGCACCCAGTGACGGTAAATGCAACCTATATA
AAGCAGCTCAGACTAATTTCAAAAGCCTGTTAAGAAATCTGCCCTCAGAGAATGAAAGGGGT
TACAAAGCCGCCGGCGTGTCCGAGAATATTTTCCTGAAGAACGCCGCTGCTTATTTTATACTC
GTGAATCTACTCATAAAGGCAGCCGCAATCCTTTCAGTGTCCAGCTTTCTGTTTGTTAACACAC
CATATGCGGGCGAGCCGGCTCCTTTCAAGGCTGCAGCAAAATACAAGCTTGCCACATCAGTAT
TGAAAGCAGCTGTGTTTTTGATATTCTTTGATCTTTTTTTAAACTACTACATACCTCATCAGTCT
AGTCTTAAAGCAGCCGGGCTACTGGGGAACGTCTCTACTGTGGGGGCCGTCTTACTTGGAGGA
GTTGGCCTCGTGTTGAACCTCGCGTGCGCAGGTCTGGCCTACAAAAAAGCGAAATTCATCAAG
TCTCTGTTCCACATTTTTAAAGCCGCATTCTATTTCATACTAGTGAACCTTCTCAAAGCTTTCCT
GATCTTCTTCGATCTATTCCTCGTAAAAGCGCTATTCTTCATTATCTTTAACAAAAATTATTAC
GGCAAGCAAGAAAATTGGTACTCACTCAAGTTTGTAGAAGCTCTGTTCCAGGAATACAACGCC
GCTGCTAAATTCGTTGCAGCTTGGACCCTGAAAGCAGCTGCAAAGATCCTATCGGTCTTCTTTC
TCGCTAATGCCGTATTAGCAGGACTTCTAGGCAACGTGAACTTTCAAGACGAAGAGAATATAG
GCATCTACAAAGCCGCAGCACTGTACATTTCATTCTACTTCATCAAGGCCTTCATACTGGTCAA
CCTTCTGATATTTCATAATGCAGCACTGCCATATGGGAGAACCAACTTGAAAGCGGCCCACGT
GTTGAGCCACAACTCCTACGAGAAGAACGCCGCCGCGAAATATCTCGTCATTGTCTTCCTGAT
TTGA (SEQ ID NO:124)

TB.1 (SEQ ID NO:125)
MQVQIQSLFLLLLWVPGSRGRMSRVTTFTVKALVLLMLPVVNLMIGTAAAVVKALVLLMLPVGA
GLMTAVYLVGAAAMALLRLPVKRMFAANLGVNSLYFGGICVGRLPLVLPAVNAAAAKFVAAWT
LKAAAKAAARLMIGTAAAGFVVALIPLVNAMTYAAPLFVGAAAAMALLRLPLV

ATGCAGGTGCAGATCCAGAGCCTGTTTCTGCTCCTCCTGTGGGTGCCCGGATCCAGAGGAAGG
ATGAGCAGAGTGACCACATTCACTGTCAAGGCCCTGGTGCTCCTGATGCTCCCCGTCGTGAAC
CTGATGATCGGCACCGCTGCAGCCGTCGTGAAAGCTCTCGTCCTGCTCATGCTCCCTGTGGGA
GCAGGGCTGATGACAGCCGTGTACCTGGTCGGCGCTGCAGCCATGGCCCTCCTGCGGCTGCCA
GTGAAGCGCATGTTTGCTGCAAATCTGGGAGTCAACTCCCTCTATTTCGGGGGCATTTGCGTG
GGAAGGCTGCCCCTCGTGCTGCCTGCTGTGAATGCAGCCGCTGCCAAATTTGTCGCCGCTTGG
ACTCTGAAGGCAGCCGCTAAGGCCGCTGCAAGACTGATGATCGGGACCGCCGCTGCCGGCTT
CGTGGTCGCCCTGATTCCCCTGGTGAACGCCATGACATACGCAGCTCCTCTGTTTGTGGGAGC
CGCTGCAGCCATGGCTCTCCTGCGGCTGCCACTGGTGTGA (SEQ ID NO:126)

FIGURE 18J

BCL A2 #90 (SEQ ID NO:127)
MQVQIQSLFLLLLWVPGSRGIMIGHLVGVNRLLQETELVNAKVAEIVHFLNAKVFGSLAFVNAYL
SGANLNVGAAYLQLVFGIEVNAAAKFVAAWTLKAAAKAAAVVLGVVFGINSMPPPGTRVNAAA
ATVGIMIGVNAKLCPVQLWV

ATGCAGGTGCAGATCCAGAGCCTGTTTCTGCTCCTCCTGTGGGTGCCCGGGTCCAGAGGAATT
ATGATCGGCCATCTGGTGGGCGTCAACAGACTGCTGCAGGAAACCGAGCTGGTGAATGCCAA
GGTGGCCGAAATTGTGCACTTTCTCAACGCAAAGGTGTTTGGTTCCCTGGCTTTTGTCAATGCC
TATCTGAGCGGCGCTAACCTCAACGTCGGAGCCGCCTACCTCCAGCTGGTCTTCGGCATCGAG
GTCAACGCTGCTGCAAAATTCGTGGCAGCTTGGACCCTCAAGGCTGCAGCAAAGGCTGCCGCC
GTCGTGCTCGGAGTGGTGTTCGGGATCAACTCTATGCCACCTCCCGGGACTAGGGTCAATGCT
GCCGCCGCAACAGTGGGAATCATGATTGGGGTGAATGCCAAACTGTGCCCAGTGCAACTGTG
GGTGTGA (SEQ ID NO:128)

BCL A2 #88 (SEQ ID NO:129)
MQVQIQSLFLLLLWVPGSRGVVLGVVFGINAAAAKFVAAWTLKAAAKVAEIVHFLNAYLSGANL
NVGAAYLQLVFGIEVNIMIGHLVGVNRLLQETELVNAKVFGSLAFVNAKLCPVQLWVNAAAATV
GIMIGVNSMPPPGTRV

ATGCAGGTGCAGATCCAGAGCCTGTTTCTGCTCCTCCTGTGGGTGCCCGGGTCCAGAGGAGTC
GTGCTGGGAGTCGTCTTCGGCATTAATGCCGCCGCTGCAAAGTTCGTGGCTGCCTGGACCCTG
AAGGCCGCAGCTAAAGTGGCAGAGATCGTGCACTTTCTGAACGCCTACCTGAGCGGAGCAAA
TCTGAACGTCGGCGCTGCCTATCTGCAGCTCGTGTTTGGAATTGAAGTGAACATCATGATTGG
ACATCTGGTGGGCGTGAACAGGCTGCTCCAGGAAACTGAGCTGGTCAACGCTAAAGTGTTCG
GGTCTCTCGCCTTTGTGAACGCTAAGCTCTGCCCCGTCCAACTCTGGGTCAATGCCGCAGCCG
CTACAGTGGGGATCATGATCGGCGTGAACTCCATGCCTCCACCAGGGACCAGAGTGTGA
(SEQ ID NO:130)

BCL A2 #63 (SEQ ID NO:131)
MQVQIQSLFLLLLWVPGSRGKLCPVQLWVNAAAATVGIMIGVNIMIGHLVGVNRLLQETELVNA
KVAEIVHFLNAKVFGSLAFVNAYLSGANLNVGAAYLQLVFGIEVNAAAKFVAAWTLKAAAKAA
AVVLGVVFGINSMPPPGTRV

ATGCAGGTGCAGATCCAGAGCCTGTTTCTGCTCCTCCTGTGGGTGCCCGGGTCCAGAGGAAAG
CTCTGCCCCGTGCAACTGTGGGTCAACGCCGCCGCCGCAACCGTCGGCATTATGATCGGGGTG
AACATCATGATCGGACACCTGGTCGGCGTGAACAGGCTGCTGCAGGAGACAGAACTGGTCAA
TGCCAAGGTGGCTGAAATTGTCCATTTCCTGAATGCCAAAGTGTTCGGCTCTCTCGCTTTCGTG
AACGCTTATCTGAGCGGAGCTAACCTCAACGTGGGGGCCGCATACCTCCAGCTCGTCTTTGGG
ATTGAGGTGAATGCCGCAGCTAAATTTGTCGCTGCCTGGACCCTGAAGGCAGCAGCCAAGGCT
GCCGCAGTGGTGCTGGGAGTGGTGTTTGGAATCAATTCCATGCCTCCACCAGGCACTAGAGTG
TGAGGATCC (SEQ ID NO:132)

FIGURE 18K

Prostate 1 (SEQ ID NO:133)
LTFFWLDRSVKAAAVLVHPQWVLTVKAAALLQERGVAYIKAALLLSIALSVNPLVCNGVLQGVK
AAIMYSAHDTTVKAAAFLTPKKLQCVNAMMNDQLMFLNAGLPSIPVHPVKAAALGTTCYVGAAI
LLWQPIPVNFLRPRSLQCVKAFLTLSVTWIGVNALLYSLVHNLGAATLMSAMTNL ATGCAGGTGCAGATCCAGAGCCTGTTTCTGCTCCTCCTGTGGGTGCCCGGGTCCAGAGGATTG
ACATTTTTTGGCTGGATAGATCGGTTAAGGCTGCAGCCGTGCTTGTTCATCCCCAGTGGGTCT
TGACCGTAAAGGCTGCCGCGCTGCTACAAGAAAGAGGGGTCGCATACATCAAAGCTGCTCTC
CTCTTGAGTATTGCGCTAAGTGTAAACCCGCTAGTTTGTAATGGGGTGTTACAAGGTGTGAAA
GCGGCGATTATGTACAGTGCCCACGACACTACCGTAAAAGCAGCCGCTTTCCTGACCCCAAAA
AAACTCCAATGCGTGAACGCAATGATGAATGATCAGCTGATGTTTTTAAACGCTGGCTTACCT
TCTATACCGGTTCATCCAGTCAAGGCCGCGGCATTGGGTACGACGTGTTATGTTGGAGCAGCG
ATACTTCTTTGGCAGCCCATACCAGTAAATTTTTTAAGACCTAGATCCTTACAATGCGTCAAAG
CATTCCTTACACTCTCAGTAACTTGGATCGGAGTCAATGCTCTGCTATATAGCCTCGTACACAA
CTTGGGCGCGGCCACACTTATGAGTGCAATGACGAATTTAGCTAAGTTCGTGGCGGCCTGGAC
TCTAAAGGCCGCAGCA (SEQ ID NO:134)

HIV-1043 (SEQ ID NO:135)
MEKVYLAWVPAHKGIGGGPGPGQKQITKIQNFRVYYRGPGPGWEFVNTPPLVKLWYQGPGPGYR
KILRQRKIDRLIDGPGPGQHLLQLTVWGIKQLQGPGPGGEIYKRWIILGLNKIVRMYGPGPGQGQM
VHQAISPRTLNGPGPGIKQFINMWQEVGKAMYGPGPGWAGIKQEFGIPYNPQGPGPGKTAVQMA
VFIHNFKRGPGPGSPAIFQSSMTKILEPGPGPGEVNIVTDSQYALGIIGPGPGHSNWRAMASDFNLPP
GPGPGAETFYVDGAANRETKGPGPGGAVVIQDNSDIKVVPGPGPGFRKYTAFTIPSINNE

ATGGAGAAGGTGTACCTGGCCTGGGTTCCAGCCCACAAAGGCATCGGGGGAGGGCCCGGACC
TGGGCAGAAACAGATCACCAAGATCCAGAACTTCCGGGTATACTACCGGGGACCTGGTCCAG
GTTGGGAGTTTGTGAACACACCACCCTTAGTAAAGCTCTGGTACCAGGGCCCCGGTCCCGGAT
ACCGTAAAATCCTGAGGCAAAGAAAGATAGATCGCCTCATTGATGGCCCGGGCCCAGGCCAG
CACCTTCTGCAGCTTACAGTGTGGGGAATTAAACAGCTGCAGGGGCCGGGCCCCGGGGGGGA
AATTTATAAAAGGTGGATCATTCTGGGTCTGAACAAGATCGTCCGCATGTATGGCCCTGGACC
CGGACAGGGGCAGATGGTCCACCAAGCAATCAGCCCTCGAACCTTGAATGGACCGGGCCCAG
GAATCAAGCAATTCATTAACATGTGGCAAGAAGTTGGTAAGGCTATGTACGGTCCCGGCCCTG
GATGGGCAGGGATAAAACAGGAGTTTGGAATCCCTTACAATCCCCAGGGTCCTGGGCCAGGT
AAAACGGCAGTGCAGATGGCCGTGTTCATTCATAATTTTAAGCGGGGCCCTGGACCTGGCAGC
CCAGCTATATTTCAAAGTTCGATGACCAAAATCTTGGAGCCCGGCCCAGGGCCGGGCGAAGT
GAACATTGTCACAGATTCTCAGTATGCCCTCGGCATCATAGGGCCCGGACCAGGGCATTCCAA
TTGGCGCGCCATGGCGTCTGACTTTAATCTACCTCCTGGGCCAGGCCCTGGCGCGGAAACTTT
CTATGTGGACGGCGCTGCAAACAGGGAGACTAAGGGACCCGGACCCGGCGGCGCTGTAGTCA
TTCAGGACAACTCAGACATCAAGGTGGTTCCCGGTCCAGGCCCCGGGTTCAGAAAGTATACCG
CCTTCACTATTCCGTCCATCAACAATGAGTGA (SEQ ID NO:136)

FIGURE 18L

HIV-1043 PADRE (SEQ ID NO:137)
MEKVYLAWVPAHKGIGGGPGPGQKQITKIQNFRVYYRGPGPGWEFVNTPPLVKLWYQGPGPGYR
KILRQRKIDRLIDGPGPGQHLLQLTVWGIKQLQGPGPGGEIYKRWIILGLNKIVRMYGPGPGQGQM
VHQAISPRTLNGPGPGIKQFINMWQEVGKAMYGPGPGWAGIKQEFGIPYNPQGPGPGKTAVQMA
VFIHNFKRGPGPGSPAIFQSSMTKILEPGPGPGEVNIVTDSQYALGIIGPGPGHSNWRAMASDFNLPP
GPGPGAETFYVDGAANRETKGPGPGGAVVIQDNSDIKVVPGPGPGFRKYTAFTIPSINNEGPGPGA
KFVAAWTLKAAA

ATGGAGAAGGTGTACCTGGCCTGGGTTCCAGCCCACAAAGGCATCGGGGGAGGGCCCGGACC
TGGGCAGAAACAGATCACCAAGATCCAGAACTTCCGGGTATACTACCGGGGACCTGGTCCAG
GTTGGGAGTTTGTGAACACACCACCCTTAGTAAAGCTCTGGTACCAGGGCCCCGGTCCCGGAT
ACCGTAAAATCCTGAGGCAAAGAAAGATAGATCGCCTCATTGATGGCCCGGGCCCAGGCCAG
CACCTTCTGCAGCTTACAGTGTGGGGAATTAAACAGCTGCAGGGGCCGGGCCCCGGGGGGGA
AATTTATAAAAGGTGGATCATTCTGGGTCTGAACAAGATCGTCCGCATGTATGGCCCTGGACC
CGGACAGGGGCAGATGGTCCACCAAGCAATCAGCCTCGAACCTTGAATGGACCGGGCCCAG
GAATCAAGCAATTCATTAACATGTGGCAAGAAGTTGGTAAGGCTATGTACGGTCCCGGCCCTG
GATGGGCAGGGATAAAACAGGAGTTTGGAATCCCTTACAATCCCCAGGGTCCTGGGCCAGGT
AAAACGGCAGTGCAGATGGCCGTGTTCATTCATAATTTTAAGCGGGGCCCTGGACCTGGCAGC
CCAGCTATATTTCAAAGTTCGATGACCAAAATCTTGGAGCCCGGCCCAGGGCCGGGCGAAGT
GAACATTGTCACAGATTCTCAGTATGCCCTCGGCATCATAGGGCCCGGACCAGGGCATTCCAA
TTGGCGCGCCATGGCGTCTGACTTTAATCTACCTCCTGGGCCAGGCCCTGGCGCGGAAACTTT
CTATGTGGACGGCGCTGCAAACAGGGAGACTAAGGGACCCGGACCCGGCGGCGCTGTAGTCA
TTCAGGACAACTCAGACATCAAGGTGGTTCCCGGTCCAGGCCCCGGGTTCAGAAAGTATACCG
CCTTCACTATTCCGTCCATCAACAATGAGGGCCCCGGCCCAGGTGCCAAGTTCGTGGCTGCCT
GGACCCTGAAGGCTGCCGCTTGA (SEQ ID NO:138)

HIV 75mer (SEQ ID NO:139)
EKVYLAWVPAHKGIGGPGPGQGQMVHQAISPRTLNGPGPGSPAIFQSSMTKILEPGPGPGFRKYTA
FTIPSINNE GAGAAGGTGTACCTGGCCTGGGTGCCTGCCCACAAGGGAATCGGAGGACCTGGCCCTGGACA
GGGACAGATGGTGCACCAGGCCATCAGCCCTAGGACCCTGAACGGACCTGGACCTGGAAGCC
CTGCCATCTTCCAGAGCAGCATGACCAAGATCCTGGAGCCCGGACCTGGACCTGGATTCAGGA
AGTACACCGCCTTCACCATCCCCAGCATCAACAACGAGTGA (SEQ ID NO:140)

FIGURE 18M

PfHTL (SEQ ID NO:141)
MQVQIQSLFLLLLWVPGSRGRHNWVNHAVPLAMKLIGPGPGKCNLYADSAWENVKNGPGPGKS
KYKLATSVLAGLLGPGPGQTNFKSLLRNLGVSEGPGPGSSVFNVVNSSIGLIMGPGPGVKNVIGPF
MKAVCVEGPGPGMNYYGKQENWYSLKKGPGPGGLAYKFVVPGAATPYGPGPGPDSIQDSLKESR
KLNGPGPGLLIFHINGKIIKNSEGPGPGAGLLGNVSTVLLGGVGPGPGKYKIAGGIAGGLALLGPGP
GMRKLAILSVSSFLFV

ATGGGAATGCAGGTGCAGATCCAGAGCCTGTTTCTGCTCCTCCTGTGGGTGCCCGGATCCAGA
GGAAGGCACAACTGGGTGAATCATGCTGTGCCCCTGGCTATGAAGCTGATCGGCCCTGGACC
AGGGAAATGCAACCTCTACGCAGACAGCGCCTGGGAGAACGTCAAGAATGGCCCCGGACCTG
GGAAATCCAAGTATAAGCTCGCTACCTCTGTGCTGGCAGGCCTGCTCGGACCAGGCCCCGGAC
AGACAAATTTCAAAAGCCTGCTCAGAAACCTGGGAGTGTCCGAGGGGCCTGGCCCAGGATCT
AGCGTCTTTAATGTGGTCAACTCCTCTATTGGGCTCATCATGGGACCCGGACCTGGGGTGAAA
AATGTCATTGGCCCATTCATGAAGGCCGTGTGTGTCGAAGGACCCGGGCCTGGCATGAACTAC
TATGGAAAGCAAGAAAATTGGTACAGCCTGAAGAAAGGCCCTGGGCCAGGCGGACTGGCTTA
CAAGTTTGTGGTCCCAGGGGCAGCCACTCCCTATGGGCCTGGGCCAGGCCCCGATTCCATCCA
GGACTCTCTCAAAGAGAGCCGGAAACTGAACGGACCCGGGCCTGGACTGCTCATTTTCCACAT
CAATGGCAAAATTATCAAGAACAGCGAGGGACCTGGGCCAGGCGCCGGACTGCTGGGGAACG
TGTCCACCGTCCTGCTCGGCGGAGTGGGGCCCGGCCCTGGGAAGTACAAGATCGCTGGAGGG
ATCGCAGGCGGACTGGCCCTCCTGGGCCCAGGACCAGGGATGCGCAAACTGGCTATTCTCTCT
GTCTCCAGCTTTCTGTTTGTGTGA (SEQ ID NO:142)

FIGURE 18N

| Protein | Sequence | Restriction | (SEQ ID NO:) |
| --- | --- | --- | --- |
| HIV gag 386 | VLAEAMSQV | HLA-A2 | 143 |
| HIV gag 271 | MTNNPPIPV | HLA-A2 | 144 |
| HIV pol 774 | MASDFNLPPV | HLA-A2 | 145 |
| HIV pol 448 | KLVGKLNWA | HLA-A2 | 146 |
| HIVpol 163 | LVGPTPVNI | HLA-A2 | 147 |
| HIV pol 498 | ILKEPVHGV | HLA-A2 | 148 |
| HIV pol 879 | KAACWWAGI | HLA-A2 | 149 |
| HIV pol 132 | KMIGGIGGFI | HLA-A2 | 150 |
| HIV pol 772 | RAMASDFNL | HLA-A2 | 151 |
| HIV pol 183 | TLNFPISPI | HLA-A2 | 152 |
| HIV env 134 | KLTPLCVTL | HLA-A2 | 153 |
| HIV env 651 | LLQLTVWGI | HLA-A2 | 154 |
| HIV env 163 | SLLNATDIAV | HLA-A2 | 155 |
| HIV nef 221 | LTFGWCFKL | HLA-A2 | 156 |
| HIV vpr 59 | AIIRILQQL | HLA-A2 | 157 |
| HIV vpr 62 | RILQQLLFI | HLA-A2 | 158 |
| HIV pol 929 | QMAVFIHNFK | HLA-A3 | 159 |
| HIV pol 722 | KVYLAWVPAHK | HLA-A3 | 160 |
| HIV pol 971 | KIQNFRVYYR | HLA-A3 | 161 |
| HIV pol 347 | AIFQSSMTK | HLA-A3 | 162 |
| HIV pol 98 | VTIKIGGQLK | HLA-A3 | 163 |
| HIV env 61 | TTLFCASDAK | HLA-A3 | 164 |
| HIV env 47 | VTVYYGVPVWK | HLA-A3 | 165 |
| HIV nef 100 | QVPLRPMTYK | HLA-A3 | 166 |
| HIV vif 7 | VMIVWQVDR | HLA-A3 | 167 |
| HIV gag 162 | QMVHQAISPR | HLA-A3 | 168 |
| HIV gag 545 | YPLASLRSLF | HLA-B7 | 169 |
| HIV gag 237 | HPVHAGPIA | HLA-B7 | 170 |
| HIV pol 186 | FPISPIETV | HLA-B7 | 171 |
| HIV pol 893 | IPYNPQSQGVV | HLA-B7 | 172 |
| HIV env 259 | IPIHYCAPA | HLA-B7 | 173 |
| HIV env 250 | CPKVSFEPI | HLA-B7 | 174 |
| HIV nef 94 | FPVRPQVPL | HLA-B7 | 175 |
| HIV rev 75 | VPLQLPPL | HLA-B7 | 176 |
| HIV pol 684 | EVNIVTDSQY | HLA-A1 | 177 |
| HIV gag 317 | FRDYVDRFY | HLA-A1 | 178 |
| HIV pol 368 | VIYQYMDDLY | HLA-A1 | 179 |
| HIV pol 295 | VTVLDVGDAY | HLA-A1 | 180 |
| HIV pol 533 | IYQEPFKNL | HLA-A24 | 181 |
| HIV pol 244 | PYNTPVFAI | HLA-A24 | 182 |
| HIV pol 530 | TYQIYQEPF | HLA-A24 | 183 |
| HIV pol 597 | YWQATWIPEW | HLA-A24 | 184 |
| HIV env 681 | IWGCSGKLI | HLA-A24 | 185 |
| HIV env 671 | RYLKDQQLL | HLA-A24 | 186 |

FIG. 19A

| Protein | Sequence | Restriction | (SEQ ID NO:) |
|---|---|---|---|
| HIV env 55 | VWKEATTTLF | HLA-A24 | 187 |
| HIV vpr 46 | IYETYGDTW | HLA-A24 | 188 |
| HIV vpr 14 | PYNEWTLEL | HLA-A24 | 189 |
| HIV gag 298 | KRWIILGLNKIVRMY | HLA-DR | 190 |
| HIV pol 596 | WEFVNTPPLVKLWYQ | HLA-DR | 191 |
| HIV pol 956 | QKQITKIQNFRVYYR | HLA-DR | 192 |
| HIV pol 712 | KVYLAWVPAHKGIGG | HLA-DR | 193 |
| HIV gag 294 | GEIYKRWIILGLNKI | HLA-DR | 194 |
| HIV pol 711 | EKVYLAWVPAHKGIG | HLA-DR | 195 |
| HIV env 729 | QHLLQLTVWGIKQLQ | HLA-DR | 196 |
| HIV gag 171 | QGQMVHQAISPRTLN | HLA-DR | 197 |
| HIV pol 335 | SPAIFQSSMTKILEP | HLA-DR | 198 |
| HIV env 566 | IKQFINMWQEVGKAMY | HLA-DR | 199 |
| HIV pol 303 | FRKYTAFTIPSINNE | HLA-DR | 200 |
| HIV pol 758 | HSNWRAMASDFNLPP | HLA-DR | 201 |
| HIV pol 915 | KTAVQMAVFIHNFKR | HLA-DR | 202 |
| HIV vpu 31 | YRKILRQRKIDRLID | HLA-DR3 | 203 |
| HIV pol 874 | WAGIKQEFGIPYNPQ | HLA-DR3 | 204 |
| HIV pol 674 | EVNIVTDSQYALGII | HLA-DR3 | 205 |
| HIV pol 619 | AETFYVDGAANRETK | HLA-DR3 | 206 |
| HIV pol 989 | GAVVIQDNSDIKVVP | HLA-DR3 | 207 |
| HCV NS4 1812 | LLFNILGGWV | HLA-A2 | 208 |
| HCV NS1/E2 728 | FLLLADARV | HLA-A2 | 209 |
| HCV NS4 1590 | YLVAYQATV | HLA-A2 | 210 |
| HCV NS5 2611 | RLIVFPDLGV | HLA-A2 | 211 |
| HCV CORE 132 | DLMGYIPLV | HLA-A2 | 212 |
| HCV NS4 1920 | WMNRLIAFA | HLA-A2 | 213 |
| HCV NS4 1666 | VLVGGVLAA | HLA-A2 | 214 |
| HCV NS4 1769 | HMWNFISGI | HLA-A2 | 215 |
| HCV NS4 1851 | ILAGYGAGV | HLA-A2 | 216 |
| HCV CORE 35 | YLLPRRGPRL | HLA-A2 | 217 |
| HCV NS1/E2 726 | LLFLLLADA | HLA-A2 | 218 |
| HCV LORF 1131 | YLVTRHADV | HLA-A2 | 219 |
| HCV CORE 51 | KTSERSQPR | HLA-A3 | 220 |
| HCV CORE 43 | RLGVRATRK | HLA-A3 | 221 |
| HCV ENV1 290 | QLFTFSPRR | HLA-A3 | 222 |
| HCV NS1/E2 632 | RMYVGGVEHR | HLA-A3 | 223 |
| HCV NS3 1396 | LIFCHSKKK | HLA-A3 | 224 |
| HCV NS4 1863 | GVAGALVAFK | HLA-A3 | 225 |
| HCV NS4 1864 | VAGALVAFK | HLA-A3 | 226 |
| HCV NS3 1262 | LGFGAYMSK | HLA-A3 | 227 |
| HCV Core 169 | LPGCSFSIF | HLA-B7 | 228 |
| HCV NS5 2922 | LSAFSLHSY | HLA-A1 | 229 |
| HCV NS3 1128 | CTCGSSDLY | HLA-A1 | 230 |
| HCV NS5 2180 | LTDPSHITA | HLA-A1 | 231 |

FIG. 19B

| Protein | Sequence | Restriction | (SEQ ID NO:) |
|---|---|---|---|
| HCV Core 126 | LTCGFADLMGY | HLA-A1 | 232 |
| HCV NS3 1305 | LADGGCSGGAY | HLA-A1 | 233 |
| HCV NS4 1765 | FWAKHMWNF | HLA-A24 | 234 |
| HCV NS5 2875 | RMILMTHFF | HLA-A24 | 235 |
| HCV NS5 2639 | VMGSSYGF | HLA-A24 | 236 |
| HCV NS4 1765 | FWAKHMWNFI | HLA-A24 | 237 |
| P. falciparum SSP2-230 | FMKAVCVEV | HLA-A2 | 238 |
| P. falciparum EXP1-83 | GLLGVVSTV | HLA-A2 | 239 |
| P. falciparum CSP-7 | ILSVSSFLFV | HLA-A2 | 240 |
| P. falciparum LSA1-94 | QTNFKSLLR | HLA-A3 | 241 |
| P. falciparum LSA1-105 | GVSENIFLK | HLA-A3 | 242 |
| P. falciparum SSP2-522 | LLACAGLAYK | HLA-A3 | 243 |
| P. falciparum SSP2-539 | TPYAGEPAPF | HLA-B7 | 244 |
| P. falciparum LSA1-1663 | LPSENERGY | HLA-A1 | 245 |
| P. falciparum EXP1-73 | KYKLATSVL | HLA-A24 | 246 |
| P. falciparum CSP-12 | SFLFVEALF | HLA-A24 | 247 |
| P. falciparum LSA1-10 | YFILVNLLI | HLA-A24 | 248 |
| P. falciparum SSP2-14 | FLIFFDLFLV | HLA-A2 | 249 |
| P. falciparum EXP1-80 | VLAGLLGVV | HLA-A2 | 250 |
| P. falciparum EXP1-91 | VLLGGVGLVL | HLA-A2 | 251 |
| P. falciparum SSP2-523 | LACAGLAYK | HLA-A3 | 252 |
| P. falciparum EXP1-10 | ALFFIIFNK | HLA-A3 | 253 |
| P. falciparum LSA1-11 | FILVNLLIFH | HLA-A3 | 254 |
| P. falciparum SSP2-126 | LPYGRTNL | HLA-B7 | 255 |
| P. falciparum CSP-15 | FVEALFQEY | HLA-A1 | 256 |
| P. falciparum LSA1-1794 | FQDEENIGIY | HLA-A1 | 257 |
| P. falciparum LSA1-9 | FYFILVNLL | HLA-A24 | 258 |
| P. falciparum SSP2-8 | KYLVIVFLI | HLA-A24 | 259 |
| P. falciparum CSP-394 | GLIMVLSFL | HLA-A2 | 260 |
| P. falciparum EXP1-2 | KILSVFFLA | HLA-A2 | 261 |
| P. falciparum CSP-344 | VTCGNGIQVR | HLA-A3 | 262 |
| P. falciparum LSA1-59 | HVLSHNSYEK | HLA-A3 | 263 |
| P. falciparum SSP2-207 | PSDGKCNLY | HLA-A1 | 264 |
| P. falciparum LSA1-1671 | YYIPHQSSL | HLA-A24 | 265 |
| P. falciparum LSA1-1876 | KFIKSLFHIF | HLA-A24 | 266 |
| P. falciparum SSP2-13 | VFLIFFDLFL | HLA-A24 | 267 |
| P. falciparum LSA1-1881 | LFHIFDGDNEI | HLA-A24 | 268 |
| P. falciparum CSP-55 | YYGKQENWYSL | HLA-A24 | 269 |
| P. falciparum LSA1-5 | LYISFYFI | HLA-A24 | 270 |
| P. falciparum CSP-2 | MRKLAILSVSSFLFV | HLA-DR | 271 |
| P. falciparum CSP-53 | MNYYGKQENWYSLKK | HLA-DR | 272 |
| P. falciparum CSP-375 | SSVFNVVNSSIGLIM | HLA-DR | 273 |
| P. falciparum SSP2-61 | RHNWVNHAVPLAMKLI | HLA-DR | 274 |
| P. falciparum SSP2-165 | PDSIQDSLKESRKLN | HLA-DR3 | 275 |
| P. falciparum SSP2-211 | KCNLYADSAWENVKN | HLA-DR3 | 276 |

FIG. 19C

| Protein | Sequence | Restriction | (SEQ ID NO:) |
| --- | --- | --- | --- |
| P. falciparum SSP2-223 | VKNVIGPFMKAVCVE | HLA-DR | 277 |
| P. falciparum SSP2-509 | KYKIAGGIAGGLALL | HLA-DR | 278 |
| P. falciparum SSP2-527 | GLAYKFVVPGAATPY | HLA-DR | 279 |
| P. falciparum EXP1-71 | KSKYKLATSVLAGLL | HLA-DR | 280 |
| P. falciparum EXP1-82 | AGLLGNVSTVLLGGV | HLA-DR | 281 |
| P. falciparum LSA1-16 | LLIFHINGKIIKNSE | HLA-DR | 282 |
| P. falciparum LSA1-94 | QTNFKSLLRNLGVSE | HLA-DR | 283 |
| HBV core 18 | FLPSDFFPSV | HLA-A2 | 284 |
| HBV env 183 | FLLTRILTI | HLA-A2 | 285 |
| HBV env 335 | WLSLLVPFV | HLA-A2 | 286 |
| HBV pol 455 | GLSRYVARL | HLA-A2 | 287 |
| HBV pol 538 | YMDDVVLGV | HLA-A2/A1 | 288 |
| HBV pol 773 | ILRGTSFVYV | HLA-A2 | 289 |
| HBV pol 562 | FLLSLGIHL | HLA-A2 | 290 |
| HBV pol 642 | ALMPLYACI | HLA-A2 | 291 |
| HBV env 338 | GLSPTVWLSV | HLA-A2 | 292 |
| HBV core 141 | STLPETTVVRR | HLA-A3 | 293 |
| HBV pol 149 | HTLWKAGILYK | HLA-A3/A1 | 294 |
| HBV pol 150 | TLWKAGILYK | HLA-A3 | 295 |
| HBV pol 388 | LVVDFSQFSR | HLA-A3 | 296 |
| HBV pol 47 | NVSIPWTHK | HLA-A3 | 297 |
| HBV pol 531 | SAICSVVRR | HLA-A3 | 298 |
| HBV pol 629 | KVGNFTGLY | HLA-A3/A1 | 299 |
| HBV pol 665 | QAFTFSPTYK | HLA-A3 | 300 |
| HBV core 19 | LPSDFFPSV | HLA-B7 | 301 |
| HBV env 313 | IPIPSSWAF | HLA-B7 | 302 |
| HBV pol 354 | TPARVTGGVF | HLA-B7 | 303 |
| TB | RMSRVTTFTV | HLA-A2 | 304 |
| TB | ALVLLMLPVV | HLA-A2 | 305 |
| TB | LMIGTAAAVV | HLA-A2 | 306 |
| TB | ALVLLMLPV | HLA-A2 | 307 |
| TB | GLMTAVYLV | HLA-A2 | 308 |
| TB | MALLRLPV | HLA-A2 | 309 |
| TB | RMFAANLGV | HLA-A2 | 310 |
| TB | SLYFGGICV | HLA-A2 | 311 |
| TB | RLPLVLPAV | HLA-A2 | 312 |
| TB | RLMIGTAAA | HLA-A2 | 313 |
| TB | FVVALIPLV | HLA-A2 | 314 |
| TB | MTYAAPLFV | HLA-A2 | 315 |
| TB | AMALLRLPLV | HLA-A2 | 316 |
| p53 139 | KLCPVQLWV | HLA-A2 | 317 |
| CEA 687 | ATVGIMIGV | HLA-A2 | 318 |
| CEA 691 | IMIGHLVGV | HLA-A2 | 319 |
| Her2/neu 689 | RLLQETELV | HLA-A2 | 320 |
| MAGE3 112 | KVAEIVHFL | HLA-A2 | 321 |

FIG. 19D

| Protein | Sequence | Restriction | (SEQ ID NO:) |
|---|---|---|---|
| Her2/neu 369 | KVFGSLAFV | HLA-A2 | 322 |
| CEA 605 | YLSGANLNV | HLA-A2 | 323 |
| MAGE2 157 | YLQLVFGIEV | HLA-A2 | 324 |
| Her2/neu 665 | VVLGVVFGI | HLA-A2 | 325 |
| p53 149 | SMPPPGTRV | HLA-A2 | 326 |
| PAP.21.T2 | LTFFWLDRSV | HLA-A2 | 327 |
| PAP.112 | TLMSAMTNL | HLA-A2 | 328 |
| PAP.284 | IMYSAHDTTV | HLA-A2 | 329 |
| PSM.288.V10 | GLPSIPVHPV | HLA-A2 | 330 |
| PSM.441 | LLQERGVAYI | HLA-A2 | 331 |
| PSM.469L2 | LLYSLVHNL | HLA-A2 | 332 |
| PSM.663 | MMNDQLMFL | HLA-A2 | 333 |
| PSA.3.V11 | FLTLSVTWIGV | HLA-A2 | 334 |
| PSA.143.V8 | ALGTTCYV | HLA-A2 | 335 |
| PSA.161 | FLTPKKLQCV | HLA-A2 | 336 |
| HuK2.4.L2 | LLLSIALSV | HLA-A2 | 337 |
| HuK2.53.V11 | VLVHPQWVLTV | HLA-A2 | 338 |
| HuK2.165 | FLRPRSLQCV | HLA-A2 | 339 |
| HuK2.216.V11 | PLVCNGVLQGV | HLA-A2 | 340 |

FIG. 19E

SEQUENCE LISTING

<160> NUMBER OF SEQ ID NOS: 382

<210> SEQ ID NO 1
<211> LENGTH: 22
<212> TYPE: PRT
<213> ORGANISM: Artificial Sequence
<220> FEATURE:
<223> OTHER INFORMATION: Oligonucleotide for minigene HBV.1 with epitope identity core 18

<400> SEQUENCE: 1

```
Thr Leu Lys Ala Ala Ala Phe Leu Pro Ser Asp Phe Phe Pro Ser Val
 1               5                  10                  15

Phe Leu Leu Ser Leu Gly
            20
```

<210> SEQ ID NO 2
<211> LENGTH: 22
<212> TYPE: PRT
<213> ORGANISM: Artificial Sequence
<220> FEATURE:
<223> OTHER INFORMATION: Oligonucleotide for minigene pMIn1 with epitope identity core 18

<400> SEQUENCE: 2

```
Thr Leu Lys Ala Ala Ala Phe Leu Pro Ser Asp Phe Phe Pro Ser Val
 1               5                  10                  15

Lys Leu Thr Pro Leu Cys
            20
```

<210> SEQ ID NO 3
<211> LENGTH: 21
<212> TYPE: PRT
<213> ORGANISM: Artificial Sequence
<220> FEATURE:
<223> OTHER INFORMATION: Oligonucleotide for minigene HCV1 with epitope identity core 132

<400> SEQUENCE: 3

```
Ile Leu Gly Gly Trp Val Asp Leu Met Gly Tyr Ile Pro Leu Val Tyr
 1               5                  10                  15

Leu Val Ala Tyr Gln
            20
```

<210> SEQ ID NO 4
<211> LENGTH: 20
<212> TYPE: PRT
<213> ORGANISM: Artificial Sequence
<220> FEATURE:
<223> OTHER INFORMATION: Oligonucleotide for minigene HCV2 with epitope identity core 132

<400> SEQUENCE: 4

```
Val Pro Gly Ser Arg Gly Asp Leu Met Gly Tyr Ile Pro Leu Val Ala
 1               5                  10                  15

Lys Phe Val Ala
            20
```

<210> SEQ ID NO 5
<211> LENGTH: 9
<212> TYPE: PRT
<213> ORGANISM: Artificial Sequence
<220> FEATURE:
<223> OTHER INFORMATION: Oligopeptide

```
<400> SEQUENCE: 5

Val Leu Ala Glu Ala Met Ser Gln Val
1               5

<210> SEQ ID NO 6
<211> LENGTH: 9
<212> TYPE: PRT
<213> ORGANISM: Artificial Sequence
<220> FEATURE:
<223> OTHER INFORMATION: Oligopeptide

<400> SEQUENCE: 6

Ile Leu Lys Glu Pro Val His Gly Val
1               5

<210> SEQ ID NO 7
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 7

Xaa Xaa Xaa Xaa Phe Xaa Xaa Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 8

Xaa Xaa Xaa Xaa Phe Xaa Xaa Ile
1               5

<210> SEQ ID NO 9
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 9

Xaa Xaa Xaa Xaa Phe Xaa Xaa Met
1               5

<210> SEQ ID NO 10
<211> LENGTH: 8
<212> TYPE: PRT
<213> ORGANISM: Artificial Sequence
<220> FEATURE:
```

```
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 10

Xaa Xaa Xaa Xaa Phe Xaa Xaa Val
 1               5

<210> SEQ ID NO 11
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 11

Xaa Xaa Xaa Xaa Tyr Xaa Xaa Leu
 1               5

<210> SEQ ID NO 12
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 12

Xaa Xaa Xaa Xaa Tyr Xaa Xaa Ile
 1               5

<210> SEQ ID NO 13
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid

<400> SEQUENCE: 13

Xaa Xaa Xaa Xaa Tyr Xaa Xaa Met
 1               5

<210> SEQ ID NO 14
<211> LENGTH: 8
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(8)
<223> OTHER INFORMATION: Xaa = Any Amino Acid
```

```
<400> SEQUENCE: 14

Xaa Xaa Xaa Xaa Tyr Xaa Xaa Val
1               5

<210> SEQ ID NO 15
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 15

Xaa Xaa Xaa Xaa Phe Xaa Xaa Xaa Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 16

Xaa Xaa Xaa Xaa Phe Xaa Xaa Xaa Ile
1               5

<210> SEQ ID NO 17
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 17

Xaa Xaa Xaa Xaa Phe Xaa Xaa Xaa Met
1               5

<210> SEQ ID NO 18
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 18

Xaa Xaa Xaa Xaa Phe Xaa Xaa Xaa Val
1               5

<210> SEQ ID NO 19
```

```
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 19

Xaa Xaa Xaa Xaa Tyr Xaa Xaa Xaa Leu
 1               5

<210> SEQ ID NO 20
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 20

Xaa Xaa Xaa Xaa Tyr Xaa Xaa Xaa Ile
 1               5

<210> SEQ ID NO 21
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 21

Xaa Xaa Xaa Xaa Tyr Xaa Xaa Xaa Met
 1               5

<210> SEQ ID NO 22
<211> LENGTH: 9
<212> TYPE: PRT
<213> ORGANISM: Artificial Sequence
<220> FEATURE:
<223> OTHER INFORMATION: Motif utilized for junctional minimization
      (murine Kb)
<220> FEATURE:
<221> NAME/KEY: VARIANT
<222> LOCATION: (1)...(9)
<223> OTHER INFORMATION: Xaa = Any Amino Acid

<400> SEQUENCE: 22

Xaa Xaa Xaa Xaa Tyr Xaa Xaa Xaa Val
 1               5

<210> SEQ ID NO 23
<211> LENGTH: 8
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
```

-continued

<222> LOCATION: (1)...(8)
<223> OTHER INFORMATION: Xaa = Any Amino Acid

<400> SEQUENCE: 23

Xaa Xaa Xaa Xaa Asn Xaa Xaa Leu
 1               5

<210> SEQ ID NO 24
<211> LENGTH: 8
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(8)
<223> OTHER INFORMATION: Xaa = Any Amino Acid

<400> SEQUENCE: 24

Xaa Xaa Xaa Xaa Asn Xaa Xaa Ile
 1               5

<210> SEQ ID NO 25
<211> LENGTH: 8
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(8)
<223> OTHER INFORMATION: Xaa = Any Amino Acid

<400> SEQUENCE: 25

Xaa Xaa Xaa Xaa Asn Xaa Xaa Met
 1               5

<210> SEQ ID NO 26
<211> LENGTH: 8
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(8)
<223> OTHER INFORMATION: Xaa = Any Amino Acid

<400> SEQUENCE: 26

Xaa Xaa Xaa Xaa Asn Xaa Xaa Val
 1               5

<210> SEQ ID NO 27
<211> LENGTH: 9
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(9)
<223> OTHER INFORMATION: Xaa = Any Amino Acid

<400> SEQUENCE: 27

Xaa Xaa Xaa Xaa Asn Xaa Xaa Xaa Leu
 1               5

<210> SEQ ID NO 28
<211> LENGTH: 9

```
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(9)
<223> OTHER INFORMATION: Xaa = Any Amino Acid

<400> SEQUENCE: 28

Xaa Xaa Xaa Xaa Asn Xaa Xaa Xaa Ile
 1               5

<210> SEQ ID NO 29
<211> LENGTH: 9
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(9)
<223> OTHER INFORMATION: Xaa = Any Amino Acid

<400> SEQUENCE: 29

Xaa Xaa Xaa Xaa Asn Xaa Xaa Xaa Met
 1               5

<210> SEQ ID NO 30
<211> LENGTH: 9
<212> TYPE: PRT
<213> ORGANISM: Artificial Sequence
<220> FEATURE:
<223> OTHER INFORMATION: Motif utilized for junctional minimization (Db)
<220> FEATURE:
<221> NAME/KEY: VARIANT
<222> LOCATION: (1)...(9)
<223> OTHER INFORMATION: Xaa = Any Amino Acid

<400> SEQUENCE: 30

Xaa Xaa Xaa Xaa Asn Xaa Xaa Xaa Val
 1               5

<210> SEQ ID NO 31
<211> LENGTH: 9
<212> TYPE: PRT
<213> ORGANISM: Artificial Sequence
<220> FEATURE:
<223> OTHER INFORMATION: Motif utilized for junctional minimization
      (human A2)
<220> FEATURE:
<221> NAME/KEY: VARIANT
<222> LOCATION: (1)...(9)
<223> OTHER INFORMATION: Xaa = Any Amino Acid

<400> SEQUENCE: 31

Xaa Leu Xaa Xaa Xaa Xaa Xaa Xaa Val
 1               5

<210> SEQ ID NO 32
<211> LENGTH: 9
<212> TYPE: PRT
<213> ORGANISM: Artificial Sequence
<220> FEATURE:
<223> OTHER INFORMATION: Motif utilized for junctional minimization
      (human A2)
<220> FEATURE:
<221> NAME/KEY: VARIANT
<222> LOCATION: (1)...(9)
<223> OTHER INFORMATION: Xaa =

-continued

```
<400> SEQUENCE: 32

Xaa Met Xaa Xaa Xaa Xaa Xaa Xaa Val
 1               5

<210> SEQ ID NO 33
<211> LENGTH: 10
<212> TYPE: PRT
<213> ORGANISM: Artificial Sequence
<220> FEATURE:
<223> OTHER INFORMATION: Motif utilized for junctional minimization
      (human A2)
<220> FEATURE:
<221> NAME/KEY: VARIANT
<222> LOCATION: (1)...(10)
<223> OTHER INFORMATION: Xaa = Any Amino Acid

<400> SEQUENCE: 33

Xaa Leu Xaa Xaa Xaa Xaa Xaa Xaa Xaa Val
 1               5                   10

<210> SEQ ID NO 34
<211> LENGTH: 10
<212> TYPE: PRT
<213> ORGANISM: Artificial sequence
<220> FEATURE:
<223> OTHER INFORMATION: Motif utilized for junctional minimization
      (human A2)
<220> FEATURE:
<221> NAME/KEY: VARIANT
<222> LOCATION: (1)...(10)
<223> OTHER INFORMATION: Xaa = Any Amino Acid

<400> SEQUENCE: 34

Xaa Met Xaa Xaa Xaa Xaa Xaa Xaa Xaa Val
 1               5                   10

<210> SEQ ID NO 35
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 35

Xaa Leu Xaa Xaa Xaa Xaa Xaa Xaa Lys
 1               5

<210> SEQ ID NO 36
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 36

Xaa Leu Xaa Xaa Xaa Xaa Xaa Xaa Arg
 1               5

<210> SEQ ID NO 37
```

```
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 37

Xaa Leu Xaa Xaa Xaa Xaa Xaa Xaa Tyr
 1               5

<210> SEQ ID NO 38
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 38

Xaa Ile Xaa Xaa Xaa Xaa Xaa Xaa Lys
 1               5

<210> SEQ ID NO 39
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 39

Xaa Ile Xaa Xaa Xaa Xaa Xaa Xaa Arg
 1               5

<210> SEQ ID NO 40
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 40

Xaa Ile Xaa Xaa Xaa Xaa Xaa Xaa Tyr
 1               5

<210> SEQ ID NO 41
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
```

```
<221> NAME/KEY: VARIANT
<222> LOCATION: (1)...(9)
<223> OTHER INFORMATION: Xaa = Any Amino Acid

<400> SEQUENCE: 41

Xaa Met Xaa Xaa Xaa Xaa Xaa Xaa Lys
 1               5

<210> SEQ ID NO 42
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 42

Xaa Met Xaa Xaa Xaa Xaa Xaa Xaa Arg
 1               5

<210> SEQ ID NO 43
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 43

Xaa Met Xaa Xaa Xaa Xaa Xaa Xaa Tyr
 1               5

<210> SEQ ID NO 44
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 44

Xaa Val Xaa Xaa Xaa Xaa Xaa Xaa Lys
 1               5

<210> SEQ ID NO 45
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 45

Xaa Val Xaa Xaa Xaa Xaa Xaa Xaa Arg
```

```
1               5

<210> SEQ ID NO 46
<211> LENGTH: 9
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(9)
<223> OTHER INFORMATION: Xaa = Any Amino Acid

<400> SEQUENCE: 46

Xaa Val Xaa Xaa Xaa Xaa Xaa Xaa Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 47

Xaa Leu Xaa Xaa Xaa Xaa Xaa Xaa Xaa Lys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 48

Xaa Ile Xaa Xaa Xaa Xaa Xaa Xaa Xaa Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 49

Xaa Met Xaa Xaa Xaa Xaa Xaa Xaa Xaa Lys
1               5                   10

<210> SEQ ID NO 50
<211> LENGTH: 10
<212> TYPE: PRT
<213> ORGANISM: Artificial Sequence
```

```
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 50

Xaa Val Xaa Xaa Xaa Xaa Xaa Xaa Xaa Lys
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 51

Xaa Leu Xaa Xaa Xaa Xaa Xaa Xaa Xaa Arg
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 52

Xaa Ile Xaa Xaa Xaa Xaa Xaa Xaa Xaa Arg
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 53

Xaa Met Xaa Xaa Xaa Xaa Xaa Xaa Xaa Arg
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid
```

```
<400> SEQUENCE: 54

Xaa Val Xaa Xaa Xaa Xaa Xaa Xaa Xaa Arg
 1               5                   10

<210> SEQ ID NO 55
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 55

Xaa Leu Xaa Xaa Xaa Xaa Xaa Xaa Xaa Tyr
 1               5                   10

<210> SEQ ID NO 56
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 56

Xaa Ile Xaa Xaa Xaa Xaa Xaa Xaa Xaa Tyr
 1               5                   10

<210> SEQ ID NO 57
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 57

Xaa Met Xaa Xaa Xaa Xaa Xaa Xaa Xaa Tyr
 1               5                   10

<210> SEQ ID NO 58
<211> LENGTH: 10
<212> TYPE: PRT
<213> ORGANISM: Artificial Sequence
<220> FEATURE:
<223> OTHER INFORMATION: Motif utilized for junctional minimization
      (human A3/A11)
<220> FEATURE:
<221> NAME/KEY: VARIANT
<222> LOCATION: (1)...(10)
<223> OTHER INFORMATION: Xaa = Any Amino Acid

<400> SEQUENCE: 58

Xaa Val Xaa Xaa Xaa Xaa Xaa Xaa Xaa Tyr
 1               5                   10
```

-continued

<210> SEQ ID NO 59
<211> LENGTH: 9
<212> TYPE: PRT
<213> ORGANISM: Artificial Sequence
<220> FEATURE:
<223> OTHER INFORMATION: Motif utilized for junctional minimization
(human B7)
<220> FEATURE:
<221> NAME/KEY: VARIANT
<222> LOCATION: (1)...(9)
<223> OTHER INFORMATION: Xaa = Any Amino Acid

<400> SEQUENCE: 59

Xaa Pro Xaa Xaa Xaa Xaa Xaa Xaa Leu
1 5

<210> SEQ ID NO 60
<211> LENGTH: 9
<212> TYPE: PRT
<213> ORGANISM: Artificial Sequence
<220> FEATURE:
<223> OTHER INFORMATION: Motif utilized for junctional minimization
(human B7)
<220> FEATURE:
<221> NAME/KEY: VARIANT
<222> LOCATION: (1)...(9)
<223> OTHER INFORMATION: Xaa = Any Amino Acid

<400> SEQUENCE: 60

Xaa Pro Xaa Xaa Xaa Xaa Xaa Xaa Ile
1 5

<210> SEQ ID NO 61
<211> LENGTH: 9
<212> TYPE: PRT
<213> ORGANISM: Artificial Sequence
<220> FEATURE:
<223> OTHER INFORMATION: Motif utilized for junctional minimization
(human B7)
<220> FEATURE:
<221> NAME/KEY: VARIANT
<222> LOCATION: (1)...(9)
<223> OTHER INFORMATION: Xaa = Any Amino Acid

<400> SEQUENCE: 61

Xaa Pro Xaa Xaa Xaa Xaa Xaa Xaa Met
1 5

<210> SEQ ID NO 62
<211> LENGTH: 9
<212> TYPE: PRT
<213> ORGANISM: Artificial Sequence
<220> FEATURE:
<223> OTHER INFORMATION: Motif utilized for junctional minimization
(human B7)
<220> FEATURE:
<221> NAME/KEY: VARIANT
<222> LOCATION: (1)...(9)
<223> OTHER INFORMATION: Xaa = Any Amino Acid

<400> SEQUENCE: 62

Xaa Pro Xaa Xaa Xaa Xaa Xaa Xaa Val
1 5

<210> SEQ ID NO 63
<211> LENGTH: 9
<212> TYPE: PRT
<213> ORGANISM: Artificial Sequence
<220> FEATURE:
<223> OTHER INFORMATION: Motif utilized for junctional minimization
(human B7)

```
<220> FEATURE:
<221> NAME/KEY: VARIANT
<222> LOCATION: (1)...(9)
<223> OTHER INFORMATION: Xaa = Any Amino Acid

<400> SEQUENCE: 63

Xaa Pro Xaa Xaa Xaa Xaa Xaa Xaa Phe
 1               5

<210> SEQ ID NO 64
<211> LENGTH: 10
<212> TYPE: PRT
<213> ORGANISM: Artificial Sequence
<220> FEATURE:
<223> OTHER INFORMATION: Motif utilized for junctional minimization
      (human B7)
<220> FEATURE:
<221> NAME/KEY: VARIANT
<222> LOCATION: (1)...(10)
<223> OTHER INFORMATION: Xaa = Any Amino Acid

<400> SEQUENCE: 64

Xaa Pro Xaa Xaa Xaa Xaa Xaa Xaa Xaa Leu
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Motif utilized for junctional minimization
      (human B7)
<220> FEATURE:
<221> NAME/KEY: VARIANT
<222> LOCATION: (1)...(10)
<223> OTHER INFORMATION: Xaa = Any Amino Acid

<400> SEQUENCE: 65

Xaa Pro Xaa Xaa Xaa Xaa Xaa Xaa Xaa Ile
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Motif utilized for junctional minimization
      (human B7)
<220> FEATURE:
<221> NAME/KEY: VARIANT
<222> LOCATION: (1)...(10)
<223> OTHER INFORMATION: Xaa = Any Amino Acid

<400> SEQUENCE: 66

Xaa Pro Xaa Xaa Xaa Xaa Xaa Xaa Xaa Met
 1               5                  10

<210> SEQ ID NO 67
<211> LENGTH: 10
<212> TYPE: PRT
<213> ORGANISM: Artificial Sequence
<220> FEATURE:
<223> OTHER INFORMATION: Motif utilized for junctional minimization
      (human B7)
<220> FEATURE:
<221> NAME/KEY: VARIANT
<222> LOCATION: (1)...(10)
<223> OTHER INFORMATION: Xaa = Any Amino Acid

<400> SEQUENCE: 67
```

```
Xaa Pro Xaa Xaa Xaa Xaa Xaa Xaa Xaa Val
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Motif utilized for junctional minimization
      (human B7)
<220> FEATURE:
<221> NAME/KEY: VARIANT
<222> LOCATION: (1)...(10)
<223> OTHER INFORMATION: Xaa = Any Amino Acid

<400> SEQUENCE: 68

Xaa Pro Xaa Xaa Xaa Xaa Xaa Xaa Xaa Phe
1               5                   10

<210> SEQ ID NO 69
<211> LENGTH: 13
<212> TYPE: PRT
<213> ORGANISM: Artificial Sequence
<220> FEATURE:
<223> OTHER INFORMATION: PADRE sequence

<400> SEQUENCE: 69

Ala Lys Phe Val Ala Ala Trp Thr Leu Lys Ala Ala Ala
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Oligopeptide

<400> SEQUENCE: 70

Val Leu Ala Glu Ala Met Ser Gln Val
1               5

<210> SEQ ID NO 71
<211> LENGTH: 9
<212> TYPE: PRT
<213> ORGANISM: Artificial Sequence
<220> FEATURE:
<223> OTHER INFORMATION: Oligopeptide

<400> SEQUENCE: 71

Ile Leu Lys Glu Pro Val His Gly Val
1               5

<210> SEQ ID NO 72
<211> LENGTH: 9
<212> TYPE: PRT
<213> ORGANISM: Artificial Sequence
<220> FEATURE:
<223> OTHER INFORMATION: Oligopeptide

<400> SEQUENCE: 72

Thr Leu Asn Phe Pro Ile Ser Pro Ile
1               5

<210> SEQ ID NO 73
<211> LENGTH: 10
<212> TYPE: PRT
<213> ORGANISM: Artificial Sequence
<220> FEATURE:
```

```
<223> OTHER INFORMATION: Oligopeptide

<400> SEQUENCE: 73

Ser Leu Leu Asn Ala Thr Asp Ile Ala Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Oligopeptide

<400> SEQUENCE: 74

Gln Met Ala Val Phe Ile His Asn Phe Lys
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Oligopeptide

<400> SEQUENCE: 75

Val Thr Val Tyr Tyr Gly Val Pro Val Trp Lys
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Oligopeptide

<400> SEQUENCE: 76

Phe Pro Val Arg Pro Gln Pro Leu
1               5

<210> SEQ ID NO 77
<211> LENGTH: 10
<212> TYPE: PRT
<213> ORGANISM: Artificial Sequence
<220> FEATURE:
<223> OTHER INFORMATION: Oligopeptide

<400> SEQUENCE: 77

Tyr Pro Leu Ala Ser Leu Arg Ser Leu Phe
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Oligopeptide

<400> SEQUENCE: 78

Val Ile Tyr Gln Tyr Met Asp Asp Leu Tyr
1               5                   10

<210> SEQ ID NO 79
<211> LENGTH: 9
<212> TYPE: PRT
<213> ORGANISM: Artificial Sequence
<220> FEATURE:
<223> OTHER INFORMATION: Oligopeptide
```

```
<400> SEQUENCE: 79

Ile Tyr Gln Glu Pro Phe Lys Asn Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Oligopeptide

<400> SEQUENCE: 80

Ile Trp Gly Cys Ser Gly Lys Leu Ile
1               5

<210> SEQ ID NO 81
<211> LENGTH: 277
<212> TYPE: PRT
<213> ORGANISM: Artificial Sequence
<220> FEATURE:
<223> OTHER INFORMATION: HIV-1090

<400> SEQUENCE: 81

Met Gly Met Gln Val Gln Ile Gln Ser Leu Phe Leu Leu Leu Leu Trp
1               5                   10                  15

Val Pro Gly Ser Arg Gly Lys Leu Val Gly Lys Leu Asn Trp Ala Gly
                20                  25                  30

Ala Ala Ile Leu Lys Glu Pro Val His Gly Val Asn Ala Ala Cys Pro
            35                  40                  45

Lys Val Ser Phe Glu Pro Ile Lys Ile Pro Ile His Tyr Cys Ala Pro
        50                  55                  60

Ala Lys Ala Lys Phe Val Ala Ala Trp Thr Leu Lys Ala Ala Ala Lys
65                  70                  75                  80

Ala Phe Pro Val Arg Pro Gln Val Pro Leu Gly Ala Ala Lys Leu Thr
                85                  90                  95

Pro Leu Cys Val Thr Leu Gly Ala Ala Ala Val Leu Ala Glu Ala Met
            100                 105                 110

Ser Gln Val Lys Val Tyr Leu Ala Trp Val Pro Ala His Lys Gly Ala
        115                 120                 125

Ala Ala Ala Ile Phe Gln Ser Ser Met Thr Lys Lys Thr Thr Leu Phe
    130                 135                 140

Cys Ala Ser Asp Ala Lys Asn Ile Pro Tyr Asn Pro Gln Ser Gln Gly
145                 150                 155                 160

Val Val Lys His Pro Val His Ala Gly Pro Ile Ala Asn Val Thr Val
                165                 170                 175

Tyr Tyr Gly Val Pro Val Trp Lys Lys Ala Ala Ala Gln Met Ala Val
            180                 185                 190

Phe Ile His Asn Phe Lys Asn Ala Ala Ala Tyr Pro Leu Ala Ser Leu
        195                 200                 205

Arg Ser Leu Phe Asn Leu Thr Phe Gly Trp Cys Phe Lys Leu Asn Arg
    210                 215                 220

Ile Leu Gln Gln Leu Leu Phe Ile Asn Ala Lys Ile Gln Asn Phe Arg
225                 230                 235                 240

Val Tyr Tyr Arg Lys Ala Ala Val Thr Ile Lys Ile Gly Gly Gln Leu
                245                 250                 255

Lys Lys Val Pro Leu Gln Leu Pro Pro Leu Lys Ala Met Thr Asn Asn
            260                 265                 270
```

Pro Pro Ile Pro Val
        275

<210> SEQ ID NO 82
<211> LENGTH: 834
<212> TYPE: DNA
<213> ORGANISM: Artificial Sequence
<220> FEATURE:
<223> OTHER INFORMATION: Encoding sequence for HIV-1090

<400> SEQUENCE: 82

```
atgggaatgc aggtgcagat ccagagcctg tttctgctcc tcctgtgggt gcccggatcc    60
agaggaaagc tggtgggcaa actcaactgg gccggagctg caatcctgaa ggagcccgtc   120
cacggggtga atgccgcttg ccctaaagtc agcttcgaac caattaagat ccccattcat   180
tactgtgcac ctgccaaagc taagtttgtg ccgcttgga ccctcaaggc cgctgcaaaa   240
gccttcccag tgaggcccca ggtgcctctg gcgccgcta aactcacacc actgtgcgtc   300
actctgggag ccgctgcagt gctggcagag ccatgtccc aagtgaaggt gtatctggct   360
tgggtgcccg ccacaagggg gccgctgca gccatctttc agtctagcat gaccaagaaa   420
acaactctgt tctgtgcctc cgacgctaag aacatccctt ataatccaca gtctcagggc   480
gtggtcaagc atcccgtgca cgccggacct attgctaacg tgaccgtgta ctatggggtc   540
ccagtgtgga agaaagccgc tgcacagatg gccgtgttta ttcacaattt caaaaacgcc   600
gctgcatacc cctcgccag cctgagatcc ctcttcaacc tgacattcgg ctggtgcttt   660
aagctgaacc ggatcctgca gcaactgctc tttatcaatg ctaaaatcca gaacttccgc   720
gtctactata ggaaggctgc agtgactatc aaaattggcg acaactgaa gaaagtgcct   780
ctccagctgc cccctctcaa ggcaatgacc aacaatcccc ctatcccagt ctga         834
```

<210> SEQ ID NO 83
<211> LENGTH: 280
<212> TYPE: PRT
<213> ORGANISM: Artificial Sequence
<220> FEATURE:
<223> OTHER INFORMATION: HIV-CPT

<400> SEQUENCE: 83

Met Gly Met Gln Val Gln Ile Gln Ser Leu Phe Leu Leu Leu Leu Trp
  1               5                  10                  15

Val Pro Gly Ser Arg Gly Ile Pro Ile His Tyr Cys Ala Pro Ala Lys
             20                  25                  30

Ala Ala Lys Ile Gln Asn Phe Arg Val Tyr Tyr Arg Lys Ala Ala Val
         35                  40                  45

Thr Ile Lys Ile Gly Gly Gln Leu Lys Lys Ala Lys Phe Val Ala Ala
     50                  55                  60

Trp Thr Leu Lys Ala Ala Ala Lys Val Pro Leu Gln Leu Pro Pro Leu
 65                  70                  75                  80

Lys Ala Ile Phe Gln Ser Ser Met Thr Lys Lys Leu Thr Pro Leu Cys
                 85                  90                  95

Val Thr Leu Gly Ala Gln Met Ala Val Phe Ile His Asn Phe Lys Gly
            100                 105                 110

Ala Lys Val Tyr Leu Ala Trp Val Pro Ala His Lys Asn Ala Ile Pro
        115                 120                 125

Tyr Asn Pro Gln Ser Gln Gly Val Val Lys Ala Ile Leu Lys Glu Pro
    130                 135                 140

Val His Gly Val Gly Ala Ala Leu Thr Phe Gly Trp Cys Phe Lys
145                 150                 155                 160

Leu Asn Ala Val Leu Ala Glu Ala Met Ser Gln Val Asn Arg Ile Leu
            165                 170                 175

Gln Gln Leu Leu Phe Ile Asn Ala Ala Cys Pro Lys Val Ser Phe
        180                 185                 190

Glu Pro Ile Lys Val Thr Val Tyr Tyr Gly Val Pro Val Trp Lys Lys
        195                 200                 205

Ala Ala His Pro Val His Ala Gly Pro Ile Ala Asn Ala Ala Tyr
    210                 215                 220

Pro Leu Ala Ser Leu Arg Ser Leu Phe Asn Ala Ala Thr Thr Leu
225                 230                 235                 240

Phe Cys Ala Ser Asp Ala Lys Asn Lys Leu Val Gly Lys Leu Asn Trp
            245                 250                 255

Ala Asn Ala Ala Ala Phe Pro Val Arg Pro Gln Val Pro Leu Asn Met
            260                 265                 270

Thr Asn Asn Pro Pro Ile Pro Val
            275                 280

<210> SEQ ID NO 84
<211> LENGTH: 843
<212> TYPE: DNA
<213> ORGANISM: Artificial Sequence
<220> FEATURE:
<223> OTHER INFORMATION: Encoding sequence for HIV-CPT

<400> SEQUENCE: 84
atggggatgc aggtgcagat ccagagcctg tttctgctcc tcctgtgggt gcccggatcc    60
agaggaatcc ccattcacta ctgcgcccct gctaaggcag ccaaaatcca gaacttcagg   120
gtgtattaca gaaaggctgc agtcaccatt aaaatcggcg acaactgaa gaaagccaag   180
tttgtggccg cttggacact caaggccgct gcaaaggtcc cactgcagct ccccccctctg   240
aaggccatct tccagagctc catgactaag aaactgaccc cactgtgtgt gacactcggg   300
gcccagatgg ctgtgttcat ccataatttt aaaggcgcca aggtctacct ggcttgggtg   360
cccgcacaca gaacgccat tccttacaat ccacagtctc aaggagtggt caaagctatt   420
ctgaaggagc ccgtgcacgg ggtgggcgcc gctgcactca ctttcggatg gtgctttaaa   480
ctgaacgccg tgctggctga agccatgagc caggtcaatc ggatcctgca gcaactgctc   540
ttcattaacg ccgctgcatg tcctaaggtg tccttcgagc caatcaaagt gaccgtgtat   600
tacggggtcc ccgtgtggaa gaaagccgct catcctgtcc acgcaggccc aatcgccaac   660
gccgctgcat atccctcgc ctctctgcgc agcctgttta cgccgctgc aacaaccctc   720
ttttgcgcct ccgacgctaa gaataaactg gtgggaaagc tgaactgggc caacgcagct   780
gcattccctg tgaggccaca ggtccccctc aatatgacta caatccccc tatcccagtg   840
tga                                                                 843

<210> SEQ ID NO 85
<211> LENGTH: 211
<212> TYPE: PRT
<213> ORGANISM: Artificial Sequence
<220> FEATURE:
<223> OTHER INFORMATION: HIV-FT

<400> SEQUENCE: 85

Met Gln Val Gln Ile Gln Ser Leu Phe Leu Leu Leu Trp Val Pro
1               5                   10                  15

Gly Ser Arg Gly Lys Leu Val Gly Lys Leu Asn Trp Ala Met Ala Ser
            20                  25                  30

Asp Phe Asn Leu Pro Pro Val Ala Ile Phe Gln Ser Ser Met Thr Lys
            35                  40                  45

Val Thr Ile Lys Ile Gly Gly Gln Leu Lys Arg Ile Leu Gln Gln Leu
    50                  55                  60

Leu Phe Ile Met Ala Val Phe Ile His Asn Phe Lys Ile Pro Tyr Asn
65                  70                  75                  80

Pro Gln Ser Gln Gly Val Val Thr Thr Leu Phe Cys Ala Ser Asp Ala
                85                  90                  95

Lys Ile Leu Lys Glu Pro Val His Gly Val Gln Met Ala Val Phe Ile
            100                 105                 110

His Asn Phe Lys Gly Ala Ala Val Phe Ile His Asn Phe Lys Arg Cys
            115                 120                 125

Pro Lys Val Ser Phe Glu Pro Ile Lys Ile Gln Asn Phe Arg Val Tyr
            130                 135                 140

Tyr Arg Leu Thr Phe Gly Trp Cys Phe Lys Leu Gln Val Pro Leu Arg
145                 150                 155                 160

Pro Met Thr Tyr Lys Met Thr Asn Asn Pro Pro Ile Pro Val Thr Val
                165                 170                 175

Tyr Tyr Gly Val Pro Val Trp Lys Val Leu Ala Glu Ala Met Ser Gln
            180                 185                 190

Val Ile Pro Ile His Tyr Cys Ala Pro Ala Lys Leu Thr Pro Leu Cys
            195                 200                 205

Val Thr Leu
    210

<210> SEQ ID NO 86
<211> LENGTH: 633
<212> TYPE: DNA
<213> ORGANISM: Artificial Sequence
<220> FEATURE:
<223> OTHER INFORMATION: Encoding sequence for HIV-FT

<400> SEQUENCE: 86
atgcaggtgc agatccagag cctgtttctg ctcctcctgt gggtgcccgg atccagagga      60
aagctggtgg ggaagctgaa ctgggccatg gccagcgatt tcaacctgcc ccccgtggcc     120
atcttccaga gcagcatgac caaggtgacc atcaagatcg gggggcagct gaagaggatc     180
ctgcagcagc tgctgttcat catggccgtg ttcatccaca acttcaagat ccccTacaac     240
ccccagagcc agggggtggt gaccacc ctg ttctgcgcca gcgatgccaa gatcctgaag     300
gagcccgtgc acggggtgca gatggccgtg ttcatccaca acttcaaggg cgccgccgtg     360
ttcatccaca acttcaagag gtgccccaag gtgagcttcg agcccatcaa gatccagaac     420
ttcagggtgt actacaggct gaccttcggg tggtgcttca gctgcaggt gcccctgagg      480 cccatgacct acaagatgac caacaacccc cccatcccccg tgaccgtgta ctacggggtg     540
cccgtgtgga aggtgctggc cgaggccatg agccaggtga tccccatcca ctactgcgcc     600
cccgccaagc tgaccccccct gtgcgtgacc ctg                                 633

<210> SEQ ID NO 87
<211> LENGTH: 585
<212> TYPE: PRT
<213> ORGANISM: Artificial Sequence
<220> FEATURE:
<223> OTHER INFORMATION: HIV-TC

<400> SEQUENCE: 87

```
Met Gly Met Gln Val Gln Ile Gln Ser Leu Phe Leu Leu Leu Leu Trp
1               5                   10                  15

Val Pro Gly Ser Arg Gly Tyr Trp Gln Ala Thr Trp Ile Pro Glu Trp
            20                  25                  30

Lys Ala Ile Phe Gln Ser Ser Met Thr Lys Lys Val Tyr Leu Ala Trp
        35                  40                  45

Val Pro Ala His Lys Asn Ala Ala Cys Pro Lys Val Ser Phe Glu Pro
    50                  55                  60

Ile Lys His Pro Val His Ala Gly Pro Ile Ala Asn Leu Thr Phe Gly
65                  70                  75                  80

Trp Cys Phe Lys Leu Asn Lys Met Ile Gly Gly Ile Gly Gly Phe Ile
                85                  90                  95

Lys Phe Arg Asp Tyr Val Asp Arg Phe Tyr Lys Ala Ala Arg Ile
            100                 105                 110

Leu Gln Gln Leu Leu Phe Ile Asn Thr Thr Leu Phe Cys Ala Ser Asp
        115                 120                 125

Ala Lys Asn Gln Met Val His Gln Ala Ile Ser Pro Arg Gly Ala Lys
    130                 135                 140

Leu Val Gly Lys Leu Asn Trp Ala Gly Ala Ala Ile Tyr Glu Thr
145                 150                 155                 160

Tyr Gly Asp Thr Trp Lys Ala Ala Gln Val Pro Leu Arg Pro Met Thr
                165                 170                 175

Tyr Lys Gly Ala Ala Ala Val Thr Val Leu Asp Val Gly Asp Ala Tyr
            180                 185                 190

Asn Ala Ala Ala Arg Tyr Leu Lys Asp Gln Gln Leu Leu Asn Thr Leu
        195                 200                 205

Asn Phe Pro Ile Ser Pro Ile Asn Met Thr Asn Asn Pro Pro Ile Pro
    210                 215                 220

Val Asn Ala Pro Tyr Asn Thr Pro Val Phe Ala Ile Lys Ala Ala Ala
225                 230                 235                 240

Val Pro Leu Gln Leu Pro Leu Lys Ala Ala Ile Pro Tyr Asn Pro
                245                 250                 255

Gln Ser Gln Gly Val Val Lys Ala Leu Leu Gln Leu Thr Val Trp Gly
            260                 265                 270

Ile Gly Ala Ala Ile Leu Lys Glu Pro Val His Gly Val Asn Ala Ala
        275                 280                 285

Ala Phe Pro Ile Ser Pro Ile Glu Thr Val Lys Val Trp Lys Glu Ala
    290                 295                 300

Thr Thr Thr Leu Phe Lys Ala Ala Val Thr Ile Lys Ile Gly Gly
305                 310                 315                 320

Gln Leu Lys Lys Ile Tyr Gln Glu Pro Phe Lys Asn Leu Lys Ala Ala
                325                 330                 335

Ala Val Leu Ala Glu Ala Met Ser Gln Val Asn Leu Val Gly Pro Thr
            340                 345                 350

Pro Val Asn Ile Gly Ala Ala Glu Val Asn Ile Val Thr Asp Ser
        355                 360                 365

Gln Tyr Lys Ala Ala Ile Pro Ile His Tyr Cys Ala Pro Ala Lys
    370                 375                 380

Ala Val Ile Tyr Gln Tyr Met Asp Asp Leu Tyr Lys Ala Ala Ala Gln
385                 390                 395                 400

Met Ala Val Phe Ile His Asn Phe Lys Asn Ala Ala Thr Tyr Gln Ile
```

-continued

```
                405                 410                 415

Tyr Gln Glu Pro Phe Lys Pro Tyr Asn Glu Trp Thr Leu Glu Leu Lys
            420                 425                 430

Ala Lys Ile Gln Asn Phe Arg Val Tyr Tyr Arg Lys Ala Phe Pro Val
        435                 440                 445

Arg Pro Gln Val Pro Leu Gly Ala Ala Ala Ile Trp Gly Cys Ser Gly
    450                 455                 460

Lys Leu Ile Lys Val Met Ile Val Trp Gln Val Asp Arg Asn Ala Ala
465                 470                 475                 480
Lys Ala Ala Cys Trp Trp Ala Gly Ile Lys Ala Lys Phe Val Ala Ala
                485                 490                 495
Trp Thr Leu Lys Ala Ala Ala Lys Leu Thr Pro Leu Cys Val Thr Leu
            500                 505                 510
Asn Ala Ala Met Ala Ser Asp Phe Asn Leu Pro Pro Val Lys Ser Leu
        515                 520                 525
Leu Asn Ala Thr Asp Ile Ala Val Asn Val Thr Val Tyr Tyr Gly Val
    530                 535                 540

Pro Val Trp Lys Lys Ala Ala Ala Ala Ile Ile Arg Ile Leu Gln Gln
545                 550                 555                 560
Leu Lys Arg Ala Met Ala Ser Asp Phe Asn Leu Asn Ala Ala Ala Tyr
                565                 570                 575
Pro Leu Ala Ser Leu Arg Ser Leu Phe
            580                 585

<210> SEQ ID NO 88
<211> LENGTH: 1758
<212> TYPE: DNA
<213> ORGANISM: Artificial Sequence
<220> FEATURE:
<223> OTHER INFORMATION: Encoding sequence for HIV-TC

<400> SEQUENCE: 88
atggggatgc aggtgcagat ccagagcctg tttctgctcc tcctgtgggt gcccggatct      60
agaggatact ggcaagctac ttggattcca gaatggaaag ctatctttca atcctcaatg     120
acgaagaagg tatacctggc atgggtccca gcacacaaga acgccgcttg cccaaaggtg     180
tcctttgaac ccattaaaca cccagtgcac gcagggccaa tagcgaattt gacattcggg     240
tggtgcttca aactaaacaa aatgatcggc ggcattggag gctttatcaa gtttagagat     300
tacgtggacc gattctataa agccgctgcc cgtatactcc agcagctact attcatcaac     360
accactctct tctgcgcttc agacgctaag aaccaaatgg tacaccaagc cataagccct     420
agaggagcca agctcgtagg gaaattaaat tgggcgggtg cagcagcaat ctacgagact     480
tacggcgata cctggaaagc agcccaggtt ccgttacgcc caatgaccta taaaggcgca     540
gcagcagtaa cagttctaga tgtaggagac gcttacaacg ctgccgcaag atacctaaaa     600
gatcagcagt tactcaacac actaaatttc ccaattagcc cgataaacat gacaaataac     660
ccaccaattc ccgtcaatgc tccctacaac actccagtat tcgcaatcaa agccgctgct     720
gtccccctgc agctccctcc tctgaaagct gcgatacctt acaacccaca gagccaaggt     780
gttgtcaaag cactgcttca gctaacagtt tggggaattg gtgctgcaat tctaaaagag     840
ccagttcatg gggttaacgc cgccgccttc ccaatcagtc ctattgagac tgtgaaagta     900
tggaaagaag ccacaaccac actttttaag gcagccgcag ttacaattaa aatagggggc     960
caacttaaga aaatatacca ggaacctttc aagaatctca aagccgctgc agtgctcgcc    1020
```

-continued

```
gaggctatgt cacaggtgaa tttggtcgga ccaacacccg taaacatcgg agccgcagcc    1080
gaagtgaaca tagtcaccga ctcacagtac aaagccgctg caatacccat acattattgt    1140
gctcccgcaa aggccgtgat ctatcaatat atggacgacc tgtataaggc cgccgcgcag    1200
atggcagtct ttatccacaa ctttaaaaac gcagctactt atcagatcta ccaggaacca    1260
ttcaaaccgt acaatgagtg gaccttggaa ctaaaggcca aaattcagaa cttcagggta    1320
tattatagaa aagcatttcc agtgaggccc caggtgcctc tgggtgccgc agcaatatgg    1380
ggatgttctg gaaaactgat caaggtgatg attgtatggc aagtggacag aaatgcagct    1440
aaggcagcct gttggtgggc aggtataaaa gcaaagttcg tggcagcatg gacgcttaaa    1500
gcagccgcaa aactcactcc tctctgcgtg acacttaatg cagccatggc ctctgatttc    1560
aaccttcccc ctgtaaaatc cctgcttaat gcgacagata tcgcagtcaa cgtaacagta    1620
tattatggcg tgccagtctg gaaaaaagcc gccgcggcca taattcggat actgcagcag    1680
ctgaaaagag ctatggcgag tgacttcaac ctgaatgcgg ccgcctaccc cttggcatcg    1740
ttaaggtcac tattttga                                                  1758
```

<210> SEQ ID NO 89
<211> LENGTH: 255
<212> TYPE: PRT
<213> ORGANISM: Artificial Sequence
<220> FEATURE:
<223> OTHER INFORMATION: HCV.1

<400> SEQUENCE: 89

```
Met Gly Met Gln Val Gln Ile Gln Ser Leu Phe Leu Leu Leu Leu Trp
 1               5                  10                  15

Val Pro Gly Ser Arg Gly Leu Leu Phe Asn Ile Leu Gly Gly Trp Val
            20                  25                  30

Asp Leu Met Gly Tyr Ile Pro Leu Val Tyr Leu Val Ala Tyr Gln Ala
        35                  40                  45

Thr Val Ile Leu Ala Gly Tyr Gly Ala Gly Val Arg Leu Ile Val Phe
    50                  55                  60

Pro Asp Leu Gly Val His Met Trp Asn Phe Ile Ser Gly Ile Tyr Leu
65                  70                  75                  80

Leu Pro Arg Arg Gly Pro Arg Leu Tyr Leu Val Thr Arg His Ala Asp
                85                  90                  95

Val Val Leu Val Gly Gly Val Leu Ala Ala Leu Leu Phe Leu Leu Leu
            100                 105                 110

Ala Asp Ala Phe Leu Leu Leu Ala Asp Ala Arg Val Trp Met Asn Arg
        115                 120                 125

Leu Ile Ala Phe Ala Cys Thr Cys Gly Ser Ser Asp Leu Tyr Leu Ser
    130                 135                 140

Ala Phe Ser Leu His Ser Tyr Gly Val Ala Gly Ala Leu Val Ala Phe
145                 150                 155                 160

Lys Leu Pro Gly Cys Ser Phe Ser Ile Phe Lys Thr Ser Glu Arg Ser
                165                 170                 175

Gln Pro Arg Leu Ile Phe Cys His Ser Lys Lys Phe Trp Ala Lys
            180                 185                 190

His Met Trp Asn Phe Ile Pro Phe Tyr Gly Lys Ala Ile Arg Met Tyr
        195                 200                 205

Val Gly Gly Val Glu His Arg Gln Leu Phe Thr Phe Ser Pro Arg Arg
    210                 215                 220

Arg Leu Gly Val Arg Ala Thr Arg Lys Val Gly Ile Tyr Leu Leu Pro
```

```
                225                 230                 235                 240

Asn Arg Ala Lys Phe Val Ala Ala Trp Thr Leu Lys Ala Ala Ala
                245                 250                 255

<210> SEQ ID NO 90
<211> LENGTH: 747
<212> TYPE: DNA
<213> ORGANISM: Artificial Sequence
<220> FEATURE:
<223> OTHER INFORMATION: Encoding sequence for HCV.1

<400> SEQUENCE: 90
gaattcgccg ccaccatgca ggtgcagatc cagagcctgt ttctgctcct cctgtgggtg      60
cccggatcca gaggactgct gttcaacatc ctggggggt gggtggatct gatggggtac     120 atcccctgg tgtacctggt ggcctaccag gccaccgtga tcctggccgg gtacggggcc     180
ggggtgaggc tgatcgtgtt ccccgatctg ggggtgcaca tgtggaactt catcagcggg     240
atctacctgc tgcccaggag aggacctaga ctgtacctgg tgactagaca cgctgatgtg     300
gtgctggtgg aggagtgct ggctgctctg ctgtttctgc tgctggctga tgctttcctg     360
ctgctggctg atgctagagt gtggatgaac agactgatcg ctttcgcttg tacatgtgga     420
agctccgatc tgtatctgag cgctttcagc ctgcacagct acggagtggc tggagctctg     480
gtggctttta agctgcctgg atgtagcttt agcatcttta agaccagcga agaagccag     540 cctagactga tcttttgtca gcaagaag aagttttggg ctaagcacat gtggaatttt     600
atcccttcct atggaaaggc tatcagaatg tatgtggag gagtggaaca cagacagctg     660
tttacattta gccctagaag agagctggga gtgagagcta caagaaaggt gggaatctat     720
ctgctgccta atagatgaaa gcttggg                                         747

<210> SEQ ID NO 91
<211> LENGTH: 281
<212> TYPE: PRT
<213> ORGANISM: Artificial Sequence
<220> FEATURE:
<223> OTHER INFORMATION: HCV.2

<400> SEQUENCE: 91

Met Gly Met Gln Val Gln Ile Gln Ser Leu Phe Leu Leu Leu Leu Trp
  1               5                  10                  15

Val Pro Gly Ser Arg Gly Asp Leu Met Gly Tyr Ile Pro Leu Val Ala
                 20                  25                  30

Lys Phe Val Ala Ala Trp Thr Leu Lys Ala Ala Ala Leu Leu Phe Leu
             35                  40                  45

Leu Leu Ala Asp Ala Leu Ile Phe Cys His Ser Lys Lys Lys Gln Leu
         50                  55                  60

Phe Thr Phe Ser Pro Arg Arg Tyr Leu Val Thr Arg His Ala Asp Val
 65                  70                  75                  80

Tyr Leu Leu Pro Arg Arg Gly Pro Arg Leu Cys Thr Cys Gly Ser Ser
                 85                  90                  95

Asp Leu Tyr His Met Trp Asn Phe Ile Ser Gly Ile Phe Trp Ala Lys
                100                 105                 110

His Met Trp Asn Phe Ala Lys Phe Val Ala Ala Trp Thr Leu Lys Ala
            115                 120                 125

Ala Ala Ile Leu Ala Gly Tyr Gly Ala Gly Val Tyr Leu Val Ala Tyr
        130                 135                 140

Gln Ala Thr Val Gly Val Ala Gly Ala Leu Val Ala Phe Lys Ile Pro
```

```
                145                 150                 155                 160
Phe Tyr Gly Lys Ala Ile Arg Met Tyr Val Gly Gly Val Glu His Arg
                165                 170                 175

Val Leu Val Gly Gly Val Leu Ala Ala Phe Leu Leu Ala Asp Ala
            180                 185                 190

Arg Val Leu Pro Gly Cys Ser Phe Ser Ile Phe Ala Lys Phe Val Ala
            195                 200                 205

Ala Trp Thr Leu Lys Ala Ala Ala Lys Thr Ser Glu Arg Ser Gln Pro
        210                 215                 220

Arg Arg Leu Gly Val Arg Ala Thr Arg Lys Arg Leu Ile Val Phe Pro
225                 230                 235                 240

Asp Leu Gly Val Trp Met Asn Arg Leu Ile Ala Phe Ala Leu Ser Ala
                245                 250                 255

Phe Ser Leu His Ser Tyr Leu Leu Phe Asn Ile Leu Gly Gly Trp Val
                260                 265                 270

Val Gly Ile Tyr Leu Leu Pro Asn Arg
            275                 280

<210> SEQ ID NO 92
<211> LENGTH: 789
<212> TYPE: DNA
<213> ORGANISM: Artificial Sequence
<220> FEATURE:
<223> OTHER INFORMATION: Encoding sequence for HCV.2

<400> SEQUENCE: 92
gaattcgccg ccaccatggg aatgcaggtg cagatccaga gcctgtttct gctcctcctg     60
tgggtgcccg gatccagagg agatctgatg ggatatatcc ctctggtggc taagtttgtg    120
gctgcttgga cactgaaggc tgctgctctg ctgtttctgc tgctggctga tgctctgatc    180
ttctgtcaca gcaagaagaa gcagctgttt acatttagcc aagaagata tctggtgaca    240 agacacgctg atgtgtatct gctgcctaga cgcggaccta gactgtgtac atgtggaagc    300
tccgatctgt atcacatgtg aactttatc agcggaatct tttgggctaa gcacatgtgg    360
aatttcatcc tggctggata tggagctgga gtgtatctgg tggcttatca ggctacagtg    420
ggagtggctg gagctctggt ggcttttcaag atcccattct atggaaaggc tatcagaatg    480
tatgtgggag gagtggaaca cagagtgctg gtgggaggag tgctggctgc tttcctgctg    540
ctggctgatg ctagagtgct gccaggatgt agctttagca tcttcaagac ttccgaacgc    600
tcccagccta agactggg agtgagagct acaaggaaga gactgatcgt gtttccagat    660 ctggagtgt ggatgaatag actgatcgct ttcgctctga gcgctttcag cctgcacagc    720
tatctgctgt tcaacatcct gggaggatgg gtggtgggaa tctatctgct gccaaacaga    780
tgaaagctt                                                            789

<210> SEQ ID NO 93
<211> LENGTH: 107
<212> TYPE: PRT
<213> ORGANISM: Artificial Sequence
<220> FEATURE:
<223> OTHER INFORMATION: HCV.3s1

<400> SEQUENCE: 93

Met Gly Met Gln Val Gln Ile Gln Ser Leu Phe Leu Leu Leu Leu Trp
1               5                  10                  15

Val Pro Gly Ser Arg Gly Tyr Leu Val Ala Tyr Gln Ala Thr Val Ala
            20                  25                  30
```

Lys Phe Val Ala Ala Trp Thr Leu Lys Ala Ala Leu Leu Phe Leu
            35                  40                  45

Leu Leu Ala Asp Ala Leu Ile Phe Cys His Ser Lys Lys Tyr Leu
        50                  55                  60

Val Thr Arg His Ala Asp Val Leu Gly Phe Gly Ala Tyr Met Ser Lys
65                  70                  75                  80

Cys Thr Cys Gly Ser Ser Asp Leu Tyr His Met Trp Asn Phe Ile Ser
                85                  90                  95

Gly Ile Phe Trp Ala Lys His Met Trp Asn Phe
                100                 105

<210> SEQ ID NO 94
<211> LENGTH: 345
<212> TYPE: DNA
<213> ORGANISM: Artificial Sequence
<220> FEATURE:
<223> OTHER INFORMATION: Encoding sequence for HCV.3s1

<400> SEQUENCE: 94
gaattcgccg ccaccatggg aatgcaggtg cagatccaaa gcctgtttct gctcctcctg      60
tgggtgcccg atccagagg atacctcgtc gcctaccagg ccactgtggc taaattcgtg     120
gcagcctgga cactgaaagc tgcagctctg ctcttcctgc tcctggccga tgcactcatc     180
ttctgccatt ccaagaaaaa gtatctggtc accagacatg ctgacgtgct ggggtttggc     240
gcctacatga gcaagtgcac ctgtggcagc tccgacctgt atcacatgtg gaactttatt     300
tctggaatct tttgggccaa gcacatgtgg aatttctgaa agctt                     345

<210> SEQ ID NO 95
<211> LENGTH: 106
<212> TYPE: PRT
<213> ORGANISM: Artificial Sequence
<220> FEATURE:
<223> OTHER INFORMATION: HCV.3s2

<400> SEQUENCE: 95

Met Gly Met Gln Val Gln Ile Gln Ser Leu Phe Leu Leu Leu Leu Trp
1               5                   10                  15

Val Pro Gly Ser Arg Gly Val Leu Val Gly Gly Val Leu Ala Ala Ala
            20                  25                  30

Lys Phe Val Ala Ala Trp Thr Leu Lys Ala Ala Phe Leu Leu Leu
            35                  40                  45

Ala Asp Ala Arg Val Leu Ser Ala Phe Ser Leu His Ser Tyr Ile Leu
        50                  55                  60

Ala Gly Tyr Gly Ala Gly Val Trp Met Asn Arg Leu Ile Ala Phe Ala
65                  70                  75                  80

Ile Pro Phe Tyr Gly Lys Ala Ile Val Ala Gly Ala Leu Val Ala Phe
                85                  90                  95

Lys Val Gly Ile Tyr Leu Leu Pro Asn Arg
                100                 105

<210> SEQ ID NO 96
<211> LENGTH: 342
<212> TYPE: DNA
<213> ORGANISM: Artificial Sequence
<220> FEATURE:
<223> OTHER INFORMATION: Encoding sequence for HCV.3s2

<400> SEQUENCE: 96

```
gaattcgccg ccaccatggg aatgcaggtg cagatccaaa gcctgtttct gctcctcctg    60
tgggtgcccg atccagagg  agtcctggtg ggcggcgtcc tggccgctgc taagtttgtc   120
gctgcttgga cactgaaggc agccgctttc ctgctcctgg cagacgccag ggtgctgtct   180
gccttcagcc tccactccta catcctcgca gggtatggcg caggcgtgtg gatgaatcgg   240
ctgatcgcct ttgccattcc attctatggg aaagccattg tggctggcgc cctggtggca   300
ttcaaggtcg ggatctacct cctgcctaac cgctgaaagc tt                      342
```

<210> SEQ ID NO 97
<211> LENGTH: 80
<212> TYPE: PRT
<213> ORGANISM: Artificial Sequence
<220> FEATURE:
<223> OTHER INFORMATION: HCV.3s2(-3)

<400> SEQUENCE: 97

Met Gly Met Gln Val Gln Ile Gln Ser Leu Phe Leu Leu Leu Leu Trp
1               5                   10                  15

Val Pro Gly Ser Arg Gly Val Leu Val Gly Gly Val Leu Ala Ala Ala
            20                  25                  30

Lys Phe Val Ala Ala Trp Thr Leu Lys Ala Ala Ala Phe Leu Leu Leu
        35                  40                  45

Ala Asp Ala Arg Val Leu Ser Ala Phe Ser Leu His Ser Tyr Ile Leu
    50                  55                  60

Ala Gly Tyr Gly Ala Gly Val Trp Met Asn Arg Leu Ile Ala Phe Ala
65                  70                  75                  80

<210> SEQ ID NO 98
<211> LENGTH: 264
<212> TYPE: DNA
<213> ORGANISM: Artificial Sequence
<220> FEATURE:
<223> OTHER INFORMATION: Encoding sequence for HCV.3s2(-3)

<400> SEQUENCE: 98

```
gaattcgccg ccaccatggg aatgcaggtg cagatccaaa gcctgtttct gctcctcctg    60
tgggtgcccg atccagagg  agtcctggtg ggcggcgtcc tggccgctgc taagtttgtc   120
gctgcttgga cactgaaggc agccgctttc ctgctcctgg cagacgccag ggtgctgtct   180
gccttcagcc tccactccta catcctcgca gggtatggcg caggcgtgtg gatgaatcgg   240
ctgatcgcct ttgcctgagg atcc                                          264
```

<210> SEQ ID NO 99
<211> LENGTH: 130
<212> TYPE: PRT
<213> ORGANISM: Artificial Sequence
<220> FEATURE:
<223> OTHER INFORMATION: HCV.3s3

<400> SEQUENCE: 99

Met Gly Met Gln Val Gln Ile Gln Ser Leu Phe Leu Leu Leu Leu Trp
1               5                   10                  15

Val Pro Gly Ser Arg Gly Asp Leu Met Gly Tyr Ile Pro Leu Val Ala
            20                  25                  30

Lys Phe Val Ala Ala Trp Thr Leu Lys Ala Ala Ala Arg Leu Gly Val
        35                  40                  45

Arg Ala Thr Arg Lys Leu Leu Phe Asn Ile Leu Gly Gly Trp Val Arg
    50                  55                  60

```
Met Tyr Val Gly Gly Val Glu His Arg Arg Leu Ile Val Phe Pro Asp
 65                  70                  75                  80

Leu Gly Val Gly Val Ala Gly Ala Leu Val Ala Phe Lys Leu Pro Gly
                 85                  90                  95

Cys Ser Phe Ser Ile Phe Lys Thr Ser Glu Arg Ser Gln Pro Arg Gln
                100                 105                 110

Leu Phe Thr Phe Ser Pro Arg Arg Tyr Leu Leu Pro Arg Arg Gly Pro
            115                 120                 125

Arg Leu
    130

<210> SEQ ID NO 100
<211> LENGTH: 414
<212> TYPE: DNA
<213> ORGANISM: Artificial Sequence
<220> FEATURE:
<223> OTHER INFORMATION: Encoding sequence for HCV.3s3

<400> SEQUENCE: 100
gaattcgccg ccaccatggg aatgcaggtg cagatccaaa gcctgtttct gctcctcctg      60
tgggtgcccg gatccagagg agacctgatg ggctacatcc ctctcgtggc caagtttgtg     120
gcagcttgga ccctgaaggc cgctgccaga ctgggagtgc gcgctacacg gaaactcctg     180
tttaacatcc tgggagggtg ggtgcggatg tacgtcggag cgtcgagca cagaaggctc      240 attgtctttc cagatctcgg cgtgggcgtc gcaggcgcac tcgtggcctt caaactgcca     300
gggtgcagct tcagcatttt caagacctcc gaacgctccc aacccagaca gctgttcact     360
ttctctcctc ggaggtatct gctgcccaga cgcggaccca ggctgtgaaa gctt          414

<210> SEQ ID NO 101
<211> LENGTH: 98
<212> TYPE: PRT
<213> ORGANISM: Artificial Sequence
<220> FEATURE:
<223> OTHER INFORMATION: HCV.PC3

<400> SEQUENCE: 101

Met Gly Met Gln Val Gln Ile Gln Ser Leu Phe Leu Leu Leu Leu Trp
  1               5                  10                  15

Val Pro Gly Ser Arg Gly Leu Leu Phe Asn Ile Leu Gly Gly Trp Val
                 20                  25                  30

Lys Ala Lys Phe Val Ala Ala Trp Thr Leu Lys Ala Ala Ala Leu Ala
             35                  40                  45

Asp Gly Gly Cys Ser Gly Gly Ala Tyr Arg Leu Ile Val Phe Pro Asp
         50                  55                  60

Leu Gly Val Lys Phe Trp Ala Lys His Met Trp Asn Phe Ile Gly Val
 65                  70                  75                  80

Ala Gly Ala Leu Val Ala Phe Lys Lys Gln Leu Phe Thr Phe Ser Pro
                 85                  90                  95

Arg Arg

<210> SEQ ID NO 102
<211> LENGTH: 318
<212> TYPE: DNA
<213> ORGANISM: Artificial Sequence
<220> FEATURE:
<223> OTHER INFORMATION: Encoding sequence for HCV.PC3

<400> SEQUENCE: 102
```

-continued

```
gaattcgccg ccaccatggg aatgcaggtg cagatccaaa gcctgttcct gctcctcctg      60
tgggtgcccg gatccagagg actgctcttc aacatcctgg gcggatgggt gaaggccaag     120
ttcgtggctg cctggaccct gaaggctgcc gctctggccg acgggggatg cagcggcgga     180
gcttacaggc tcattgtctt tcccgatctc ggagtcaaat tttgggcaaa gcacatgtgg     240
aatttcatcg gggtggccgg agccctggtc gcttttaaaa agcagctctt caccttctcc     300
ccaagacggt gaggtacc                                                   318
```

<210> SEQ ID NO 103
<211> LENGTH: 107
<212> TYPE: PRT
<213> ORGANISM: Artificial Sequence
<220> FEATURE:
<223> OTHER INFORMATION: HCV.PC4

<400> SEQUENCE: 103

```
Met Gly Met Gln Val Gln Ile Gln Ser Leu Phe Leu Leu Leu Leu Trp
 1               5                  10                  15
Val Pro Gly Ser Arg Gly Arg Leu Gly Val Arg Ala Thr Arg Lys Lys
            20                  25                  30
Ala Lys Phe Val Ala Ala Trp Thr Leu Lys Ala Ala Lys Thr Ser
        35                  40                  45
Glu Arg Ser Gln Pro Arg Asn Leu Pro Gly Cys Ser Phe Ser Ile Phe
    50                  55                  60
Asn Asp Leu Met Gly Tyr Ile Pro Leu Val Lys Tyr Leu Leu Pro Arg
65                  70                  75                  80
Arg Gly Pro Arg Leu Asn Thr Leu Cys Gly Phe Ala Asp Leu Met Gly
                85                  90                  95
Tyr Arg Met Tyr Val Gly Gly Val Glu His Arg
            100                 105
```

<210> SEQ ID NO 104
<211> LENGTH: 345
<212> TYPE: DNA
<213> ORGANISM: Artificial Sequence
<220> FEATURE:
<223> OTHER INFORMATION: Encoding sequence for HCV.PC4

<400> SEQUENCE: 104

```
gaattcgccg ccaccatggg aatgcaggtg cagatccaaa gcctgttcct gctcctcctg      60
tgggtgcccg gatccagagg aaggctgggc gtgagagcca cccggaagaa ggccaagttc     120
gtggctgcct ggaccctgaa ggctgccgct aaaacaagcg agcgctccca gcccaggaac     180
ctgcctggat gctctttcag catctttaat gacctcatgg gtacattcc actggtgaag     240
tatctgctcc ccagacgggg ccctcgcctg aacactctct gtggatttgc tgatctgatg     300
gggtacagga tgtatgtcgg cggagtcgaa cacagatgag gtacc                    345
```

<210> SEQ ID NO 105
<211> LENGTH: 308
<212> TYPE: PRT
<213> ORGANISM: Artificial Sequence
<220> FEATURE:
<223> OTHER INFORMATION: HCV.2431(1P)

<400> SEQUENCE: 105

```
Met Gly Met Gln Val Gln Ile Gln Ser Leu Phe Leu Leu Leu Leu Trp
 1               5                  10                  15
Val Pro Gly Ser Arg Gly Val Leu Val Gly Gly Val Leu Ala Ala Ala
```

-continued

```
            20                  25                  30

Phe Leu Leu Leu Ala Asp Ala Arg Val Leu Ser Ala Phe Ser Leu His
        35                  40                  45

Ser Tyr Ile Leu Ala Gly Tyr Gly Ala Gly Val Trp Met Asn Arg Leu
    50                  55                  60

Ile Ala Phe Ala Gly Ala Ala Ala Arg Leu Gly Val Arg Ala Thr Arg
65                  70                  75                  80

Lys Lys Ala Ala Ala Lys Thr Ser Glu Arg Ser Gln Pro Arg Asn Leu
                85                  90                  95

Pro Gly Cys Ser Phe Ser Ile Phe Asn Asp Leu Met Gly Tyr Ile Pro
            100                 105                 110

Leu Val Lys Tyr Leu Leu Pro Arg Arg Gly Pro Arg Leu Asn Thr Leu
        115                 120                 125

Cys Gly Phe Ala Asp Leu Met Gly Tyr Arg Met Tyr Val Gly Gly Val
    130                 135                 140

Glu His Arg Lys Leu Leu Phe Asn Ile Leu Gly Gly Trp Val Lys Ala
145                 150                 155                 160
Ala Ala Leu Ala Asp Gly Gly Cys Ser Gly Gly Ala Tyr Arg Leu Ile
                165                 170                 175
Val Phe Pro Asp Leu Gly Val Lys Phe Trp Ala Lys His Met Trp Asn
            180                 185                 190
Phe Ile Gly Val Ala Gly Ala Leu Val Ala Phe Lys Lys Gln Leu Phe
        195                 200                 205

Thr Phe Ser Pro Arg Arg Asn Gly Tyr Leu Val Ala Tyr Gln Ala Thr
    210                 215                 220

Val Ala Ala Ala Leu Leu Phe Leu Leu Leu Ala Asp Ala Leu Ile Phe
225                 230                 235                 240
Cys His Ser Lys Lys Lys Tyr Leu Val Thr Arg His Ala Asp Val Leu
                245                 250                 255
Gly Phe Gly Ala Tyr Met Ser Lys Cys Thr Cys Gly Ser Ser Asp Leu
            260                 265                 270
Tyr His Met Trp Asn Phe Ile Ser Gly Ile Phe Trp Ala Lys His Met
        275                 280                 285

Trp Asn Phe Lys Ala Ala Ala Ala Lys Phe Val Ala Ala Trp Thr Leu
    290                 295                 300

Lys Ala Ala Ala
305
```

<210> SEQ ID NO 106
<211> LENGTH: 948
<212> TYPE: DNA
<213> ORGANISM: Artificial Sequence
<220> FEATURE:
<223> OTHER INFORMATION: Encoding sequence for HCV.2431(1P)

<400> SEQUENCE: 106

```
gaattcgccg ccaccatggg aatgcaggtg cagatccaaa gcctgtttct gctcctcctg     60
tgggtgcccg gctccagagg agtcctggtg ggcggcgtcc tggcagccgc tttcctgctc    120
ctggcagacg ccagggtgct gtctgccttc agcctccact cctacatcct cgcagggtat    180
ggcgcaggcg tgtggatgaa tcggctgatc gcctttgccg gcgctgccgc aaggctgggc    240
gtgagagcca cccggaagaa ggctgccgct aaaacaagcg agcgctccca gcccaggaac    300
ctgcctggat gctctttcag catctttaat gacctcatgg ggtacattcc actggtgaag    360
tatctgctcc ccagacgggg ccctcgcctg aacactctct gtggatttgc tgatctgatg    420
```

```
gggtacagga tgtatgtcgg cggagtcgaa cacagaaaac tgctcttcaa catcctgggc    480
ggatgggtga aggctgccgc tctggccgac gggggatgca gcggcggagc ttacaggctc    540
attgtctttc ccgatctcgg agtcaaattt tgggcaaagc acatgtggaa tttcatcggg    600
gtggccggag ccctggtcgc ttttaaaaag cagctcttca ccttctcccc aagacggaac    660
ggatacctcg tcgcctacca ggccactgtg gctgcagctc tgctcttcct gctcctggcc    720
gatgcactca tcttctgcca ttccaagaaa aagtatctgg tcaccagaca tgctgacgtg    780
ctggggtttg gcgcctacat gagcaagtgc acctgtggca gctccgacct gtatcacatg    840
tggaacttta tttctggaat cttttgggcc aagcacatgt ggaattttaa ggccgcagca    900
gctaaattcg tggcagcctg gacactgaaa gcagctgcat gaggatcc    948
```

<210> SEQ ID NO 107
<211> LENGTH: 308
<212> TYPE: PRT
<213> ORGANISM: Artificial Sequence
<220> FEATURE:
<223> OTHER INFORMATION: HCV.4312(1P)

<400> SEQUENCE: 107

```
Met Gly Met Gln Val Gln Ile Gln Ser Leu Phe Leu Leu Leu Leu Trp
 1               5                  10                  15

Val Pro Gly Ser Arg Gly Arg Leu Gly Val Arg Ala Thr Arg Lys Lys
            20                  25                  30

Ala Ala Ala Lys Thr Ser Glu Arg Ser Gln Pro Arg Asn Leu Pro Gly
        35                  40                  45

Cys Ser Phe Ser Ile Phe Asn Asp Leu Met Gly Tyr Ile Pro Leu Val
    50                  55                  60

Lys Tyr Leu Leu Pro Arg Arg Gly Pro Arg Leu Asn Thr Leu Cys Gly
65                  70                  75                  80

Phe Ala Asp Leu Met Gly Tyr Arg Met Tyr Val Gly Gly Val Glu His
                85                  90                  95

Arg Lys Leu Leu Phe Asn Ile Leu Gly Gly Trp Val Lys Ala Ala Ala
            100                 105                 110

Leu Ala Asp Gly Gly Cys Ser Gly Gly Ala Tyr Arg Leu Ile Val Phe
        115                 120                 125

Pro Asp Leu Gly Val Lys Phe Trp Ala Lys His Met Trp Asn Phe Ile
    130                 135                 140

Gly Val Ala Gly Ala Leu Val Ala Phe Lys Lys Gln Leu Phe Thr Phe
145                 150                 155                 160

Ser Pro Arg Arg Asn Gly Tyr Leu Val Ala Tyr Gln Ala Thr Val Ala
                165                 170                 175

Ala Ala Leu Leu Phe Leu Leu Leu Ala Asp Ala Leu Ile Phe Cys His
            180                 185                 190

Ser Lys Lys Lys Tyr Leu Val Thr Arg His Ala Asp Val Leu Gly Phe
        195                 200                 205

Gly Ala Tyr Met Ser Lys Cys Thr Cys Gly Ser Ser Asp Leu Tyr His
    210                 215                 220

Met Trp Asn Phe Ile Ser Gly Ile Phe Trp Ala Lys His Met Trp Asn
225                 230                 235                 240

Phe Lys Lys Ala Ala Ala Val Leu Val Gly Gly Val Leu Ala Ala Ala
                245                 250                 255

Phe Leu Leu Leu Ala Asp Ala Arg Val Leu Ser Ala Phe Ser Leu His
            260                 265                 270
```

Ser Tyr Ile Leu Ala Gly Tyr Gly Ala Gly Val Trp Met Asn Arg Leu
            275                 280                 285

Ile Ala Phe Ala Asn Ala Ala Ala Lys Phe Val Ala Ala Trp Thr Leu
        290                 295                 300

Lys Ala Ala Ala
305

<210> SEQ ID NO 108
<211> LENGTH: 948
<212> TYPE: DNA
<213> ORGANISM: Artificial Sequence
<220> FEATURE:
<223> OTHER INFORMATION: Encoding sequence for HCV.4312(1P)

<400> SEQUENCE: 108
gaattcgccg ccaccatggg aatgcaggtg cagatccaaa gcctgtttct gctcctcctg      60
tgggtgcccg gctccagagg aaggctgggc gtgagagcca cccggaagaa ggctgccgct     120
aaaacaagcg agcgctccca gcccaggaac ctgcctggat gctctttcag catctttaat     180
gacctcatgg ggtacattcc actggtgaag tatctgctcc ccagacgggg ccctcgcctg     240
aacactctct gtggatttgc tgatctgatg gggtacagga tgtatgtcgg cggagtcgaa     300
cacagaaaac tgctcttcaa catcctgggc ggatgggtga aggctgccgc tctggccgac     360
gggggatgca gcggcggagc ttacaggctc attgtctttc ccgatctcgg agtcaaattt     420
tgggcaaagc acatgtggaa tttcatcggg gtggccggag ccctggtcgc ttttaaaaag     480
cagctcttca ccttctcccc aagacggaac ggatacctcg tcgcctacca ggccactgtg     540
gctgcagctc tgctcttcct gctcctggcc gatgcactca tcttctgcca ttccaagaaa     600
aagtatctgg tcaccagaca tgctgacgtg ctggggtttg gcgcctacat gagcaagtgc     660
acctgtggca gctccgacct gtatcacatg tggaacttta tttctggaat cttttgggcc     720
aagcacatgt ggaattttaa gaaagccgct gcagtcctgg tgggcggcgt cctggcagcc     780
gctttcctgc tcctggcaga cgccaggggtg ctgtctgcct tcagcctcca ctcctacatc     840
ctcgcagggt atggcgcagg cgtgtggatg aatcggctga tcgcctttgc caatgctgca     900
gctaaattcg tggcagcctg gacactgaaa gcagctgcat gaggatcc               948

<210> SEQ ID NO 109
<211> LENGTH: 123
<212> TYPE: PRT
<213> ORGANISM: Artificial Sequence
<220> FEATURE:
<223> OTHER INFORMATION: AOSI.K

<400> SEQUENCE: 109

Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Lys Phe Leu Leu Ser Leu Gly Ile
    50                  55                  60

His Leu Tyr Met Asp Asp Val Val Leu Gly Val Gly Leu Ser Arg Tyr
65                  70                  75                  80

Val Ala Arg Leu Phe Leu Leu Thr Arg Ile Leu Thr Ile Ser Thr Leu
                85                  90                  95

Pro Glu Thr Thr Val Val Arg Arg Gln Ala Phe Thr Phe Ser Pro Thr
            100                 105                 110

Tyr Lys Trp Leu Ser Leu Leu Val Pro Phe Val
        115                 120

<210> SEQ ID NO 110
<211> LENGTH: 372
<212> TYPE: DNA
<213> ORGANISM: Artificial Sequence
<220> FEATURE:
<223> OTHER INFORMATION: Encoding sequence for AOSI.K

<400> SEQUENCE: 110
atgggaatgc aggtgcagat ccagagcctg tttctgctcc tcctgtgggt gcccgggtcc     60
agaggacaca ccctgtggaa ggccggaatc ctgtataagg ccaagttcgt ggctgcctgg    120
accctgaagg ctgccgcttt cctgcctagc gatttctttc ctagcgtgaa gttcctgctg    180
tccctgggaa tccacctgta tatggatgac gtggtgctgg agtgggact gtccaggtac    240 gtggctaggc tgttcctgct gaccagaatc ctgaccatct ccaccctgcc agagaccacc    300
gtggtgagga ggcaggcctt cacctttagc cctacctata gtggctgag cctgctggtg    360 ccctttgtgt ga                                                        372

<210> SEQ ID NO 111
<211> LENGTH: 206
<212> TYPE: PRT
<213> ORGANISM: Artificial Sequence
<220> FEATURE:
<223> OTHER INFORMATION: HBV.1

<400> SEQUENCE: 111

Met Gly Met Gln Val Gln Ile Gln Ser Leu Phe Leu Leu Leu Leu Trp
 1               5                  10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Phe Leu Leu Ser Leu Gly Ile His
    50                  55                  60

Leu Tyr Met Asp Asp Val Val Leu Gly Val Gly Leu Ser Arg Tyr Val
65                  70                  75                  80

Ala Arg Leu Phe Leu Leu Thr Arg Ile Leu Thr Ile Ser Thr Leu Pro
                85                  90                  95

Glu Thr Thr Val Val Arg Arg Gln Ala Phe Thr Phe Ser Pro Thr Tyr
            100                 105                 110

Lys Trp Leu Ser Leu Leu Val Pro Phe Val Ile Pro Ile Pro Ser Ser
        115                 120                 125

Trp Ala Phe Thr Pro Ala Arg Val Thr Gly Gly Val Phe Lys Val Gly
    130                 135                 140

Asn Phe Thr Gly Leu Tyr Leu Pro Ser Asp Phe Phe Pro Ser Val Thr
145                 150                 155                 160

Leu Trp Lys Ala Gly Ile Leu Tyr Lys Asn Val Ser Ile Pro Trp Thr
                165                 170                 175

His Lys Leu Val Val Asp Phe Ser Gln Phe Ser Arg Ser Ala Ile Cys
            180                 185                 190

Ser Val Val Arg Arg Ala Leu Met Pro Leu Tyr Ala Cys Ile
        195                 200                 205

<210> SEQ ID NO 112
<211> LENGTH: 621
<212> TYPE: DNA
<213> ORGANISM: Artificial Sequence
<220> FEATURE:
<223> OTHER INFORMATION: Encoding sequence for HBV.1

<400> SEQUENCE: 112

```
atgggaatgc aggtgcagat ccagagcctg tttctgctcc tcctgtgggt gcccgggtcc      60
agaggacaca ccctgtggaa ggccggaatc ctgtataagg ccaagttcgt ggctgcctgg     120
accctgaagg ctgccgcttt cctgcctagc gatttctttc ctagcgtgtt cctgctgtcc     180
ctgggaatcc acctgtatat ggatgacgtg gtgctgggag tgggactgtc caggtacgtg     240
gctaggctgt tcctgctgac cagaatcctg accatctcca ccctgccaga gaccaccgtg     300
gtgaggaggc aggccttcac ctttagcccc acctataagt ggctgagcct gctggtgccc     360
tttgtgatcc ctatccctag ctcctgggct ttcacccag ccagggtgac cggaggagtg      420
tttaaggtgg aaacttcac cggcctgtat ctgcccagcg atttctttcc tagcgtgacc      480
ctgtggaagg ccgggatcct gtacaagaat gtgtccatcc cttggaccca caagctggtg     540
gtggactttt cccagttcag cagatccgct atctgctccg tggtgaggag agctctgatg     600
ccactgtatg cctgtatctg a                                               621
```

<210> SEQ ID NO 113
<211> LENGTH: 219
<212> TYPE: PRT
<213> ORGANISM: Artificial Sequence
<220> FEATURE:
<223> OTHER INFORMATION: HBV.2

<400> SEQUENCE: 113

```
Met Gly Met Gln Val Gln Ile Gln Ser Leu Phe Leu Leu Leu Leu Trp
  1               5                  10                  15
Val Pro Gly Ser Arg Gly His Thr Leu Trp Lys Ala Gly Ile Leu Tyr
                 20                  25                  30
Lys Ala Lys Phe Val Ala Ala Trp Thr Leu Lys Ala Ala Ala Phe Leu
             35                  40                  45
Pro Ser Asp Phe Phe Pro Ser Val Asn Phe Leu Ser Leu Gly Ile
         50                  55                  60
His Leu Tyr Met Asp Asp Val Val Leu Gly Val Gly Leu Ser Arg Tyr
 65                  70                  75                  80
Val Ala Arg Leu Phe Leu Leu Thr Arg Ile Leu Thr Ile Ser Thr Leu
                 85                  90                  95
Pro Glu Thr Thr Val Val Arg Arg Gln Ala Phe Thr Phe Ser Pro Thr
            100                 105                 110
Tyr Lys Gly Ala Ala Ala Trp Leu Ser Leu Leu Val Pro Phe Val Asn
            115                 120                 125
Ile Pro Ile Pro Ser Ser Trp Ala Phe Lys Thr Pro Ala Arg Val Thr
        130                 135                 140
Gly Gly Val Phe Lys Val Gly Asn Phe Thr Gly Leu Tyr Asn Leu Pro
145                 150                 155                 160
Ser Asp Phe Phe Pro Ser Val Lys Thr Leu Trp Lys Ala Gly Ile Leu
                165                 170                 175
Tyr Lys Asn Val Ser Ile Pro Trp Thr His Lys Gly Ala Ala Leu Val
            180                 185                 190
```

Val Asp Phe Ser Gln Phe Ser Arg Asn Ser Ala Ile Cys Ser Val Val
        195                 200                 205

Arg Arg Ala Leu Met Pro Leu Tyr Ala Cys Ile
    210                 215

<210> SEQ ID NO 114
<211> LENGTH: 660
<212> TYPE: DNA
<213> ORGANISM: Artificial Sequence
<220> FEATURE:
<223> OTHER INFORMATION: Encoding sequence for HBV.2

<400> SEQUENCE: 114
atgggaatgc aggtgcagat ccagagc

<210> SEQ ID NO 116
<211> LENGTH: 513
<212> TYPE: DNA
<213> ORGANISM: Artificial Sequence
<220> FEATURE:
<223> OTHER INFORMATION: Encoding sequence for PfCTL.1

<400> SEQUENCE: 116

```
atgggaatgc aggtgcagat ccagagcctg tttctgctcc tcctgtgggt gcccggatcc    60
agaggaatcc tgagcgtgtc ctctttcctg tttgtcaacg ccgctgcaca gaccaatttc   120
aagagcctcc tgaggaacct cccctccgag aacgaaagag gctacaaagc cgctgcactg   180
ctcgcctgcg ctggactggc ctataagaaa gccgctgcag ccaagttcgt ggccgcttgg   240
acactgaagg ccgctgcaaa agcctttatg aaggctgtct gtgtggaggt caatgccgct   300
gcatctttcc tgtttgtgga ggccctcttt aacgctactc cttacgcagg gaaccagcc    360
cccttcaagg ccgctgcaaa atataagctg gcaaccagcg tgctgaaggc tggcgtgtcc   420
gagaatattt ttctgaaaaa cgccgctgca tacttcatcc tggtgaatct gctcattaag   480
gccggactcc tggggtggt ctctacagtg tga                                 513
```

<210> SEQ ID NO 117
<211> LENGTH: 157
<212> TYPE: PRT
<213> ORGANISM: Artificial Sequence
<220> FEATURE:
<223> OTHER INFORMATION: PfCTL.2

<400> SEQUENCE: 117

```
Met Gln Val Gln Ile Gln Ser Leu Phe Leu Leu Leu Trp Val Pro
  1               5                  10                  15
Gly Ser Arg Gly Phe Val Glu Ala Leu Phe Gln Glu Tyr Asn Ala Ala
             20                  25                  30
Ala Lys Tyr Leu Val Ile Val Phe Leu Ile Asn Ala Leu Ala Cys Ala
         35                  40                  45
Gly Leu Ala Tyr Lys Lys Phe Tyr Phe Ile Leu Val Asn Leu Leu Lys
     50                  55                  60
Ala Ala Leu Phe Phe Ile Ile Phe Asn Lys Asn Ala Ala Ala Lys Phe
 65                  70                  75                  80
Val Ala Ala Trp Thr Leu Lys Ala Ala Ala Lys Phe Ile Leu Val Asn
                 85                  90                  95
Leu Leu Ile Phe His Asn Phe Gln Asp Glu Glu Asn Ile Gly Ile Tyr
                100                 105                 110
Lys Leu Pro Tyr Gly Arg Thr Asn Leu Lys Ala Ala Ala Val Leu Leu
            115                 120                 125
Gly Gly Val Gly Leu Val Leu Asn Phe Leu Ile Phe Phe Asp Leu Phe
        130                 135                 140
Leu Val Lys Ala Val Leu Ala Gly Leu Leu Gly Val Val
145                 150                 155
```

<210> SEQ ID NO 118
<211> LENGTH: 480
<212> TYPE: DNA
<213> ORGANISM: Artificial Sequence
<220> FEATURE:
<223> OTHER INFORMATION: Encoding sequence for PfCTL.2

<400> SEQUENCE: 118

```
atgggaatgc aggtgcagat ccagagcctg tttctgctcc tcctgtgggt gcccggatcc    60
agaggattcg tggaggccct gtttcaggaa tacaacgccg ctgcaaagta tctcgtcatc   120
gtgttcctga tcaatgctct ggcatgcgcc ggcctcgctt acaaaaagtt ttacttcatt   180
ctggtcaacc tgctcaaggc cgctctgttc tttatcattt caataaaaa cgccgcagct    240 aagtttgtgg ccgcatggac cctgaaggcc gctgcaaaat tcatcctcgt gaatctgctc   300
atttttcaca acttccaaga cgaggaaaat atcggaattt ataagctgcc ctacgggagg   360
acaaacctga agccgctgc agtcctgctc ggcggagtgg ggctggtgct caattttctg   420
atcttctttg atctgttcct ggtgaaggcc gtcctggccg cctgctcgg agtcgtgtga    480
```

<210> SEQ ID NO 119
<211> LENGTH: 169
<212> TYPE: PRT
<213> ORGANISM: Artificial Sequence
<220> FEATURE:
<223> OTHER INFORMATION: PfCTL.3

<400> SEQUENCE: 119

```
Met Gln Val Gln Ile Gln Ser Leu Phe Leu Leu Leu Leu Trp Val Pro
 1               5                  10                  15

Gly Ser Arg Gly Val Phe Leu Ile Phe Phe Asp Leu Phe Leu Asn Ala
            20                  25                  30

Ala Ala Pro Ser Asp Gly Lys Cys Asn Leu Tyr Lys Ala Ala Ala Val
        35                  40                  45

Thr Cys Gly Asn Gly Ile Gln Val Arg Lys Leu Phe His Ile Phe Asp
    50                  55                  60

Gly Asp Asn Glu Ile Lys Ala His Val Leu Ser His Asn Ser Tyr Glu
65                  70                  75                  80

Lys Asn Tyr Tyr Gly Lys Gln Glu Asn Trp Tyr Ser Leu Lys Lys Ile
                85                  90                  95

Leu Ser Val Phe Phe Leu Ala Asn Ala Ala Lys Phe Ile Lys Ser
            100                 105                 110

Leu Phe His Ile Phe Lys Ala Ala Ala Leu Tyr Ile Ser Phe Tyr Phe
        115                 120                 125

Ile Lys Ala Lys Phe Val Ala Ala Trp Thr Leu Lys Ala Ala Ala Lys
    130                 135                 140

Ala Ala Ala Tyr Tyr Ile Pro His Gln Ser Ser Leu Lys Ala Ala Ala
145                 150                 155                 160

Gly Leu Ile Met Val Leu Ser Phe Leu
                165
```

<210> SEQ ID NO 120
<211> LENGTH: 516
<212> TYPE: DNA
<213> ORGANISM: Artificial Sequence
<220> FEATURE:
<223> OTHER INFORMATION: Encoding sequence for PfCTL.3

<400> SEQUENCE: 120

```
atgggaatgc aggtgcagat ccagagcctg tttctgctcc tcctgtgggt gcccggatcc    60
agaggagtgt tcctgatctt ctttgacctg ttcctgaacg ccgctgcacc cagcgatggc   120
aagtgcaatc tctacaaggc cgctgcagtg acctgtggaa acgggattca ggtcaggaaa   180
ctctttcaca cttcgacgg cgataacgag atcaaggccc atgtgctgtc ccacaattct   240
tatgaaaaaa actactatgg aaagcaagag aattggtaca gcctgaagaa aattctgtcc   300
```

```
gtgttctttc tcgccaacgc cgctgcaaag tttatcaagt ctctgttcca tattttcaag    360
gccgctgcac tctacatcag cttctatttt attaaagcca aatttgtggc cgcttggaca    420
ctgaaggccg ctgcaaaagc cgctgcatac tatatccctc accagagctc cctgaaggcc    480
gctgcagggc tgatcatggt gctctctttc ctgtga                              516
```

<210> SEQ ID NO 121
<211> LENGTH: 456
<212> TYPE: PRT
<213> ORGANISM: Artificial Sequence
<220> FEATURE:
<223> OTHER INFORMATION: PfCTL/HTL(N)

<400> SEQUENCE: 121

```
Met Gln Val Gln Ile Gln Ser Leu Phe Leu Leu Leu Trp Val Pro
 1               5                  10                  15

Gly Ser Arg Gly Ser Ser Val Phe Asn Val Val Asn Ser Ser Ile Gly
            20                  25                  30

Leu Ile Met Val Leu Ser Phe Leu Gly Pro Gly Pro Gly Leu Tyr Ile
            35                  40                  45

Ser Phe Tyr Phe Ile Leu Val Asn Leu Leu Ile Phe His Ile Asn Gly
        50                  55                  60

Lys Ile Ile Lys Asn Ser Glu Gly Pro Gly Pro Gly Pro Asp Ser Ile
65                  70                  75                  80

Gln Asp Ser Leu Lys Glu Ser Arg Lys Leu Ser Gly Pro Gly Pro Gly
                85                  90                  95

Val Leu Ala Gly Leu Leu Gly Val Val Ser Thr Val Leu Leu Gly Gly
            100                 105                 110

Val Gly Leu Val Leu Gly Pro Gly Pro Gly Leu Pro Ser Glu Asn Glu
            115                 120                 125

Arg Gly Tyr Tyr Ile Pro His Gln Ser Ser Leu Gly Pro Gly Pro Gly
        130                 135                 140

Gln Thr Asn Phe Lys Ser Leu Leu Arg Asn Leu Gly Val Ser Glu Asn
145                 150                 155                 160

Ile Phe Leu Lys Gly Pro Gly Pro Gly Phe Gln Asp Glu Glu Asn Ile
                165                 170                 175

Gly Ile Tyr Gly Pro Gly Pro Gly Lys Tyr Leu Val Ile Val Phe Leu
            180                 185                 190

Ile Phe Phe Asp Leu Phe Leu Val Gly Pro Gly Pro Gly Lys Phe Ile
            195                 200                 205

Lys Ser Leu Phe His Ile Phe Asp Gly Asp Asn Glu Ile Gly Pro Gly
        210                 215                 220

Pro Gly Lys Ser Lys Tyr Lys Leu Ala Thr Ser Val Leu Ala Gly Leu
225                 230                 235                 240

Leu Gly Pro Gly Pro Gly Leu Pro Tyr Gly Lys Thr Asn Leu Gly Pro
                245                 250                 255

Gly Pro Gly Arg His Asn Trp Val Asn His Ala Val Pro Leu Ala Met
            260                 265                 270

Lys Leu Ile Gly Pro Gly Pro Gly Met Arg Lys Leu Ala Ile Leu Ser
            275                 280                 285

Val Ser Ser Phe Leu Phe Val Glu Ala Leu Phe Gln Glu Tyr Gly Pro
        290                 295                 300

Gly Pro Gly Val Thr Cys Gly Asn Gly Ile Gln Val Arg Gly Pro Gly
305                 310                 315                 320
```

```
Pro Gly Met Asn Tyr Tyr Gly Lys Gln Glu Asn Trp Tyr Ser Leu Lys
            325                 330                 335

Lys Gly Pro Gly Pro Gly Pro Ser Asp Gly Lys Cys Asn Leu Tyr Ala
        340                 345                 350

Asp Ser Ala Trp Glu Asn Val Lys Asn Val Ile Gly Pro Phe Met Lys
        355                 360                 365

Ala Val Cys Val Glu Val Gly Pro Gly Pro Lys Ile Leu Ser Val
    370                 375                 380

Phe Phe Leu Ala Leu Phe Phe Ile Ile Phe Asn Lys Gly Pro Gly Pro
385                 390                 395                 400

Gly His Val Leu Ser His Asn Ser Tyr Glu Lys Gly Pro Gly Pro Gly
                405                 410                 415

Lys Tyr Lys Ile Ala Gly Gly Ile Ala Gly Gly Leu Ala Leu Leu Ala
        420                 425                 430

Cys Ala Gly Leu Ala Tyr Lys Phe Val Val Pro Gly Ala Ala Thr Pro
    435                 440                 445

Tyr Ala Gly Glu Pro Ala Pro Phe
    450                 455

<210> SEQ ID NO 122
<211> LENGTH: 1385
<212> TYPE: DNA
<213> ORGANISM: Artificial Sequence
<220> FEATURE:
<223> OTHER INFORMATION: Encoding sequence for PfCTL/HTL(N)

<400> SEQUENCE: 122
atgggaatgc aggtgcagat ccagagcctg tttctgctcc tcctgtgggt gcccggatcc      60
agaggaagta gtgtgttcaa tgttgtgaac tcatcaattg gtctgatcat ggtgctgagc     120
tttctcgggc cagggccagg attatatatt tctttctact tcatccttgt caacctgtta     180
atattccaca ttaacggcaa ataataaag aacagtgaag ccctgggcc tgggcctgac      240 tcgatccagg attctctaaa agaatcgagg aagctctccg gaccaggccc tggtgtactc     300
gccgggttgc tgggagtagt tagcacagtg ctgttaggag gcgtcggcct cgtcttagga     360
cctggaccag gtctgccgtc cgaaaacgaa agaggatact acatacctca ccagagcagc     420
ctcggcccag gccccggaca aaccaatttc aaatccctct gcgaaatct aggagtgagc      480 gagaacatat ttcttaaagg acccggtccc ggctttcagg acgaggagaa tataggtatt     540
tacggtccag gacctggaaa ataccagtg atcgtattcc taatttttt tgacctattt      600 ctggtgggcc caggtcccgg aaagttcatt aaatcactct ccacattttt tgacggagat     660
aacgagatag gacccggtcc cgggaaatca agtacaaac tagccacttc agtgctggcc     720
ggccttctag ggccgggccc agggctcccc tatggaaaga caaatcttgg ccccggtcca     780
ggacggcaca actgggtgaa tcatgcggtt ccattggcca tgaaactaat cgggcccggt     840
ccaggcatgc gcaaacttgc aattctaagc gtaagttcat ttctgttcgt agaggcactg     900
tttcaagaat atggcccagg acctggcgtc acatgtggga atgggatcca ggtgagagga     960
ccgggacctg gtatgaacta ttacggtaaa caggaaaatt ggtactccct gaaaaagggt    1020
ccaggccccg gccctcaga tggtaagtgc aacctgtatg ctgactcagc atgggagaac    1080
gtaaaaaatg taataggccc attcatgaag gcagtttgtg tcgaagtcgg accaggccca    1140
ggaaaaatac tttctgtctt cttcctagct ctcttcttca tcatcttcaa caagggacca    1200
gggccaggtc acgtgttatc ccataactct tatgaaaaag gccaggacc tgggaaatac    1260
```

```
aaaatcgcag agggatcgc cggcgggcta gcgctccttg cctgcgcagg cttggcttac    1320
aaattcgttg taccaggagc tgcaacaccc tatgcaggag aacctgcccc attttgaaga    1380
tctgc                                                                1385
```

<210> SEQ ID NO 123
<211> LENGTH: 419
<212> TYPE: PRT
<213> ORGANISM: Artificial Sequence
<220> FEATURE:
<223> OTHER INFORMATION: Pf33

<400> SEQUENCE: 123

```
Met Gly Met Gln Val Gln Ile Gln Ser Leu Phe Leu Leu Leu Leu Trp
 1               5                  10                  15

Val Pro Gly Ser Arg Gly Phe Met Lys Ala Val Cys Val Glu Val Asn
            20                  25                  30

Val Thr Cys Gly Asn Gly Ile Gln Val Arg Lys Gly Leu Ile Met Val
        35                  40                  45

Leu Ser Phe Leu Asn Ala Ala Leu Phe His Ile Phe Asp Gly Asp Asn
 50                  55                  60

Glu Ile Lys Ala Ala Leu Leu Ala Cys Ala Gly Leu Ala Tyr Lys Lys
65                  70                  75                  80

Ser Phe Leu Phe Val Glu Ala Leu Phe Asn Ala Ala Pro Ser Asp Gly
                85                  90                  95

Lys Cys Asn Leu Tyr Lys Ala Ala Gln Thr Asn Phe Lys Ser Leu Leu
           100                 105                 110

Arg Asn Leu Pro Ser Glu Asn Glu Arg Gly Tyr Lys Ala Ala Gly Val
       115                 120                 125

Ser Glu Asn Ile Phe Leu Lys Asn Ala Ala Ala Tyr Phe Ile Leu Val
   130                 135                 140

Asn Leu Leu Ile Lys Ala Ala Ala Ile Leu Ser Val Ser Ser Phe Leu
145                 150                 155                 160

Phe Val Asn Thr Pro Tyr Ala Gly Glu Pro Ala Pro Phe Lys Ala Ala
                165                 170                 175

Ala Lys Tyr Lys Leu Ala Thr Ser Val Leu Lys Ala Ala Val Phe Leu
           180                 185                 190

Ile Phe Phe Asp Leu Phe Leu Asn Tyr Tyr Ile Pro His Gln Ser Ser
       195                 200                 205

Leu Lys Ala Ala Gly Leu Leu Gly Asn Val Ser Thr Val Gly Ala Val
   210                 215                 220

Leu Leu Gly Gly Val Gly Leu Val Leu Asn Leu Ala Cys Ala Gly Leu
225                 230                 235                 240

Ala Tyr Lys Lys Ala Lys Phe Ile Lys Ser Leu Phe His Ile Phe Lys
                245                 250                 255

Ala Ala Phe Tyr Phe Ile Leu Val Asn Leu Leu Lys Ala Phe Leu Ile
           260                 265                 270

Phe Phe Asp Leu Phe Leu Val Lys Ala Leu Phe Phe Ile Ile Phe Asn
       275                 280                 285

Lys Asn Tyr Tyr Gly Lys Gln Glu Asn Trp Tyr Ser Leu Lys Phe Val
   290                 295                 300

Glu Ala Leu Phe Gln Glu Tyr Asn Ala Ala Ala Lys Phe Val Ala Ala
305                 310                 315                 320

Trp Thr Leu Lys Ala Ala Ala Lys Ile Leu Ser Val Phe Phe Leu Ala
                325                 330                 335
```

Asn Ala Val Leu Ala Gly Leu Leu Gly Asn Val Asn Phe Gln Asp Glu
            340                 345                 350

Glu Asn Ile Gly Ile Tyr Lys Ala Ala Ala Leu Tyr Ile Ser Phe Tyr
            355                 360                 365

Phe Ile Lys Ala Phe Ile Leu Val Asn Leu Leu Ile Phe His Asn Ala
        370                 375                 380

Ala Leu Pro Tyr Gly Arg Thr Asn Leu Lys Ala Ala His Val Leu Ser
385                 390                 395                 400

His Asn Ser Tyr Glu Lys Asn Ala Ala Ala Lys Tyr Leu Val Ile Val
                405                 410                 415

Phe Leu Ile

<210> SEQ ID NO 124
<211> LENGTH: 1269
<212> TYPE: DNA
<213> ORGANISM: Artificial Sequence
<220> FEATURE:
<223> OTHER INFORMATION: Encoding sequence for Pf33

<400> SEQUENCE: 124
gccgccacca tgggaatgca ggtgcagatc cagagcctgt ttctgctcct cctgtgggtg        60
cccggatcca gaggatttat gaaagctgtc tgtgtagagg tgaatgtaac atgcggtaac       120
ggaattcagg tgagaaaggg actcatcatg gtactcagct ttctgaacgc agccctgttc       180
cacatctttg acggagacaa tgaaatcaaa gccgcattgc tcgcctgtgc cggactagcc       240
tataaaaaga gtttcctttt cgttgaagca ctatttaacg cagcacccag tgacggtaaa       300
tgcaacctat ataaagcagc tcagactaat ttcaaaagcc tgttaagaaa tctgccctca       360
gagaatgaaa ggggttacaa agccgccggc gtgtccgaga atattttcct gaagaacgcc       420
gctgcttatt ttatactcgt gaatctactc ataaaggcag ccgcaatcct ttcagtgtcc       480
agctttctgt ttgttaacac accatatgcg ggcgagccgg ctcctttcaa ggctgcagca       540
aaatacaagc ttgccacatc agtattgaaa gcagctgtgt ttttgatatt ctttgatctt       600
tttttaaact actacatacc tcatcagtct agtcttaaag cagccgggct actggggaac       660
gtctctactg tgggggccgt cttacttgga ggagttggcc tcgtgttgaa cctcgcgtgc       720
gcaggtctgg cctacaaaaa agcgaaattc atccagtctc tgttccacat ttttaaagcc       780
gcattctatt tcatactagt gaaccttctc aaagctttcc tgatcttctt cgatctattc       840
ctcgtaaaag cgctattctt cattatcttt aacaaaaatt attacggcaa gcaagaaaat       900
tggtactcac tcaagtttgt agaagctctg ttccaggaat acaacgccgc tgctaaattc       960
gttgcagctt ggaccctgaa agcagctgca agatcctat cggtcttctt tctcgctaat      1020
gccgtattag caggacttct aggcaacgtg aactttcaag acgaagagaa tataggcatc      1080
tacaaagccg cagcactgta catttcattc tacttcatca aggccttcat actggtcaac      1140
cttctgatat tcataatgc agcactgcca tatgggagaa ccaacttgaa agcggcccac      1200
gtgttgagcc acaactccta cgagaagaac gccgccgcga aatatctcgt cattgtcttc      1260
ctgatttga                                                             1269

<210> SEQ ID NO 125
<211> LENGTH: 180
<212> TYPE: PRT
<213> ORGANISM: Artificial Sequence
<220> FEATURE:
<223> OTHER INFORMATION: TB.1

```
<400> SEQUENCE: 125

Met Gln Val Gln Ile Gln Ser Leu Phe Leu Leu Leu Leu Trp Val Pro
 1               5                   10                  15

Gly Ser Arg Gly Arg Met Ser Arg Val Thr Thr Phe Thr Val Lys Ala
             20                  25                  30

Leu Val Leu Leu Met Leu Pro Val Val Asn Leu Met Ile Gly Thr Ala
         35                  40                  45

Ala Ala Val Val Lys Ala Leu Val Leu Met Leu Pro Val Gly Ala
     50                  55                  60

Gly Leu Met Thr Ala Val Tyr Leu Val Gly Ala Ala Met Ala Leu
65               70                  75                  80

Leu Arg Leu Pro Val Lys Arg Met Phe Ala Ala Asn Leu Gly Val Asn
             85                  90                  95

Ser Leu Tyr Phe Gly Gly Ile Cys Val Gly Arg Leu Pro Leu Val Leu
             100                 105                 110

Pro Ala Val Asn Ala Ala Ala Ala Lys Phe Val Ala Ala Trp Thr Leu
             115                 120                 125

Lys Ala Ala Ala Lys Ala Ala Ala Arg Leu Met Ile Gly Thr Ala Ala
130                 135                 140

Ala Gly Phe Val Val Ala Leu Ile Pro Leu Val Asn Ala Met Thr Tyr
145                 150                 155                 160

Ala Ala Pro Leu Phe Val Gly Ala Ala Ala Met Ala Leu Leu Arg
                 165                 170                 175

Leu Pro Leu Val
             180

<210> SEQ ID NO 126
<211> LENGTH: 543
<212> TYPE: DNA
<213> ORGANISM: Artificial Sequence
<220> FEATURE:
<223> OTHER INFORMATION: Encoding sequence for TB.1

<400> SEQUENCE: 126 atgca

```
            1               5                   10                  15
Gly Ser Arg Gly Ile Met Ile Gly His Leu Val Gly Val Asn Arg Leu
                20                  25                  30

Leu Gln Glu Thr Glu Leu Val Asn Ala Lys Val Ala Glu Ile Val His
                35                  40                  45

Phe Leu Asn Ala Lys Val Phe Gly Ser Leu Ala Phe Val Asn Ala Tyr
    50                  55                  60

Leu Ser Gly Ala Asn Leu Asn Val Gly Ala Ala Tyr Leu Gln Leu Val
65                  70                  75                  80

Phe Gly Ile Glu Val Asn Ala Ala Lys Phe Val Ala Ala Trp Thr
                85                  90                  95

Leu Lys Ala Ala Lys Ala Ala Val Val Leu Gly Val Val Phe
                100                 105                 110

Gly Ile Asn Ser Met Pro Pro Gly Thr Arg Val Asn Ala Ala Ala
            115                 120                 125

Ala Thr Val Gly Ile Met Ile Gly Val Asn Ala Lys Leu Cys Pro Val
    130                 135                 140

Gln Leu Trp Val
145

<210> SEQ ID NO 128
<211> LENGTH: 447
<212> TYPE: DNA
<213> ORGANISM: Artificial Sequence
<220> FEATURE:
<223> OTHER INFORMATION: Encoding sequence for BCL A2 #90

<400> SEQUENCE: 128
atgcaggtgc agatccagag cctgtttctg ctcctcctgt gggtgcccgg gtccagagga      60
attatgatcg gccatctggt gggcgtcaac agactgctgc aggaaaccga gctggtgaat     120
gccaaggtgg ccgaaattgt gcactttctc aacgcaaagg tgtttggttc cctggctttt     180
gtcaatgcct atctgagcgg cgctaacctc aacgtcggag ccgcctacct ccagctggtc     240
ttcggcatcg aggtcaacgc tgctgcaaaa ttcgtggcag cttggaccct caaggctgca     300
gcaaaggctg ccgccgtcgt gctcggagtg gtgttcggga tcaactctat gccacctccc     360
gggactaggg tcaatgctgc cgccgcaaca gtgggaatca tgattggggt gaatgccaaa     420
ctgtgcccag tgcaactgtg ggtgtga                                         447

<210> SEQ ID NO 129
<211> LENGTH: 144
<212> TYPE: PRT
<213> ORGANISM: Artificial Sequence
<220> FEATURE:
<223> OTHER INFORMATION: BCL A2 #88

<400> SEQUENCE: 129

Met Gln Val Gln Ile Gln Ser Leu Phe Leu Leu Leu Leu Trp Val Pro
1               5                   10                  15

Gly Ser Arg Gly Val Val Leu Gly Val Val Phe Gly Ile Asn Ala Ala
                20                  25                  30

Ala Ala Lys Phe Val Ala Ala Trp Thr Leu Lys Ala Ala Ala Lys Val
                35                  40                  45

Ala Glu Ile Val His Phe Leu Asn Ala Tyr Leu Ser Gly Ala Asn Leu
    50                  55                  60

Asn Val Gly Ala Ala Tyr Leu Gln Leu Val Phe Gly Ile Glu Val Asn
65                  70                  75                  80
```

Ile Met Ile Gly His Leu Val Gly Val Asn Arg Leu Leu Gln Glu Thr
                85                  90                  95

Glu Leu Val Asn Ala Lys Val Phe Gly Ser Leu Ala Phe Val Asn Ala
            100                 105                 110

Lys Leu Cys Pro Val Gln Leu Trp Val Asn Ala Ala Ala Ala Thr Val
        115                 120                 125

Gly Ile Met Ile Gly Val Asn Ser Met Pro Pro Gly Thr Arg Val
    130                 135                 140

<210> SEQ ID NO 130
<211> LENGTH: 435
<212> TYPE: DNA
<213> ORGANISM: Artificial Sequence
<220> FEATURE:
<223> OTHER INFORMATION: Encoding sequence for BCL A2 #88

<400> SEQUENCE: 130
atgcaggtgc agatccagag cctgtttctg ctcctcctgt gggtgcccgg gtccagagga      60
gtcgtgctgg agtcgtcttc ggcattaat gccgccgctg caaagttcgt ggctgcctgg     120
accctgaagg ccgcagctaa agtggcagag atcgtgcact ttctgaacgc ctacctgagc    180
ggagcaaatc tgaacgtcgg cgctgcctat ctgcagctcg tgtttggaat tgaagtgaac    240
atcatgattg acatctggt gggcgtgaac aggctgctcc aggaaactga gctggtcaac     300
gctaaagtgt tcgggtctct cgcctttgtg aacgctaagc tctgccccgt ccaactctgg    360
gtcaatgccg cagccgctac agtggggatc atgatcggcg tgaactccat gcctccacca    420
gggaccagag tgtga                                                     435

<210> SEQ ID NO 131
<211> LENGTH: 147
<212> TYPE: PRT
<213> ORGANISM: Artificial Sequence
<220> FEATURE:
<223> OTHER INFORMATION: BCL A2 #63

<400> SEQUENCE: 131

Met Gln Val Gln Ile Gln Ser Leu Phe Leu Leu Leu Leu Trp Val Pro
 1               5                  10                  15

Gly Ser Arg Gly Lys Leu Cys Pro Val Gln Leu Trp Val Asn Ala Ala
            20                  25                  30

Ala Ala Thr Val Gly Ile Met Ile Gly Val Asn Ile Met Ile Gly His
        35                  40                  45

Leu Val Gly Val Asn Arg Leu Leu Gln Glu Thr Glu Leu Val Asn Ala
    50                  55                  60

Lys Val Ala Glu Ile Val His Phe Leu Asn Ala Lys Val Phe Gly Ser
65                  70                  75                  80

Leu Ala Phe Val Asn Ala Tyr Leu Ser Gly Ala Asn Leu Asn Val Gly
                85                  90                  95

Ala Ala Tyr Leu Gln Leu Val Phe Gly Ile Glu Val Asn Ala Ala Ala
            100                 105                 110

Lys Phe Val Ala Ala Trp Thr Leu Lys Ala Ala Lys Ala Ala Ala
        115                 120                 125

Val Val Leu Gly Val Val Phe Gly Ile Asn Ser Met Pro Pro Gly
    130                 135                 140

Thr Arg Val
145

```
<210> SEQ ID NO 132
<211> LENGTH: 450
<212> TYPE: DNA
<213> ORGANISM: Artificial Sequence
<220> FEATURE:
<223> OTHER INFORMATION: Encoding sequence for BCL A2 #63

<400> SEQUENCE: 132
atgcaggtgc agatccagag cctgtttctg ctcctcctgt gggtgcccgg gtccagagga      60
aagctctgcc ccgtgcaact gtgggtcaac gccgccgccg caaccgtcgg cattatgatc     120
ggggtgaaca tcatgatcgg acacctggtc ggcgtgaaca ggctgctgca ggagacagaa     180
ctggtcaatg ccaaggtggc tgaaattgtc catttcctga atgccaaagt gttcggctct     240
ctcgctttcg tgaacgctta tctgagcgga gctaacctca acgtggggc cgcatacctc      300 cagctcgtct ttgggattga ggtgaatgcc gcagctaaat tgtcgctgc ctggaccctg      360 aaggcagcag ccaaggctgc cgcagtggtg ctgggagtgg tgtttggaat caattccatg     420
cctccaccag gcactagagt gtgaggatcc                                      450

<210> SEQ ID NO 133
<211> LENGTH: 183
<212> TYPE: PRT
<213> ORGANISM: Artificial Sequence
<220> FEATURE:
<223> OTHER INFORMATION: Prostate 1

<400> SEQUENCE: 133

Leu Thr Phe Phe Trp Leu Asp Arg Ser Val Lys Ala Ala Ala Val Leu
 1               5                  10                  15

Val His Pro Gln Trp Val Leu Thr Val Lys Ala Ala Ala Leu Leu Gln
             20                  25                  30

Glu Arg Gly Val Ala Tyr Ile Lys Ala Ala Leu Leu Leu Ser Ile Ala
         35                  40                  45

Leu Ser Val Asn Pro Leu Val Cys Asn Gly Val Leu Gln Gly Val Lys
     50                  55                  60

Ala Ala Ile Met Tyr Ser Ala His Asp Thr Thr Val Lys Ala Ala Ala
 65                  70                  75                  80

Phe Leu Thr Pro Lys Lys Leu Gln Cys Val Asn Ala Met Met Asn Asp
                 85                  90                  95

Gln Leu Met Phe Leu Asn Ala Gly Leu Pro Ser Ile Pro Val His Pro
            100                 105                 110

Val Lys Ala Ala Ala Leu Gly Thr Thr Cys Tyr Val Gly Ala Ala Ile
        115                 120                 125

Leu Leu Trp Gln Pro Ile Pro Val Asn Phe Leu Arg Pro Arg Ser Leu
    130                 135                 140

Gln Cys Val Lys Ala Phe Leu Thr Leu Ser Val Thr Trp Ile Gly Val
145                 150                 155                 160

Asn Ala Leu Leu Tyr Ser Leu Val His Asn Leu Gly Ala Ala Thr Leu
                165                 170                 175

Met Ser Ala Met Thr Asn Leu
            180

<210> SEQ ID NO 134
<211> LENGTH: 648
<212> TYPE: DNA
<213> ORGANISM: Artificial Sequence
<220> FEATURE:
<223> OTHER INFORMATION: Encoding sequence for Prostate 1
```

<400> SEQUENCE: 134

```
atgcaggtgc agatccagag cctgtttctg ctcctcctgt gggtgcccgg gtccagagga      60
ttgacatttt tttggctgga tagatcggtt aaggctgcag ccgtgcttgt tcatccccag     120
tgggtcttga ccgtaaaggc tgccgcgctg ctacaagaaa gaggggtcgc atacatcaaa     180
gctgctctcc tcttgagtat tgcgctaagt gtaaacccgc tagtttgtaa tggggtgtta     240
caaggtgtga agcggcgat tatgtacagt gcccacgaca ctaccgtaaa agcagccgct      300
ttcctgaccc caaaaaaact ccaatgcgtg aacgcaatga tgaatgatca gctgatgttt     360
ttaaacgctg gcttaccttc tataccggtt catccagtca aggccgcggc attgggtacg     420
acgtgttatg ttggagcagc gatacttctt tggcagccca taccagtaaa ttttttaaga     480
cctagatcct acaatgcgt caaagcattc cttacactct cagtaacttg gatcggagtc      540
aatgctctgc tatatagcct cgtacacaac ttgggcgcgg ccacacttat gagtgcaatg     600
acgaatttag ctaagttcgt ggcggcctgg actctaaagg ccgcagca                  648
```

<210> SEQ ID NO 135
<211> LENGTH: 322
<212> TYPE: PRT
<213> ORGANISM: Artificial Sequence
<220> FEATURE:
<223> OTHER INFORMATION: HIV-1043

<400> SEQUENCE: 135

```
Met Glu Lys Val Tyr Leu Ala Trp Val Pro Ala His Lys Gly Ile Gly
  1               5                  10                  15
Gly Gly Pro Gly Pro Gly Gln Lys Gln Ile Thr Lys Ile Gln Asn Phe
             20                  25                  30
Arg Val Tyr Tyr Arg Gly Pro Gly Pro Gly Trp Glu Phe Val Asn Thr
         35                  40                  45
Pro Pro Leu Val Lys Leu Trp Tyr Gln Gly Pro Gly Pro Gly Tyr Arg
     50                  55                  60
Lys Ile Leu Arg Gln Arg Lys Ile Asp Arg Leu Ile Asp Gly Pro Gly
 65                  70                  75                  80
Pro Gly Gln His Leu Leu Gln Leu Thr Val Trp Gly Ile Lys Gln Leu
                 85                  90                  95
Gln Gly Pro Gly Pro Gly Gly Glu Ile Tyr Lys Arg Trp Ile Ile Leu
            100                 105                 110
Gly Leu Asn Lys Ile Val Arg Met Tyr Gly Pro Gly Pro Gly Gln Gly
        115                 120                 125
Gln Met Val His Gln Ala Ile Ser Pro Arg Thr Leu Asn Gly Pro Gly
    130                 135                 140
Pro Gly Ile Lys Gln Phe Ile Asn Met Trp Gln Glu Val Gly Lys Ala
145                 150                 155                 160
Met Tyr Gly Pro Gly Pro Gly Trp Ala Gly Ile Lys Gln Glu Phe Gly
                165                 170                 175
Ile Pro Tyr Asn Pro Gln Gly Pro Gly Pro Gly Lys Thr Ala Val Gln
            180                 185                 190
Met Ala Val Phe Ile His Asn Phe Lys Arg Gly Pro Gly Pro Gly Ser
        195                 200                 205
Pro Ala Ile Phe Gln Ser Ser Met Thr Lys Ile Leu Glu Pro Gly Pro
    210                 215                 220
Gly Pro Gly Glu Val Asn Ile Val Thr Asp Ser Gln Tyr Ala Leu Gly
225                 230                 235                 240
```

Ile Ile Gly Pro Gly Pro Gly His Ser Asn Trp Arg Ala Met Ala Ser
            245                 250                 255

Asp Phe Asn Leu Pro Pro Gly Pro Gly Ala Glu Thr Phe Tyr
        260                 265                 270

Val Asp Gly Ala Ala Asn Arg Glu Thr Lys Gly Pro Gly Pro Gly Gly
    275                 280                 285

Ala Val Val Ile Gln Asp Asn Ser Asp Ile Lys Val Val Pro Gly Pro
    290                 295                 300

Gly Pro Gly Phe Arg Lys Tyr Thr Ala Phe Thr Ile Pro Ser Ile Asn
305                 310                 315                 320

Asn Glu

<210> SEQ ID NO 136
<211> LENGTH: 969
<212> TYPE: DNA
<213> ORGANISM: Artificial Sequence
<220> FEATURE:
<223> OTHER INFORMATION: Encoding sequence for HIV-1043

<400> SEQUENCE: 136
atggagaagg tgtacctggc ctgggttcca gcccacaaag gcatcggggg agggcccgga      60
cctgggcaga aacagatcac caagatccag aacttccggg tatactaccg gggacctggt     120
ccaggttggg agtttgtgaa cacaccaccc ttagtaaagc tctggtacca gggccccggt     180
cccggatacc gtaaaatcct gaggcaaaga aagatagatc gcctcattga tggcccgggc     240
ccaggccagc accttctgca gcttacagtg tggggaatta acagctgca ggggccgggc      300 cccgggggg aaatttataa aggtggatc attctgggtc tgaacaagat cgtccgcatg      360 tatgccctg acccggaca ggggcagatg gtccaccaag caatcagccc tcgaaccttg       420
aatggaccgg gcccaggaat caagcaattc attaacatgt ggcaagaagt tggtaaggct     480
atgtacggtc ccggccctgg atgggcaggg ataaaacagg agtttggaat cccttacaat     540
ccccagggtc ctgggccagg taaaacggca gtgcagatgg ccgtgttcat tcataatttt     600
aagcggggcc ctggacctgg cagcccagct atatttcaaa gttcgatgac caaaatcttg     660
gagcccggcc cagggccggg cgaagtgaac attgtcacag attctcagta tgccctcggc     720 atcataggc ccggaccagg gcattccaat tggcgcgcca tggcgtctga ctttaatcta      780
cctcctgggc cagggcctgg cgcggaaact ttctatgtgg acggcgctgc aaacagggag     840
actaagggac ccggacccgg cggcgctgta gtcattcagg acaactcaga catcaaggtg     900
gttcccggtc caggccccgg gttcagaaag tataccgcct tcactattcc gtccatcaac     960
aatgagtga                                                              969

<210> SEQ ID NO 137
<211> LENGTH: 340
<212> TYPE: PRT
<213> ORGANISM: Artificial Sequence
<220> FEATURE:
<223> OTHER INFORMATION: HIV-1043 PADRE

<400> SEQUENCE: 137

Met Glu Lys Val Tyr Leu Ala Trp Val Pro Ala His Lys Gly Ile Gly
1               5                   10                  15

Gly Gly Pro Gly Pro Gly Gln Lys Gln Ile Thr Lys Ile Gln Asn Phe
            20                  25                  30

Arg Val Tyr Tyr Arg Gly Pro Gly Pro Gly Trp Glu Phe Val Asn Thr

-continued

```
                35                  40                  45
Pro Pro Leu Val Lys Leu Trp Tyr Gln Gly Pro Gly Tyr Arg
 50                  55                  60
Lys Ile Leu Arg Gln Arg Lys Ile Asp Arg Leu Ile Asp Gly Pro Gly
 65                  70                  75                  80
Pro Gly Gln His Leu Leu Gln Leu Thr Val Trp Gly Ile Lys Gln Leu
                 85                  90                  95
Gln Gly Pro Gly Pro Gly Gly Glu Ile Tyr Lys Arg Trp Ile Ile Leu
                100                 105                 110
Gly Leu Asn Lys Ile Val Arg Met Tyr Gly Pro Gly Pro Gly Gln Gly
            115                 120                 125
Gln Met Val His Gln Ala Ile Ser Pro Arg Thr Leu Asn Gly Pro Gly
130                 135                 140
Pro Gly Ile Lys Gln Phe Ile Asn Met Trp Gln Glu Val Gly Lys Ala
145                 150                 155                 160
Met Tyr Gly Pro Gly Pro Gly Trp Ala Gly Ile Lys Gln Glu Phe Gly
                165                 170                 175
Ile Pro Tyr Asn Pro Gln Gly Pro Gly Pro Gly Lys Thr Ala Val Gln
                180                 185                 190
Met Ala Val Phe Ile His Asn Phe Lys Arg Gly Pro Gly Pro Gly Ser
            195                 200                 205
Pro Ala Ile Phe Gln Ser Ser Met Thr Lys Ile Leu Glu Pro Gly Pro
210                 215                 220
Gly Pro Gly Glu Val Asn Ile Val Thr Asp Ser Gln Tyr Ala Leu Gly
225                 230                 235                 240
Ile Ile Gly Pro Gly Pro Gly His Ser Asn Trp Arg Ala Met Ala Ser
                245                 250                 255
Asp Phe Asn Leu Pro Pro Gly Pro Gly Pro Gly Ala Glu Thr Phe Tyr
                260                 265                 270
Val Asp Gly Ala Ala Asn Arg Glu Thr Lys Gly Pro Gly Pro Gly Gly
            275                 280                 285
Ala Val Val Ile Gln Asp Asn Ser Asp Ile Lys Val Val Pro Gly Pro
290                 295                 300
Gly Pro Gly Phe Arg Lys Tyr Thr Ala Phe Thr Ile Pro Ser Ile Asn
305                 310                 315                 320
Asn Glu Gly Pro Gly Pro Gly Ala Lys Phe Val Ala Ala Trp Thr Leu
                325                 330                 335
Lys Ala Ala Ala
            340

<210> SEQ ID NO 138
<211> LENGTH: 1023
<212> TYPE: DNA
<213> ORGANISM: Artificial Sequence
<220> FEATURE:
<223> OTHER INFORMATION: Encoding sequence for HIV-1043 PADRE

<400> SEQUENCE: 138
atggagaagg tgtacctggc ctgggttcca gcccacaaag gcatcggggg agggcccgga      60
cctgggcaga acagatcac caagatccag aacttccggg tatactaccg gggacctggt     120
ccaggttggg agtttgtgaa cacaccaccc ttagtaaagc tctggtacca gggcccggt      180 cccggatacc gtaaaatcct gaggcaaaga aagatagatc gcctcattga tgggcccggc    240
ccaggccagc accttctgca gcttacagtg tggggaatta aacagctgca ggggccgggc    300
```

```
cccgggggg aaatttataa aaggtggatc attctgggtc tgaacaagat cgtccgcatg    360
tatggccctg acccggaca ggggcagatg gtccaccaag caatcagccc tcgaaccttg    420
aatggaccgg gcccaggaat caagcaattc attaacatgt ggcaagaagt tggtaaggct    480
atgtacggtc ccggccctgg atgggcaggg ataaaacagg agtttggaat cccttacaat    540
ccccagggtc ctgggccagg taaaacggca gtgcagatgg ccgtgttcat tcataatttt    600
aagcggggcc ctgacctgg cagcccagct atatttcaaa gttcgatgac caaaatcttg     660
gagcccggcc cagggccggg cgaagtgaac attgtcacag attctcagta tgccctcggc    720
atcatagggc ccgaccagg gcattccaat tggcgcgcca tggcgtctga ctttaatcta     780
cctcctgggc caggccctgg cgcggaaact ttctatgtgg acggcgctgc aaacagggag    840
actaagggac ccgacccgg cggcgctgta gtcattcagg acaactcaga catcaaggtg     900
gttcccggtc caggccccgg gttcagaaag tataccgcct tcactattcc gtccatcaac    960
aatgagggcc ccggcccagg tgccaagttc gtggctgcct ggaccctgaa ggctgccgct   1020
tga                                                                1023
```

<210> SEQ ID NO 139
<211> LENGTH: 75
<212> TYPE: PRT
<213> ORGANISM: Artificial Sequence
<220> FEATURE:
<223> OTHER INFORMATION: HIV 75 mer
<400> SEQUENCE: 139

```
Glu Lys Val Tyr Leu Ala Trp Val Pro Ala His Lys Gly Ile Gly Gly
 1               5                  10                  15

Pro Gly Pro Gly Gln Gly Gln Met Val His Gln Ala Ile Ser Pro Arg
            20                  25                  30

Thr Leu Asn Gly Pro Gly Pro Gly Ser Pro Ala Ile Phe Gln Ser Ser
        35                  40                  45

Met Thr Lys Ile Leu Glu Pro Gly Pro Gly Pro Gly Phe Arg Lys Tyr
    50                  55                  60

Thr Ala Phe Thr Ile Pro Ser Ile Asn Asn Glu
65                  70                  75
```

<210> SEQ ID NO 140
<211> LENGTH: 228
<212> TYPE: DNA
<213> ORGANISM: Artificial Sequence
<220> FEATURE:
<223> OTHER INFORMATION: Encoding sequence for HIV 75mer
<400> SEQUENCE: 140

```
gagaaggtgt acctggcctg ggtgcctgcc cacaagggaa tcggaggacc tggccctgga    60
cagggacaga tggtgcacca ggccatcagc cctaggaccc tgaacggacc tggacctgga   120
agccctgcca tcttccagag cagcatgacc aagatcctgg agcccggacc tggacctgga   180
ttcaggaagt acaccgcctt caccatcccc agcatcaaca acgagtga               228
```

<210> SEQ ID NO 141
<211> LENGTH: 276
<212> TYPE: PRT
<213> ORGANISM: Artificial Sequence
<220> FEATURE:
<223> OTHER INFORMATION: PfHTL
<400> SEQUENCE: 141

```
Met Gln Val Gln Ile Gln Ser Leu Phe Leu Leu Leu Trp Val Pro
 1               5                  10                  15

Gly Ser Arg Gly Arg His Asn Trp Val Asn His Ala Val Pro Leu Ala
             20                  25                  30

Met Lys Leu Ile Gly Pro Gly Pro Gly Lys Cys Asn Leu Tyr Ala Asp
         35                  40                  45

Ser Ala Trp Glu Asn Val Lys Asn Gly Pro Gly Pro Gly Lys Ser Lys
 50                  55                  60

Tyr Lys Leu Ala Thr Ser Val Leu Ala Gly Leu Leu Gly Pro Gly Pro
 65                  70                  75                  80

Gly Gln Thr Asn Phe Lys Ser Leu Leu Arg Asn Leu Gly Val Ser Glu
                 85                  90                  95

Gly Pro Gly Pro Gly Ser Ser Val Phe Asn Val Val Asn Ser Ser Ile
                100                 105                 110

Gly Leu Ile Met Gly Pro Gly Pro Gly Val Lys Asn Val Ile Gly Pro
            115                 120                 125

Phe Met Lys Ala Val Cys Val Glu Gly Pro Gly Pro Gly Met Asn Tyr
        130                 135                 140

Tyr Gly Lys Gln Glu Asn Trp Tyr Ser Leu Lys Lys Gly Pro Gly Pro
145                 150                 155                 160

Gly Gly Leu Ala Tyr Lys Phe Val Val Pro Gly Ala Ala Thr Pro Tyr
            165                 170                 175

Gly Pro Gly Pro Gly Pro Asp Ser Ile Gln Asp Ser Leu Lys Glu Ser
                180                 185                 190

Arg Lys Leu Asn Gly Pro Gly Pro Gly Leu Leu Ile Phe His Ile Asn
            195                 200                 205

Gly Lys Ile Ile Lys Asn Ser Glu Gly Pro Gly Pro Gly Ala Gly Leu
210                 215                 220

Leu Gly Asn Val Ser Thr Val Leu Leu Gly Gly Val Gly Pro Gly Pro
225                 230                 235                 240

Gly Lys Tyr Lys Ile Ala Gly Gly Ile Ala Gly Gly Leu Ala Leu Leu
            245                 250                 255

Gly Pro Gly Pro Gly Met Arg Lys Leu Ala Ile Leu Ser Val Ser Ser
            260                 265                 270

Phe Leu Phe Val
        275

<210> SEQ ID NO 142
<211> LENGTH: 837
<212> TYPE: DNA
<213> ORGANISM: Artificial Sequence
<220> FEATURE:
<223> OTHER INFORMATION: Encoding sequence for PfHTL

<400> SEQUENCE: 142
atgggaatgc aggtgcagat ccagagcctg tttctgctcc tcctgtgggt gcccggatcc    60
agaggaaggc acaactgggt gaatcatgct gtgcccctgg ctatgaagct gatcggccct   120
ggaccaggga aatgcaacct ctacgcagac agcgcctggg agaacgtcaa gaatggcccc   180
ggacctggga atccaagta taagctcgct acctctgtgc tggcaggcct gctcggacca   240
ggccccggac agacaaattt caaaagcctg ctcagaaacc tggagtgtc cgagggggcct   300 ggcccaggat ctagcgtctt taatgtggtc aactcctcta ttgggctcat catgggaccc   360
ggacctgggg tgaaaaatgt cattggccca ttcatgaagg ccgtgtgtgt cgaaggaccc   420
gggcctggca tgaactacta tggaaagcaa gaaaattggt acagcctgaa gaaaggccct   480
```

-continued

```
gggccaggcg gactggctta caagtttgtg gtcccagggg cagccactcc ctatgggcct       540
gggccaggcc ccgattccat ccaggactct ctcaaagaga gccggaaact gaacggaccc       600
gggcctggac tgctcatttt ccacatcaat ggcaaaatta tcaagaacag cgagggacct       660
gggccaggcg ccggactgct ggggaacgtg tccaccgtcc tgctcggcgg agtggggccc       720
ggccctggga agtacaagat cgctggaggg atcgcaggcg gactggccct cctgggccca       780
ggaccaggga tgcgcaaact ggctattctc tctgtctcca gctttctgtt tgtgtga         837
```

<210> SEQ ID NO 143
<211> LENGTH: 9
<212> TYPE: PRT
<213> ORGANISM: Transgenic mouse

<400> SEQUENCE: 143

Val Leu Ala Glu Ala Met Ser Gln Val
 1               5

<210> SEQ ID NO 144
<211> LENGTH: 9
<212> TYPE: PRT
<213> ORGANISM: Transgenic mouse

<400> SEQUENCE: 144

Met Thr Asn Asn Pro Pro Ile Pro Val
 1               5

<210> SEQ ID NO 145
<211> LENGTH: 10
<212> TYPE: PRT
<213> ORGANISM: Transgenic mouse

<400> SEQUENCE: 145

Met Ala Ser Asp Phe Asn Leu Pro Pro Val
 1               5                  10

<210> SEQ ID NO 146
<211> LENGTH: 9
<212> TYPE: PRT
<213> ORGANISM: Transgenic mouse

<400> SEQUENCE: 146

Lys Leu Val Gly Lys Leu Asn Trp Ala
 1               5

<210> SEQ ID NO 147
<211> LENGTH: 9
<212> TYPE: PRT
<213> ORGANISM: Transgenic mouse

<400> SEQUENCE: 147

Leu Val Gly Pro Thr Pro Val Asn Ile
 1               5

<210> SEQ ID NO 148
<211> LENGTH: 9
<212> TYPE: PRT
<213> ORGANISM: Transgenic mouse

<400> SEQUENCE: 148

Ile Leu Lys Glu Pro Val His Gly Val
 1               5

```
<210> SEQ ID NO 149
<211> LENGTH: 9
<212> TYPE: PRT
<213> ORGANISM: Transgenic mouse

<400> SEQUENCE: 149

Lys Ala Ala Cys Trp Trp Ala Gly Ile
1               5

<210> SEQ ID NO 150
<211> LENGTH: 10
<212> TYPE: PRT
<213> ORGANISM: Transgenic mouse

<400> SEQUENCE: 150

Lys Met Ile Gly Gly Ile Gly Gly Phe Ile
1               5                   10

<210> SEQ ID NO 151
<211> LENGTH: 9
<212> TYPE: PRT
<213> ORGANISM: Transgenic mouse

<400> SEQUENCE: 151

Arg Ala Met Ala Ser Asp Phe Asn Leu
1               5

<210> SEQ ID NO 152
<211> LENGTH: 9
<212> TYPE: PRT
<213> ORGANISM: Transgenic mouse

<400> SEQUENCE: 152

Thr Leu Asn Phe Pro Ile Ser Pro Ile
1               5

<210> SEQ ID NO 153
<211> LENGTH: 9
<212> TYPE: PRT
<213> ORGANISM: Transgenic mouse

<400> SEQUENCE: 153

Lys Leu Thr Pro Leu Cys Val Thr Leu
1               5

<210> SEQ ID NO 154
<211> LENGTH: 9
<212> TYPE: PRT
<213> ORGANISM: Transgenic mouse

<400> SEQUENCE: 154

Leu Leu Gln Leu Thr Val Trp Gly Ile
1               5

<210> SEQ ID NO 155
<211> LENGTH: 10
<212> TYPE: PRT
<213> ORGANISM: Transgenic mouse

<400> SEQUENCE: 155

Ser Leu Leu Asn Ala Thr Asp Ile Ala Val
1               5                   10

<210> SEQ ID NO 156
```

```
<211> LENGTH: 9
<212> TYPE: PRT
<213> ORGANISM: Transgenic mouse

<400> SEQUENCE: 156

Leu Thr Phe Gly Trp Cys Phe Lys Leu
1               5

<210> SEQ ID NO 157
<211> LENGTH: 9
<212> TYPE: PRT
<213> ORGANISM: Transgenic mouse

<400> SEQUENCE: 157

Ala Ile Ile Arg Ile Leu Gln Gln Leu
1               5

<210> SEQ ID NO 158
<211> LENGTH: 9
<212> TYPE: PRT
<213> ORGANISM: Transgenic mouse

<400> SEQUENCE: 158

Arg Ile Leu Gln Gln Leu Leu Phe Ile
1               5

<210> SEQ ID NO 159
<211> LENGTH: 10
<212> TYPE: PRT
<213> ORGANISM: Transgenic mouse

<400> SEQUENCE: 159

Gln Met Ala Val Phe Ile His Asn Phe Lys
1               5                   10

<210> SEQ ID NO 160
<211> LENGTH: 11
<212> TYPE: PRT
<213> ORGANISM: Transgenic mouse

<400> SEQUENCE: 160

Lys Val Tyr Leu Ala Trp Val Pro Ala His Lys
1               5                   10

<210> SEQ ID NO 161
<211> LENGTH: 10
<212> TYPE: PRT
<213> ORGANISM: Transgenic mouse

<400> SEQUENCE: 161

Lys Ile Gln Asn Phe Arg Val Tyr Tyr Arg
1               5                   10

<210> SEQ ID NO 162
<211> LENGTH: 9
<212> TYPE: PRT
<213> ORGANISM: Transgenic mouse

<400> SEQUENCE: 162

Ala Ile Phe Gln Ser Ser Met Thr Lys
1               5

<210> SEQ ID NO 163
<211> LENGTH: 10
<212> TYPE: PRT
```

```
<213> ORGANISM: Transgenic mouse

<400> SEQUENCE: 163

Val Thr Ile Lys Ile Gly Gly Gln Leu Lys
1               5                   10

<210> SEQ ID NO 164
<211> LENGTH: 10
<212> TYPE: PRT
<213> ORGANISM: Transgenic mouse

<400> SEQUENCE: 164

Thr Thr Leu Phe Cys Ala Ser Asp Ala Lys
1               5                   10

<210> SEQ ID NO 165
<211> LENGTH: 11
<212> TYPE: PRT
<213> ORGANISM: Transgenic mouse

<400> SEQUENCE: 165

Val Thr Val Tyr Tyr Gly Val Pro Val Trp Lys
1               5                   10

<210> SEQ ID NO 166
<211> LENGTH: 10
<212> TYPE: PRT
<213> ORGANISM: Transgenic mouse

<400> SEQUENCE: 166

Gln Val Pro Leu Arg Pro Met Thr Tyr Lys
1               5                   10

<210> SEQ ID NO 167
<211> LENGTH: 9
<212> TYPE: PRT
<213> ORGANISM: Transgenic mouse

<400> SEQUENCE: 167

Val Met Ile Val Trp Gln Val Asp Arg
1               5

<210> SEQ ID NO 168
<211> LENGTH: 10
<212> TYPE: PRT
<213> ORGANISM: Transgenic mouse

<400> SEQUENCE: 168

Gln Met Val His Gln Ala Ile Ser Pro Arg
1               5                   10

<210> SEQ ID NO 169
<211> LENGTH: 10
<212> TYPE: PRT
<213> ORGANISM: Transgenic mouse

<400> SEQUENCE: 169

Tyr Pro Leu Ala Ser Leu Arg Ser Leu Phe
1               5                   10

<210> SEQ ID NO 170
<211> LENGTH: 9
<212> TYPE: PRT
<213> ORGANISM: Transgenic mouse
```

```
<400> SEQUENCE: 170

His Pro Val His Ala Gly Pro Ile Ala
1               5

<210> SEQ ID NO 171
<211> LENGTH: 9
<212> TYPE: PRT
<213> ORGANISM: Transgenic mouse

<400> SEQUENCE: 171

Phe Pro Ile Ser Pro Ile Glu Thr Val
1               5

<210> SEQ ID NO 172
<211> LENGTH: 11
<212> TYPE: PRT
<213> ORGANISM: Transgenic mouse

<400> SEQUENCE: 172

Ile Pro Tyr Asn Pro Gln Ser Gln Gly Val Val
1               5                   10

<210> SEQ ID NO 173
<211> LENGTH: 9
<212> TYPE: PRT
<213> ORGANISM: Transgenic mouse

<400> SEQUENCE: 173

Ile Pro Ile His Tyr Cys Ala Pro Ala
1               5

<210> SEQ ID NO 174
<211> LENGTH: 9
<212> TYPE: PRT
<213> ORGANISM: Transgenic mouse

<400> SEQUENCE: 174

Cys Pro Lys Val Ser Phe Glu Pro Ile
1               5

<210> SEQ ID NO 175
<211> LENGTH: 9
<212> TYPE: PRT
<213> ORGANISM: Transgenic mouse

<400> SEQUENCE: 175

Phe Pro Val Arg Pro Gln Val Pro Leu
1               5

<210> SEQ ID NO 176
<211> LENGTH: 8
<212> TYPE: PRT
<213> ORGANISM: Transgenic mouse

<400> SEQUENCE: 176

Val Pro Leu Gln Leu Pro Pro Leu
1               5

<210> SEQ ID NO 177
<211> LENGTH: 10
<212> TYPE: PRT
<213> ORGANISM: Transgenic mouse

<400> SEQUENCE: 177
```

```
Glu Val Asn Ile Val Thr Asp Ser Gln Tyr
1               5                   10

<210> SEQ ID NO 178
<211> LENGTH: 9
<212> TYPE: PRT
<213> ORGANISM: Transgenic mouse

<400> SEQUENCE: 178

Phe Arg Asp Tyr Val Asp Arg Phe Tyr
1               5

<210> SEQ ID NO 179
<211> LENGTH: 10
<212> TYPE: PRT
<213> ORGANISM: Transgenic mouse

<400> SEQUENCE: 179

Val Ile Tyr Gln Tyr Met Asp Asp Leu Tyr
1               5                   10

<210> SEQ ID NO 180
<211> LENGTH: 10
<212> TYPE: PRT
<213> ORGANISM: Transgenic mouse

<400> SEQUENCE: 180

Val Thr Val Leu Asp Val Gly Asp Ala Tyr
1               5                   10

<210> SEQ ID NO 181
<211> LENGTH: 9
<212> TYPE: PRT
<213> ORGANISM: Transgenic mouse

<400> SEQUENCE: 181

Ile Tyr Gln Glu Pro Phe Lys Asn Leu
1               5

<210> SEQ ID NO 182
<211> LENGTH: 9
<212> TYPE: PRT
<213> ORGANISM: Transgenic mouse

<400> SEQUENCE: 182

Pro Tyr Asn Thr Pro Val Phe Ala Ile
1               5

<210> SEQ ID NO 183
<211> LENGTH: 9
<212> TYPE: PRT
<213> ORGANISM: Transgenic mouse

<400> SEQUENCE: 183

Thr Tyr Gln Ile Tyr Gln Glu Pro Phe
1               5

<210> SEQ ID NO 184
<211> LENGTH: 10
<212> TYPE: PRT
<213> ORGANISM: Transgenic mouse

<400> SEQUENCE: 184

Tyr Trp Gln Ala Thr Trp Ile Pro Glu Trp
1               5                   10
```

<210> SEQ ID NO 185
<211> LENGTH: 9
<212> TYPE: PRT
<213> ORGANISM: Transgenic mouse

<400> SEQUENCE: 185

Ile Trp Gly Cys Ser Gly Lys Leu Ile
1               5

<210> SEQ ID NO 186
<211> LENGTH: 9
<212> TYPE: PRT
<213> ORGANISM: Transgenic mouse

<400> SEQUENCE: 186

Arg Tyr Leu Lys Asp Gln Gln Leu Leu
1               5

<210> SEQ ID NO 187
<211> LENGTH: 10
<212> TYPE: PRT
<213> ORGANISM: Transgenic mouse

<400> SEQUENCE: 187

Val Trp Lys Glu Ala Thr Thr Thr Leu Phe
1               5                   10

<210> SEQ ID NO 188
<211> LENGTH: 9
<212> TYPE: PRT
<213> ORGANISM: Transgenic mouse

<400> SEQUENCE: 188

Ile Tyr Glu Thr Tyr Gly Asp Thr Trp
1               5

<210> SEQ ID NO 189
<211> LENGTH: 9
<212> TYPE: PRT
<213> ORGANISM: Transgenic mouse

<400> SEQUENCE: 189

Pro Tyr Asn Glu Trp Thr Leu Glu Leu
1               5

<210> SEQ ID NO 190
<211> LENGTH: 15
<212> TYPE: PRT
<213> ORGANISM: Transgenic mouse

<400> SEQUENCE: 190

Lys Arg Trp Ile Ile Leu Gly Leu Asn Lys Ile Val Arg Met Tyr
1               5                   10                  15

<210> SEQ ID NO 191
<211> LENGTH: 15
<212> TYPE: PRT
<213> ORGANISM: Transgenic mouse

<400> SEQUENCE: 191

Trp Glu Phe Val Asn Thr Pro Pro Leu Val Lys Leu Trp Tyr Gln
1               5                   10                  15

```
<210> SEQ ID NO 192
<211> LENGTH: 15
<212> TYPE: PRT
<213> ORGANISM: Transgenic mouse

<400> SEQUENCE: 192

Gln Lys Gln Ile Thr Lys Ile Gln Asn Phe Arg Val Tyr Tyr Arg
 1               5                  10                  15

<210> SEQ ID NO 193
<211> LENGTH: 15
<212> TYPE: PRT
<213> ORGANISM: Transgenic mouse

<400> SEQUENCE: 193

Lys Val Tyr Leu Ala Trp Val Pro Ala His Lys Gly Ile Gly Gly
 1               5                  10                  15

<210> SEQ ID NO 194
<211> LENGTH: 15
<212> TYPE: PRT
<213> ORGANISM: Transgenic mouse

<400> SEQUENCE: 194

Gly Glu Ile Tyr Lys Arg Trp Ile Ile Leu Gly Leu Asn Lys Ile
 1               5                  10                  15

<210> SEQ ID NO 195
<211> LENGTH: 15
<212> TYPE: PRT
<213> ORGANISM: Transgenic mouse

<400> SEQUENCE: 195

Glu Lys Val Tyr Leu Ala Trp Val Pro Ala His Lys Gly Ile Gly
 1               5                  10                  15

<210> SEQ ID NO 196
<211> LENGTH: 15
<212> TYPE: PRT
<213> ORGANISM: Transgenic mouse

<400> SEQUENCE: 196

Gln His Leu Leu Gln Leu Thr Val Trp Gly Ile Lys Gln Leu Gln
 1               5                  10                  15

<210> SEQ ID NO 197
<211> LENGTH: 15
<212> TYPE: PRT
<213> ORGANISM: Transgenic mouse

<400> SEQUENCE: 197

Gln Gly Gln Met Val His Gln Ala Ile Ser Pro Arg Thr Leu Asn
 1               5                  10                  15

<210> SEQ ID NO 198
<211> LENGTH: 15
<212> TYPE: PRT
<213> ORGANISM: Transgenic mouse

<400> SEQUENCE: 198

Ser Pro Ala Ile Phe Gln Ser Ser Met Thr Lys Ile Leu Glu Pro
 1               5                  10                  15

<210> SEQ ID NO 199
<211> LENGTH: 16
```

```
<212> TYPE: PRT
<213> ORGANISM: Transgenic mouse

<400> SEQUENCE: 199

Ile Lys Gln Phe Ile Asn Met Trp Gln Glu Val Gly Lys Ala Met Tyr
 1               5                  10                  15

<210> SEQ ID NO 200
<211> LENGTH: 15
<212> TYPE: PRT
<213> ORGANISM: Transgenic mouse

<400> SEQUENCE: 200

Phe Arg Lys Tyr Thr Ala Phe Thr Ile Pro Ser Ile Asn Asn Glu
 1               5                  10                  15

<210> SEQ ID NO 201
<211> LENGTH: 15
<212> TYPE: PRT
<213> ORGANISM: Transgenic mouse

<400> SEQUENCE: 201

His Ser Asn Trp Arg Ala Met Ala Ser Asp Phe Asn Leu Pro Pro
 1               5                  10                  15

<210> SEQ ID NO 202
<211> LENGTH: 15
<212> TYPE: PRT
<213> ORGANISM: Transgenic mouse

<400> SEQUENCE: 202

Lys Thr Ala Val Gln Met Ala Val Phe Ile His Asn Phe Lys Arg
 1               5                  10                  15

<210> SEQ ID NO 203
<211> LENGTH: 15
<212> TYPE: PRT
<213> ORGANISM: Transgenic mouse

<400> SEQUENCE: 203

Tyr Arg Lys Ile Leu Arg Gln Arg Lys Ile Asp Arg Leu Ile Asp
 1               5                  10                  15

<210> SEQ ID NO 204
<211> LENGTH: 15
<212> TYPE: PRT
<213> ORGANISM: Transgenic mouse

<400> SEQUENCE: 204

Trp Ala Gly Ile Lys Gln Glu Phe Gly Ile Pro Tyr Asn Pro Gln
 1               5                  10                  15

<210> SEQ ID NO 205
<211> LENGTH: 15
<212> TYPE: PRT
<213> ORGANISM: Transgenic mouse

<400> SEQUENCE: 205

Glu Val Asn Ile Val Thr Asp Ser Gln Tyr Ala Leu Gly Ile Ile
 1               5                  10                  15

<210> SEQ ID NO 206
<211> LENGTH: 15
<212> TYPE: PRT
<213> ORGANISM: Transgenic mouse
```

```
<400> SEQUENCE: 206

Ala Glu Thr Phe Tyr Val Asp Gly Ala Ala Asn Arg Glu Thr Lys
1               5                   10                  15

<210> SEQ ID NO 207
<211> LENGTH: 15
<212> TYPE: PRT
<213> ORGANISM: Transgenic mouse

<400> SEQUENCE: 207

Gly Ala Val Val Ile Gln Asp Asn Ser Asp Ile Lys Val Val Pro
1               5                   10                  15

<210> SEQ ID NO 208
<211> LENGTH: 10
<212> TYPE: PRT
<213> ORGANISM: Transgenic mouse

<400> SEQUENCE: 208

Leu Leu Phe Asn Ile Leu Gly Gly Trp Val
1               5                   10

<210> SEQ ID NO 209
<211> LENGTH: 9
<212> TYPE: PRT
<213> ORGANISM: Transgenic mouse

<400> SEQUENCE: 209

Phe Leu Leu Leu Ala Asp Ala Arg Val
1               5

<210> SEQ ID NO 210
<211> LENGTH: 9
<212> TYPE: PRT
<213> ORGANISM: Transgenic mouse

<400> SEQUENCE: 210

Tyr Leu Val Ala Tyr Gln Ala Thr Val
1               5

<210> SEQ ID NO 211
<211> LENGTH: 10
<212> TYPE: PRT
<213> ORGANISM: Transgenic mouse

<400> SEQUENCE: 211

Arg Leu Ile Val Phe Pro Asp Leu Gly Val
1               5                   10

<210> SEQ ID NO 212
<211> LENGTH: 9
<212> TYPE: PRT
<213> ORGANISM: Transgenic mouse

<400> SEQUENCE: 212

Asp Leu Met Gly Tyr Ile Pro Leu Val
1               5

<210> SEQ ID NO 213
<211> LENGTH: 9
<212> TYPE: PRT
<213> ORGANISM: Transgenic mouse

<400> SEQUENCE: 213
```

Trp Met Asn Arg Leu Ile Ala Phe Ala
1               5

<210> SEQ ID NO 214
<211> LENGTH: 9
<212> TYPE: PRT
<213> ORGANISM: Transgenic mouse

<400> SEQUENCE: 214

Val Leu Val Gly Gly Val Leu Ala Ala
1               5

<210> SEQ ID NO 215
<211> LENGTH: 9
<212> TYPE: PRT
<213> ORGANISM: Transgenic mouse

<400> SEQUENCE: 215

His Met Trp Asn Phe Ile Ser Gly Ile
1               5

<210> SEQ ID NO 216
<211> LENGTH: 9
<212> TYPE: PRT
<213> ORGANISM: Transgenic mouse

<400> SEQUENCE: 216

Ile Leu Ala Gly Tyr Gly Ala Gly Val
1               5

<210> SEQ ID NO 217
<211> LENGTH: 10
<212> TYPE: PRT
<213> ORGANISM: Transgenic mouse

<400> SEQUENCE: 217

Tyr Leu Leu Pro Arg Arg Gly Pro Arg Leu
1               5                   10

<210> SEQ ID NO 218
<211> LENGTH: 9
<212> TYPE: PRT
<213> ORGANISM: Transgenic mouse

<400> SEQUENCE: 218

Leu Leu Phe Leu Leu Leu Ala Asp Ala
1               5

<210> SEQ ID NO 219
<211> LENGTH: 9
<212> TYPE: PRT
<213> ORGANISM: Transgenic mouse

<400> SEQUENCE: 219

Tyr Leu Val Thr Arg His Ala Asp Val
1               5

<210> SEQ ID NO 220
<211> LENGTH: 9
<212> TYPE: PRT
<213> ORGANISM: Transgenic mouse

<400> SEQUENCE: 220

Lys Thr Ser Glu Arg Ser Gln Pro Arg

```
                  1               5

<210> SEQ ID NO 221
<211> LENGTH: 9
<212> TYPE: PRT
<213> ORGANISM: Transgenic mouse

<400> SEQUENCE: 221

Arg Leu Gly Val Arg Ala Thr Arg Lys
  1               5

<210> SEQ ID NO 222
<211> LENGTH: 9
<212> TYPE: PRT
<213> ORGANISM: Transgenic mouse

<400> SEQUENCE: 222

Gln Leu Phe Thr Phe Ser Pro Arg Arg
  1               5

<210> SEQ ID NO 223
<211> LENGTH: 10
<212> TYPE: PRT
<213> ORGANISM: Transgenic mouse

<400> SEQUENCE: 223

Arg Met Tyr Val Gly Gly Val Glu His Arg
  1               5                  10

<210> SEQ ID NO 224
<211> LENGTH: 9
<212> TYPE: PRT
<213> ORGANISM: Transgenic mouse

<400> SEQUENCE: 224

Leu Ile Phe Cys His Ser Lys Lys Lys
  1               5

<210> SEQ ID NO 225
<211> LENGTH: 10
<212> TYPE: PRT
<213> ORGANISM: Transgenic mouse

<400> SEQUENCE: 225

Gly Val Ala Gly Ala Leu Val Ala Phe Lys
  1               5                  10

<210> SEQ ID NO 226
<211> LENGTH: 9
<212> TYPE: PRT
<213> ORGANISM: Transgenic mouse

<400> SEQUENCE: 226

Val Ala Gly Ala Leu Val Ala Phe Lys
  1               5

<210> SEQ ID NO 227
<211> LENGTH: 9
<212> TYPE: PRT
<213> ORGANISM: Transgenic mouse

<400> SEQUENCE: 227

Leu Gly Phe Gly Ala Tyr Met Ser Lys
  1               5
```

<210> SEQ ID NO 228
<211> LENGTH: 9
<212> TYPE: PRT
<213> ORGANISM: Transgenic mouse

<400> SEQUENCE: 228

Leu Pro Gly Cys Ser Phe Ser Ile Phe
1               5

<210> SEQ ID NO 229
<211> LENGTH: 9
<212> TYPE: PRT
<213> ORGANISM: Transgenic mouse

<400> SEQUENCE: 229

Leu Ser Ala Phe Ser Leu His Ser Tyr
1               5

<210> SEQ ID NO 230
<211> LENGTH: 9
<212> TYPE: PRT
<213> ORGANISM: Transgenic mouse

<400> SEQUENCE: 230

Cys Thr Cys Gly Ser Ser Asp Leu Tyr
1               5

<210> SEQ ID NO 231
<211> LENGTH: 9
<212> TYPE: PRT
<213> ORGANISM: Transgenic mouse

<400> SEQUENCE: 231

Leu Thr Asp Pro Ser His Ile Thr Ala
1               5

<210> SEQ ID NO 232
<211> LENGTH: 11
<212> TYPE: PRT
<213> ORGANISM: Transgenic mouse

<400> SEQUENCE: 232

Leu Thr Cys Gly Phe Ala Asp Leu Met Gly Tyr
1               5                   10

<210> SEQ ID NO 233
<211> LENGTH: 11
<212> TYPE: PRT
<213> ORGANISM: Transgenic mouse

<400> SEQUENCE: 233

Leu Ala Asp Gly Gly Cys Ser Gly Gly Ala Tyr
1               5                   10

<210> SEQ ID NO 234
<211> LENGTH: 9
<212> TYPE: PRT
<213> ORGANISM: Transgenic mouse

<400> SEQUENCE: 234

Phe Trp Ala Lys His Met Trp Asn Phe
1               5

<210> SEQ ID NO 235

```
<211> LENGTH: 9
<212> TYPE: PRT
<213> ORGANISM: Transgenic mouse

<400> SEQUENCE: 235

Arg Met Ile Leu Met Thr His Phe Phe
 1               5

<210> SEQ ID NO 236
<211> LENGTH: 8
<212> TYPE: PRT
<213> ORGANISM: Transgenic mouse

<400> SEQUENCE: 236

Val Met Gly Ser Ser Tyr Gly Phe
 1               5

<210> SEQ ID NO 237
<211> LENGTH: 10
<212> TYPE: PRT
<213> ORGANISM: Transgenic mouse

<400> SEQUENCE: 237

Phe Trp Ala Lys His Met Trp Asn Phe Ile
 1               5                  10

<210> SEQ ID NO 238
<211> LENGTH: 9
<212> TYPE: PRT
<213> ORGANISM: P. falciparum

<400> SEQUENCE: 238

Phe Met Lys Ala Val Cys Val Glu Val
 1               5

<210> SEQ ID NO 239
<211> LENGTH: 9
<212> TYPE: PRT
<213> ORGANISM: P. falciparum

<400> SEQUENCE: 239

Gly Leu Leu Gly Val Val Ser Thr Val
 1               5

<210> SEQ ID NO 240
<211> LENGTH: 10
<212> TYPE: PRT
<213> ORGANISM: P. falciparum

<400> SEQUENCE: 240

Ile Leu Ser Val Ser Ser Phe Leu Phe Val
 1               5                  10

<210> SEQ ID NO 241
<211> LENGTH: 9
<212> TYPE: PRT
<213> ORGANISM: P. falciparum

<400> SEQUENCE: 241

Gln Thr Asn Phe Lys Ser Leu Leu Arg
 1               5

<210> SEQ ID NO 242
<211> LENGTH: 9
<212> TYPE: PRT
```

<213> ORGANISM: P. falciparum

<400> SEQUENCE: 242

Gly Val Ser Glu Asn Ile Phe Leu Lys
1               5

<210> SEQ ID NO 243
<211> LENGTH: 10
<212> TYPE: PRT
<213> ORGANISM: P. falciparum

<400> SEQUENCE: 243

Leu Leu Ala Cys Ala Gly Leu Ala Tyr Lys
1               5                   10

<210> SEQ ID NO 244
<211> LENGTH: 10
<212> TYPE: PRT
<213> ORGANISM: P. falciparum

<400> SEQUENCE: 244

Thr Pro Tyr Ala Gly Glu Pro Ala Pro Phe
1               5                   10

<210> SEQ ID NO 245
<211> LENGTH: 9
<212> TYPE: PRT
<213> ORGANISM: P. falciparum

<400> SEQUENCE: 245

Leu Pro Ser Glu Asn Glu Arg Gly Tyr
1               5

<210> SEQ ID NO 246
<211> LENGTH: 9
<212> TYPE: PRT
<213> ORGANISM: P. falciparum

<400> SEQUENCE: 246

Lys Tyr Lys Leu Ala Thr Ser Val Leu
1               5

<210> SEQ ID NO 247
<211> LENGTH: 9
<212> TYPE: PRT
<213> ORGANISM: P. falciparum

<400> SEQUENCE: 247

Ser Phe Leu Phe Val Glu Ala Leu Phe
1               5

<210> SEQ ID NO 248
<211> LENGTH: 9
<212> TYPE: PRT
<213> ORGANISM: P. falciparum

<400> SEQUENCE: 248

Tyr Phe Ile Leu Val Asn Leu Leu Ile
1               5

<210> SEQ ID NO 249
<211> LENGTH: 10
<212> TYPE: PRT
<213> ORGANISM: P. falciparum

```
<400> SEQUENCE: 249

Phe Leu Ile Phe Phe Asp Leu Phe Leu Val
1               5                   10

<210> SEQ ID NO 250
<211> LENGTH: 9
<212> TYPE: PRT
<213> ORGANISM: P. falciparum

<400> SEQUENCE: 250

Val Leu Ala Gly Leu Leu Gly Val Val
1               5

<210> SEQ ID NO 251
<211> LENGTH: 10
<212> TYPE: PRT
<213> ORGANISM: P. falciparum

<400> SEQUENCE: 251

Val Leu Leu Gly Gly Val Gly Leu Val Leu
1               5                   10

<210> SEQ ID NO 252
<211> LENGTH: 9
<212> TYPE: PRT
<213> ORGANISM: P. falciparum

<400> SEQUENCE: 252

Leu Ala Cys Ala Gly Leu Ala Tyr Lys
1               5

<210> SEQ ID NO 253
<211> LENGTH: 9
<212> TYPE: PRT
<213> ORGANISM: P. falciparum

<400> SEQUENCE: 253

Ala Leu Phe Phe Ile Ile Phe Asn Lys
1               5

<210> SEQ ID NO 254
<211> LENGTH: 10
<212> TYPE: PRT
<213> ORGANISM: P. falciparum

<400> SEQUENCE: 254

Phe Ile Leu Val Asn Leu Leu Ile Phe His
1               5                   10

<210> SEQ ID NO 255
<211> LENGTH: 8
<212> TYPE: PRT
<213> ORGANISM: P. falciparum

<400> SEQUENCE: 255

Leu Pro Tyr Gly Arg Thr Asn Leu
1               5

<210> SEQ ID NO 256
<211> LENGTH: 9
<212> TYPE: PRT
<213> ORGANISM: P. falciparum

<400> SEQUENCE: 256
```

```
Phe Val Glu Ala Leu Phe Gln Glu Tyr
 1               5

<210> SEQ ID NO 257
<211> LENGTH: 10
<212> TYPE: PRT
<213> ORGANISM: P. falciparum

<400> SEQUENCE: 257

Phe Gln Asp Glu Glu Asn Ile Gly Ile Tyr
 1               5                  10

<210> SEQ ID NO 258
<211> LENGTH: 9
<212> TYPE: PRT
<213> ORGANISM: P. falciparum

<400> SEQUENCE: 258

Phe Tyr Phe Ile Leu Val Asn Leu Leu
 1               5

<210> SEQ ID NO 259
<211> LENGTH: 9
<212> TYPE: PRT
<213> ORGANISM: P. falciparum

<400> SEQUENCE: 259

Lys Tyr Leu Val Ile Val Phe Leu Ile
 1               5

<210> SEQ ID NO 260
<211> LENGTH: 9
<212> TYPE: PRT
<213> ORGANISM: P. falciparum

<400> SEQUENCE: 260

Gly Leu Ile Met Val Leu Ser Phe Leu
 1               5

<210> SEQ ID NO 261
<211> LENGTH: 9
<212> TYPE: PRT
<213> ORGANISM: P. falciparum

<400> SEQUENCE: 261

Lys Ile Leu Ser Val Phe Phe Leu Ala
 1               5

<210> SEQ ID NO 262
<211> LENGTH: 10
<212> TYPE: PRT
<213> ORGANISM: P. falciparum

<400> SEQUENCE: 262

Val Thr Cys Gly Asn Gly Ile Gln Val Arg
 1               5                  10

<210> SEQ ID NO 263
<211> LENGTH: 10
<212> TYPE: PRT
<213> ORGANISM: P. falciparum

<400> SEQUENCE: 263

His Val Leu Ser His Asn Ser Tyr Glu Lys
 1               5                  10
```

```
<210> SEQ ID NO 264
<211> LENGTH: 9
<212> TYPE: PRT
<213> ORGANISM: P. falciparum

<400> SEQUENCE: 264

Pro Ser Asp Gly Lys Cys Asn Leu Tyr
1               5

<210> SEQ ID NO 265
<211> LENGTH: 9
<212> TYPE: PRT
<213> ORGANISM: P. falciparum

<400> SEQUENCE: 265

Tyr Tyr Ile Pro His Gln Ser Ser Leu
1               5

<210> SEQ ID NO 266
<211> LENGTH: 10
<212> TYPE: PRT
<213> ORGANISM: P. falciparum

<400> SEQUENCE: 266

Lys Phe Ile Lys Ser Leu Phe His Ile Phe
1               5                   10

<210> SEQ ID NO 267
<211> LENGTH: 10
<212> TYPE: PRT
<213> ORGANISM: P. falciparum

<400> SEQUENCE: 267

Val Phe Leu Ile Phe Phe Asp Leu Phe Leu
1               5                   10

<210> SEQ ID NO 268
<211> LENGTH: 11
<212> TYPE: PRT
<213> ORGANISM: P. falciparum

<400> SEQUENCE: 268

Leu Phe His Ile Phe Asp Gly Asp Asn Glu Ile
1               5                   10

<210> SEQ ID NO 269
<211> LENGTH: 11
<212> TYPE: PRT
<213> ORGANISM: P. falciparum

<400> SEQUENCE: 269

Tyr Tyr Gly Lys Gln Glu Asn Trp Tyr Ser Leu
1               5                   10

<210> SEQ ID NO 270
<211> LENGTH: 8
<212> TYPE: PRT
<213> ORGANISM: P. falciparum

<400> SEQUENCE: 270

Leu Tyr Ile Ser Phe Tyr Phe Ile
1               5
```

```
<210> SEQ ID NO 271
<211> LENGTH: 15
<212> TYPE: PRT
<213> ORGANISM: P. falciparum

<400> SEQUENCE: 271

Met Arg Lys Leu Ala Ile Leu Ser Val Ser Ser Phe Leu Phe Val
1               5                   10                  15

<210> SEQ ID NO 272
<211> LENGTH: 15
<212> TYPE: PRT
<213> ORGANISM: P. falciparum

<400> SEQUENCE: 272

Met Asn Tyr Tyr Gly Lys Gln Glu Asn Trp Tyr Ser Leu Lys Lys
1               5                   10                  15

<210> SEQ ID NO 273
<211> LENGTH: 15
<212> TYPE: PRT
<213> ORGANISM: P. falciparum

<400> SEQUENCE: 273

Ser Ser Val Phe Asn Val Val Asn Ser Ser Ile Gly Leu Ile Met
1               5                   10                  15

<210> SEQ ID NO 274
<211> LENGTH: 16
<212> TYPE: PRT
<213> ORGANISM: P. falciparum

<400> SEQUENCE: 274

Arg His Asn Trp Val Asn His Ala Val Pro Leu Ala Met Lys Leu Ile
1               5                   10                  15

<210> SEQ ID NO 275
<211> LENGTH: 15
<212> TYPE: PRT
<213> ORGANISM: P. falciparum

<400> SEQUENCE: 275

Pro Asp Ser Ile Gln Asp Ser Leu Lys Glu Ser Arg Lys Leu Asn
1               5                   10                  15

<210> SEQ ID NO 276
<211> LENGTH: 15
<212> TYPE: PRT
<213> ORGANISM: P. falciparum

<400> SEQUENCE: 276

Lys Cys Asn Leu Tyr Ala Asp Ser Ala Trp Glu Asn Val Lys Asn
1               5                   10                  15

<210> SEQ ID NO 277
<211> LENGTH: 15
<212> TYPE: PRT
<213> ORGANISM: P. falciparum

<400> SEQUENCE: 277

Val Lys Asn Val Ile Gly Pro Phe Met Lys Ala Val Cys Val Glu
1               5                   10                  15

<210> SEQ ID NO 278
<211> LENGTH: 15
```

```
<212> TYPE: PRT
<213> ORGANISM: P. falciparum

<400> SEQUENCE: 278

Lys Tyr Lys Ile Ala Gly Gly Ile Ala Gly Gly Leu Ala Leu Leu
 1               5                  10                  15

<210> SEQ ID NO 279
<211> LENGTH: 15
<212> TYPE: PRT
<213> ORGANISM: P. falciparum

<400> SEQUENCE: 279

Gly Leu Ala Tyr Lys Phe Val Val Pro Gly Ala Ala Thr Pro Tyr
 1               5                  10                  15

<210> SEQ ID NO 280
<211> LENGTH: 15
<212> TYPE: PRT
<213> ORGANISM: P. falciparum

<400> SEQUENCE: 280

Lys Ser Lys Tyr Lys Leu Ala Thr Ser Val Leu Ala Gly Leu Leu
 1               5                  10                  15

<210> SEQ ID NO 281
<211> LENGTH: 15
<212> TYPE: PRT
<213> ORGANISM: P. falciparum

<400> SEQUENCE: 281

Ala Gly Leu Leu Gly Asn Val Ser Thr Val Leu Leu Gly Gly Val
 1               5                  10                  15

<210> SEQ ID NO 282
<211> LENGTH: 15
<212> TYPE: PRT
<213> ORGANISM: P. falciparum

<400> SEQUENCE: 282

Leu Leu Ile Phe His Ile Asn Gly Lys Ile Ile Lys Asn Ser Glu
 1               5                  10                  15

<210> SEQ ID NO 283
<211> LENGTH: 15
<212> TYPE: PRT
<213> ORGANISM: P. falciparum

<400> SEQUENCE: 283

Gln Thr Asn Phe Lys Ser Leu Leu Arg Asn Leu Gly Val Ser Glu
 1               5                  10                  15

<210> SEQ ID NO 284
<211> LENGTH: 10
<212> TYPE: PRT
<213> ORGANISM: Transgenic mouse

<400> SEQUENCE: 284

Phe Leu Pro Ser Asp Phe Phe Pro Ser Val
 1               5                  10

<210> SEQ ID NO 285
<211> LENGTH: 9
<212> TYPE: PRT
<213> ORGANISM: Transgenic mouse
```

```
<400> SEQUENCE: 285

Phe Leu Leu Thr Arg Ile Leu Thr Ile
1               5

<210> SEQ ID NO 286
<211> LENGTH: 9
<212> TYPE: PRT
<213> ORGANISM: Transgenic mouse

<400> SEQUENCE: 286

Trp Leu Ser Leu Leu Val Pro Phe Val
1               5

<210> SEQ ID NO 287
<211> LENGTH: 9
<212> TYPE: PRT
<213> ORGANISM: Transgenic mouse

<400> SEQUENCE: 287

Gly Leu Ser Arg Tyr Val Ala Arg Leu
1               5

<210> SEQ ID NO 288
<211> LENGTH: 9
<212> TYPE: PRT
<213> ORGANISM: Transgenic mouse

<400> SEQUENCE: 288

Tyr Met Asp Asp Val Val Leu Gly Val
1               5

<210> SEQ ID NO 289
<211> LENGTH: 10
<212> TYPE: PRT
<213> ORGANISM: Transgenic mouse

<400> SEQUENCE: 289

Ile Leu Arg Gly Thr Ser Phe Val Tyr Val
1               5                   10

<210> SEQ ID NO 290
<211> LENGTH: 9
<212> TYPE: PRT
<213> ORGANISM: Transgenic mouse

<400> SEQUENCE: 290

Phe Leu Leu Ser Leu Gly Ile His Leu
1               5

<210> SEQ ID NO 291
<211> LENGTH: 9
<212> TYPE: PRT
<213> ORGANISM: Transgenic mouse

<400> SEQUENCE: 291

Ala Leu Met Pro Leu Tyr Ala Cys Ile
1               5

<210> SEQ ID NO 292
<211> LENGTH: 10
<212> TYPE: PRT
<213> ORGANISM: Transgenic mouse

<400> SEQUENCE: 292
```

```
Gly Leu Ser Pro Thr Val Trp Leu Ser Val
1               5                   10

<210> SEQ ID NO 293
<211> LENGTH: 11
<212> TYPE: PRT
<213> ORGANISM: Transgenic mouse

<400> SEQUENCE: 293

Ser Thr Leu Pro Glu Thr Thr Val Val Arg Arg
1               5                   10

<210> SEQ ID NO 294
<211> LENGTH: 11
<212> TYPE: PRT
<213> ORGANISM: Transgenic mouse

<400> SEQUENCE: 294

His Thr Leu Trp Lys Ala Gly Ile Leu Tyr Lys
1               5                   10

<210> SEQ ID NO 295
<211> LENGTH: 10
<212> TYPE: PRT
<213> ORGANISM: Transgenic mouse

<400> SEQUENCE: 295

Thr Leu Trp Lys Ala Gly Ile Leu Tyr Lys
1               5                   10

<210> SEQ ID NO 296
<211> LENGTH: 10
<212> TYPE: PRT
<213> ORGANISM: Transgenic mouse

<400> SEQUENCE: 296

Leu Val Val Asp Phe Ser Gln Phe Ser Arg
1               5                   10

<210> SEQ ID NO 297
<211> LENGTH: 9
<212> TYPE: PRT
<213> ORGANISM: Transgenic mouse

<400> SEQUENCE: 297

Asn Val Ser Ile Pro Trp Thr His Lys
1               5

<210> SEQ ID NO 298
<211> LENGTH: 9
<212> TYPE: PRT
<213> ORGANISM: Transgenic mouse

<400> SEQUENCE: 298

Ser Ala Ile Cys Ser Val Val Arg Arg
1               5

<210> SEQ ID NO 299
<211> LENGTH: 9
<212> TYPE: PRT
<213> ORGANISM: Transgenic mouse

<400> SEQUENCE: 299

Lys Val Gly Asn Phe Thr Gly Leu Tyr
```

```
<210> SEQ ID NO 300
<211> LENGTH: 10
<212> TYPE: PRT
<213> ORGANISM: Transgenic mouse

<400> SEQUENCE: 300

Gln Ala Phe Thr Phe Ser Pro Thr Tyr Lys
1               5                   10

<210> SEQ ID NO 301
<211> LENGTH: 9
<212> TYPE: PRT
<213> ORGANISM: Transgenic mouse

<400> SEQUENCE: 301

Leu Pro Ser Asp Phe Phe Pro Ser Val
1               5

<210> SEQ ID NO 302
<211> LENGTH: 9
<212> TYPE: PRT
<213> ORGANISM: Transgenic mouse

<400> SEQUENCE: 302

Ile Pro Ile Pro Ser Ser Trp Ala Phe
1               5

<210> SEQ ID NO 303
<211> LENGTH: 10
<212> TYPE: PRT
<213> ORGANISM: Transgenic mouse

<400> SEQUENCE: 303

Thr Pro Ala Arg Val Thr Gly Gly Val Phe
1               5                   10

<210> SEQ ID NO 304
<211> LENGTH: 10
<212> TYPE: PRT
<213> ORGANISM: Transgenic mouse

<400> SEQUENCE: 304

Arg Met Ser Arg Val Thr Thr Phe Thr Val
1               5                   10

<210> SEQ ID NO 305
<211> LENGTH: 10
<212> TYPE: PRT
<213> ORGANISM: Transgenic mouse

<400> SEQUENCE: 305

Ala Leu Val Leu Leu Met Leu Pro Val Val
1               5                   10

<210> SEQ ID NO 306
<211> LENGTH: 10
<212> TYPE: PRT
<213> ORGANISM: Transgenic mouse

<400> SEQUENCE: 306

Leu Met Ile Gly Thr Ala Ala Ala Val Val
1               5                   10
```

<210> SEQ ID NO 307
<211> LENGTH: 9
<212> TYPE: PRT
<213> ORGANISM: Transgenic mouse

<400> SEQUENCE: 307

Ala Leu Val Leu Leu Met Leu Pro Val
1               5

<210> SEQ ID NO 308
<211> LENGTH: 9
<212> TYPE: PRT
<213> ORGANISM: Transgenic mouse

<400> SEQUENCE: 308

Gly Leu Met Thr Ala Val Tyr Leu Val
1               5

<210> SEQ ID NO 309
<211> LENGTH: 8
<212> TYPE: PRT
<213> ORGANISM: Transgenic mouse

<400> SEQUENCE: 309

Met Ala Leu Leu Arg Leu Pro Val
1               5

<210> SEQ ID NO 310
<211> LENGTH: 9
<212> TYPE: PRT
<213> ORGANISM: Transgenic mouse

<400> SEQUENCE: 310

Arg Met Phe Ala Ala Asn Leu Gly Val
1               5

<210> SEQ ID NO 311
<211> LENGTH: 9
<212> TYPE: PRT
<213> ORGANISM: Transgenic mouse

<400> SEQUENCE: 311

Ser Leu Tyr Phe Gly Gly Ile Cys Val
1               5

<210> SEQ ID NO 312
<211> LENGTH: 9
<212> TYPE: PRT
<213> ORGANISM: Transgenic mouse

<400> SEQUENCE: 312

Arg Leu Pro Leu Val Leu Pro Ala Val
1               5

<210> SEQ ID NO 313
<211> LENGTH: 9
<212> TYPE: PRT
<213> ORGANISM: Transgenic mouse

<400> SEQUENCE: 313

Arg Leu Met Ile Gly Thr Ala Ala Ala
1               5

<210> SEQ ID NO 314

```
<211> LENGTH: 9
<212> TYPE: PRT
<213> ORGANISM: Transgenic mouse

<400> SEQUENCE: 314

Phe Val Val Ala Leu Ile Pro Leu Val
 1               5

<210> SEQ ID NO 315
<211> LENGTH: 9
<212> TYPE: PRT
<213> ORGANISM: Transgenic mouse

<400> SEQUENCE: 315

Met Thr Tyr Ala Ala Pro Leu Phe Val
 1               5

<210> SEQ ID NO 316
<211> LENGTH: 10
<212> TYPE: PRT
<213> ORGANISM: Transgenic mouse

<400> SEQUENCE: 316

Ala Met Ala Leu Leu Arg Leu Pro Leu Val
 1               5                  10

<210> SEQ ID NO 317
<211> LENGTH: 9
<212> TYPE: PRT
<213> ORGANISM: Transgenic mouse

<400> SEQUENCE: 317

Lys Leu Cys Pro Val Gln Leu Trp Val
 1               5

<210> SEQ ID NO 318
<211> LENGTH: 9
<212> TYPE: PRT
<213> ORGANISM: Transgenic mouse

<400> SEQUENCE: 318

Ala Thr Val Gly Ile Met Ile Gly Val
 1               5

<210> SEQ ID NO 319
<211> LENGTH: 9
<212> TYPE: PRT
<213> ORGANISM: Transgenic mouse

<400> SEQUENCE: 319

Ile Met Ile Gly His Leu Val Gly Val
 1               5

<210> SEQ ID NO 320
<211> LENGTH: 9
<212> TYPE: PRT
<213> ORGANISM: Transgenic mouse

<400> SEQUENCE: 320

Arg Leu Leu Gln Glu Thr Glu Leu Val
 1               5

<210> SEQ ID NO 321
<211> LENGTH: 9
<212> TYPE: PRT
```

<213> ORGANISM: Transgenic mouse

<400> SEQUENCE: 321

Lys Val Ala Glu Ile Val His Phe Leu
1               5

<210> SEQ ID NO 322
<211> LENGTH: 9
<212> TYPE: PRT
<213> ORGANISM: Transgenic mouse

<400> SEQUENCE: 322

Lys Val Phe Gly Ser Leu Ala Phe Val
1               5

<210> SEQ ID NO 323
<211> LENGTH: 9
<212> TYPE: PRT
<213> ORGANISM: Transgenic mouse

<400> SEQUENCE: 323

Tyr Leu Ser Gly Ala Asn Leu Asn Val
1               5

<210> SEQ ID NO 324
<211> LENGTH: 10
<212> TYPE: PRT
<213> ORGANISM: Transgenic mouse

<400> SEQUENCE: 324

Tyr Leu Gln Leu Val Phe Gly Ile Glu Val
1               5                   10

<210> SEQ ID NO 325
<211> LENGTH: 9
<212> TYPE: PRT
<213> ORGANISM: Transgenic mouse

<400> SEQUENCE: 325

Val Val Leu Gly Val Val Phe Gly Ile
1               5

<210> SEQ ID NO 326
<211> LENGTH: 9
<212> TYPE: PRT
<213> ORGANISM: Transgenic mouse

<400> SEQUENCE: 326

Ser Met Pro Pro Pro Gly Thr Arg Val
1               5

<210> SEQ ID NO 327
<211> LENGTH: 10
<212> TYPE: PRT
<213> ORGANISM: Transgenic mouse

<400> SEQUENCE: 327

Leu Thr Phe Phe Trp Leu Asp Arg Ser Val
1               5                   10

<210> SEQ ID NO 328
<211> LENGTH: 9
<212> TYPE: PRT
<213> ORGANISM: Transgenic mouse

```
<400> SEQUENCE: 328

Thr Leu Met Ser Ala Met Thr Asn Leu
 1               5

<210> SEQ ID NO 329
<211> LENGTH: 10
<212> TYPE: PRT
<213> ORGANISM: Transgenic mouse

<400> SEQUENCE: 329

Ile Met Tyr Ser Ala His Asp Thr Thr Val
 1               5                  10

<210> SEQ ID NO 330
<211> LENGTH: 10
<212> TYPE: PRT
<213> ORGANISM: Transgenic mouse

<400> SEQUENCE: 330

Gly Leu Pro Ser Ile Pro Val His Pro Val
 1               5                  10

<210> SEQ ID NO 331
<211> LENGTH: 10
<212> TYPE: PRT
<213> ORGANISM: Transgenic mouse

<400> SEQUENCE: 331

Leu Leu Gln Glu Arg Gly Val Ala Tyr Ile
 1               5                  10

<210> SEQ ID NO 332
<211> LENGTH: 9
<212> TYPE: PRT
<213> ORGANISM: Transgenic mouse

<400> SEQUENCE: 332

Leu Leu Tyr Ser Leu Val His Asn Leu
 1               5

<210> SEQ ID NO 333
<211> LENGTH: 9
<212> TYPE: PRT
<213> ORGANISM: Transgenic mouse

<400> SEQUENCE: 333

Met Met Asn Asp Gln Leu Met Phe Leu
 1               5

<210> SEQ ID NO 334
<211> LENGTH: 11
<212> TYPE: PRT
<213> ORGANISM: Transgenic mouse

<400> SEQUENCE: 334

Phe Leu Thr Leu Ser Val Thr Trp Ile Gly Val
 1               5                  10

<210> SEQ ID NO 335
<211> LENGTH: 8
<212> TYPE: PRT
<213> ORGANISM: Transgenic mouse

<400> SEQUENCE: 335
```

```
Ala Leu Gly Thr Thr Cys Tyr Val
 1               5

<210> SEQ ID NO 336
<211> LENGTH: 10
<212> TYPE: PRT
<213> ORGANISM: Transgenic mouse

<400> SEQUENCE: 336

Phe Leu Thr Pro Lys Lys Leu Gln Cys Val
 1               5                  10

<210> SEQ ID NO 337
<211> LENGTH: 9
<212> TYPE: PRT
<213> ORGANISM: Transgenic mouse

<400> SEQUENCE: 337

Leu Leu Leu Ser Ile Ala Leu Ser Val
 1               5

<210> SEQ ID NO 338
<211> LENGTH: 11
<212> TYPE: PRT
<213> ORGANISM: Transgenic mouse

<400> SEQUENCE: 338

Val Leu Val His Pro Gln Trp Val Leu Thr Val
 1               5                  10

<210> SEQ ID NO 339
<211> LENGTH: 10
<212> TYPE: PRT
<213> ORGANISM: Transgenic mouse

<400> SEQUENCE: 339

Phe Leu Arg Pro Arg Ser Leu Gln Cys Val
 1               5                  10

<210> SEQ ID NO 340
<211> LENGTH: 11
<212> TYPE: PRT
<213> ORGANISM: Transgenic mouse

<400> SEQUENCE: 340

Pro Leu Val Cys Asn Gly Val Leu Gln Gly Val
 1               5                  10

<210> SEQ ID NO 341
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 341

Xaa Xaa Xaa Xaa Asn Xaa Xaa Xaa Xaa Leu
 1               5                  10

<210> SEQ ID NO 342
<211> LENGTH: 10
<212> TYPE: PRT
```

```
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 342

Xaa Xaa Xaa Xaa Asn Xaa Xaa Xaa Xaa Ile
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 343

Xaa Xaa Xaa Xaa Asn Xaa Xaa Xaa Xaa Met
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 344

Xaa Xaa Xaa Xaa Asn Xaa Xaa Xaa Xaa Val
1               5                   10

<210> SEQ ID NO 345
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 345

Xaa Leu Xaa Xaa Xaa Xaa Xaa Xaa Lys
1               5

<210> SEQ ID NO 346
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 346

Xaa Leu Xaa Xaa Xaa Xaa Xaa Xaa Arg
```

1               5

<210> SEQ ID NO 347
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 347

Xaa Leu Xaa Xaa Xaa Xaa Xaa Xaa Tyr
1               5

<210> SEQ ID NO 348
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 348

Xaa Met Xaa Xaa Xaa Xaa Xaa Xaa Lys
1               5

<210> SEQ ID NO 349
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 349

Xaa Met Xaa Xaa Xaa Xaa Xaa Xaa Arg
1               5

<210> SEQ ID NO 350
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 350

Xaa Met Xaa Xaa Xaa Xaa Xaa Xaa Tyr
1               5

<210> SEQ ID NO 351
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT

```
<222> LOCATION: (1)...(9)
<223> OTHER INFORMATION: Xaa = Any Amino Acid

<400> SEQUENCE: 351

Xaa Val Xaa Xaa Xaa Xaa Xaa Xaa Lys
 1               5

<210> SEQ ID NO 352
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 352

Xaa Val Xaa Xaa Xaa Xaa Xaa Xaa Arg
 1               5

<210> SEQ ID NO 353
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 353

Xaa Val Xaa Xaa Xaa Xaa Xaa Xaa Tyr
 1               5

<210> SEQ ID NO 354
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 354

Xaa Thr Xaa Xaa Xaa Xaa Xaa Xaa Lys
 1               5

<210> SEQ ID NO 355
<211> LENGTH: 9
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 355

Xaa Thr Xaa Xaa Xaa Xaa Xaa Xaa Arg
 1               5

<210> SEQ ID NO 356
<211> LENGTH: 9
```

```
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(9)
<223> OTHER INFORMATION: Xaa = Any Amino Acid

<400> SEQUENCE: 356

Xaa Thr Xaa Xaa Xaa Xaa Xaa Xaa Tyr
 1               5

<210> SEQ ID NO 357
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 357

Xaa Leu Xaa Xaa Xaa Xaa Xaa Xaa Xaa Lys
 1               5                  10

<210> SEQ ID NO 358
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 358

Xaa Leu Xaa Xaa Xaa Xaa Xaa Xaa Xaa Arg
 1               5                  10

<210> SEQ ID NO 359
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 359

Xaa Leu Xaa Xaa Xaa Xaa Xaa Xaa Xaa Tyr
 1               5                  10

<210> SEQ ID NO 360
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 360
```

```
Xaa Met Xaa Xaa Xaa Xaa Xaa Xaa Xaa Lys
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 361

Xaa Met Xaa Xaa Xaa Xaa Xaa Xaa Xaa Arg
1               5                   10

<210> SEQ ID NO 362
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 362

Xaa Met Xaa Xaa Xaa Xaa Xaa Xaa Xaa Tyr
1               5                   10

<210> SEQ ID NO 363
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 363

Xaa Val Xaa Xaa Xaa Xaa Xaa Xaa Xaa Lys
1               5                   10

<210> SEQ ID NO 364
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 364

Xaa Val Xaa Xaa Xaa Xaa Xaa Xaa Xaa Arg
1               5                   10

<210> SEQ ID NO 365
<211> LENGTH: 10
<212> TYPE: PRT
<213> ORGANISM: Artificial Sequence
<220> FEATURE:
<223> OTHER INFORMATION: Motif Specification 206
<220> FEATURE:
```

```
<221> NAME/KEY: VARIANT
<222> LOCATION: (1)...(10)
<223> OTHER INFORMATION: Xaa = Any Amino Acid

<400> SEQUENCE: 365

Xaa Val Xaa Xaa Xaa Xaa Xaa Xaa Xaa Tyr
 1               5                   10

<210> SEQ ID NO 366
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 366

Xaa Thr Xaa Xaa Xaa Xaa Xaa Xaa Xaa Lys
 1               5                   10

<210> SEQ ID NO 367
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 367

Xaa Thr Xaa Xaa Xaa Xaa Xaa Xaa Xaa Arg
 1               5                   10

<210> SEQ ID NO 368
<211> LENGTH: 10
<212> TYPE: PRT
<213> ORGANISM: Artificial Sequence
<220> FEATURE:
<223> OTHER INFORMATION: Motif Specification 206
<220> FEATURE:
<221> NAME/KEY: VARIANT
<222> LOCATION: (1)...(10)
<223> OTHER INFORMATION: Xaa = Any Amino Acid

<400> SEQUENCE: 368

Xaa Thr Xaa Xaa Xaa Xaa Xaa Xaa Xaa Tyr
 1               5                   10

<210> SEQ ID NO 369
<211> LENGTH: 5
<212> TYPE: PRT
<213> ORGANISM: Artificial Sequence
<220> FEATURE:
<223> OTHER INFORMATION: Amino Acid Spacer

<400> SEQUENCE: 369

Gly Pro Gly Pro Gly
 1               5

<210> SEQ ID NO 370
<211> LENGTH: 8
<212> TYPE: PRT
<213> ORGANISM: Artificial
<220> FEATURE:
```

```
<223> OTHER INFORMATION: Motif Specification 206
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa = Phe or Tyr
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa = Leu, Ile, Met or Val

<400> SEQUENCE: 370

Xaa Xaa Xaa Xaa Xaa Xaa Xaa Xaa
1               5

<210> SEQ ID NO 371
<211> LENGTH: 9
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa = Phe or Tyr
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa = Leu, Ile, Met or Val

<400> SEQUENCE: 371

Xaa Xaa Xaa Xaa Xaa Xaa Xaa Xaa Xaa
1               5

<210> SEQ ID NO 372
<211> LENGTH: 9
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa = Leu, Ile, Met or Val

<400> SEQUENCE: 372

Xaa Xaa Xaa Xaa Asn Xaa Xaa Xaa Xaa
1               5

<210> SEQ ID NO 373
```

```
<211> LENGTH: 10
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa = Leu, Ile, Met or Val

<400> SEQUENCE: 373

Xaa Xaa Xaa Xaa Asn Xaa Xaa Xaa Xaa Xaa
1               5                   10

<210> SEQ ID NO 374
<211> LENGTH: 9
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa = Leu or Met
<220> FEATURE:
<221> NAME/KEY: misc_feature
<222> LOCATION: (3)..(8)
<223> OTHER INFORMATION: Xaa can be any naturally occurring amino acid

<400> SEQUENCE: 374

Xaa Xaa Xaa Xaa Xaa Xaa Xaa Xaa Val
1               5

<210> SEQ ID NO 375
<211> LENGTH: 10
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa = Leu or Met
<220> FEATURE:
<221> NAME/KEY: misc_feature
<222> LOCATION: (3)..(9)
<223> OTHER INFORMATION: Xaa can be any naturally occurring amino acid

<400> SEQUENCE: 375

Xaa Xaa Xaa Xaa Xaa Xaa Xaa Xaa Xaa Val
1               5                   10

<210> SEQ ID NO 376
<211> LENGTH: 9
<212> TYPE: PRT
<213> ORGANISM: Artificial
<220> FEATURE:
```

```
<223> OTHER INFORMATION: Motif Specification 206
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa = Leu, Met, Val or Thr
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa = Lys, Arg or Tyr

<400> SEQUENCE: 376

Xaa Xaa Xaa Xaa Xaa Xaa Xaa Xaa Xaa
1               5

<210> SEQ ID NO 377
<211> LENGTH: 10
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa = Leu, Met, Val or Thr
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa = Lys, Arg or Tyr

<400> SEQUENCE: 377

Xaa Xaa Xaa Xaa Xaa Xaa Xaa Xaa Xaa Xaa
1               5                   10

<210> SEQ ID NO 378
<211> LENGTH: 9
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa = Leu, Ile, Met, Val or Phe

<400> SEQUENCE: 378

Xaa Pro Xaa Xaa Xaa Xaa Xaa Xaa Xaa
1               5

<210> SEQ ID NO 379
```

```
-continued

<211> LENGTH: 10
<212> TYPE: PRT
<213> ORGANISM: Artificial
<220> FEATURE:
<223> OTHER INFORMATION: Motif Specification 206
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa = Leu, Ile, Met, Val or Phe

<400> SEQUENCE: 379

Xaa Pro Xaa Xaa Xaa Xaa Xaa Xaa Xaa Xaa
1               5                   10

<210> SEQ ID NO 380
<211> LENGTH: 4
<212> TYPE: PRT
<213> ORGANISM: Artificial Sequence
<220> FEATURE:
<223> OTHER INFORMATION: Amino Acid Spacer

<400> SEQUENCE: 380

Gly Ala Ala Ala
1

<210> SEQ ID NO 381
<211> LENGTH: 4
<212> TYPE: PRT
<213> ORGANISM: Artificial Sequence
<220> FEATURE:
<223> OTHER INFORMATION: Amino Acid Spacer

<400> SEQUENCE: 381

Asn Ala Ala Ala
1

<210> SEQ ID NO 382
<211> LENGTH: 4
<212> TYPE: PRT
<213> ORGANISM: Artificial Sequence
<220> FEATURE:
<223> OTHER INFORMATION: Amino Acid Spacer

<400> SEQUENCE: 382

Lys Ala Ala Ala
1
```

METHOD AND SYSTEM FOR OPTIMIZING MINIGENES AND PEPTIDES ENCODED THEREBY

CROSS-REFERENCES TO RELATED APPLICATIONS

This application is a continuation-in-part of International Application No. PCT/US00/35568 PCT, entitled "Optimized Minigenes and Peptides Encoded Thereby," filed on 28 Dec. 2000, to Sette et al., which claims priority to U.S. Application Ser. No. 60/173,390 filed 28 Dec. 1999. This application also claims the benefit of the 16 Apr. 2001 filing date for U.S. Application Ser. No. 60/284,221, entitled "Optimized Minigenes and Peptides Encoded Thereby," to Sette et al. Each of these documents is hereby incorporated by reference in its entirety.

STATEMENT AS TO RIGHTS TO INVENTIONS MADE UNDER FEDERALLY SPONSORED RESEARCH AND DEVELOPMENT

This invention was made with Federal Funding assistance. Accordingly, the U.S. government may have certain rights to the invention.

BACKGROUND OF THE INVENTION

The Sequence Listing written in file Sequence Listing 2060 0320003.txt, 149,504 bytes, created on May 10, 2004 on two identical copies of compact discs for application Ser. No. 09/894,018, Sette et al., Method and System for Optimizing Minigenes and Peptides Encoded Thereby, is herein incorporated-by-reference.

This present invention relates to the field of biology. In particular, it relates to multi-epitope (multi-epitope) vaccines and methods of designing such vaccines to provide increased immunogenicity. In certain embodiments, the multi-epitope vaccine is encoded by a minigene that provides optimized immunogenicity of the construct.

The technology relevant to multi-epitope ("minigene") vaccines is developing. Several independent studies have established that induction of simultaneous immune responses against multiple epitopes can be achieved. For example, responses against a large number of T cell specificities can be induced and detected. In natural situations, Doolan et al (*Immunity*, Vol. 7(1):97-112 (1997)) simultaneously detected recall T cell responses, against as many as 17 different *P. falciparum* epitopes using PBMC from a single donor. Similarly, Bertoni and colleagues (*J Clin Invest*, Vol. 100(3):503-13 (1997)) detected simultaneous CTL responses against 12 different HBV-derived epitopes in a single donor. In terms of immunization with multi-epitope DNA minigene vaccines, several examples have been reported where multiple T cell responses were induced. For example, minigene vaccines composed of approximately ten MHC Class I epitopes in which all epitopes were immunogenic and/or antigenic have been reported. Specifically, minigene vaccines composed of 9 EBV (Thomson et al., *Proc Natl Acad Sci* USA, Vol. 92(13): 5845-9 (1995)), 7HIV (Woodberry et al., *J Virol*, Vol. 73(7): 5320-5 (1999)), 10 murine (Thomson et al., *J Immunol*, Vol. 160(4):1717-23 (1998)) and 10 tumor-derived (Mateo et al.,*J Immunol*, Vol. 163(7):4058-63 (1999)) epitopes have been shown to be active. It has also been shown that a multi-epitope DNA plasmid encoding nine different HLA-A2.1- and A11-restricted epitopes derived from HBV and HIV induced CTL against all epitopes (Ishioka et al., *J Immunol*, Vol. 162(7): 3915-25 (1999)).

Thus, minigene vaccines containing multiple MHC Class I and Class II (i.e., CTL) epitopes can be designed, and presentation and recognition can be obtained for all epitopes. However, the immunogenicity of multi-epitope constructs appears to be strongly influenced by a number of variables, a number of which have heretofore been unknown. For example, the immunogenicity (or antigenicity) of the same epitope expressed in the context of different vaccine constructs can vary over several orders of magnitude. Thus, there exists a need to identify strategies to optimize multi-epitope vaccine constructs. Such optimization is important in terms of induction of potent immune responses and ultimately, for clinical efficacy. Accordingly, the present invention provides strategies to optimize antigenicity and immunogenicity of multi-epitope vaccines encompassing a large number of epitopes, and optimized multi-epitope vaccines, particularly minigene vaccines, generated in accordance with these strategies.

The following paragraphs provide a brief review of some of the main variables potentially influencing minigene immunogenicity, epitope processing, and presentation on antigen presenting cells (APCs) in association with Class I and Class II MHC molecules.

Immunodominance

Of the many thousand possible peptides that are encoded by a complex foreign pathogen, only a small fraction ends up in a peptide form capable of binding to MHC Class I antigens and thus of being recognized by T cells. This phenomenon, of obvious potential impact on the development of a multi-epitope vaccine, is known as immunodominance (Yewdell et al., *Annu Rev Immunol*, 17:51-88 (1999)). Several major variables contribute to immunodominance. Herein, we describe variables affecting the generation of the appropriate peptides, both in qualitative and quantitative terms, as a result of intracellular processing.

Junctional Epitopes

A junctional epitope is defined as an epitope created due to the juxtaposition of two other epitopes. The new epitope is composed of a C-terminal section derived from a first epitope, and an N-terminal section derived from a second epitope. Creation of junctional epitopes is a potential problem in the design of multi-epitope minigene vaccines, for both Class I and Class II restricted epitopes for the following reasons. Firstly, when developing a minigene composed of, or containing, human epitopes, which are typically tested for immunogenicity in HLA transgenic laboratory animals, the creation of murine epitopes could create undesired immunodominance effects. Secondly, the creation of new, unintended epitopes for human HLA Class I or Class II molecules could elicit in vaccine recipients, new T cell specificities that are not expressed by infected cells or tumors that are the targets-induced T cell responses. These responses are by definition irrelevant and ineffective and could even be counterproductive, by creating undesired immunodominance effects.

The existence of junctional epitopes has been documented in a variety of different experimental situations. Gefter and collaborators first demonstrated the effect in a system in which two different Class II restricted epitopes were juxtaposed and colinearly synthesized (Perkins et al., *J Immunol*, Vol. 146(7):2137-44 (1991)). The effect was so marked that the immune system recognition of the epitopes could be completely "silenced" by these new junctional epitopes (Wang et al., *Cell Immunol*, Vol. 143(2):284-97 (1992)). Helper T cells directed against junctional epitopes were also observed in humans as a result of immunization with a synthetic lipopeptide, which was composed of an HLA-A2-restricted HBV-derived immunodominant CTL epitope, and a universal Tetanus Toxoid-derived HTL epitope (Livingston et al, *J Immunol*, Vol. 159(3):1383-92 (1997)). Thus, the creation of junctional epitopes are a major consideration in the design of multi-epitope constructs.

The present invention provides methods of addressing this problem and avoiding or minimizing the occurrence of junctional epitopes.

Flanking Regions

Class I restricted epitopes are generated by a complex process (Yewdell et al., *Annu Rev Immunol*, 17:51-88 (1999)). Limited proteolysis involving endoproteases and potential trimming by exoproteases is followed by translocation across the endoplasmic reticulum (ER) membrane by transporters associated with antigen processing (TAP) molecules. The major cytosolic protease complex involved in generation of antigenic peptides, and their precursors, is the proteosome (Niedermann et al., *Immunity*, Vol. 2(3):289-99 (1995)), although ER trimming of CTL precursors has also been demonstrated (Paz et al., *Immunity* Vol. 11(2):241-51 (1999)). It has long been debated whether or not the residues immediately flanking the C and N terminus of the epitope, have an influence on the efficiency of epitope generation.

The yield and availability of processed epitope has been implicated as a major variable in determining immunogenicity and could thus clearly have a major impact on overall minigene potency in that the magnitude of immune response can be directly proportional to the amount of epitope bound by MHC and displayed for T cell recognition. Several studies have provided evidence that this is indeed the case. For example, induction of virus-specific CTL that is essentially proportional to epitope density (Wherry et al., *J Immunol*, Vol. 163(7):3735-45 (1999)) has been observed. Further, recombinant minigenes, which encode a preprocessed optimal epitope, have been used to induce higher levels of epitope expression than naturally observed with full-length protein (Anton et al., *J Immunol*, Vol. 158(6):2535-42 (1997)). In general, minigene priming has been shown to be more effective than priming with the whole antigen (Restifo et al., *J Immunol*, Vol. 154(9):4414-22 (1995); Ishioka et al., *J Immunol*, Vol. 162(7):3915-25 (1999)), even though some exceptions have been noted (Iwasaki et al., *Vaccine*, Vol. 17(15-16): 2081-8 (1999)).

Early studies concluded that residues within the epitope (Hahn et al., *J Exp Med*, Vol. 176(5):1335-41 (1992)) primarily regulate immunogenicity. Similar conclusions were reached by other studies, mostly based on grafting an epitope in an unrelated gene, or in the same gene, but in a different location (Chimini et al., *J Exp Med*, Vol. 169(1):297-302 (1989); Hahn et al., *J Exp Med*, Vol. 174(3):733-6 (1991)). Other experiments however (Del Val et al., *Cell*, Vol. 66(6): 1145-53 (1991); Hahn et al., *J Exp Med*, Vol. 176(5):1335-41 (1992)), suggested that residues localized directly adjacent to the CTL epitope can directly influence recognition (Couillin et al., *J Exp Med*, Vol. 180(3):1129-34 (1994); Bergmann et al., *J Virol*. Vol. 68(8):5306-10 (1994)). In the context of minigene vaccines, the controversy has been renewed. Shastri and coworkers (Shastri et al., *J Immunol*, Vol. 155(9):4339-46 (1995)) found that T cell responses were not significantly affected by varying the N-terminal flanking residue but were inhibited by the addition of a single C-terminal flanking residue. The most dramatic inhibition was observed with isoleucine, leucine, cysteine, and proline as the C-terminal flanking residues. In contrast, Gileadi (Gileadi et al., *Eur J Immunol*, Vol. 29(7):2213-22 (1999)) reported profound effects as a function of the residues located at the N terminus of mouse influenza virus epitopes. Bergmann and coworkers found that aromatic, basic and alanine residues supported efficient epitope recognition, while G and P residues were strongly inhibitory (Bergmann et al., *J Immunol*, Vol. 157(8):3242-9 (1996)). In contrast, Lippolis (Lippolis et al., *J Virol*, Vol. 69(5):3134-46 (1995)) concluded that substituting flanking residues did not effect recognition. However, only rather conservative substitutions which are unlikely to affect proteosome specificity, were tested.

It appears that the specificity of these effects, and in general of natural epitopes, roughly correlates with proteosome specificity. For example, proteosome specificity is partly trypsin-like (Niedermann et al., *Immunity*, Vol. 2(3):289-99 (1995)), with cleavage following basic amino acids. Nevertheless, efficient cleavage of the carboxyl side of hydrophobic and acidic residues is also possible. Consistent with these specificities are the studies of Sherman and collaborators, which found that an R to H mutation at the position following the C-terminus of a p53 epitope affects proteosome-mediated processing of the protein (Theobald et al., *J Exp Med*, Vol. 188(6):1017-28 (1998)). Several other studies (Hanke et al., *J Gen Virol*, Vol. 79 (Pt 1):83-90 (1998); Thomson et al., *Proc Natl Acad Sci* USA, Vol. 92(13):5845-9 (1995)) indicated that minigenes can be constructed utilizing minimal epitopes, and that these flanking sequences appear not be required, although the potential for further optimization by the use of flanking regions was also acknowledged.

In sum, for HLA Class I epitopes, the effects of flanking regions on processing and presentation of CTL epitopes is as yet undefined. A systematic analysis of the effect of modulation of flanking regions has not been performed for minigene vaccines. Thus, analysis utilizing minigene vaccines encoding epitopes restricted by human Class I in general is needed. The present invention provides such an analysis and accordingly, provides multi-epitope vaccine constructs optimized for immunogenicity and antigenicity, and methods of designing such constructs.

HLA Class II peptide complexes are also generated as a result of a complex series of events that is distinct from HLA Class I processing. The processing pathway involves association with Invariant chain (Ii), its transport to specialized compartments, the degradation of Ii to CLIP, and HLA-DM catalyzed removal of CLIP (see (Blum et al., *Crit Rev Immunol*, Vol. 17(5-6):411-7 (1997); Arndt et al., *Immunol Res*, Vol. 16(3):261-72 (1997)) for review. Moreover, there is a potentially crucial role of various cathepsins in general, and cathepsin S and L in particular, in Ii degradation (Nakagawa et al., *Immunity*, Vol. 10(2):207-17 (1999)). In terms of generation of functional epitopes however, the process appears to be somewhat less selective (Chapman H. A., *Curr Opin Immunol*, Vol. 10(1):93-102 (1998)), and peptides of many sizes can bind to MHC Class IMHC Class II (Hunt et al., *Science*, Vol. 256(5065):1817-20 (1992)). Most or all of the possible peptides appear to be generated (Moudgil et al., *J Immunol*, Vol. 159(6):2574-9 (1997); and Thomson et al., *J Virol*, Vol. 72(3):2246-52 (1998)). Thus, as compared to the issue of flanking regions, the creation of junctional epitopes can be a more serious concern in particular embodiments.

SUMMARY OF THE INVENTION

The invention provides a method and system for optimizing the efficacy of multi-epitope vaccines so as to minimize the number of junctional epitopes and maximize, or at least increase, the immunogenicity and/or antigenicity of multiepitope vaccines. Also disclosed are multi-epitope constructs and nucleicic acids encoding such constructs (minigenes).

In one embodiment of the invention, a computerized method for designing a multi-epitope construct having multiple epitopes includes the steps of: storing a plurality of input parameters in a memory of a computer system, the input parameters including a plurality of epitopes, at least one motif for identifying junctional epitopes, a plurality of amino acid insertions and at least one enhancement weight value for each insertion; generating a list of epitope pairs from the plurality of epitopes; determining for each epitope pair at least one optimum combination of amino acid insertions based on the at least one motif, the plurality of insertions and the at least one enhancement weight value for each insertion; and identifying at least one optimum arrangement of the plurality of epitopes, wherein a respective one of the at least one optimum combination of amino acid insertions is inserted at a respective junction of two epitopes, so as to provide an optimized multi-epitope construct. In a preferred embodiment, the step of identifying at least one optimum arrangement of epitopes may be accomplished by performing either an exhaustive search wherein all permutations of arrangements of the plurality of epitopes are evaluated or a stochastic search wherein only a subset of all permutations of arrangements of the plurality of epitopes are evaluated.

In a further embodiment, the method determines for each epitope pair at least one optimum combination of amino acid insertions by calculating a function value (F) for each possible combination of insertions for each epitope pair, wherein the number of insertions in a combination may range from 0 to a maximum number of insertions (MaxInsertions) value input by a user, and the function value is calculated in accordance with the equation $F=(C+N)/J$, when $J>0$, and $F=2(C+N)$, when $J=0$, wherein C equals the enhancement weight value of a C+1 flanking amino acid, N equals the enhancement weight value of an N−1 flanking amino acid, and J equals the number of junctional epitopes detected for each respective combination of insertions in an epitope pair based on said at least one motif.

In another embodiment of the invention, a computer system for designing a multi-epitope construct having multiple epitopes, includes: a memory for storing a plurality of input parameters such as a plurality of epitopes, at least one motif for identifying junctional epitopes, a plurality of amino acid insertions and at least one enhancement weight value for each insertion; a processor for retrieving the input parameters from memory and generating a list of epitope pairs from the plurality of epitopes; wherein the processor further determines for each epitope pair at least one optimum combination of amino acid insertions, based on the at least one motif, the plurality of insertions and the at least one enhancement weight value for each insertion. The processor further identifies at least one optimum arrangement of the plurality of epitopes, wherein a respective one of the optimum combinations of amino acid insertions are inserted at a respective junction of two epitopes, to provide an optimized multi-epitope construct; and a display monitor, coupled to the processor, for displaying at least one optimum arrangement of the plurality of epitopes to a user.

In a further embodiment, the invention provides a data storage device storing a computer program for designing a multi-epitope construct having multiple epitopes, the computer program, when executed by a computer system, performing a process that includes the steps of: retrieving a plurality of input parameters from a memory of a computer system, the input parameters including, for example, a plurality of epitopes, at least one motif for identifying junctional epitopes, a plurality of amino acid insertions and at least one enhancement weight value for each insertion; generating a list of epitope pairs from the plurality of epitopes; determining for each epitope pair at least one optimum combination of amino acid insertions based on the at least one motif, the plurality of insertions and the at least one enhancement weight value for each insertion; and identifying at least one optimum arrangement of the plurality of epitopes, wherein a respective one of the at least one optimum combination of amino acid insertions is inserted at a respective junction of two epitopes, so as to provide an optimized multi-epitope construct.

In another embodiment, the invention provides a method and system for designing a multi-epitope construct that comprises multiple epitopes. The method comprising steps of: (i) sorting the multiple epitopes to minimize the number of junctional epitopes; (ii) introducing a flanking amino acid residue at a C+1 position of an epitope to be included within the multi-epitope construct; (iii) introducing one or more amino acid spacer residues between two epitopes of the multi-epitope construct, wherein the spacer prevents the occurrence of a junctional epitope; and, (iv) selecting one or more multi-epitope constructs that have a minimal number of junctional epitopes, a minimal number of amino acid spacer residues, and a maximum number of flanking amino acid residues at a C+1 position relative to each epitope. In some embodiments, the spacer residues are independently selected from residues that are not known HLA Class II primary anchor residues. In particular embodiments, introducing the spacer residues prevents the occurrence of an HTL epitope. Such a spacer often comprises at least 5 amino acid residues independently selected from the group consisting of G, P, and N. In some embodiments the spacer is GPGPG (SEQ ID NO:369).

In some embodiments, introducing the spacer residues prevents the occurrence of a CTL epitope and further, wherein the spacer is 1, 2, 3, 4, 5, 6, 7, or 8 amino acid residues independently selected from the group consisting of A and G. Often, the flanking residue is introduced at the C+1 position of a CTL epitope and is selected from the group consisting of K, R, N, G, and A. In some embodiments, the flanking residue is adjacent to the spacer sequence. The method of the invention can also include substituting an N-terminal residue of an epitope that is adjacent to a C-terminus of an adjacent epitope within the multi-epitope construct with a residue selected from the group consisting of K, R, N, G, and A.

In some embodiments, the method of the invention can also further comprise a step of predicting a structure of the multi-epitope construct, and further, selecting one or more constructs that have a maximal structure, i.e., that are processed by an HLA processing pathway to produce all of the epitopes comprised by the construct. Often, the epitopes comprised by the multi-epitope construct are encoded by a minigene. In some embodiments, the multi-epitope construct encoded by the minigene is EP-HIV-1090 as set out in FIG. 9, HIV-CPT as set out in FIG. 9, or HIV-TC as set out in FIG. 9.

In another embodiment of the invention, a system for optimizing multi-epitope minigenes includes a computer system having a processor (e.g., central processing unit) and at least one memory coupled to the processor for storing instructions executed by the processor and data to be manipulated (i.e., processed) by the processor. The computer system further includes an input device (e.g., keyboard) coupled to the processor and the at least one memory for allowing a user to input desired parameters and information to be accessed by the processor. The processor may be a single CPU or a plurality of different processing devices/circuits integrated onto a single integrated circuit chip. Alternatively, the processor may be a collection of discrete processing devices/circuits selectively coupled to one another via either direct wire/conductor connections or via a data bus. Similarly, the at least one memory may be one large memory device (e.g., EPROM), or a collection of a plurality of discrete memory devices (e.g., EEPROM, EPROM, RAM, DRAM, SDRAM, Flash, etc.) selectively coupled to one another for selectively storing data and/or program information (i.e., instructions executed by the processor). Those of ordinary skill in the art would easily be able to implement a desired computer system architecture to perform the operations and functions disclosed herein.

In one embodiment, the computer system includes a display monitor for displaying information, instructions, images, graphics, etc. The computer system receives user inputs via a keyboard. These user input parameters may include, for example, the number of insertions (i.e., flanking residues and spacer residues), the peptides to be processed, the C+1 and N−1 weighting values for each amino acid, and the motifs to use for searching for junctional epitopes. Based on these input values/parameters, the computer system executes a "Junctional Analyzer" software program which automatically determines the number of junctional epitope for each peptide pair and also calculates an "enhancement" value for each combination of flanking residues and spacers that may be inserted at the junction of each peptide pair. The results of the junctional analyzer program are then used in either an exhaustive or stochastic search program which determines the "optimal" combination or linkage of the entire set of peptides to create a multi-epitope polypeptide, or minigene, having a minimal number of junctional epitopes and a maximum functional (e.g., immunogenicity) value.

In one embodiment, if the number of peptides to be processed by the computer system is less than fourteen, an exhaustive search program is executed by the computer system which examines all permutations of the peptides making up the polypeptide to find the permutation with the "best" or "optimal" function value. In one embodiment, the function value is calculated using the equation $(Ce+Ne)/J$ when J is greater than zero and $2*(Ce+Ne)$ when J is equal to zero, where Ce is the enhancement "weight" value of an amino acid at the C+1 position of a peptide, Ne is the enhancement "weight" value of an amino acid at the N−1 position of a peptide, and J is the number of junctional epitopes contained in the polypeptide minigene. Thus, maximizing this function value will identify the peptide pairs having the least number of junctional epitopes and the maximum enhancement weight value for flanking residues. If the number of peptides to be processed is fourteen or more, the computer system executes a stochastic search program that uses a "Monte Carlo" technique to examine many regions of the permutation space to find the best estimate of the optimum arrangement of peptides (e.g., having the maximum function value).

In a further embodiment, the computer system allows a user to input parameter values which format or limit the output results of the exhaustive or stochastic search program. For example, a user may input the maximum number of results having the same function value ("MaxDuplicateFunctionValue=X") to limit the number of permutations that are generated as a result of the search. Since it is possible for the search programs to find many arrangements that give the same function value, it may be desirable to prevent the output file from being filled by a large number of equivalent solutions. Once this limit is reached no more results are reported until a larger or "better" function value is found. As another example, the user may input the maximum number of "hits" per probe during a stochastic search process. This parameter prevents the stochastic search program from generating too much output on a single probe. In a preferred embodiment, the number of permutations examined in a single probe is limited by several factors: the amount of time set for each probe in the input text file; the speed of the computer, and the values of the parameters "MaxHitsPerProbe" and "MaxDuplicateFunctionValues." The algorithms used to generate and select permutations for analysis may be in accordance with well-known recursive algorithms found in many computer science text books. For example, six permutations of three things taken three at a time would be generated in the following sequence: ABC; ACB; BAC; BCA; CBA; CAB. As a further example of an input parameter, a user may input how the stochastic search is performed, e.g., randomly, statistically or other methodology; the maximum time allowed for each probe (e.g., 5 minutes); and the number of probes to perform.

Also disclosed herein are multi-epitope constructs designed by the methods described above and hereafter. The multi-epitope constructs include spacer nucleic acids between a subset of the epitope nucleic acids or all of the epitope nucleic acids. One or more of the spacer nucleic acids may encode amino acid sequences different from amino acid sequences encoded by other spacer nucleic acids to optimize epitope processing and to minimize the presence of junctional epitopes.

DEFINITIONS

The following definitions are provided to enable one of ordinary skill in the art to understand some of the preferred embodiments of invention disclosed herein. It is understood, however, that these definitions are exemplary only and should not be used to limit the scope of the invention as set forth in the claims. Those of ordinary skill in the art will be able to construct slight modifications to the definitions below and utilize such modified definitions to understand and practice the invention disclosed herein. Such modifications, which would be obvious to one of ordinary skill in the art, as they may be applicable to the claims set forth below, are considered to be within the scope of the present invention.

Throughout this disclosure, "binding data" results are often expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand. Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide. Binding may also be determined using other assay systems including those using: live cells (e.g., Ceppellini et al., *Nature* 339:392, 1989; Christnick et al., *Nature* 352:67, 1991; Busch et al., *Int.*

*Immunol.* 2:443, 19990;Hill et al., *J. Immunol.* 147:189,1991; del Guercio et al., *J. Immunol.* 154:685, 1995), cell free systems using detergent lysates (e.g., Cerundolo et al., *J. Immunol.* 21:2069, 1991), immobilized purified MHC (e.g., Hill et al., *J. Immunol.* 152, 2890, 1994; Marshall et al., *J. Immunol.* 152:4946, 1994), ELISA systems (e.g., Reay et al., *EMBO J.* 11:2829, 1992), surface plasmon resonance (e.g., Khilko et al., *J. Biol. Chem.* 268:15425, 1993); high flux soluble phase assays (Hammer et al., *J. Exp. Med.* 180:2353, 1994), and measurement of class I MHC stabilization or assembly (e.g., Ljunggren et al., *Nature* 346:476, 1990; Schumacher et al., *Cell* 62:563, 1990; Townsend et al., *Cell* 62:285, 1990; Parker et al., *J. Immunol.* 149:1896, 1992).

The designation of a residue position in an epitope as the "carboxyl terminus" or the "carboxyl terminal position" refers to the residue position at the end of the epitope that is nearest to the carboxyl terminus of a peptide, which is designated using conventional nomenclature as defined below. "C+1" refers to the residue or position immediately following the C-terminal residue of the epitope, ie., refers to the residue flanking the C-terminus of the epitope. The "carboxyl terminal position" of the epitope occurring at the carboxyl end of the multi-epitope construct may or may not actually correspond to the carboxyl terminal end of polypeptide. In preferred embodiments, the epitopes employed in the optimized multi-epitope constructs are motif-bearing epitopes and the carboxyl terminus of the epitope is defined with respect to primary anchor residues corresponding to a particular motif.

The designation of a residue position in an epitope as "amino terminus" or "amino-terminal position" refers to the residue position at the end of the epitope which is nearest to the amino terminus of a peptide, which is designated using conventional nomenclature as defined below. "N–1" refers to the residue or position immediately adjacent to the epitope at the amino terminal end (position number 1) of an eptiope. The "amino terminal position" of the epitope occurring at the amino terminal end of the multi-epitope construct may or may not actually corresponds to the amino terminal end of the polypeptide. In preferred embodiments, the epitopes employed in the optimized multi-epitope constructs are motif-bearing epitopes and the amino terminus of the epitope is defined with respect to primary anchor residues corresponding to a particular motif.

A "computer" or "computer system" generally includes: a processor; at least one information storage/retrieval apparatus such as, for example, a hard drive, a disk drive or a tape drive; at least one input apparatus such as, for example, a keyboard, a mouse, a touch screen, or a microphone; and display structure. Additionally, the computer may include a communication channel in communication with a network such that remote users may communicate with the computer via the network to perform minigene optimization functions disclosed herein. Such a computer may include more or less than what is listed above. The network may be a local area network (LAN), wide area network (WAN) or a global network such as the world wide web (e.g., the internet).

A "construct" as used herein generally denotes a composition that does not occur in nature. A construct can be produced by synthetic technologies, e.g., recombinant DNA preparation and expression or chemical synthetic techniques for nucleic or amino acids. A construct can also be produced by the addition or affiliation of one material with another such that the result is not found in nature in that form. A "multi-epitope construct" comprises multiple epitope nucleic acids that encode peptide epitopes of any length that can bind to a molecule functioning in the immune system, preferably a class I HLA and a T-cell receptor or a class II HLA and a T-cell receptor. All of the epitope nucleic acids in a multi-epitope construct can encode class I HLA epitopes or class II HLA epitopes. Class I HLA-encoding epitope nucleic acids are referred to as CTL epitope nucleic acids, and class II HLA-encoding epitope nucleic acids are referred to as HTL epitope nucleic acids. Some multi-epitope constructs can have a subset of the multi-epitope nucleic acids encoding class I HLA epitopes and another subset of the multi-epitope nucleic acids encoding class II HLA epitopes. The CTL epitope nucleic acids preferably encode an epitope peptide of about eight to about thirteen amino acids in length, more preferably about eight to about eleven amino acids in length, and most preferably about nine amino acids in length. The HTL epitope nucleic acids can encode an epitope peptide of about seven to about twenty three, preferably about seven to about seventeen, more preferably about eleven to about fifteen, and most preferably about thirteen amino acids in length. The multi-epitope constructs described herein preferably include five or more, ten or more, fifteen or more, twenty or more, or twenty-five or more epitope nucleic acids. All of the epitope nucleic acids in a multi-epitope construct may be from one organism (e.g., the nucleotide sequence of every epitope nucleic acid may be present in HIV strains), or the multi-epitope construct may include epitope nucleic acids present in two or more different organisms (e.g., some epitopes from HIV and some from HCV). As described hereafter, one or more epitope nucleic acids in the multi-epitope construct may be flanked by a spacer nucleic acid.

A "multi-epitope vaccine," which is synonyous with a "polyepitopic vaccine," is a vaccine comprising multiple epitopes.

"Cross-reactive binding" indicates that a peptide is bound by more than one HLA molecule; a synonym is "degenerate binding."

A "cryptic epitope" elicits a response by immunization with an isolated peptide, but the response is not cross-reactive in vitro when intact whole protein that comprises the epitope is used as an antigen.

A "dominant epitope" is an epitope that induces an immune response upon immunization with a whole native antigen (see, e.g., Sercarz, et al., *Annu. Rev. Immunol.* 11:729-766, 1993). Such a response is cross-reactive in vitro with an isolated peptide epitope.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the bounds of the invention.

A "flanking residue" is a residue that is positioned next to an epitope. A flanking residue can be introduced or inserted at a position adjacent to the N-terminus or the C-terminus of an epitope.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

"Heteroclitic analogs" are defined herein as a peptide with increased potency for a specific T cell, as measured by increased responses to a given dose, or by a requirement of lesser amounts to achieve the same response. Advantages of heteroclitic analogs include that the epitopes can be more potent, or more economical (since a lower amount is required to achieve the same effect). In addition, modified epitopes might overcome antigen-specific T cell unresponsiveness (T cell tolerance).

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994)).

An "HLA supertype or HLA family," as used herein, describes sets of HLA molecules grouped based on shared peptide-binding specificities. HLA class I molecules that share similar binding affinity for peptides bearing certain amino acid motifs are grouped into such HLA supertypes. The terms HLA superfamily, HLA supertype family, HLA family, and HLA xx-like molecules (where xx denotes a particular HLA type), are synonyms.

As used herein, "high affinity" with respect to HLA class I molecules is defined as binding with an $IC_{50}$, or $K_D$ value, of 50 nM or less; "intermediate affinity" with respect to HLA class I molecules is defined as binding with an $IC_{50}$ or $K_D$ value of between about 50 and about 500 nM. "High affinity" with respect to binding to HLA class II molecules is defined as binding with an $IC_{50}$ or $K_D$ value of 100 nM or less; "intermediate affinity" with respect to binding to HLA class II molecules is defined as binding with an $IC_{50}$ or $K_D$ value of between about 100 and about 1000 nM.

An "$IC_{50}$" is the concentration of peptide in a binding assay at which 50% inhibition of binding of a reference peptide is observed. Depending on the conditions in which the assays are run (i.e., limiting HLA proteins and labeled peptide concentrations), these values may approximate $K_D$ values.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

"Introducing" an amino acid residue at a particular position in a multi-epitope construct, e.g., adjacent, at the C-terminal side, to the C-terminus of the epitope, encompasses configuring multiple epitopes such that a desired residue is at a particular position, e.g., adjacent to the epitope, or such that a deleterious residue is not adjacent to the C-terminus of the epitope. The term also includes inserting an amino acid residue, preferably a preferred or intermediate amino acid residue, at a particular position. An amino acid residue can also be introduced into a sequence by substituting one amino acid residue for another. Preferably, such a substitution is made in accordance with analoging principles set forth, e.g., in U.S. Ser. No. 09/260,714 filed Mar. 1, 1999, now abandoned and PCT application number PCT/US00/19774.

The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

"Link" or "join" refers to any method known in the art for functionally connecting peptides, including, without limitation, recombinant fusion, covalent bonding, disulfide bonding, ionic bonding, hydrogen bonding, and electrostatic bonding.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, $3^{RD}$ ED., Raven Press, New York, 1993.

As used herein, "middle of the peptide" is a position in a peptide that is neither an amino or a carboxyl terminus.

A "minimal number of junctional epitopes" as used herein refers to a number of junctional epitopes that is lower than what would be created using a random selection criteria.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "negative binding residue" or "deleterious residue" is an amino acid which, if present at certain positions (typically not primary anchor positions) in a peptide epitope, results in decreased binding affinity of the peptide for the peptide's corresponding HLA molecule.

"Optimizing" refers to increasing the immunogenicity or antigenicity of a multi-epitope construct having at least one epitope pair by sorting epitopes to minimize the occurrence of junctional epitopes, inserting flanking residues that flank the C-terminus or N-terminus of an epitope, and inserting spacer residue to further prevent the occurrence of junctional epitopes or to provide a flanking residue. An increase in immunogenicity or antigenicity of an optimized multi-epitope construct is measured relative to a multi-epitope construct that has not been constructed based on the optimization parameters and is using assays known to those of skill in the art, e.g., assessment of immunogenicity in HLA transgenic mice, ELISPOT, interferon-gamma release assays, tetramer staining, chromium release assays, and presentation on dendritic cells.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing peptides of the invention are 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

A "PanDR binding peptide or PADRE® peptide" is a member of a family of molecules that binds more than one HLA class II DR molecule. The pattern that defines the PADRE® family of molecules can be thought of as an HLA Class II supermotif. PADRE® binds to most HLA-DR molecules and stimulates in vitro and in vivo human helper T lymphocyte (HTL) responses.

"Pharmaceutically acceptable" refers to a generally non-toxic, inert, and/or physiologically compatible composition.

"Presented to an HLA Class I processing pathway" means that the multi-epitope constructs are introduced into a cell such that they are largely processed by an HLA Class I processing pathway. Typically, multi-epitope constructs are introduced into the cells using expression vectors that encode the multi-epitope constructs. HLA Class II epitopes that are encoded by such a minigene are also presented on Class II molecules, although the mechanism of entry of the epitopes into the Class II processing pathway is not defined.

A "primary anchor residue" or a "primary MHC anchor" is an amino acid at a specific position along a peptide sequence that is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, for example, the primary anchor residues of an HLA class I epitope are located at position 2 (from the amino terminal position) and at the carboxyl terminal position of a 9-residue peptide epitope in accordance with the invention. The primary anchor positions for each motif and supermotif are described, for example, in Tables I and III of PCT/US00/27766, or PCT/US00/19774. Preferred amino acids that can serve as in the anchors for most Class II epitopes consist of M and F in position one and V, M, S, T, A and C in position six. Tolerated amino acids that can occupy these positions for most Class II epitopes consist of L, I, V, W, and Y in position one and P, L and I in position six. The presence of these amino acids in positions one and six in Class II epitopes defines the HLA-DR1, 4, 7 supermotif. The HLA-DR3 binding motif is defined by preferred amino acids from the group of L, I, V, M, F, Y and A in position one and D, E, N, Q, S and T in position four and K, R and H in position six. Other amino acids may be tolerated in these positions but they are not preferred.

Furthermore, analog peptides can be created by altering the presence or absence of particular residues in these primary anchor positions. Such analogs are used to modulate the binding affinity of a peptide comprising a particular motif or supermotif.

"Promiscuous recognition" occurs where a distinct peptide is recognized by the same T cell clone in the context of various HLA molecules. Promiscuous recognition or binding is synonymous with cross-reactive binding.

A "protective immune response" or "therapeutic immune response" refers to a CTL and/or an HTL response to an antigen derived from an infectious agent or a tumor antigen, which in some way prevents or at least partially arrests disease symptoms, side effects or progression. The immune response may also include an antibody response that has been facilitated by the stimulation of helper T cells.

The term "residue" refers to an amino acid or amino acid mimetic incorporated into a peptide or protein by an amide bond or amide bond mimetic.

A "secondary anchor residue" is an amino acid at a position other than a primary anchor position in a peptide that may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue which is present at a higher frequency among high or intermediate affinity binding peptides, or a residue otherwise associated with high or intermediate affinity binding. For example, analog peptides can be created by altering the presence or absence of particular residues in these secondary anchor positions. Such analogs are used to finely modulate the binding affinity of a peptide comprising a particular motif or supermotif. The terminology "fixed peptide" is sometimes used to refer to an analog peptide.

"Sorting epitopes" refers to determining or designing an order of the epitopes in a multi-epitope construct.

A "spacer" refers to a sequence that is inserted between two epitopes in a multi-epitope construct to prevent the occurrence of junctional epitopes and/or to increase the efficiency of processing. A multi-epitope construct may have one or more spacer nucleic acids. A spacer nucleic acid may flank each epitope nucleic acid in a construct, or the spacer nucleic acid to epitope nucleic acid ratio may be about 2 to 10, about 5 to 10, about 6 to 10, about 7 to 10, about 8 to 10, or about 9 to 10, where a ratio of about 8 to 10 has been determined to yield favorable results for some constructs.

The spacer nucleic acid may encode one or more amino acids. A spacer nucleic acid flanking a class I HLA epitope in a multi-epitope construct is preferably between one and about eight amino acids in length. A spacer nucleic acid flanking a class II HLA epitope in a multi-epitope construct is preferably greater than five, six, seven, or more amino acids in length, and more preferably five or six amino acids in length.

The number of spacers in a construct, the number of amino acids in a spacer, and the amino acid composition of a spacer can be selected to optimize epitope processing and/or minimize junctional epitopes. It is preferred that spacers are selected by concomitantly optimizing epitope processing and junctional motifs. Suitable amino acids for optimizing epitope processing are described herein. Also, suitable amino acid spacing for minimizing the number of junctional epitopes in a construct are described herein for class I and class II HLAs. For example, spacers flanking class II HLA epitopes preferably include G, P, and/or N residues as these are not generally known to be primary anchor residues (see, e.g., PCT/US00/19774). A particularly preferred spacer for flanking a class II HLA epitope includes alternating G and P residues, for example, $(GP)_n$, $(PG)_n$, $(GP)_nG$, $(PG)_nP$, and so forth, where n is an integer between one and ten, preferably two or about two, and where a specific example of such a spacer is GPGPG (SEQ ID NO:369).

In some multi-epitope constructs, it is sufficient that each spacer nucleic acid encodes the same amino acid sequence. In multi-epitope constructs having two spacer nucleic acids encoding the same amino acid sequence, the spacer nucleic acids encoding those spacers may have the same or different nucleotide sequences, where different nucleotide sequences may be preferred to decrease the likelihood of unintended recombination events when the multi-epitope construct is inserted into cells.

In other multi-epitope constructs, one or more of the spacer nucleic acids may encode different amino acid sequences. While many of the spacer nucleic acids may encode the same amino acid sequence in a multi-epitope construct, one, two, three, four, five or more spacer nucleic acids may encode different amino acid sequences, and it is possible that all of the spacer nucleic acids in a multi-epitope construct encode different amino acid sequences. Spacer nucleic acids may be optimized with respect to the epitope nucleic acids they flank by determining whether a spacer sequence will maximize epitope processing and/or minimize junctional epitopes, as described herein.

Multi-epitope constructs may be distinguished from one another according to whether the spacers in one construct optimize epitope processing or minimize junctional epitopes over another construct, and preferably, constructs may be distinguished where one construct is concomitantly optimized for epitope processing and junctional epitopes over the other. Computer assisted methods and in vitro and in vivo laboratory methods for determining whether a construct is optimized for epitope processing and junctional motifs are described herein.

A "subdominant epitope" is an epitope which evokes little or no response upon immunization with whole antigens which comprise the epitope, but for which a response can be obtained by immunization with an isolated epitope, and this response (unlike the case of cryptic epitopes) is detected when whole protein is used to recall the response in vitro or in vivo.

A "supermotif" is an amino acid sequence for a peptide that provides binding specificity shared by HLA molecules encoded by two or more HLA alleles. Preferably, a supermotif-bearing peptide is recognized with high or intermediate affinity (as defined herein) by two or more HLA antigens.

"Synthetic peptide" refers to a peptide that is not naturally occurring, but is man-made using such methods as chemical synthesis or recombinant DNA technology.

A "TCR contact residue" or "T cell receptor contact residue" is an amino acid residue in an epitope that is understood to be bound by a T cell receptor; these are defined herein as not being any primary MHC anchor. T cell receptor contact residues are defined as the position/positions in the peptide where all analogs tested induce T-cell recognition relative to that induced with a wildtype peptide.

The term "homology," as used herein, refers to a degree of complementarity between two nucleotide sequences. The word "identity" may substitute for the word "homology" when a nucleic acid has the same nucleotide sequence as another nucleic acid. Sequence homology and sequence identity can also be determined by hybridization studies under high stringency and/or low stringency, and disclosed herein are nucleic acids that hybridize to the multi-epitope constructs under low stringency or under high stringency. Also, sequence homology and sequence identity can be determined by analyzing sequences using algorithms and computer programs known in the art. Such methods be used to assess whether a nucleic acid is identical or homologous to the multi-epitope constructs disclosed herein. The invention pertains in part to nucleotide sequences having 80% or more, 85% or more, 90% or more, 95% or more, 97% or more, 98% or more, or 99% or more identity to the nucleotide sequence of a multi-epitope construct disclosed herein.

As used herein, the term "stringent conditions" refers to conditions which permit hybridization between nucleotide sequences and the nucleotide sequences of the disclosed multi-epitope constructs. Suitable stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. In particular, hybridization could occur under high stringency conditions at 42° C. in 50% formamide, 5× SSPE, 0.3% SDS, and 200 µg/ml sheared and denatured salmon sperm DNA or at 42° C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. Hybridization could occur under reduced stringency conditions in about 35% to 25% formamide at about 30° C. to 35° C. For example, reduced stringency conditions could occur at 35° C. in 35% formamide, 5× SSPE, 0.3% SDS, and 200 µg/ml sheared and denatured salmon sperm DNA. The temperature range corresponding to a particular level of stringency can be further narrowed by calculating the purine to pyrimidine ratio of the nucleic acid of interest and adjusting the temperature accordingly. Variations on the above ranges and conditions are well known in the art.

In addition to utilizing hybridization studies to assess sequence identity or sequence homology, known computer programs may be used to determine whether a particular nucleic acid is homologous to a multi-epitope construct disclosed herein. An example of such a program is the Bestfit program (Wisconsin Sequence Analysis Package, Version 8 for Unix, Genetics Computer Group, University Research Park, 575 Science Drive, Madison, Wis. 53711), and other sequence alignment programs are known in the art and may be utilized for determining whether two or more nucleotide sequences are homologous. Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence, the parameters may be set such that the percentage of identity is calculated over the full length of the reference nucleotide sequence and that gaps in homology of up to 5% of the total number of nucleotides in the reference sequence are allowed.

The nomenclature used to describe peptide compounds follows the conventional practice wherein the amino group is presented to the left (the N-terminus) and the carboxyl group to the right (the C-terminus) of each amino acid residue. When amino acid residue positions are referred to in an epitope, they are numbered in an amino to carboxyl direction with position one being the position closest to the amino terminal end of the epitope, or the peptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three-letter or single-letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for the amino acids are shown below.

| Single Letter Symbol | Three Letter Symbol | Amino Acids |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |

-continued

| Single Letter Symbol | Three Letter Symbol | Amino Acids |
| --- | --- | --- |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Amino acid "chemical characteristics" are defined as: Aromatic (F,W,Y); Aliphatic-hydrophobic (L, I, V, M); Small polar (S, T, C); Large polar (Q, N); Acidic (D, E); Basic (R, H, K); Proline; Alanine; and Glycine.

Acronyms used herein are as follows:
APC: Antigen presenting cell
CD3: Pan T cell marker
CD4: Helper T lymphocyte marker
CD8: Cytotoxic T lymphocyte marker
CEA: Carcinoembryonic antigen
CFA: Complete Freund's Adjuvant
CTL: Cytotoxic T lymphocytes
DC: Dendritic cells. DC functioned as potent antigen presenting cells by stimulating cytokine release from CTL lines that were specific for a model peptide derived from hepatitis B virus (HBV). In vitro experiments using DC pulsed ex vivo with an HBV peptide epitope have stimulated CTL immune responses in vitro following delivery to naïve mice.
DMSO: Dimethylsulfoxide
ELISA: Enzyme-linked immunosorbant assay
E:T: Effector:target ratio
FCS: Fetal calf serum
G-CSF: Granulocyte colony-stimulating factor
GM-CSF: Granulocyte-macrophage (monocyte)-colony stimulating factor
HBV: Hepatitis B virus
HER2/Neu: c-erbB-2
HLA: Human leukocyte antigen
HLA-DR: Human leukocyte antigen class II
HPLC: High Performance Liquid Chromatography
HTC: Helper T cells
HTL: Helper T Lymphocyte
ID: Identity
IFA: Incomplete Freund's Adjuvant
IFNγ: Interferon gamma
IL-4: Interleukin-4 cytokine
IV: Intravenous
$LU_{30\%}$: Cytotoxic activity required to achieve 30% lysis at a 100:1 (E:T) ratio
MAb: Monoclonal antibody
MAGE: Melanoma antigen
MLR: Mixed lymphocyte reaction
MNC: Mononuclear cells
PB: Peripheral blood
PBMC: Peripheral blood mononuclear cell
SC: Subcutaneous
S.E.M.: Standard error of the mean
QD: Once a day dosing
TAA: Tumor associated antigen
TCR: T cell receptor
TNF: Tumor necrosis factor
WBC: White blood cells This application may be relevant to U.S. Ser. No. 09/189,702 filed Nov. 10, 1998, currently pending, which is a CIP of U.S. Ser. No. 08/205,713 filed Mar. 4, 1994 now abandoned, which is a CIP of Ser. No. 08/159,184 filed Nov. 29, 1993 and now abandoned, which is a CIP of Ser. No. 08/073,205 filed Jun. 4, 1993 and now abandoned, which is a CIP of Ser. No. 08/027,146 filed Mar. 5, 1993 and now abandoned. The present application is also related to U.S. Ser. No. 09/226,775 now abandoned, which is a CIP of U.S. Ser. No. 08/815,396 now abandoned, which claims the benefit of U.S. Ser. No. 60/013,113, now abandoned. Furthermore, the present application is related to U.S. Ser. No. 09/017,735 now abandoned, which is a CIP of abandoned U.S. Ser. Nos. 08/589,108; 08/753,622 now abandoned, U.S. Ser. No. 08/822,382 now abandoned, abandoned U.S. Ser. Nos. 60/013,980, 08/454,033 now abandoned, U.S. Ser. No. 09/116,424 now abandoned, and U.S. Ser. No. 08/349,177 now abandoned. The present application is also related to U.S. Ser. No. 09/017,524 now abandoned, U.S. Ser. No. 08/821,739 now abandoned, abandoned U.S. Ser. Nos. 60/013,833, 08/758,409 now abandoned, U.S. Ser. No. 08/589,107 now abandoned, U.S. Ser. No. 08/451,913 now abandoned, U.S. Ser. No. 08/186,266 now U.S. Pat. No. 5,662,907, U.S. Ser. No. 09/116,061 now abandoned, and U.S. Ser. No. 08/347,610 now abandoned, which is a CIP of U.S. Ser. No. 08/159,339 now U.S. Pat. No. 6,037,135, which is a CIP of abandoned U.S. Ser. No. 08/103,396, which is a CIP of abandoned U.S. Ser. No. 08/027,746, which is a CIP of abandoned U.S. Ser. No. 07/926,666. The present application may also be relevant to U.S. Ser. No. 09/017,743 now abandoned, U.S. Ser. No. 08/753,615 now abandoned; U.S. Ser. No. 08/590,298 now abandoned, U.S. Ser. No. 09/115,400 now abandoned, and U.S. Ser. No. 08/452,843 now abandoned, which is a CIP of U.S. Ser. No. 08/344,824 now abandoned, which is a CIP of abandoned U.S. Ser. No. 08/278,634. The present application may also be related to provisional U.S. Ser. No. 60/087,192 now abandoned and U.S. Ser. No. 09/009,953 now abandoned, which is a CIP of abandoned U.S. Ser. No. 60/036,713 and abandoned U.S. Ser. No. 60/037,432. In addition, the present application may be relevant to U.S. Ser. No. 09/098,584 now abandoned, and U.S. Ser. No. 09/239,043 now U.S. Pat. No. 6,689,363. The present application may also be relevant to co-pending U.S. Ser. No. 09/583,200 filed May 30, 2000 currently pending, U.S. Ser. No. 09/260,714 filed Mar. 1, 1999 now abandoned, and U.S. Provisional Application 60/239,008, now abandoned. All of the above applications are incorporated herein by reference.

BRIEF DESCRIPTION OF THE DRAWINGS

FIG. 1 illustrates data on three different multi-epitope constructs, incorporating 20 to 25 different CTL epitopes each.

FIG. 2b illustrates the capacity of 2 nanomoles of these different constructs to prime for proliferative responses to the various epitopes in $IA^b$ positive mice, compared to the responses induced by equimolar amounts of a pool of the same peptides (3 micrograms of each peptide).

FIGS. 11A-B illustrate an exemplary input text file containing user input parameters used for executing a Junctional Analyzer program, in accordance with one embodiment of the invention. (SEQ ID NOS: 70-80; SEQ ID NOS: 7-22; SEQ ID NOS: 27-34; SEQ ID NOS: 59-68 and SEQ ID NOS: 341-368).

FIGS. 13A-D illustrate an exemplary output text file containing output results of a Junctional Analyzer program, in accordance with one embodiment of the invention (SEQ ID NOS: 7-22; SEQ ID NOS: 27-34; SEQ ID NOS: 59-68; SEQ ID NOS: 341-368 and SEQ ID NOS: 70-80).

FIG. 17 is a schematic depicting the epitopes present in HIV 75mer, EP-HIV-1043, and EP-HIV-1043-PADRE®.

FIGS. 18A-N show the amino acid sequences and nucleic acid sequences of certain multi-epitope constructs (SEQ ID NOS: 81-142).

FIGS. 19A-D show the amino acid sequences for epitopes present in certain multi-epitope constructs (SEQ ID NOS: 143-340).

DETAILED DESCRIPTION OF THE PREFERRED EMBODIMENTS

Figure 2:
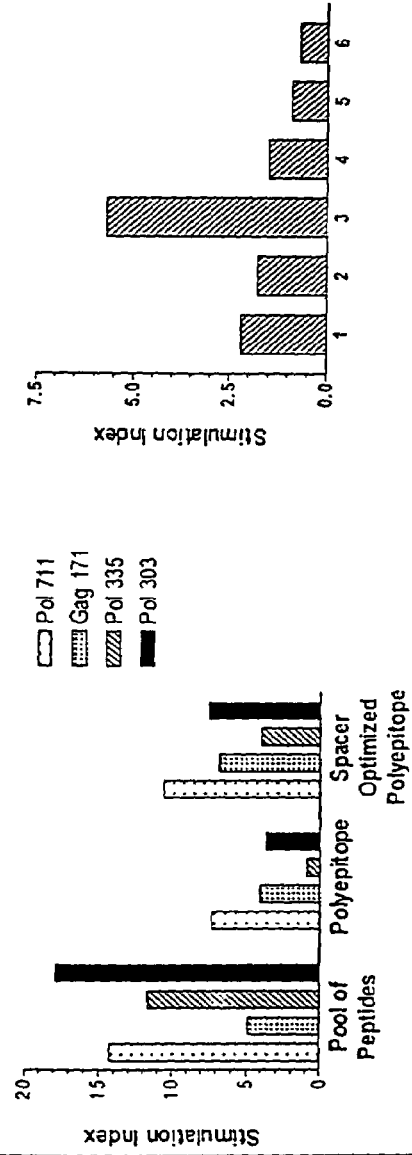
FIG. 2 illustrates two different synthetic polypeptides (FIG. 2a) where the first construct incorporates four different epitopes linearly cosynthesized, and the second construct incorporates a GPGPG (SEQ ID NO: 369) spacer.

The invention is described in detail below with reference to the figures wherein like elements are referenced with like numerals throughout. The invention relates to a method and system of designing multi-epitope vaccines with optimized immunogenicity. In preferred embodiments, the vaccine comprises CTL and HTL epitopes. Vaccines in accordance with the invention allow for significant, non-ethnically biased population coverage, and can preferably focus on epitopes conserved amongst different viral or other antigenic isolates. Through the method and system disclosed herein, vaccines can be optimized with regard to the magnitude and breadth of responses, and can allow for the simplest epitope configuration. Finally, general methods are provided to evaluate immunogenicity of a multi-epitope vaccine in humans.

The method of the invention comprises designing a multi-epitope construct based on principles identified herein. In one aspect, the invention provides for simultaneous induction of responses against specific CTL and HTL epitopes, using single promoter minigene vaccines. Such minigene constructs can contain many different epitopes, preferably greater than 10, often greater than 20, 25, 30, 25, 40, 45, 50, 55, 60, 65, 70, or more.

In a preferred embodiment, a computer system identifies one or more optimal multi-epitope constructs for a minigene by performing the following functions and/or analyses:

(i) the epitopes to be incorporated into the multi-epitope construct are sorted to provide an order that minimizes the number of junctional epitopes formed. A more detailed discussion of this sorting procedure is provided below with reference to FIGS. 11 and 12. Preferably, as a secondary consideration in ordering epitopes, epitopes are positioned such that residues at the N-terminus of an epitope that promote CTL immunogenicity are juxtaposed to the C-terminus of another CTL epitope.

(ii) flanking residues that enhance immunogenicity may be inserted at the flanking positions of epitopes. In particular embodiments, flanking residues are inserted at the C+1 position of CTL epitopes.

(iii) spacer sequences may be inserted between epitopes to prevent occurance of junctional epitopes. In particular embodiments, the spacer sequences can also include a residue that promotes immunogenicity at the N-terminus of the linker such that the residue flanks the C-terminus of a CTL epitope.

In particular embodiments to prevent HTL junctional epitopes, a spacer composed of amino acid residues that do not correspond to any known HLA Class II anchor residue, are used, e.g, alternating G and P residues (a GP spacer) is included between two HTL epitopes.

Another aspect of the invention, (consideration (ii) above) involves the introduction or substitution of particular amino acid residues at positions that flank epitopes, e.g., a position immediately adjacent to the C-terminus of the epitope, thereby generating multi-epitope constructs with enhanced antigenicity and immunogenicity compared to constructs that do not contain the particular residue introduced or substituted at that site, i.e., non-optimized minigenes. The methods of optimizing multi-epitope constructs comprise a step of introducing a flanking residue, preferably K, N, G, R, or A at the C+1 position of the epitope, i.e., the position immediately adjacent to the C-terminus of the epitope. In an alternative embodiment, residues that contribute to decreased immunogenicity, i.e., negatively charged residues, e.g., D, aliphatic residues (I, L, M, V) or aromatic non-trytophan residues, are replaced. The flanking residue can be introduced by positioning appropriate epitopes to provide the favorable flanking residue, or by inserting a specific residue.

As noted in the background section, minigenes encoding up to 10 epitopes have been used to induce responses against a number of different epitopes. The data relating to an experimental minigene, pMin .1 has been published (Ishioka et al., *J Immunol*, Vol. 162(7):3915-25 (1999)). Disclosed herein, are parameters for designing and evaluating multi-epitope constructs with optimized immunogenicity that address myriad disease indications of interest.

Figure 1:
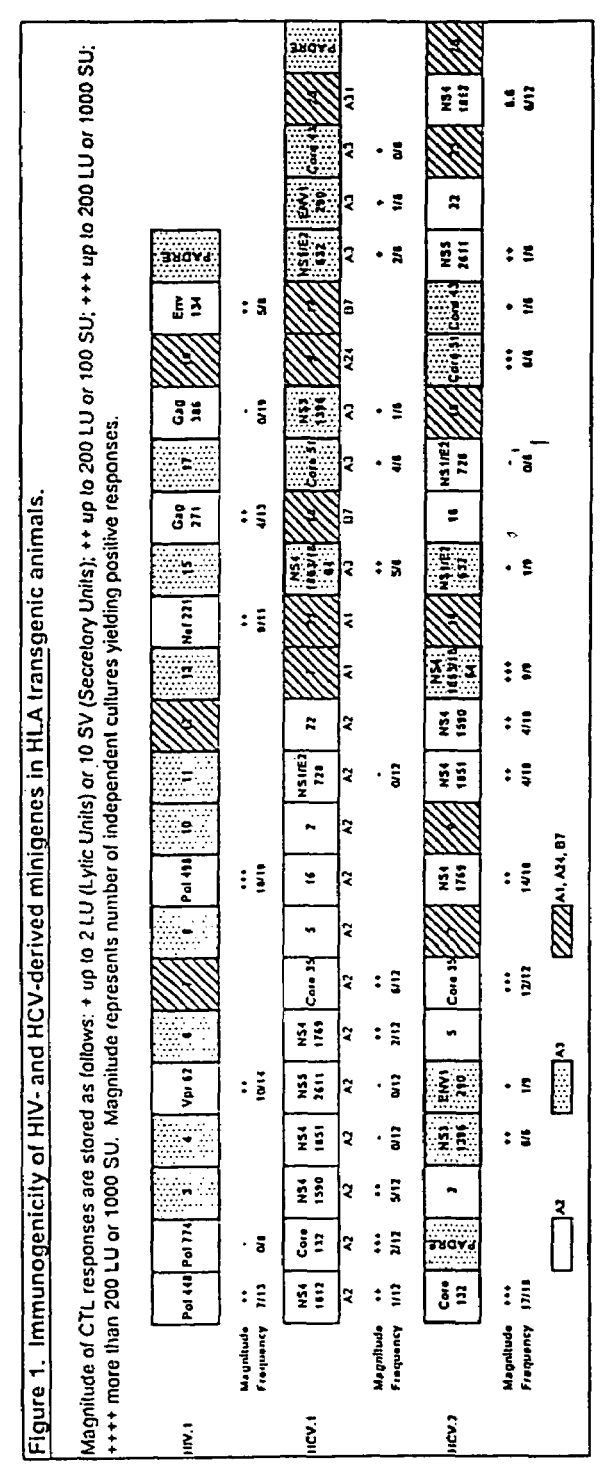

Design parameters were identified based on a number of studies. In a preliminary evaluation of multi-epitope constructs, data on three different multi-epitope constructs, incorporating 20 to 25 different CTL epitopes each, are presented (FIG. 1). One construct is based on HIV-derived epitopes, (HIV-1), while the other two incorporate HCV-derived epitopes (HCV1 and HCV2, respectively). The immunogenicity of these different minigenes has been measured in either A2 or A11 HLA transgenic mice (A1, A24 and B7 restricted epitopes were not evaluated).

Thus, eleven days after a single i.m. DNA vaccine injection, responses against 8 to 14 different representative epitopes were evaluated following a single six day in vitro restimulation, utilizing assays to measure CTL activity (either chromium release or in situ IFN production, as described herein). Priming of epitope specific CTL could be demonstrated for 6/8 (75%), 10/14 (72%) and 13/14 (93%) of the epitopes tested in the case of HIV-1, HCV1 and HCV2, respectively. Thus, multi-epitope minigenes, capable of simultaneously priming CTL responses against a large number of epitopes, can be readily designed. However, it should be emphasized that CTL priming for some epitopes was not detected and, in several of the 36 cases considered, responses were infrequent, or varied significantly in magnitude over at least three orders of magnitude (1000-fold). These results strongly suggested that a more careful analysis and optimization of the minigene constructs was required to.

The possibility that the suboptimal performance of priming for certain epitopes might be related to minigene size was also examined. In fact, most of the published reports describe minigenes of up to ten epitopes, and the few instances in which 20-epitope minigenes have been reported, activity directed against only two or three epitopes was measured. To address this possibility, two smaller minigenes (HIV-1.1 and HIV-1.2) each encompassing ten epitopes, and corresponding to one half of the HIV-1 minigene, were synthesized and tested. Responses against four representative epitopes were measured.

TABLE 1

Immunogenicity appears to be independent of minigene size.

CTL response to different minigenes

| CTL Epitope | HIV 1 (20 mer) | | HIV 1.1 (10 mer) | | HIV 1.2 (10 mer) | |
|---|---|---|---|---|---|---|
| | Frequenc | Magnitude[2] | Frequency | Magnitude | Frequenc | Magnitude |
| Pol 774 | 0/8 | * | 0/4 | * | NA[3] | NA |
| Pol 498 | 18/19 | 46.7 | 4/4 | 16.4 | NA | NA |
| Gag 271 | 4/13 | 4.0 | NA | NA | 0/4 | * |
| Env 134 | 5/8 | 16.1 | NA | NA | 4/4 | 14.8 |

[1] Represents the fraction of independent cultures yielding positive responses
[2] Lytic Units (LU)
[3] Not Applicable It was found that the responses induced by the smaller minigenes were comparable, and if anything, lower than those induced by the twenty-epitope construct (Table 1.) Accordingly, factors relating to minigene size are unlikely explanations for the observed suboptimal priming to certain epitopes and thus other parameters, disclosed herein, are used to design efficacious multi-epitope constructs.

The Minimization of Junctional Motifs

One of the considerations in designing multi-epitope constructs is the inadvertent creation of junctional epitopes when placing epitopes adjacent to each other. The presence of such epitopes in a minigene could significantly affect minigene performance. Strategies to guard against this undesired effect are disclosed herein for application to the development of multi-epitope or minigene vaccines. Junctional epitopes can first be minimized by sorting the epitopes to identify an order in which the numbers of junctional epitopes is minimized. Such a sorting procedure can be performed using a computer or by eye, if necessary, or depending on the number of epitopes to be included in the multi-epitope construct.

For example, a computer program that finds patterns, e.g., Panorama, manufactured by ProVUE Development, Huntington Beach, Calif., U.S.A., can be used in accordance with one embodiment of the invention. A very large number of different epitope arrangements can be considered in designing a particular minigene construct. A computer program accepts as input, the particular set of epitopes considered, and the motifs to be scanned in order to evaluate whether there are any junctional epitopes bearing these motifs. For example, a program can simulate building a minigene, and in an euristic computational algorithm, examine epitope pairs to avoid or minimize the occurrance of junctional motifs. The program can for example, evaluate $6 \times 10^5$ (about half a million) minigene configurations/second.

A complete analysis of a 10-epitope construct using a computer program as described in the preceding paragraph requires examining 10 factorial≅$3.6 \times 10^6$ combinations and can be completed in six seconds. A fourteen-epitope construct can be completely analyzed in a couple of days. Thus, analysis time goes up very rapidly as larger minigenes are considered. However, a complete analysis is not always required and the program can be run for any desired length of time. In either case, the computer system of the present invention identifies and provides at least one configuration having a minimum number of junctional epitopes.

An example of the results of this type of approach is presented in Table 2. The number of junctional motifs in ten different random assortments of the same epitopes contained in the HCV1 minigene, which incorporates 25 epitopes, and is the result of a two day computer analysis, is presented in this Table. In the non-optimized assortments, a large number of A2, A11 and $K^b$ motifs were found, in the 25 to 38 range, with an average of 31. By comparison, only two such junctional motifs are present in the HCV1 minigene assortment. In conclusion, a computer program can be utilized to effectively minimize the number of junctional motifs present in minigene constructs.

TABLE 2

Occurrence of junctional epitopes.

| minigene construct | selection criteria | junctional motifs |
| --- | --- | --- |
| HCV.a | random | 33 |
| HCV.b | random | 26 |
| HCV.c | random | 28 |
| HCV.d | random | 27 |
| HCV.e | random | 30 |
| HCV.f | random | 26 |
| HCV.g | random | 38 |
| HCV.h | random | 33 |
| HCV.i | random | 33 |
| HCV.j | random | 34 |
| HCV.1 | minimized | 2 |

Eliminating Class II Junctional Epitopes and Testing for Class II Restricted Responses In Vivo As a further element in eliminating junctional epitopes, spacer sequences can be inserted between two epitopes that create a junctional epitope when juxtaposed.

In one embodiment, to correct the problem of junctional epitopes for HTL epitopes, a spacer of, for example, five amino acids in length is inserted between the two epitopes. The amino acid residues incorporated into such a spacer are preferably those amino acid residues that are not known to be primary anchor residues for any of the HLA Class II binding motifs. Such residues include G, P, and N. In a preferred embodiment, a spacer with the sequence GPGPG (SEQ ID NO: 369) is inserted between two epitopes. Previous work has demonstrated that the GP spacer is particularly effective in disrupting Class II binding interactions (Sette et al., *J Immunol.*, 143:1268-73 (1989)). All known human Class II binding motifs and the mouse $IA^b$ (the Class II expressed by HLA transgenic mice) do not tolerate either G or P at this main anchor positions, which are spaced four residues apart. This approach virtually guarantees that no Class II restricted epitopes can be formed as junctional epitopes.

In an example validating this design consideration, we synthesized polypeptides incorporating HIV-derived HTL epitopes. These epitopes are broadly cross-reactive HLA DR binding epitopes. It was then determined that these epitopes also efficiently bind the murine $IA^b$ Class II molecule. A diagram illustrating the two different synthetic polypeptides considered is shown in FIG. 2a.

The first construct incorporates four different epitopes linearly arranged, while the second construct incorporates the GPGPG (SEQ ID NO: 369) spacer. Synthetic peptides corresponding to the three potential junctional epitopes were also synthesized.

The capacity of 2 nanomoles of these different constructs to prime for proliferative responses to the various epitopes in $IA^b$ positive mice was tested, and compared to the responses induced by equimolar amounts of a pool of the same peptides (3 micrograms of each peptide). Specifically, groups of 3 mice were injected with peptides in CFA emulsions, 11 days after injection their lymph node cells were cultured in vitro for an additional 3 days, and thymidine incorporation was measured in the last 24 hours of culture. It was found (FIG. 2b) that, as predicted on the basis of their high affinity $IA^b$ binding capacity, all four epitopes induced good proliferation responses. Stimulation index (SI) values in the 4.9 to 17.9 range were observed when these peptides were injected in a pool. However, when the linear polypeptide incorporating the same epitopes was tested, the response directed against Pol 335 was lost. This was associated with appearance of a response directed against a junctional epitope spanning Gag 171 and Pol 335. The use of the GPGPG (SEQ ID NO:369) spacer eliminated this problem, presumably by destroying the junctional epitope, and the Pol 335 response was regained. The responses observed were of magnitude similar to those observed with the pool of isolated peptides.

These results demonstrate that responses against multiple HIV-derived Class II epitopes can be simultaneously induced, and also illustrate how $IA^b$/DR crossreactivity can be utilized to investigate the immunogenicity of various constructs incorporating HTL epitope candidates. Finally, they demonstrate that appropriate spacers can be employed to effectively disrupt Class II junctional epitopes that would otherwise interfere with effective vaccine immunogenicity.

In the case of Class I restricted responses, one case of a naturally occurring junctional epitope and the consequent inhibition of epitope specific responses has been presented by McMichael and coworkers (Tussey et al., *Immunity*, Vol. 3(1): 65-77 (1995)). To address the problem of junctional epitopes for Class I, similar analyses can be performed. For example, a specific computer program is employed to identify potential Class I restricted junctional epitopes, by screening for selected murine motifs and for the most common human Class I HLA A and B motifs.

Spacer sequences can also similarly be employed to prevent CTL junctional epitopes. Often, very small residues such as A or G are preferred spacer residues. G also occurs relatively infrequently as a preferred primary anchor residue (see, e.g., PCT/US00/24802) of an HLA Class I binding motif. These spacers can vary in length, e.g., spacer sequences can typically be 1, 2, 3, 4, 5, 6, 7, or 8 amino acid residues in length and are sometimes longer. Smaller lengths are often preferred because of physical constraints in producing the multi-epitope construct.

The Influence of Flanking Regions on CTL Minigene Immunogenicity

Another factor to be considered in designing minigenes is to insert residues that favor immunogenicity at the position flanking the C-terminus of a CTL epitope.

Disclosed herein are studies that identify residues that increase immunogenicity and, accordingly, residues that are inserted in multi-epitope constructs to optimize immunogenicity.

The molecular context in which an epitope was expressed often dramatically influenced the frequency and/or magnitude of priming of CTL specific for that epitope in HLA transgenic mice. Two examples are shown in Table 3.

TABLE 3

Differences in effectiveness of T cell priming for
specific epitopes in different minigenes.

| Epitope Identity | Minigene Identity | Flanking Sequence (N terminus) | Epitope Sequence | Flanking Sequence (C-terminus) | (SEQ ID NO:) | Immune Response Frequency | Immune Response Magnitude[1] |
|---|---|---|---|---|---|---|---|
| Core 18 | HBV.1 | TLKAAA | FLPSDFFPSV | FLLSLG | 1 | 6/6 | 5.5 |
|  | pMin1 | TLKAAA | FLPSDFFPSV | KLTPLC | 2 | 6/6 | 1074.5 |
| Core 132 | HCV1 | ILGGWV | DLMGYIPLV | YLVAYQ | 3 | 2/12 | 107.7 |
|  | HCV2 | VPGSRG | DLMGYIPLV | AKFVA | 4 | 17/18 | 929.2 |

[1]IFNγ secretory units

The immunogenicity of the HBV Core 18 epitope expressed in the pMin5 minigene was approximately 200-fold lower in magnitude than that observed in the case of the pMin1 minigene. Similarly, the immunogenicity of the HCV Core 132 epitope expressed in the context of the HCV1 minigene was marginal, with significant T cell priming demonstrable in only 2 of 12 different independent CTL experiments/cultures performed. These two positive experiments yielded responses of approximately 100 SU of IFNγ. However, when the same epitope was expressed in the context of the HCV2 minigene, positive responses were observed in 17/18 cases, and with average magnitudes approximately five-fold higher.

Immunogenicity of HIV-FT in HLA-A*0201/Kb Transgenic Mice

Figure 3:
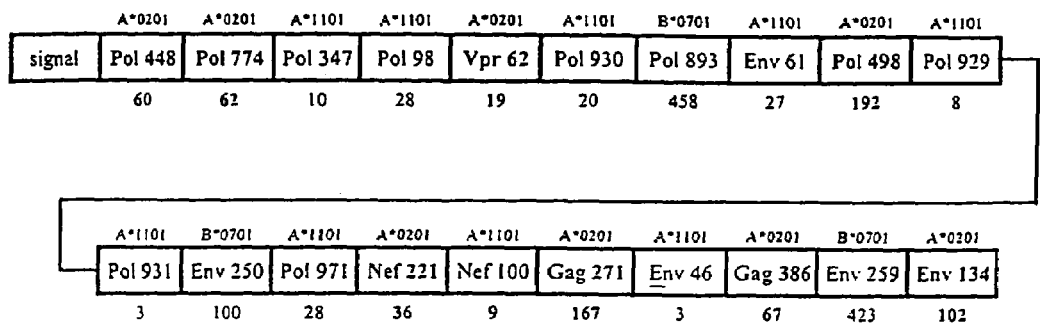
FIG. 3 depicts the structure of multi-epitope DNA constructs. The HLA restriction is shown above each epitope, the A*0201 epitopes are bolded. The HLA binding affinity ($IC_{50}$ nM) is provided below each epitope. (a) Schematic of HIV- FT illustrating order of the encoded epitopes. (b) Schematics of the of the HBV-specific constructs. The C+1 amino acid relative to Core 18 is indicated with an arrow. The HBV-specific constructs with single amino acid insertions at the $C_1$ position of Core 18 are illustrated as HBV.1X.
Figure 3:
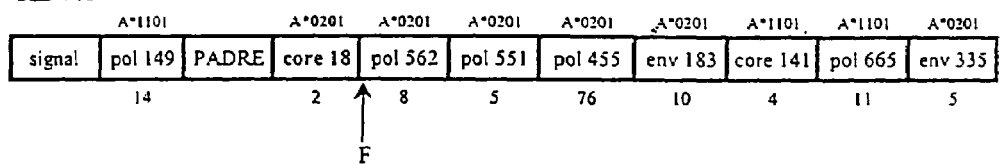
Figure 3:
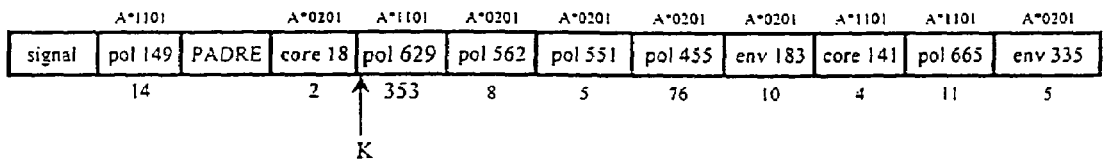
Figure 3:
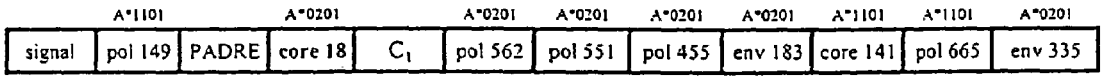

An HIV multi-epitope DNA vaccine, HIV-FT (FIG. 3a) encodes 20 HIV-derived CTL epitopes. Of these 20 epitopes, eight are restricted by HLA-A*0201, nine by HLA-A*1101 and three by HLA-B*0702. All epitopes bound their relevant restriction element with high or moderate affinity. All of the HLA-A*0201 restricted epitopes bound purified HLA-A*0201 molecules with roughly similar affinities, with $IC_{50}$ values in the 19-192 nM range (FIG. 3a). The HLA-A*0201 epitopes chosen for inclusion in HIV-FT are recognized in HIV-1 infected individuals and were also highly effective in priming for recall CTL responses when emulsified with IFA and utilized to prime HLA-A*0201/$K^b$ transgenic mice. The construct was designed to encode the epitopes sequentially without any intervening spacer sequences between them and a consensus Igk signal sequence was fused to the 5' end of the construct to facilitate transport of the encoded antigen into the endoplasmic reticulum (Ishioka et al., *J. Immunol.* 162:3915-3925, 1999).

Figure 4:
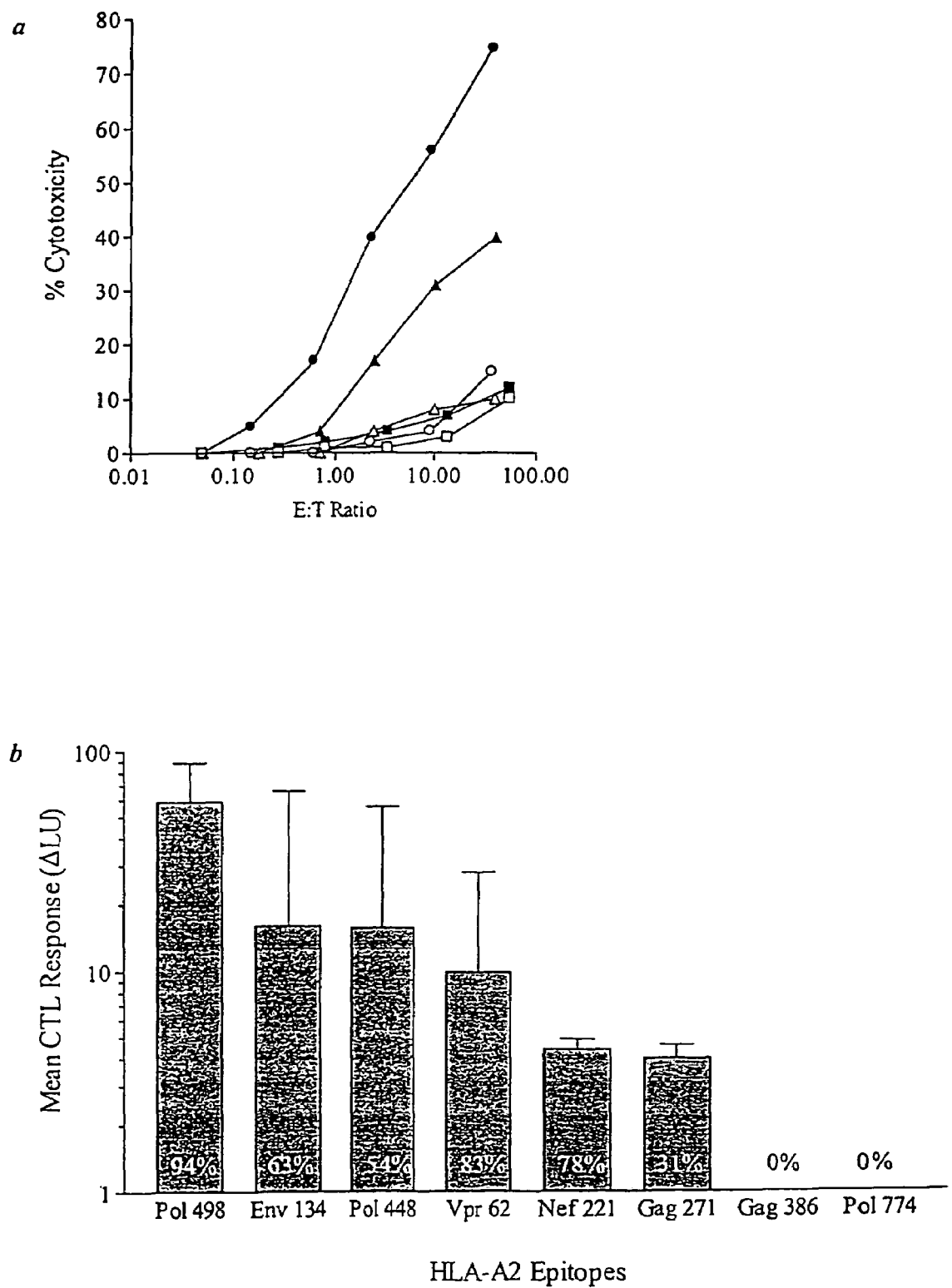
FIG. 4 illustrates the immunogenicity of the HLA-A*0201 epitopes in HIV-FT in HLA-A*0201/$K^b$ transgenic mice. (a) Representative CTL responses against epitopes Pol 498 (circles), Vpr 62 (triangle), Gag 386 (squares). Cytotoxicity was assayed in a $^{51}Cr$ release assay against Jurkat-HLA-A*0201/$K^b$ target cells in the presence (filled symbols) or absence (open symbols) of each peptide. (b) Summary of CTL responses of immunogenicity of HW-FT in HLA-A*0201/$K^b$ transgenic mice. Bars indicate the geometric mean CTL response of positive cultures. The frequency of positive CTL cultures is also indicated.

The ability of HIV-FT to prime recall CTL responses in vivo was evaluated by intramuscular immunization of HLA-A*0201/$K^b$ transgenic mice. Splenocytes from animals immunized with 100 μg of HIV-FT plasmid DNA were stimulated with each of the HLA-A*0201 epitopes encoded in HIV-FT and assayed for peptide-specific CTL activity after six days of culture. Representative CTL responses against three of the epitopes in HIV-FT are shown in FIG. 4a. To more conveniently compile results from different experiments the percent cytotoxicity values for each splenocyte culture were expressed in lytic units (Vitiello, et al., *J. Clin. Invest* 95:341-349, 1995). Of the eight HLA-A*0201 restricted epitopes encoded in HIV-FT, Pol 498, Env 134, Pol 448, Vpr 62, Nef 221, and Gag 271, primed for CTL responses following DNA immunization, (FIG. 4b). The magnitude of the CTL responses varied over greater than a 10-fold range, from as high as nearly 50 LU against Pol 498, too as little as 4 LU against Nef 221 and Gag 271. Similarly, the frequency of recall CTL responses varied between epitopes, with the Pol 498 epitope inducing responses in 94% of the experiments while CTL responses to Gag 271 were detected in only 31% of the experiments. In conclusion, DNA immunization with HIV-FT, which sequentially encodes the epitopes without any spacer amino acids, induced recall CTL responses against the majority of the epitopes analyzed. However, the magnitude and the frequency of the responses varied greatly between epitopes.

Correlation Between Epitope Immunogenicity and Levels of HIV-FT Epitope Presentation in Transfected Cell Lines The differential immunogenicity of the HLA-A*0201 epitopes in HIV-FT was then assessed. Differential MHC binding affinity could be excluded as all of the epitopes bind HLA-A*0201 with high affinity (FIG. 3a). In addition, lack of a suitable repertoire of TCR specificities in HLA-A*0201/$K^b$ transgenic mice could be excluded since all epitopes yielded comparable CTL responses following immunization of HLA transgenic mice with the optimal preprocessed peptide emulsified in IFA. Variations in the relative amounts of each epitope presented for T cell recognition may account for the differences in epitope immunogenicity.

To test this, Jurkat cells, a human T cell line, expressing the HLA-A*0201/$K^b$ gene (Vitiello et al., *J. Exp. Med.* 173, 1007-1015, 1991) were transfected with the HIV-FT expressed in an episomal vector. A human cell line was selected for use to eliminate any possible artifacts that may be associated with potential differences in the processing capabilities between humans and mice. This transfected cell line matches the human MHC presentation with human antigen processing capabilities and provides support for the subsequent development of CTL epitope-based DNA vaccines for use in humans.

Peptide-specific CTL lines detected presentation in the transfected targets of four of the HLA-A*0201 epitopes encoded in the HIV-FT, Pol 498, Env 134, Pol 448 and Nef 221. To quantitate the level at which each of these epitopes was produced and presented, the CTL lines specific for the various epitopes were incubated with untransfected targets and variable amounts of each epitope or peptides. These CTL dose response curves were utilized as standard curves to determine the peptide concentration inducing levels of IFNγ secretion equivalent to those observed in response to the HIV-FT transfected target cells. This value is referred to as a "peptide equivalent dose" and taken as a relative measure of the amount of epitope presented on the transfected cell.

Table 4 summarizes the findings of this analysis for eight of the HLA-A*0201 epitopes encoded in the HIV-FT. Peptide equivalent doses varied from a high of 33.3 ng/ml for Nef 221 to less than 0.4 ng/ml peptide equivalents for epitopes Gag 271, Gag 386 and Pol 774. Cumulatively these results indicate that in human cells lines transfected with HIV-FT there is at least a 100-fold variation exists in the levels of presentation of the different HLA-A*0201 restricted epitopes. All of the epitopes that were presented at detectable levels in antigenicity assays were also immunogenic in vivo. The only epitope that was immunogenic and not antigenic was Gag 271. In this case, immunization of HLA-A*0201/Kb transgenic mice with HIV-FT induced a weak CTL response in less than a third of the cultures tested. The other two epitopes, which were presented below the limit of sensitivity for the antigenicity analysis, Gag 386 and Pol 774, were non-immunogenic. In conclusion these results suggest that the heterogeneity in CTL responses induced by HIV-FT immunization can at least in part be attributed to suboptimal epitope presentation.

TABLE 4

Comparison of HIV-FT immunogenicity and antigenicity

| | HIV-FT Immunogenicity | | HIV-FT Antigenicity Peptide | |
|---|---|---|---|---|
| Epitope | magnitude[1] | frequency[2] | Equivalents[3] | n[4] |
| Pol 498 | 58.8 (2.2) | 94% (16/17) | 23.8 (2.0) | 4 |
| Env 134 | 16.1 (5.0) | 63% (5/8) | 6.2 (1.2) | 3 |
| Pol 448 | 15.7 (2.6) | 54% (7/13) | 24.7 (3.9) | 3 |
| Vpr 62 | 9.9 (1.9) | 83% (10.12) | ND | — |
| Nef 221 | 4.4 (1.3) | 78% (7/9) | 33.3 (6.0) | 3 |
| Gag 271 | 4.0 (1.4) | 31% (4/13) | <0.4 | 6 |
| Gag 386 | 0 | 0% (0/17) | <0.4 | 3 |
| Pol 774 | 0 | 0% (0/8) | <0.4 | 1 |

[1] magnitude expressed as LU (ref); the correlation coefficient relative to peptide equivalents R + 0.44
[2] frequency of positive cultures (number cultures > 2LU/total tested); the correlation coefficient relative to peptide equivalents R + 0.8.
[3] magnitude expressed in ng/ml
[4] number of independent experiments Flanking Amino Acids Influence CTL Epitope Immunogenicity in Vivo Following Vaccination As described herein, the particular amino acids flanking individual CTL epitopes is one factor that influences or enhances the efficiency with which an epitope is processed by altering the susceptibility of the antigen to proteolytic cleavage. To examine the influence of flanking amino acids on epitope immunogenicity, immunogenicity data was obtained from HLA-A*0201,-A*1101 and -B*0701 transgenic mice immunized with a number of unrelated experimental multi-epitope DNA constructs encoding minimal CTL epitopes without intervening sequences. A database representing 94 different epitope/flanking residue combinations was compiled to determine the possible influence the immediately flanking amino acids on epitope immunogenicity. A given epitope and flanking amino acid combination was included only once to prevent artificial skewing of the analysis because of redundancies. Epitope immunogenicity in HLA transgenic was considered optimal if greater than 100 SU or 20 LU in at least 30% of the cultures measured. CTL responses were typically scored in one of four categories: (+++), outstanding-more than 200 LU or 1000 SU; (++), good-20-200 LU or 100-1000 SU; (+), intermediate-2 to 20 LU or 10 to 100 SU; and (+/−), weak or negative-less than 2 LU or 10 SU. The numbers of optimal versus sub-optimal responses were categorized based on the chemical type of amino acid in the flanking positions and the significance of differences were determined using a chi-square test.

Figure 5:
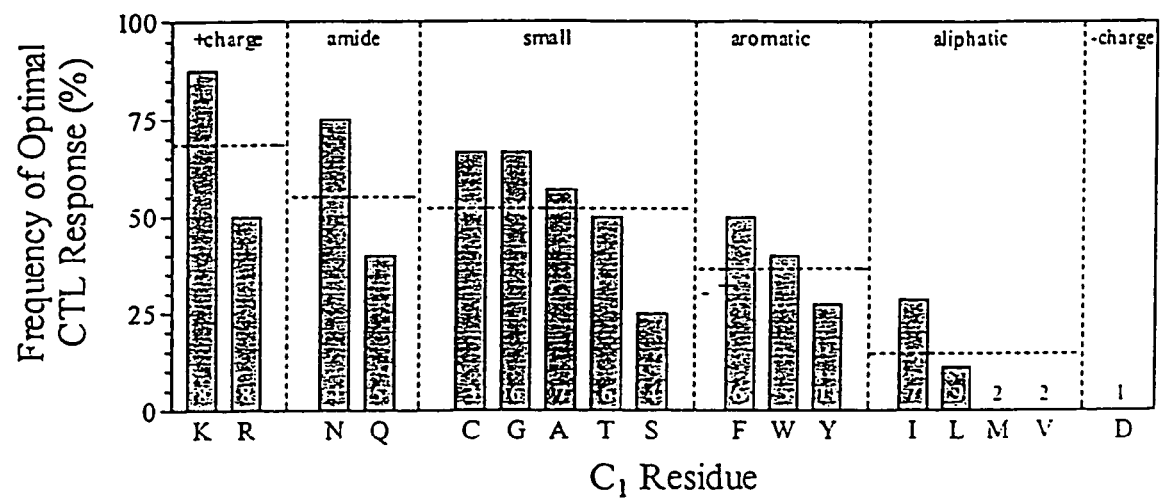
FIG. 5 shows the influence of the C+1 amino acid on epitope immunogenicity. A database incorporating CTL responses from a variety of minigenes representing 94 epitope/C+1 amino acid combinations was analyzed to determine the frequency (%) of instances in which a particular combination was associated with an optimal CTL response. CTL responses were considered optimal if greater than 100 SU or 20 LU in at least 30% of the cultures measured. The number of times a given epitope/C+1 amino acid combination was observed is also provided.

This analysis did not find any associations between the type of amino acids present at the amino-terminus of an epitope and immunogenicity. However, significant effects of the carboxyl-terminus flanking residue, the C+1 residue, were identified. Positively charged amino acids, K or R were most frequently associated with optimal CTL responses, a frequency of 68% (FIG. 5). The presence of amino acids N and Q at the C+1 residue was also associated with strong CTL responses in 55.5% of the cases examined; when epitopes were flanked at the C+1 position by N, they induced optimal CTL responses in 3/4 cases. In general, small residues such as C, G, A, T, and S promoted intermediate CTL responses inducing strong responses in 54% of the combinations available for analysis. Conversely, epitopes flanked by aromatic and aliphatic amino acids induced optimal in vivo responses in only 36% and 17% of the cases, respectively. The negatively charged residue, D, yielded a suboptimal CTL response. The influence of C+1 amino acid on epitope immunogenicity was found to be statistically significant using a chi-square test (P<0.03). No significant influence on epitope immunogenicity was noted when similar analysis was performed for C-terminal residues more distal than the C+1 position.

Direct Evaluation of the Effect of the C1 Residue on Epitope Immunogenicity

To directly evaluate the effect of preferred versus deleterious types of amino acids in the C+1 flanking position, two multi-epitope constructs, referred to as HBV.1 and HBV.2 (FIG. 3b) were evaluated. As with HIV-FT, these HBV constructs encode the epitopes sequentially without intervening spacers. Indeed, the HBV.1 and HBV.2 were generated by replacing the HIV-1 epitopes in pMin1, an experimental multi-epitope construct previously characterized (Ishioka, supra) with similar HBV-derived epitopes.

Figure 6:
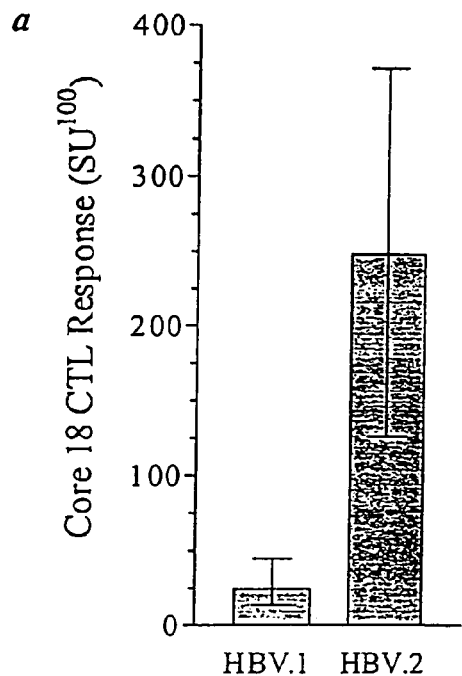
FIG. 6 shows CTL responses to HBV-specific constructs (a) CTL responses to Core 18 epitope following DNA immunization of HLA-A*0201/$K^b$ transgenic mice. (b) CTL responses to HBV Core 18 following DNA immunization of HLA-A*0201/$K^b$ transgenic mice with constructs which vary by a single amino acid insertion at the C+1 position of Core 18.
Figure 6:
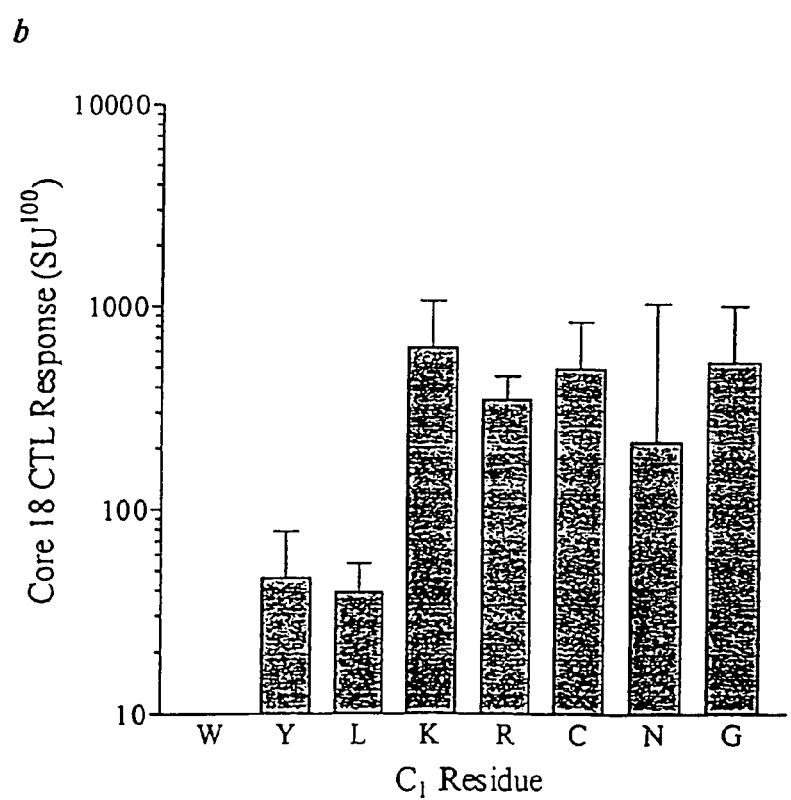

For HBV.1, the HIV-1 epitope directly following the highly immunogenic HBV Core 18 epitope was replaced with the HBV Pol 562 epitope. This altered the C+1 residue from a K to an F. The second construct, HBV.2, was produced by the insertion of an additional epitope, HBV Pol 629, between the HBV Core 18 and Pol 562 epitopes; a change that replaced the C+1 amino acid with a K residue. When the immunogenicity of the Core 18 epitope presented in these different contexts was evaluated in HLA-A*0201/$K^b$ transgenic mice, it was determined that the Core 18 epitope was virtually non-immunogenic in HBV.1 but strongly immunogenic in HBV.2 (FIG. 6a). The reduction of in vivo immunogenicity for this epitope was as would be predicted by our previous analysis.

To further test the effects of the C+1 flanking amino acid on CTL epitope immunogenicity, a set of constructs that differ from HBV.1 by the insertion of single amino acids at the C+1 position relative to the Core 18 epitope (FIG. 3b) was evaluated. Little or no CTL response was observed against the Core 18 epitope when flanked at the C+1 position by W, Y, or L (FIG. 6b). In contrast, insertion of a single K residue dramatically increased the CTL response to Core 18. The responses were comparable to those observed in HBV.2 in which the Core 18 epitope is flanked by Pol 629, an epitope with a K at the N-terminus of the epitope. Enhancement of the Core 18 CTL response was also observed to insertion of R, C, N, or G. The effect of these insertions is specific, as the immunogenicity of other epitopes within these constructs did not exhibit significant changes in CTL responses (data not shown). In conclusion, these data indicate that the C+1 amino acid can dramatically influence epitope immunogenicity.

Figure 7:
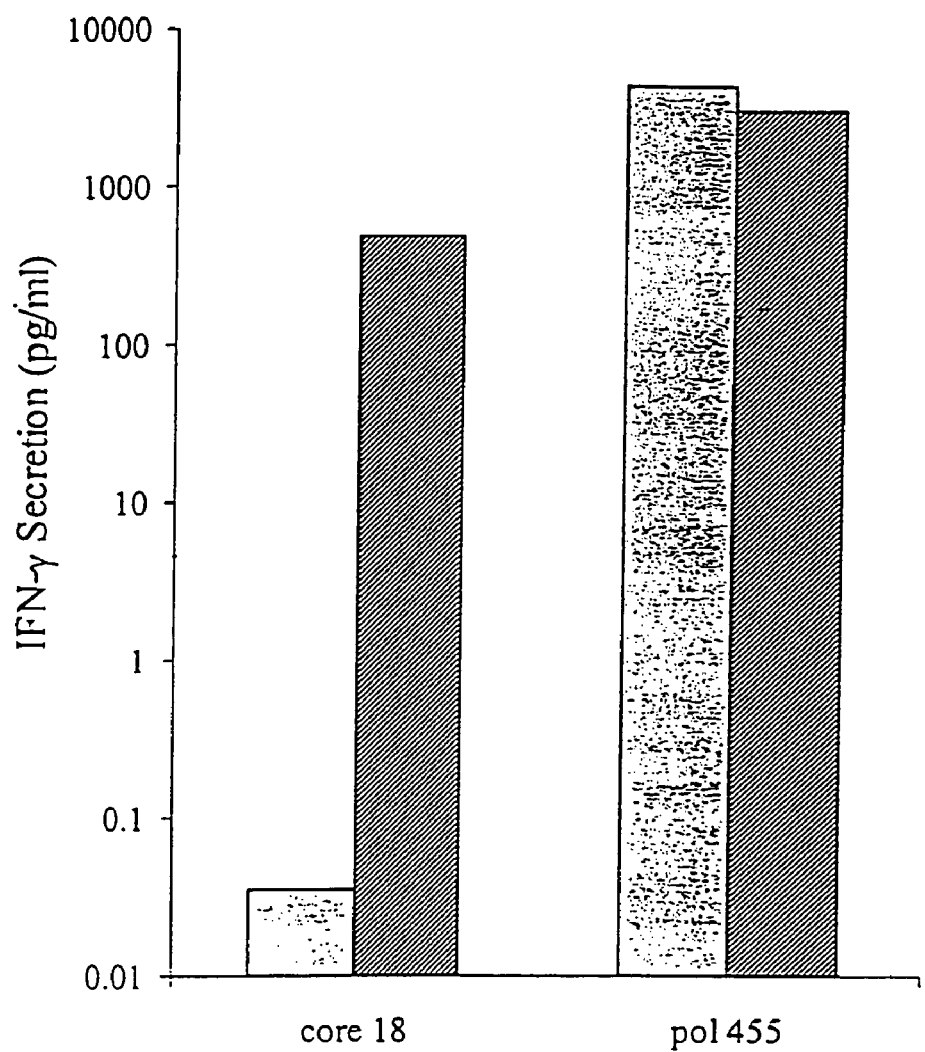
FIG. 7 shows levels of HBV Core 18 presentation in HBV.1 (shaded bars) and HBV.1K (hatched bars) transfected cell lines. Epitope presentation was quantified using peptide-specific CTL lines. Presentation of HBV Pol 455 is shown for comparative purposes.

Variations in CTL Epitope Immunogenicity Are Correlated with the Amount Presented If the variation of the immunogenicity of Core 18 associated with different C+1 residues was the result of differential sensitivity to proteolytic cleavage then large differences in the levels of epitope presentation should be detectable in different constructs. To test this, Jurkat cells, expressing the same HLA-A*0201/$K^b$ gene expressed in the transgenic mice, were transfected with an episomal vector expressing either HBV.1 or HBV.1K. The Core 18 epitope was presented at >$10^5$ higher levels when a K was in the C+1 position, compared to the presence of an F in the same position (FIG. 7). It is unlikely that this difference in Core 18 presentation is attributed to differences in gene expression between target cell lines since presentation of Pol 455 varied by less than ten-fold. These data demonstrate the striking effect that amino acids at the C+1 position can exert on efficiency of epitope presentation in multi-epitope DNA vaccines. Thus, these data show that the immunogenicity of CTL epitopes in a DNA vaccine can be optimized through design considerations that affect the level of epitope presentation. This type of optimization is applicable to epitope-based vaccines delivered using other formats, such as viral vectors as well as other expression vectors known to those of skill in the art, since the effects are exerted after the antigen is transcribed and translated.

In summary, for flanking residues, it was found that either very small residues such as A, C or G, or large residues such as Q, W, K, or R were generally associated with good or outstanding responses. The absence of a C+1 residue because of a stop codon in the minigene, or the presence of intermediate size residues such as S or T was associated with a more intermediate response pattern. Finally, in the case of a negatively charged residue, D; aliphatic (V, I, L, M) or aromatic-non tryptophan residues (Y, F), relatively poor responses were observed. These results show that the particular residue flanking the epitope's C-terminus can dramatically influence the response frequency and magnitude. Flanking residues at the C+1 position can also be introduced in combination with spacer sequences. Thus, a residue that favors immunogenicity, preferably, K, R, N, A, or G, is included as a flanking residue of a spacer.

Sorting and Optimization of Multi-epitope Constructs

To develop multi-epitope constructs using the invention, the epitopes for inclusion in the multi-epitope construct are sorted and optimized using the parameters defined herein. Sorting and optimization can be performed using a computer or, for fewer numbers of epitopes, not using a computer.

Figure 10:
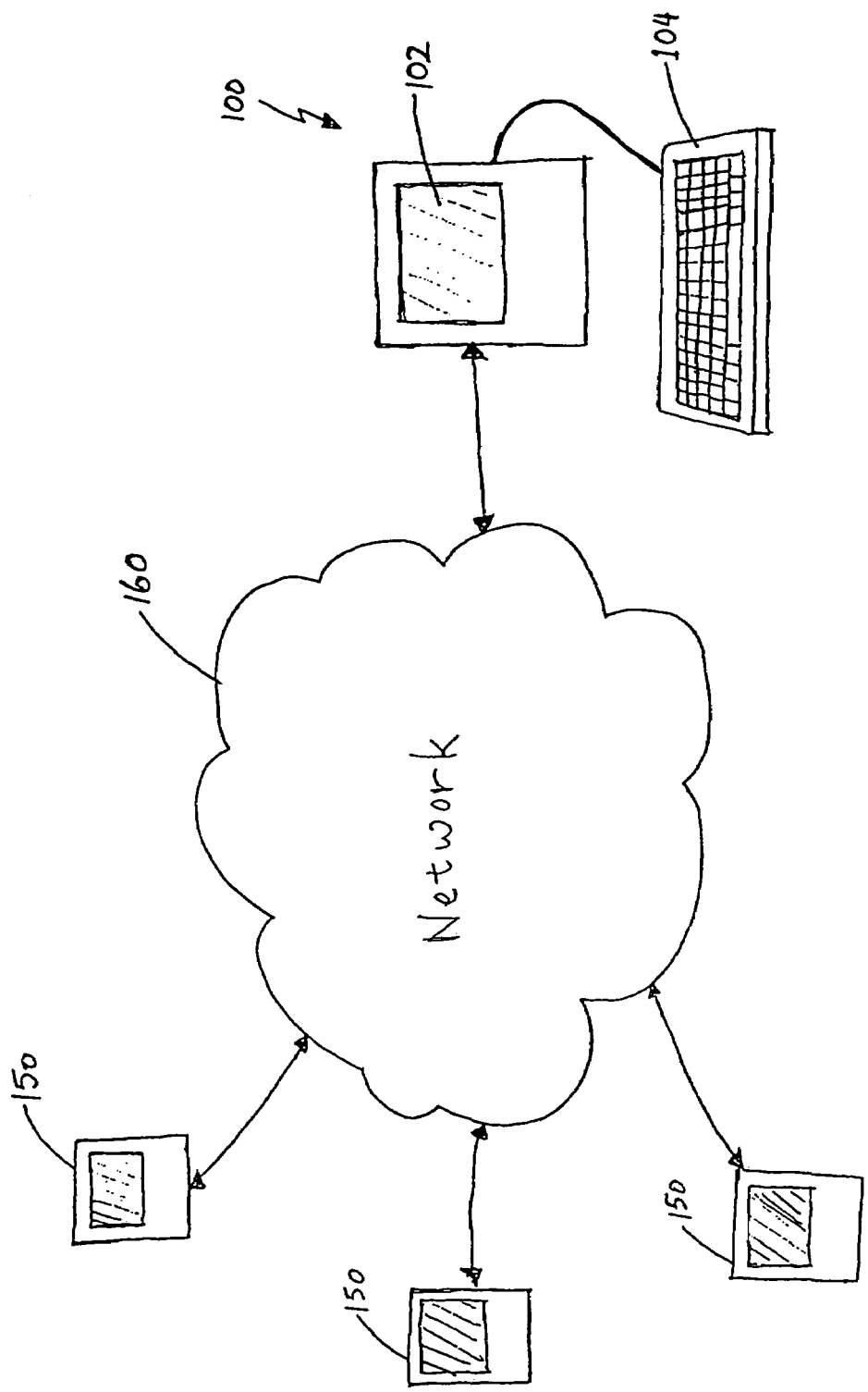
FIG. 10 illustrates a computer system for performing automatic optimization of multi-epitope minigenes in accordance with one embodiment of the invention.

Computerized optimization can typically be performed as follows. The following provides an example of a computerized system that identifies and optimizes, e.g., provides for a minimal number of junctional epitopes and a maximal number of flanking residues, epitope combinations. FIG. 10 illustrates a computer system 100 for performing the optimization of multi-epitope constructs, in accordance with one embodiment of the invention. The computer system 100 may be a conventional-type computer which includes processing circuitry, e.g., a central processing unit (CPU), memory, e.g., a hard disk drive (ROM), a random access memory (RAM), cache, and other components, devices and circuitry (not shown) typically found in computers today. In a preferred embodiment, the computer system 100 includes, among other components and devices, a Macintosh G3 333 MHz processor, a six Gigabit (GB) hard drive, 96 Megabits of RAM, and 512 Kilabits (KB) of cache memory, capable of searching 600,000 to 700,000 permutations per second. The computer system 100 further includes a monitor 102 for displaying text, graphics and other information to a user and a keyboard 104 for allowing a user to input data, commands, and other information to the computer system 100.

As shown in FIG. 10, in one embodiment, the computer system 100 may communicate with one or more remote computers 150 through a computer network 160 such that registered users at remote locations can perform the junctional analyses and minigene optimization procedures described herein by logging on at the remote computers 150 and supplying a required password or user identification. The computer network 160 may be a local area network (LAN), a wide area network (WAN), or the world-wide web (i.e., Internet). These types of networks are well-known in the art and, therefore, a discussion of these networks and their communication protocols is not provided herein.

In a preferred embodiment, the computer system 100 stores a software program, e.g., object code, in the hard drive memory of the computer system 100. This object code is executed by the CPU for performing the functions described herein. One component, or module, of the software program carries out the function of analyzing and identifying junctional epitopes at the peptide junctions of the polypeptide minigene as well as evaluating combinations of spacer and flanking residues at these junctions. This software module is referred to herein as the "Junctional Analyzer" module or program. In a preferred embodiment, the Junctional Analyzer analyzes and processes peptides entered by a user in accordance with other criteria, data and operating parameters described below.

FIGS. 11A-B (hereinafter FIG. 11) illustrate an exemplary input text file 200 containing user input data and parameters which is used by the Junctional Analyzer program, in accordance with one embodiment of the invention. As shown in FIG. 11, various types of input data are provided to the program. First, a user may enter a set of peptides or epitopes 202 for processing. A set of weights 204 for each amino acid when it appears in a C+1 and N−1 position is also entered into the text file by the user. In one embodiment, the weight values are determined by statistical or empirical analysis of experimental results which reflect the immunogenicity or antigenicity "enhancement" effects of each amino acid when it is placed at the C+1 or N−1 positions of a polypeptide. However, the assignment of weight values for each amino acid may be performed by any number of methodologies, including in vitro and in vivo studies, which would be apparent to those of ordinary skill in the art, depending on the desired criteria used to determine the weight values. Some examples of such experiments or studies are described in further detail below.

In a preferred embodiment, a database containing different epitope/flanking residue combinations is stratified on the basis of epitope immunogenicity and the number of optimal versus suboptimal responses are sorted to rank the amino acids and assign enhancement weight values. The text file also contains a set of motifs 206 to use in detecting junctional epitopes. In a preferred embodiment, the user may also enter a maximum number of amino acids (spacers and flanking) to insert between each pair of peptides (MaxInsertions) 208 to function as spacers and/or flanking residues. Other parameters, values or commands (collectively referred to herein as "parameters") to control the operation of the program may also be entered such as, for example: "OutputToScreen (Y/N)" 210; "OutputToFile (Y/N)" 212; the minimum function value to accept as a valid result ("MinimumAccepted") 214; the maximum number of results having the same function value ("MaxDuplicateFunctionValue") 216; the maximum time allowed for a search in minutes ("SearchTime") 218; whether an Exhaustive Search is desired ("Exhaustive=Y/N") 220; the number of Stochastic search probes ("NumStochasticProbes") 222; the maximum number of hits allowed per single probe during a stochastic search ("MaxHitsPerProbe") 224; and whether the start of each probe should be random or other ("RandomProbeStart(Y/N)") 226. These parameters are provided for purposes of illustration only. Other parameters to control the operation and output format of the program may be entered as would be obvious to those of ordinary skill in the art.

The motifs 206 in the text file 200 provide a "mask" or structural model for identifying junctional epitopes. For example the first motif 206a shown in FIG. 11, XXXX(FY)XX(LIMV) (SEQ ID NO: 370), defines an epitope that is eight amino acids in length. The value "X" indicates that any amino acid may be at that position of the epitope. The value "(FY)" indicates that either an F amino acid or a Y amino acid may be in the fifth position of the epitope. Similarly, "(LIMV)" indicates that any one of the listed amino acids, L, I, M or V, may be in the eighth position of the epitope. Therefore if a sequence of eight amino acids spanning a junction of two peptides satisfies the above motif criteria, it is identified as a junctional epitope.

Figure 12:
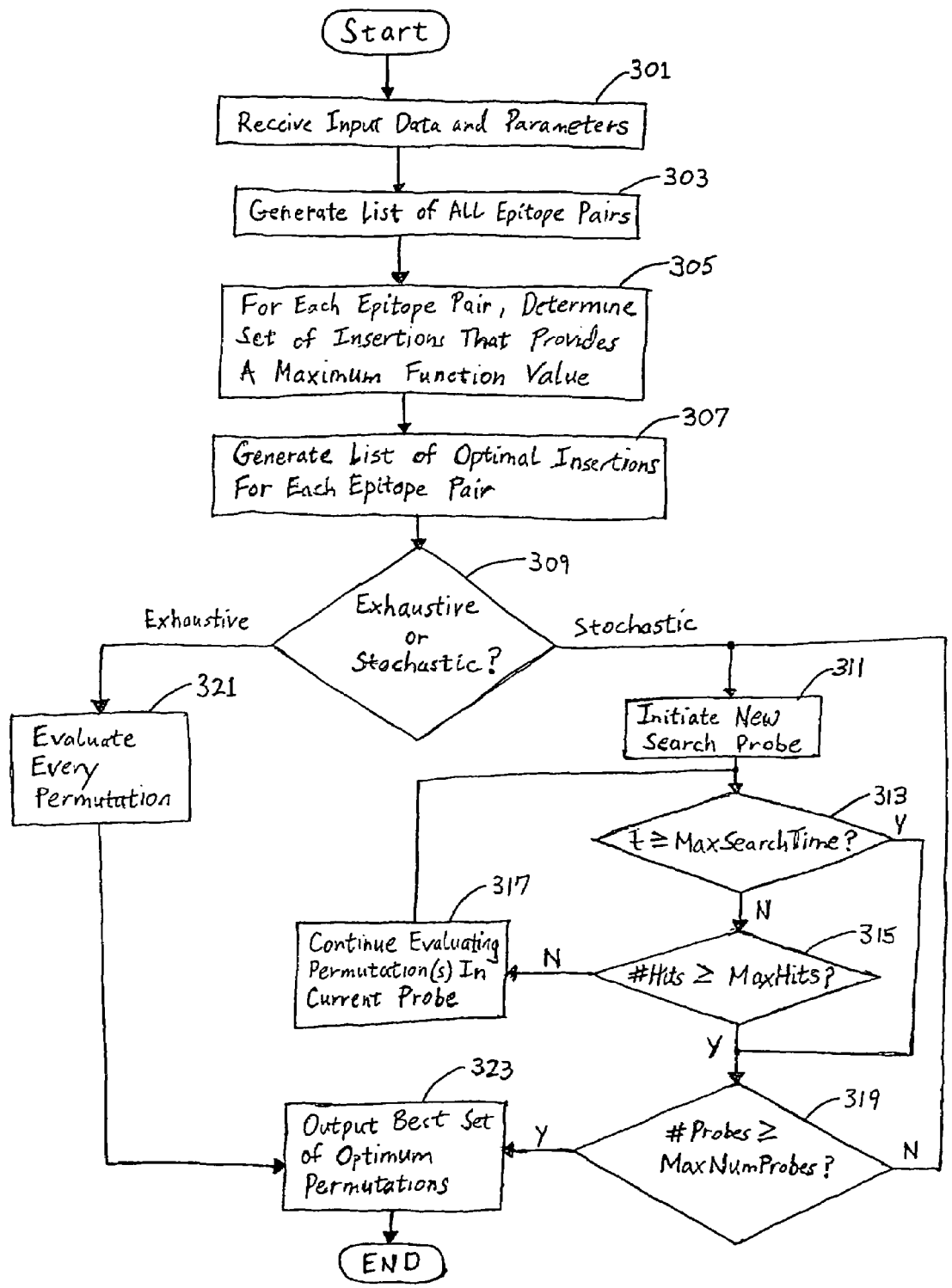
FIG. 12 illustrates a flow chart diagram of a software program for identifying optimal multi-epitope constructs for minigenes, in accordance with one embodiment of the invention.

FIG. 12 illustrates a flow chart diagram of one embodiment of the Junctional Analyzer program. At step 301, the program receives user inputs and instructions for performing the junctional analysis operation. In a preferred embodiment, the program uses an input text file 200 as shown in FIG. 11 to input parameters 202-226. As is well-known in the art, such a text file may be derived, for example, from a Microsoft Excel™ spreadsheet file or document, to specify desired input parameters (e.g., epitopes, motifs, flanking residue weight values, maximum number of hits, maximum search time, etc.) for its operation. At step 303, the Junctional Analyzer program generates a list of all epitope pairs. For example, if ten epitopes are entered by the user, there will be a total of ninety (10×9) epitope (peptide) pairs. Next, at step 305, for each pair of peptides or epitopes, the program determines the set of insertions that results in the minimum number of junctional epitopes and/or the maximum effect from the C+1 and N−1 contribution of spacing residues. To make this determination, the program calculates a function value for each possible combination of spacers for each peptide pair, where the number of spacers can range from 0 to MaxInsertions 208 (FIG. 11) and any arrangement of known or pre-specified amino acids may be considered. In a preferred embodiment, the function value is calculated using the following equation: F=(C+N)/J, where C is the enhancement weight value for a flanking amino acid located at the C+1 position of an epitope, N is the enhancement weight value for a flanking amino acid located at the N−1 position of an epitope, and J is the number of junctional epitopes present. Since multiple motifs may be satisfied at one junction of a peptide pair, J may be a number greater than one. When J=0, F=2(C+N). This second equation was chosen because for a fixed value of (C+N), the function value F will double when J changes from two to one, and will double again when J changes from one to zero. It is understood, however, that the above equations are exemplary only and that other equations for evaluating peptide pairs can be easily added to the program at any time. Modifications or changes to the above equations, depending on the desired criteria for emphasis or evaluation, would be readily apparent to those of ordinary skill in the art. At step 307, the program outputs the optimum combination of insertions (spacing and/or flanking residues) for each pair of peptides and the maximum function value for each pair of peptides. In a preferred embodiment, at step 307, the output from this program is generated as an output text file that lists, for each pair of peptides, the insertion that yields the maximum function result.

FIGS. 13A-D (hereinafter FIG. 13) illustrate an exemplary output text file 400 that lists, for each peptide pair, the spacer combination having the maximum function value. In the example shown in FIG. 13, eleven peptides, labeled A-K 202 (FIG. 11), were processed, the Motifs 206 were used to detect junctional epitopes, the enhancement weight values for each potential flanking residue 204 were used, and MaxInsertions 208 was set to four. Other parameters for controlling the operation and format of the Junctional Analyzer program were set as illustrated by the parameter settings 402. For purposes of convenience, in a preferred embodiment, these input parameters are repeated in the output text file 400. The output text file 400 includes an output table 404 which contain the results of steps 305 (FIG. 12). The first column (Col. 1) of the output table 404 indicates the first peptide of a pair. The second column (Col. 2) of the output table lists the first amino acid insertions which function both as a spacer and the C+1 flanking amino acid. The third column lists a second spacer amino acid. The fourth column lists a third spacer amino acid. The fifth column lists a fourth spacer amino acid which is also the N−1 flanking amino acid for the second peptide of the pair which is listed in column six. The seventh column lists the enhancement weight value of the C+1 flanking amino acid listed in column two. The eighth column lists the enhancement weight value of the N−1 flanking amino acid listed in column six 412. The ninth column lists the sum of the C+1 and N−1 enhancement weight values. The tenth column lists the number of junctional epitopes found in the peptide pair and the eleventh column lists the maximum function value for the peptide pair based on the equations listed above. For example, the first row of the output table 404 shows that for the peptide pair A-B, corresponding to the peptides VLAE-AMSQV-ILKEPVHGV (SEQ ID NO: 5-6), the spacer combination of three amino acids, CAL, eliminates all junctional epitopes and provides a maximum function value of 8.80. It is understood, however, that other output options may be implemented in accordance with the invention. For example, the output table 404 may show the top 32 results for each pair of peptides, or show every result for all possible insertions in the order evaluated, or trace the motif search process to generate large output files, depending on the level of detail and/or analysis desired by the user.

In a preferred embodiment, the information contained in the output table 404 is used to perform either an "Exhaustive J Search" or a "Stochastic J Search" to identify a polypeptide construct linking all eleven peptides, including optimum spacer combinations. For eleven peptides, for example, there will be ten junctions. Therefore the permutation which yields the largest sum of function values taking into account all ten junctions is identified as the "optimum" permutation(s) of the multi-epitope constructs. In one embodiment, for the convenience of the user, the output text file 400 will also contain the original list of peptides/epitopes 202, the weight values used 204, the motifs used 206, and MaxInsertion value 208, and other parameter settings 402 entered into the input text file 200 of FIG. 11.

The "Exhaustive J Search" looks at all permutations of the peptides and selects the ones that have the largest function sum. However, due to the factorial nature of permutations, as the number of peptides to be processed increases, the time required to complete an Exhaustive J Search increases almost exponentially. For example, using a standard Macintosh 333 MHz computer, the estimated running time for 13 peptides is approximately 2.9 hours and would be approximately 40 hours for 14 peptides. The "Stochastic J Search" is designed to search many areas of the permutation sequence, rather than the entire permutation space, and report the best function sum that it finds. By reporting only permutations that meet or exceed the current maximum function total, it is possible to search a much broader area of the permutation sequence. This technique has been successful with as many as 20 peptides. The time to perform an exhaustive search of 20 peptides is estimated to be on the order of 1.3×105 years.

Referring again to FIG. 12, at step 309, the program determines whether to perform an Exhaustive or Stochastic search of the possible permutations of polypeptides from the output text file 400. In a preferred embodiment, the determination at step 309 is made by the user who inputs whether the search will be Exhaustive or Stochastic as indicated by the input parameter, Exhaustive (Y/N) 220 (FIG. 11). In other embodiments, the program may automatically select either a Stochastic or Exhaustive search depending on the number of peptides to be processed. For example, if less than 14 epitopes are to be included, an Exhaustive search routine is automatically selected by the program. The Exhaustive search program examines all permutations of the epitopes making up the multi-epitope construct to find the one(s) with the best value for the sum of the optimizing function for all pairs of epitopes. This is guaranteed to find the "best" permutation(s) since all are examined. If 14 or more epitopes are to be included in the multi-epitope construct, a Stochastic search is used. In a preferred embodiment, the Stochastic search uses a Monte Carlo technique, known to those of skill in the art, to examine many regions of the permutation space to find the best estimate of the optimum arrangement of the peptides. However, other methods of Stochastic searching may be implemented in accordance with the invention. For example, rather than randomly picking a starting permutation for each stochastic probe, the program may require that each probe begin with a permutation beginning with a different one of the peptides entered by the user. For example, if there were just three peptides, A, B and C, the three probes would begin with, for example, ABC, BAC and CBA. This method provides a fairly uniform coverage of the possible permutations.

If a Stochastic search has been selected, next, at step 311, the program begins the Stochastic search by initiating a probe. Next, at step 313, the program determines if the maximum search time per probe has been exceeded. If the maximum search time has not been reached, next, at step 315, the program determines whether a single probe has reached or exceeded the maximum number of "hits" per probe. In one embodiment, a probe hit is registered when a permutation's function value sum is the same as or greater than the largest function sum previously registered for one or more previously analyzed permutations. If the maximum number of hits per probe has not been reached, then, at step 317, the current stochastic probe evaluates the next permutation or set of permutations and the process returns step 313. If at step 315 it is determined that the maximum number of hits per probe has been reached or exceeded, then, the program proceeds to step 319, where the program determines whether a maximum number of probes have already been executed. Also, if at step 313, it is determined that the maximum time limit per probe has been reached or exceeded, the program proceeds to step 319 to determine if the maximum number of probes have been completed. If, at step 319, it is determined that the maximum number of probes has not been reached, the program returns to step 311 and a new search probe is initiated. If at step 319 it is determined that the maximum number of probes have been executed, the program then proceeds to step 323 where it outputs the best set of optimum permutations identified up to that point. This "best set" may consist of only those permutations having the highest function sum or, alternatively, may consist of the permutations having the top three highest function sums, for example, or any other output criteria desired by the user.

In one preferred embodiment, if a probe has received a maximum number of hits specified per probe, any unused time for that probe is divided by the remaining probes to decide how much time should be allocated to each of the remaining probes. In other words, if a probe terminates early because of finding too many hits then the remaining probes are allocated more time. Such functionality is easily implemented by those of ordinary skill in the computer programming arts.

If at step 309, an Exhaustive search has been selected, then, at step 321, an exhaustive search is initiated which analyzes every permutation, as described above. At the completion of the Exhaustive analysis, the program proceeds to step 323 where it outputs the "best set" of optimum permutations found. As mentioned above, this "best set" may include those permutations with the highest sum function values, or the top three highest sum function values, or permutations meeting any desired criteria specified by the user (e.g., top 30 permutations with the highest function values).

For each of the decision steps or determination steps discussed above (e.g., steps 313, 315 and 319), the program may be set to perform a query at periodic intervals (e.g., every five seconds) or, alternatively, the program may be set to perform a query after a specified number of permutations (e.g., five) have been analyzed or after every permutation has been analyzed. Any one of these operation and timing protocols is easily implemented and adjusted by those of ordinary skill in the art.

Figure 9:
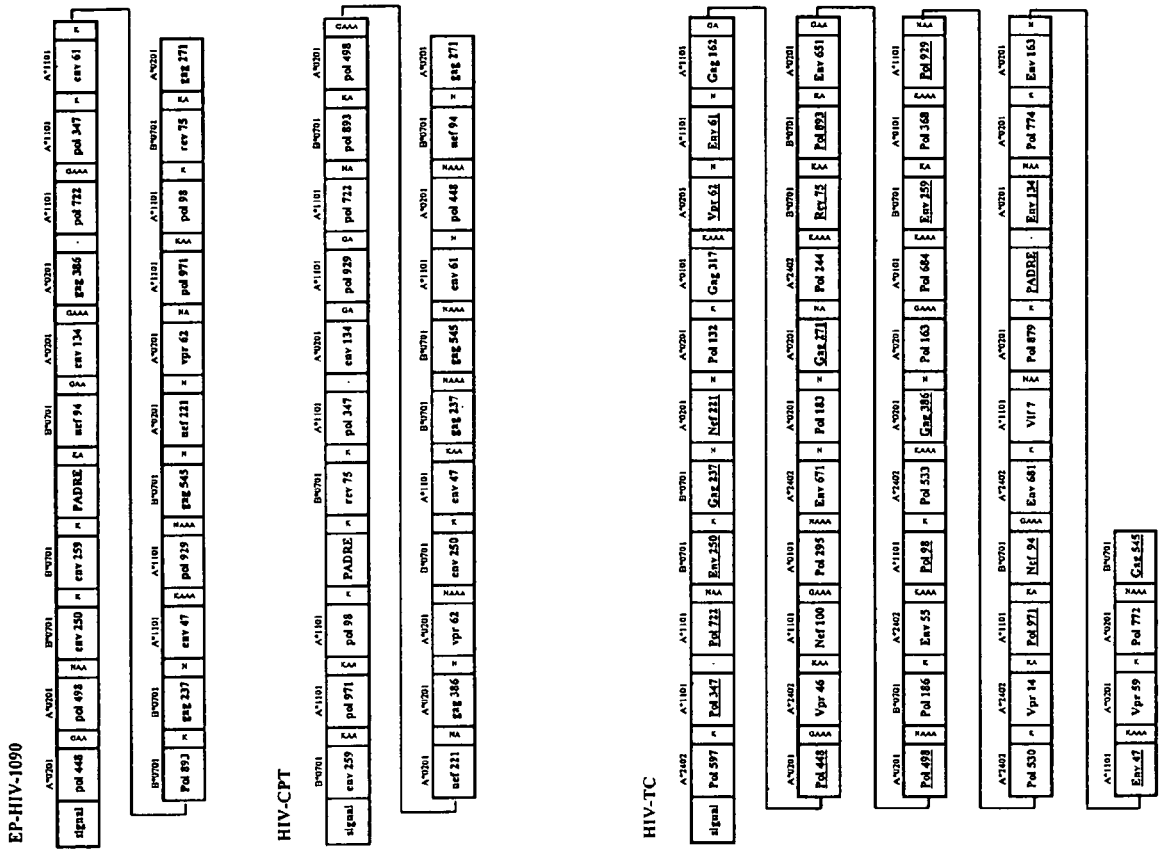
FIG. 9 shows HIV multi-epitope constructs optimized using the methods of the present invention. GAAA spacer (SEQ ID NO:380); NAAA spacer (SEQ ID NO:381); and KAAA spacer (SEQ ID NO:382).

The Program output provides a list of the best arrangements of the epitopes. Since many permutations may have the same value of the evaluation function, several are generated so that other factors can be considered in choosing the optimum arrangement. Examples of multi-epitope constructs generated using the above-described computerized techniques are illustrated in FIG. 9. An exemplary process flow implemented by the method and system of the invention is provided above. As would be readily apparent to those of ordinary skill, other factors such as charge distribution, hydrophobic/hydrophilic region analysis, or folding prediction could also be incorporated into the evaluation function to further optimize the minigene constructs.

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

Structural predictions such as charge distribution, hydrophobic/hydrophilic region analysis, or folding predictions can be performed using sequence analysis programs known to those of skill in the art, for example, hydrophobic and hydrophilic domains can be identified (see, e.g., Kyte & Doolittle, *J. Mol. Biol.* 157:105-132 (1982) and Stryer, *Biochemistry* (3$^{rd}$ ed. 1988); see also any of a number of Internet based sequence analysis programs, such as those found at dot.imgen.bcm.tmc.edu.

A three-dimensional structural model of a multi-epitope construct can also be generated. This is generally performed by entering amino acid sequence to be analyzed into the computer system. The amino acid sequence represents the primary sequence or subsequence of the protein, which encodes the structural information of the protein. The three-dimensional structural model of the protein is then generated by the interaction of the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy tenns," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model. The tertiary structure of the protein encoded by the secondary structure is then formed on the basis of the energy terms of the secondary structure. The user can enter additional variables such as whether the protein is membrane bound or soluble, its location in the body, and its cellular location, e.g., cytoplasmic, surface, or nuclear. These variables along with energy terms of the secondary structure are used to form the model of the tertiary structure. In modeling the tertiary structure, the computer program matches hydrophobic faces of secondary structure with like, and hydrophilic faces of secondary structure with like. Those multi-epitope constructs that are most readily accessible to the HLA processing apparatus are then selected.

Assessment of Immunogenicity of Multi-epitope Vaccines

The development of multi-epitope minigenes represents a unique challenge, because the species-specificity of the peptide binding to MHC. Different MHC types from different species tend to bind different sets of peptides (Rammensee et al., *Immunogenetics*, Vol. 41(4):178-228 (1995)). As a result, it is not possible to test in regular laboratory animals a construct composed of human epitopes. Alternatives to overcome this limitation are generally available. They include: 1) testing analogous constructs incorporating epitopes restricted by non-human MHC; 2) reliance on control epitopes restricted by non human MHC; 3) reliance on crossreactivity between human and non-human MHC; 4) the use of HLA transgenic animals; and 5) antigenicity assays utilizing human cells in vivo. The following is a brief overview of the development of the technology for analyzing antigenicity and immunogenicity.

Class I HLA Transgenics

The utility of HLA transgenic mice for the purpose of epitope identification (Sette et al., *J Immunol*, Vol. 153(12): 5586-92 (1994); Wentworth et al., *Int Immunol*, Vol. 8(5): 651-9 (1996); Engelhard et al., *J Immunol*, Vol. 146(4):1226-32 (1991); Man et al., *Int Immunol*, Vol. 7(4):597-605 (1995); Shirai et al., *J Immunol*, Vol. 154(6):2733-42 (1995)), and vaccine development (Ishioka et al., *J Immunol*, Vol. 162(7): 3915-25 (1999)) has been established. Most of the published reports have investigated the use of HLA A2.1K$^b$ mice but it should be noted that B*27, and B*3501 mice are also available. Furthermore, HLA A*11/K$^b$ mice (Alexander et al., *J Immunol*, Vol. 159(10):4753-61 (1997)), and HLA B7/K$^b$ and HLA A1/K$^b$ mice have also been generated.

Data from 38 different potential epitopes was analyzed to determine the level of overlap between the A2.1-restricted CTL repertoire of A2.1/K$^b$-transgenic mice and A2.1+ humans (Wentworth et al., *Eur J Immunol*, Vol. 26(1):97-101 (1996)). In both humans and mice, an MHC peptide binding affinity threshold of approximately 500 nM correlates with the capacity of a peptide to elicit a CTL response in vivo. A high level of concordance between the human data in vivo and mouse data in vivo was observed for 85% of the high-binding peptides, 58% of the intermediate binders, and 83% of the low/negative binders. Similar results were also obtained with HLA A11 and HLA B7 transgenic mice (Alexander et al., *J Immunol*, Vol. 159(10):4753-61 (1997)). Thus, because of the extensive overlap that exists between T cell receptor repertoires of HLA transgenic mouse and human CTLs, transgenic mice are valuable for assessing immunogenicity of the multi-epitope constructs described herein.

The different specificities of TAP transport as it relates to HLA A11 mice does not prevent the use of HLA-A11 transgenic mice of evaluation of immunogenicity. While both murine and human TAP efficiently transport peptides with an hydrophobic end, only human TAP has been reported to efficiently transport peptides with positively charged C terminal ends, such as the ones bound by A3, A11 and other members of the A3 supertype. This concern does not apply to A2, A1 or B7 because both murine and human TAP should be equally capable of transporting peptides bound by A2, B7 or A1. Consistent with this understanding, Vitiello (Vitiello et al., *J Exp Med*, Vol. 173(4):1007-15 (1991)) and Rotzschke (Rotzschke O, Falk K., *Curr Opin Immunol*, Vol. 6(1):45-51 (1994)) suggested that processing is similar in mouse and human cells, while Cerundolo (Rotzschke O, Falk K., *Curr Opin Immunol*, Vol. 6(1):45-51 (1994)) suggested differences in murine versus human cells, both expressing HLA A3 molecules. However, using HLA A11 transgenics, expression of HLA molecules on T and B cells in vivo has been observed, suggesting that the reported unfavorable specificity of murine TAP did not prevent stabilization and transport of A11/K$^b$ molecules in vivo (Alexander et al., *J Immunol*, Vol. 159(10): 4753-61 (1997)). These data are in agreement with the previous observation that peptides with a charged C termini could be eluted from murine cells transfected with A11 molecules (Maier et al., *Immunogenetics*; Vol. 40(4):306-8 (1994)). Responses in HLA A11 mice to complex antigens, such as influenza, and most importantly to A11 restricted epitopes encoded by multi-epitope minigenes (Ishioka et al., *J Immunol*, Vol. 162(7):3915-25 (1999)) has also been detected. Thus, the TAP issue appears to be of minor concern with transgenic mice.

Another issue of potential relevance in the use of HLA transgenic mice is the possible influence of β2 microglobulin on HLA expression and binding specificity. It is well known that human β2 binds both human and mouse MHC with higher affinity and stability than mouse β2 microglobulin (Shields et al., *Mol Immunol* Vol. 35(14-15):919-28 (1998)). It is also well known that more stable complexes of MHC heavy chain and β2 facilitate exogenous loading of MHC Class I (Vitiello et al., *Science*, Vol. 250(4986):1423-6 (1990)). We have examined the potential effect of this variable by generating mice that are double transgenics for HLA/K$^b$ and human β2. Expression of human β2 was beneficial in the case HLA B7/K$^b$ mice, and was absolutely essential to achieve good expression levels in the case of HLA A1 transgenic mice. Accordingly, HLA/K$^b$ and β2 double transgenic mice are currently and routinely bred and utilized by the present inventors. Thus, HLA transgenic mice can be used to model HLA-restricted recognition of four major HLA specificities (namely A2, A11, B7 and A1) and transgenic mice for other HLA specificities can be developed as suitable models for evaluation of immunogenicity.

Antigenicity Testing for Class I Epitopes

Several independent lines of experimentation indicate that the density of Class I/peptide complexes on the cell surface may correlate with the level of T cell priming. Thus, measuring the levels at which an epitope is generated and presented on an APC's surface provides an avenue to indirectly evaluate the potency of minigene vaccines in human cells in vitro. As a complement to the use of HLA Class I transgenic mice, this approach has the advantage of examining processing in human cells. (Ishioka et al., *J Immunol*, Vol. 162(7):3915-25 (1999))

Several possible approaches to experimentally quantitate processed peptides are available. The amount of peptide on the cell surface can be quantitated by measuring the amount of peptide eluted from the APC surface (Sijts et al., *J Immunol*, Vol. 156(2):683-92 (1996); Demotz et al., *Nature*, Vol. 342(6250):682-4 (1989)). Alternatively, the number of peptide-MHC complexes can be estimated by measuring the amount of lysis or lymphokine release induced by infected or transfected target cells, and then determining the concentration of peptide necessary to obtain equivalent levels of lysis or lymphokine release (Kageyama et al., *J Immunol*, Vol. 154 (2):567-76 (1995)).

A similar approach has also been used to measure epitope presentation in minigene-transfected cell lines. Specifically, minigene constructs that are immunogenic in HLA transgenic mice are also processed into optimal epitopes by human cells transfected with the same minigene, and the magnitude of the response observed in transgenic mice correlates with the antigenicity observed with the transfected human target cells (Ishioka et al., *J Immunol*, Vol. 162(7):3915-25 (1999)).

Using antigenicity assays, a number of related minigenes differing in epitope order or flanking residues can be transfected into APCs, and the impact of the aforementioned variables on epitope presentation can be evaluated. This can be a preferred system for testing where a relatively large number of different constructs need to be evaluated. Although it requires large numbers of epitope-specific CTLs protocols that allow for the generation of highly sensitive CTL lines (Alexander-Miller et al., *Proc Natl Acad Sci U S A*, Vol. 93(9):4102-7 (1996)) and also for their expansion to large numbers (Greenberg P. D., Riddell S. R., *Science*, Vol. 285 (5427):546-51 (1999)) have been developed to address this potential problem.

It should also be kept in mind that, if the cell selected for the transfection is not reflective of the cell performing APC function in vivo, misleading results could be obtained. Cells of the B cell lineage, which are known "professional" APCs, are typically employed as transfection recipients. The use of transfected B cells of this type is an accepted practice in the field. Furthermore, a good correlation has already been noted between in vitro data utilizing transfected human B cells and in vivo results utilizing HLA transgenic mice, as described in more detail herein.

Measuring HTL Responses

In preferred embodiments, vaccine constructs are optimized to induce Class II restricted immune responses. One method of evaluating multi-epitope constructs including Class II epitopes, is to use HLA-DR transgenic mice. Several groups have produced and characterized HLA-DR transgenic mice (Taneja V., David C. S., *Immunol Rev*, Vol. 169:67-79 (1999)).

An alternative also exists which relies on crossreactivity between certain human MHC molecules and particular MHC molecules expressed by laboratory animals. Bertoni and colleagues (Bertoni et al., *J Immunol*, Vol. 161(8):4447-55 (1998)) have noted that appreciable crossreactivity can be demonstrated between certain HLA Class I supertypes and certain PATR molecules expressed by chimpanzees. Crossreactivity between human and macaques at the level of Class II (Geluk et al., *J Exp Med*, Vol. 177(4):979-87 (1993)) and Class I molecules (Dzuris, et al., *J Immunol.*, July 1999) has also been noted. Finally, it can also be noted that the motif recognized by human HLA B7 supertype is essentially the same as the one recognized by the murine Class I L$^d$ (Rammensee et al., *Immunogenetics*, Vol. 41(4):178-228 (1995)). Of relevance to testing HLA DR restricted epitopes in mice, it has been shown by Wall, et al (Wall et al., *J Immunol.*, 152: 4526-36 (1994)) that similarities exist in the motif of DR1 and IA$^b$. We routinely breed our transgenic mice to take advantage of this fortuitous similarity. Furthermore, we have also shown that most of our peptides bind to IA$^b$, so that we use these mice for the study of CTL and HTL immunogenicity.

Measuring and Quantitating Immune Responses from Clinical Samples

A crucial element to assess vaccine performance is to evaluate its capacity to induce immune responses in vivo. Analyses of CTL and HTL responses against the immunogen, as well as against common recall antigens are commonly used and are known in the art. Assays employed included chromium release, lymphokine secretion and lymphoproliferation assays.

More sensitive techniques such as the ELISPOT assay, intracellular cytokine staining, and tetramer staining have become available in the art. It is estimated that these newer methods are 10- to 100-fold more sensitive than the common CTL and HTL assays (Murali-Krishna et al., *Immunity*, Vol. 8(2):177-87 (1998)), because the traditional methods measure only the subset of T cells that can proliferate in vitro, and may, in fact, be representative of only a fraction of the memory T cell compartment (Ogg G.S., McMichael A. J., *Curr Opin Immunol*, Vol. 10(4):393-6 (1998)). Specifically in the case of HIV, these techniques have been used to measure antigen-specific CTL responses from patients that would have been undetectable with previous techniques (Ogg et al., *Science*, Vol. 279(5359):2103-6 (1998); Gray et al., *J Immunol*, Vol. 162(3):1780-8 (1999); Ogg et al., *J Virol*, Vol. 73(11):9153-60 (1999); Kalams et al., *J Virol*, Vol. 73(8): 6721-8 (1999); Larsson et al., *AIDS*, Vol. 13(7):767-77 (1999); Come et al., *J Acquir Immune Defic Syndr Hum Retrovirol*, Vol. 20(5):442-7 (1999)).

With relatively few exceptions, direct activity of freshly isolated cells has been difficult to demonstrate by the means of traditional assays (Ogg G. S., McMichael A. J., *Curr Opin Immunol*, Vol. 10(4):393-6 (1998)). However, the increased sensitivity of the newer techniques has allowed investigators to detect responses from cells freshly isolated from infected humans or experimental animals (Murali-Krishna et al., *Immunity*, Vol. 8(2):177-87 (1998); Ogg G. S., McMichael A. J., *Curr Opin Immunol*, Vol. 10(4):393-6 (1998)). The availability of these sensitive assays, that do not depend on an in vitro restimulation step, has greatly facilitated the study of CTL function in natural infection and cancer. In contrast, assays utilized as an endpoint to judge effectiveness of experimental vaccines are usually performed in conjunction with one or more in vitro restimulation steps (Ogg G.S., McMichael A. J., *Curr Opin Immunol*, Vol. 10(4):393-6 (1998)). In fact, with few exceptions (Hanke et al., *Vaccine*, Vol. 16(4):426-35 (1998)), freshly isolated Class I-restricted CD8+T cells have been difficult to demonstrate in response to immunization with experimental vaccines designed to elicit CTL responses. The use of sensitive assays, such as ELISPOT or in situ IFNγ ELISA, have been combined with a restimulation step to achieve maximum sensitivity; MHC tetramers are also used for this purpose.

MHC tetramers were first described in 1996 by Altman and colleagues. They produced soluble HLA-A2 Class I molecules which were folded with HIV-specific peptides containing a CTL epitope complexed together into tetramers tagged with fluorescent markers. These are used to label populations of T cells from HIV-infected individuals that recognize the epitope (Ogg G. S., McMichael A. J., *Curr Opin Immunol*, Vol. 10(4):393-6 (1998)). These cells were then quantified by flow cytometry, providing a frequency measurement for the T cells that are specific for the epitope. This technique has become very popular in HIV research as well as in other infectious diseases (Ogg G.S., McMichael A. J., *Curr Opin Immunol*, Vol. 10(4):393-6 (1998); Ogg et al., *Science*, Vol. 279(5359):2103-6 (1998); Gray et al., *J Immunol*, Vol. 162 (3):1780-8 (1999); Ogg et al., *J Virol*, Vol. 73(11):9153-60 (1999); Kalams et al., *J Virol*, Vol. 73(8):6721-8 (1999)). However, HLA polymorphism can limit the general applicability of this technique, in that the tetramer technology relies on defined HLA/peptide combinations. However, it has been shown that a variety of peptides, including HIV-derived peptides, are recognized by peptide-specific CTL lines in the context of different members of the A2, A3 and B7 supertypes (Threlkeld et al., *J Immunol*, Vol. 159(4):1648-57 (1997); Bertoni et al., *J Clin Invest*, Vol. 100(3):503-13 (1997)). Taken together these observations demonstrate that a T cell receptor (TCR) for a given MHC/peptide combination can have detectable affinity for the same peptide presented by a different MHC molecule from the same supertype.

In circumstances in which efficacy of a prophylactic vaccine is primarily correlated with the induction of a long-lasting memory response, restimulation assays can be the most appropriate and sensitive measures to monitor vaccine-induced immunological responses. Conversely, in the case of therapeutic vaccines, the main immunological correlate of activity can be the induction of effector T cell function, most aptly measured by primary assays. Thus, the use of sensitive assays allows for the most appropriate testing strategy for immunological monitoring of vaccine efficacy.

Antigenicity of Multi-epitope Minigenes in Transfected Human APC's

Antigenicity assays are performed to evaluate epitope processing and presentation in human cells. An episomal vector to efficiently transfect human target cells with epitope-based minigene vaccines is used to perform such an analysis.

Figure 8:
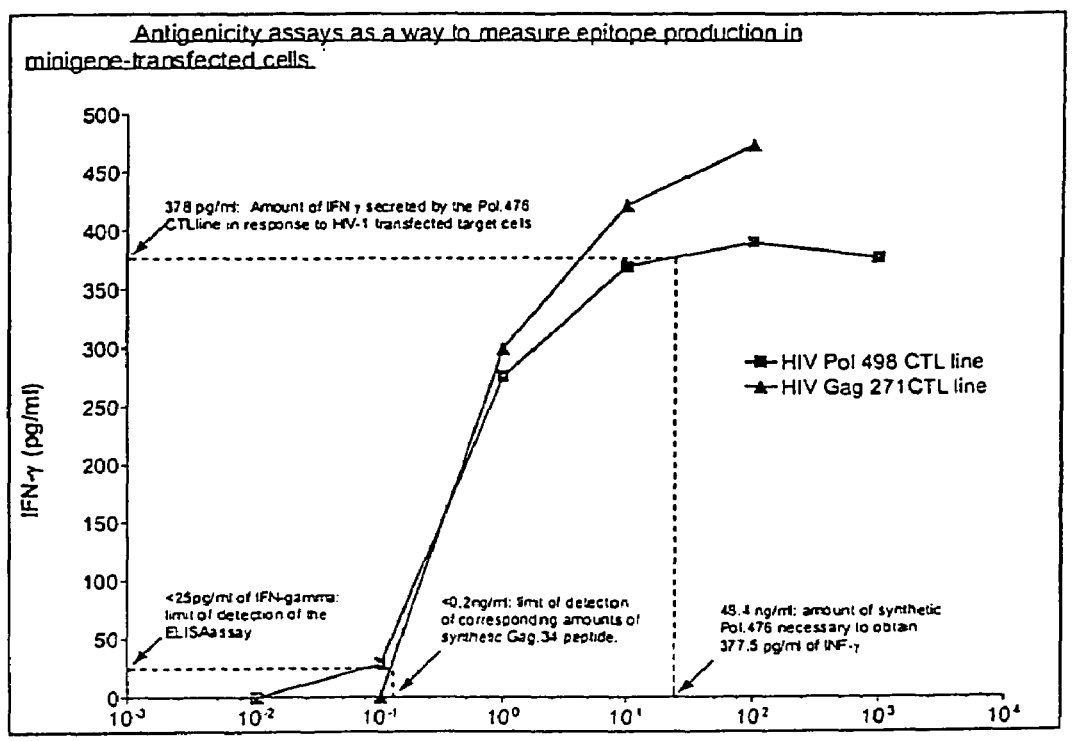
FIG. 8 depicts data for 221A2$K^b$ target cells transfected with the HIV-FT minigene. These transfected cells were assayed for their capacity to present epitopes to CTL lines derived from HLA transgenic mice and specific for various HIV-derived CTL epitopes. To correct for differences in antigen sensitivity of different CTL lines, peptide dose titrations, using untransfected cells as APC, were run in parallel.

For example, 221 A2K$^b$ target cells were transfected with an HIV-1 minigene vaccine. The 221 A2K$^b$ target cell expresses the A2K$^b$ gene that is expressed in HLA transgenic mice, but expresses no endogenous Class I (Shimizu Y, DeMars R., *J Immunol, Vol.* 142(9):3320-8 (1989)). These transfected cells were assayed for their capacity to present antigen to CTL lines derived from HLA transgenic mice and specific for various HIV-derived CTL epitopes. To correct for differences in antigen sensitivity of different CTL lines, peptide dose titrations, using untransfected cells as APC, were run in parallel. Representative data is presented in FIG. 8. In the case of HIV Pol 498-specific CTL, the transfected target cells induced the release of 378 pg/ml of IFNγ. Inspection of the peptide dose responses reveals that, 48 ng/ml of exogenously added peptide was necessary to achieve similar levels of IFNγ release. These results demonstrate that relatively large amounts of Pol 498 epitope are presented by the transfected cells, equivalent to 48 ng/ml of exogenously added peptide.

TABLE 5

Comparison between antigenicity in transfected human cells and immunogenicity in HLA transgenic mice of the HIV-1 minigene

| Epitope | Antigenicity Peptide Equivalents[1] | n[2] | Immunogenicity % response[3] | Magnitude[4] |
|---|---|---|---|---|
| HIV Pol 498 | 30.5 | (6) | 95% | 46.7 |
| HIV Env 134 | 6.2 | (3) | 62% | 16.1 |
| HIV Nef 221 | 2.1 | (5) | 82% | 3.8 |
| HIV Gag 271 | <0.2 | (6) | 31% | 4 |

[1]ng/ml;
[2]number of independent experiments;
[3]% of CTL cultures yielding positive results;
[4]Lytic Units By comparison, less than 25 pg/ml IFNY was detected utilizing the CTL specific for the Gag 271 epitope. The control peptide titration with untransfected target cells revealed that this negative result could not be ascribed to poor sensitivity of the particular CTL line utilized, because as little as 0.2 pg/ml of "peptide equivalents" (PE) could be detected. Thus, it appears that the Gag 271 epitope is not efficiently processed and presented in the HIV-1 transfected target cells. Utilizing the "peptide equivalents" figure as an approximate quantitation of the efficiency of processing, it can be estimated that at least 200-fold less Gag 271 is presented by the transfected targets, compared to the Pol 498 epitope.

The results of various independent determinations for four different epitopes contained within HIV-FT are compiled in Table 5. The amount of each epitope produced from the HIV-FT transfected cells ranged from 30.5 PE for Pol 498, to a low of less than 0.2 PE for Gag 271. The two epitopes Env 134 and Nef 221 were associated with intermediate values, of 6.1 and 2.1 PE, respectively.

These results were next correlated with the in vivo immunogenicity values observed for each epitope after immunization with the HIV-FT construct. The Pol 498 epitope was also the most immunogenic, as would be predicted. The Env 134 and Nef 221 epitopes, for which intermediate immunogenicity was observed in vivo, were also processed in vitro with intermediate efficiency by the transfected human cells. Finally, the Gag 271, for which no detectable in vitro processing was observed was also associated with in vivo immunogenicity suboptimal in both frequency and magnitude.

These data have several important implications. First, they suggest that different epitopes contained within a given minigene may be processed and presented with differential efficiency. Second, they suggest that immunogenicity is proportional to the amount of processed epitope generated. Finally, these results provide an important validation of the use of transgenic mice for the purpose of optimization of multi-epitope vaccines destined for human use.

III. Preparation of Multi-Epitope Constructs

Epitopes for inclusion in the multi-epitope constructs typically bear HLA Class I or Class II binding motifs as described, for example, in PCT applications PCT/US00/27766, or PCT/US00/19774.

Multiple HLA class II or class I epitopes present in a multi-epitope construct can be derived from the same antigen, or from different antigens. For example, a multi-epitope construct can contain one or more HLA epitopes that can be derived from two different antigens of the same virus or from two different antigens of different viruses. Epitopes for inclusion in a multi-epitope construct can be selected by one of skill in the art, e.g., by using a computer to select epitopes that contain HLA allele-specific motifs or supermotifs. The multi-epitope constructs of the invention can also encode one or more broadly cross-reactive binding, or universal, HLA class II epitopes, e.g., PADRE® (Epimmune, San Diego, Calif.), (described, for example, in U.S. Pat. No. 5,736,142) or a PADRE® family molecule.

Universal HLA Class II epitopes can be advantageously combined with other HLA Class I and Class II epitopes to increase the number of cells that are activated in response to a given antigen and provide broader population coverage of HLA-reactive alleles. Thus, the multi-epitope constructs of the invention can include HLA epitopes specific for an antigen, universal HLA class II epitopes, or a combination of specific HLA epitopes and at least one universal HLA class II epitope.

HLA Class I epitopes are generally about 8 to about 13 amino acids in length, in particular 8, 9, 10, or 11 amino acids in length. HLA Class II epitopes are generally about 6 to 25 amino acids in length, in particular about 13 to 21 amino acids in length. An HLA Class I or II epitope can be derived from any desired antigen of interest. The antigen of interest can be a viral antigen, surface receptor, tumor antigen, oncogene, enzyme, or any pathogen, cell or molecule for which an immune response is desired. Epitopes can be selected based on their ability to bind one or multiple HLA alleles. Epitopes that are analogs of naturally occuring sequences can also be included in the multi-epitope constructs described herein. Such analog peptides are described, for example, in PCT applications PCT/US97/03778, PCT/US00/19774, and co-pending U.S. Ser. No. 09/260,714 filed Mar. 1, 1999, now abandoned.

Multi-epitope constructs can be generated using methodology well known in the art. For example, polypeptides comprising the multi-epitope constructs can be synthesized and linked. Typically, multi-epitope minigenes are constructed using recombinant DNA technology.

IV. Expression Vectors and Construction of a Minigene

The multi-epitope constructs of the invention are typically provided as an expression vector comprising a minigene encoding the multi-epitope construct. Construction of such expression vectors is described, for example in PCT/US99/10646. The expression vectors contain at least one promoter element that is capable of expressing a transcription unit encoding the minigene in the appropriate cells of an organism so that the antigen is expressed and targeted to the appropriate HLA molecule. For example, for administration to a human, a promoter element that functions in a human cell is incorporated into the expression vector.

In preferred embodiments, the invention utilizes routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994); *Oligonucleotide Synthesis: A Practical Approach* (Gait, ed., 1984); Kuijpers, *Nucleic Acids Research* 18(17):5197 (1994); Duehohn, *J Org. Chem.* 59:5767-5773 (1994); *Methods in Molecular Biology*, volume 20 (Agrawal, ed.); and Tijssen, *Laboratory Techniques in Biochemistry and Molecular Biology—Hybridization with Nucleic Acid Probes*, e.g., Part I, chapter 2 "Overview of principles of hybridization and the strategy of nucleic acid probe assays" (1993)).

The nucleic acids encoding the epitopes are assembled in a minigene according to standard techniques. In general, the nucleic acid sequences encoding minigene epitopes are isolated using amplification techniques with oligonucleotide primers, or are chemically synthesized. Recombinant cloning techniques can also be used when appropriate. Oligonucleotide sequences are selected which either amplify (when using PCR to assemble the minigene) or encode (when using synthetic oligonucleotides to assemble the minigene) the desired epitopes.

Amplification techniques using primers are typically used to amplify and isolate sequences encoding the epitopes of choice from DNA or RNA (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify epitope nucleic acid sequences directly from mRNA, from cDNA, from genomic libraries or cDNA libraries. Restriction endonuclease sites can be incorporated into the primers. Minigenes amplified by the PCR reaction can be purified from agarose gels and cloned into an appropriate vector.

Synthetic oligonucleotides can also be used to construct minigenes. This method is performed using a series of overlapping oligonucleotides, representing both the sense and non-sense strands of the gene. These DNA fragments are then annealed, ligated and cloned. Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The epitopes of the minigene are typically subcloned into an expression vector that contains a strong promoter to direct transcription, as well as other regulatory sequences such as enhancers and polyadenylation sites. Suitable promoters are well known in the art and described, e.g., in Sambrook et al. and Ausubel et al. Eukaryotic expression systems for mammalian cells are well known in the art and are commercially available. Such promoter elements include, for example, cytomegalovirus (CMV), Rous sarcoma virus LTR and SV40.

The expression vector typically contains a transcription unit or expression cassette that contains all the additional elements required for the expression of the minigene in host cells. A typical expression cassette thus contains a promoter operably linked to the minigene and signals required for efficient polyadenylation of the transcript. Additional elements of the cassette may include enhancers and introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical.

Any of the conventional vectors used for expression in eukaryotic cells may be used. Expression vectors containing regulatory elements from eukaryotic viruses are typically used in eukaryotic expression vectors, e.g., SV40 vectors, CMV vectors, papilloma virus vectors, and vectors derived from Epstein Bar virus.

The multi-epitope constructs of the invention can be expressed from a variety of vectors including plasmid vectors as well as viral or bacterial vectors. Examples of viral expression vectors include attenuated viral hosts, such as vaccinia or fowlpox. As an example of this approach, vaccinia virus is used as a vector to express nucleotide sequences that encode the peptides of the invention. Upon introduction into a host bearing a tumor, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848.

A wide variety of other vectors useful for therapeutic administration or immunization, e.g. adeno and adeno-associated virus vectors, retroviral vectors, non-viral vectors such as BCG (Bacille Calmette Guerin), Salmonella typhi vectors, detoxified anthrax toxin vectors, and the like, will be apparent to those skilled in the art.

Immunogenicity and antigenicity of the multi-epitope constructs are evaluated as described herein.

Targeting Sequences

The expression vectors of the invention may encode one or more MHC epitopes operably linked to a MHC targeting sequence, and are referred to herein as "targeting nucleic acids" or "targeting sequences." The use of a MHC targeting sequence enhances the immune response to an antigen, relative to delivery of antigen alone, by directing the peptide epitope to the site of MHC molecule assembly and transport to the cell surface, thereby providing an increased number of MHC molecule-peptide epitope complexes available for binding to and activation of T cells.

MHC Class I targeting sequences can be used in the present invention, e.g., those sequences that target an MHC Class I epitope peptide to a cytosolic pathway or to the endoplasmic reticulum (see, e.g., Rammensee et al., *Immunogenetics* 41:178-228 (1995)). For example, the cytosolic pathway processes endogenous antigens that are expressed inside the cell. Although not wishing to be bound by any particular theory, cytosolic proteins are thought to be at least partially degraded by an endopeptidase activity of a proteasome and then transported to the endoplasmic reticulum by the TAP molecule (transporter associated with processing). In the endoplasmic reticulum, the antigen binds to MHC Class I molecules. Endoplasmic reticulum signal sequences bypass the cytosolic processing pathway and directly target endogenous antigens to the endoplasmic reticulum, where proteolytic degradation into peptide fragments occurs. Such MHC Class I targeting sequences are well known in the art, and include, e.g., signal sequences such as those from Ig kappa, tissue plasminogen activator or insulin. A preferred signal peptide is the human Ig kappa chain sequence. Endoplasmic reticulum signal sequences can also be used to target MHC Class II epitopes to the endoplasmic reticulum, the site of MHC Class I molecule assembly. MHC Class II targeting sequences can also be used in the invention, e.g., those that target a peptide to the endocytic pathway. These targeting sequences typically direct extracellular antigens to enter the endocytic pathway, which results in the antigen being transferred to the lysosomal compartment where the antigen is proteolytically cleaved into antigen peptides for binding to MHC Class II molecules.

As with the normal processing of exogenous antigen, a sequence that directs a MHC Class II epitope to the endosomes of the endocytic pathway and/or subsequently to lysosomes, where the MHC Class II epitope can bind to a MHC Class II molecule, is a MHC Class II targeting sequence. For example, group of MHC Class II targeting sequences useful in the invention are lysosomal targeting sequences, which localize polypeptides to lysosomes. Since MHC Class II molecules typically bind to antigen peptides derived from proteolytic processing of endocytosed antigens in lysosomes, a lysosomal targeting sequence can function as a MHC Class II targeting sequence. Lysosomal targeting sequences are well known in the art and include sequences found in the lysosomal proteins LAMP-1 and LAMP-2 as described by August et al. (U.S. Pat. No. 5,633,234, issued May 27, 1997), which is incorporated herein by reference.

Other lysosomal proteins that contain lysosomal targeting sequences include HLA-DM. HLA-DM is an endosomal/lysosomal protein that functions in facilitating binding of antigen peptides to MHC Class II molecules. Since it is located in the lysosome, HLA-DM has a lysosomal targeting sequence that can function as a MHC Class II molecule targeting sequence (Copier et al., *J Immunol.* 157:1017-1027 (1996), which is incorporated herein by reference).

The resident lysosomal protein HLA-DO can also function as a lysosomal targeting sequence. In contrast to the above described resident lysosomal proteins LAMP-I and HLA-DM, which encode specific Tyr-containing motifs that target proteins to lysosomes, HLA-DO is targeted to lysosomes by association with HLA-DM (Liljedahl et al., *EMBO J.* 15:4817-4824 (1996)), which is incorporated herein by reference. Therefore, the sequences of HLA-DO that cause association with HLA-DM and, consequently, translocation of HLA-DO to lysosomes can be used as MHC Class II targeting sequences. Similarly, the murine homolog of HLA-DO, H2-DO, can be used to derive a MHC Class II targeting sequence. A MHC Class II epitope can be fused to HLA-DO or H2-DO and targeted to lysosomes.

In another example, the cytoplasmic domains of B cell receptor subunits Ig-α and Ig-β mediate antigen internalization and increase the efficiency of antigen presentation as described in, for example, Bonnerot et al., *Immunity* 3:335-347 (1995). Therefore, the cytoplasmic domains of the Ig-α and Ig-β proteins can function as MHC Class II targeting sequences that target a MHC Class II epitope to the endocytic pathway for processing and binding to MHC Class II molecules.

Another example of a MHC Class II targeting sequence that directs MHC Class II epitopes to the endocytic pathway is a sequence that directs polypeptides to be secreted, where the polypeptide can enter the endosomal pathway. These MHC Class II targeting sequences that direct polypeptides to be secreted mimic the normal pathway by which exogenous, extracellular antigens are processed into peptides that bind to MHC Class II molecules. Any signal sequence that functions to direct a polypeptide through the endoplasmic reticulum and ultimately to be secreted can function as a MHC Class II targeting sequence so long as the secreted polypeptide can enter the endosomal/lysosomal pathway and be cleaved into peptides that can bind to MHC Class II molecules.

In another example, the Ii protein binds to MHC Class IMHC Class II molecules in the endoplasmic reticulum, where it functions to prevent peptides present in the endoplasmic reticulum from binding to the MHC Class II molecules. Therefore, fusion of a MHC Class II epitope to the Ii protein targets the MHC Class II epitope to the endoplasmic reticulum and a MHC Class II molecule. For example, the CLIP sequence of the Ii protein can be removed and replaced with a MHC Class I MHC Class II epitope sequence so that the MHC Class II epitope is directed to the endoplasmic reticulum, where the epitope binds to a MHC Class II molecule.

In some cases, antigens themselves can serve as MHC Class II or I targeting sequences and can be fused to a universal MHC Class II epitope to stimulate an immune response. Although cytoplasmic viral antigens are generally processed and presented as complexes with MHC Class I molecules, long-lived cytoplasmic proteins such as the influenza matrix protein can enter the MHC Class IMHC Class II molecule processing pathway as described in, for example, Gueguen & Long, *Proc. Natl. Acad. Sci*. USA 93:14692-14697 (1996). Therefore, long-lived cytoplasmic proteins can function as a MHC Class IMHC Class II targeting sequence. For example, an expression vector encoding influenza matrix protein fused to a universal MHC Class IMHC Class II epitope can be advantageously used to target influenza antigen and the universal MHC Class IMHC Class II epitope to the MHC Class IMHC Class II pathway for stimulating an immune response to influenza.

Other examples of antigens functioning as MHC Class IMHC Class II targeting sequences include polypeptides that spontaneously form particles. The polypeptides are secreted from the cell that produces them and spontaneously form particles, which are taken up into an antigen-presenting cell by endocytosis such as receptor-mediated endocytosis or are engulfed by phagocytosis. The particles are proteolytically cleaved into antigen peptides after entering the endosomal/lysosomal pathway.

One such polypeptide that spontaneously forms particles is HBV surface antigen (HBV-S) as described in, for example, Diminsky et al., *Vaccine* 15:637-647 (1997) or Le Borgne et al., *Virology* 240:304-315 (1998). Another polypeptide that spontaneously forms particles is HBV core antigen as described in, for example, Kuhröber et al., *International immunol.* 9:1203-1212 (1997). Still another polypeptide that spontaneously forms particles is the yeast Ty protein as described in, for example, Weber et al., *Vaccine* 13:831-834 (1995). For example, an expression vector containing HBV-S antigen fused to a universal MHC Class IMHC Class II epitope can be advantageously used to target HBV-S antigen and the universal MHC Class IMHC Class II epitope to the MHC Class IMHC Class II pathway for stimulating an immune response to HBV.

Administration In Vivo

The invention also provides methods for stimulating an immune response by administering an expression vector of the invention to an individual. Administration of an expression vector of the invention for stimulating an immune response is advantageous because the expression vectors of the invention target MHC epitopes to MHC molecules, thus increasing the number of CTL and HTL activated by the antigens encoded by the expression vector.

Initially, the expression vectors of the invention are screened in mouse to determine the expression vectors having optimal activity in stimulating a desired immune response. Initial studies are therefore carried out, where possible, with mouse genes of the MHC targeting sequences. Methods of determining the activity of the expression vectors of the invention are well known in the art and include, for example, the uptake of $^{3}$H-thymidine to measure T cell activation and the release of $^{51}$Cr to measure CTL activity as described below in Examples II and III. Experiments similar to those described in Example IV are performed to determine the expression vectors having activity at stimulating an immune response. The expression vectors having activity are further tested in human. To circumvent potential adverse immunological responses to encoded mouse sequences, the expression vectors having activity are modified so that the MHC Class IMHC Class II targeting sequences are derived from human genes. For example, substitution of the analogous regions of the human homologs of genes containing various MHC Class IMHC Class II targeting sequences are substituted into the expression vectors of the invention. Expression vectors containing human MHC Class IMHC Class II targeting sequences, such as those described in Example I below, are tested for activity at stimulating an immune response in human.

The invention also relates to pharmaceutical compositions comprising a pharmaceutically acceptable carrier and an expression vector of the invention. Pharmaceutically acceptable carriers are well known in the art and include aqueous or non-aqueous solutions, suspensions and emulsions, including physiologically buffered saline, alcohol/aqueous solutions or other solvents or vehicles such as glycols, glycerol, oils such as olive oil or injectable organic esters.

A pharmaceutically acceptable carrier can contain physiologically acceptable compounds that act, for example, to stabilize the expression vector or increase the absorption of the expression vector. Such physiologically acceptable compounds include, for example, carbohydrates, such as glucose, sucrose or dextrans, antioxidants such as ascorbic acid or glutathione, chelating agents, low molecular weight polypeptides, antimicrobial agents, inert gases or other stabilizers or excipients. Expression vectors can additionally be complexed with other components such as peptides, polypeptides and carbohydrates. Expression vectors can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The invention further relates to methods of administering a pharmaceutical composition comprising an expression vector of the invention to stimulate an immune response. The expression vectors are administered by methods well known in the art as described in, for example, Donnelly et al. (*Ann. Rev. Immunol.* 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). In one embodiment, the minigene is administered as naked nucleic acid.

A pharmaceutical composition comprising an expression vector of the invention can be administered to stimulate an immune response in a subject by various routes including, for example, orally, intravaginally, rectally, or parenterally, such as intravenously, intramuscularly, subcutaneously, intraorbitally, intracapsularly, intraperitoneally, intracistemally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An expression vector also can be administered as a topical spray, in which case one component of the composition is an appropriate propellant. The pharmaceutical composition also can be incorporated, if desired, into liposomes, microspheres or other polymer matrices as described in, for example, Felgner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer.

The expression vectors of the invention can be delivered to the interstitial spaces of tissues of an animal body as described in, for example, Felgner et al., U.S. Pat. Nos. 5,580,859 and 5,703,055. Administration of expression vectors of the invention to muscle is a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

Other effective methods of administering an expression vector of the invention to stimulate an immune response include mucosal administration as described in, for example, Carson et al., U.S. Pat. No. 5,679,647. For mucosal administration, the most effective method of administration includes intranasal administration of an appropriate aerosol containing the expression vector and a pharmaceutical composition. Suppositories and topical preparations are also effective for delivery of expression vectors to mucosal tissues of genital, vaginal and ocular sites. Additionally, expression vectors can be complexed to particles and administered by a vaccine gun.

The dosage to be administered is dependent on the method of administration and will generally be between about 0.1 μg up to about 200 μg. For example, the dosage can be from about 0.05 μg/kg to about 50 mg/kg, in particular about 0.005-5 mg/kg. An effective dose can be determined, for example, by measuring the immune response after administration of an expression vector. For example, the production of antibodies specific for the MHC Class II epitopes or MHC Class I epitopes encoded by the expression vector can be measured by methods well known in the art, including ELISA or other immunological assays. In addition, the activation of T helper cells or a CTL response can be measured by methods well known in the art including, for example, the uptake of $^3$H-thymidine to measure T cell activation and the release of $^{51}$Cr to measure CTL activity (see Examples II and III below).

The pharmaceutical compositions comprising an expression vector of the invention can be administered to mammals, particularly humans, for prophylactic or therapeutic purposes. Examples of diseases that can be treated or prevented using the expression vectors of the invention include infection with HBV, HCV, HIV and CMV as well as prostate cancer, renal carcinoma, cervical carcinoma, lymphoma, condyloma acuminatum and acquired immunodeficiency syndrome (AIDS).

In therapeutic applications, the expression vectors of the invention are administered to an individual already suffering from cancer, autoimmune disease or infected with a virus. Those in the incubation phase or acute phase of the disease can be treated with expression vectors of the invention, including those expressing all universal MHC Class II epitopes, separately or in conjunction with other treatments, as appropriate.

In therapeutic and prophylactic applications, pharmaceutical compositions comprising expression vectors of the invention are administered to a patient in an amount sufficient to elicit an effective immune response to an antigen and to ameliorate the signs or symptoms of a disease. The amount of expression vector to administer that is sufficient to ameliorate the signs or symptoms of a disease is termed a therapeutically effective dose. The amount of expression vector sufficient to achieve a therapeutically effective dose will depend on the pharmaceutical composition comprising an expression vector of the invention, the manner of administration, the state and severity of the disease being treated, the weight and general state of health of the patient and the judgment of the prescribing physician.

EXAMPLES

The following examples are offered to illustrate, but not to limit the claimed invention. It is understood that the examples and embodiments described herein are for illustrative purposes only and that various modifications or changes in light thereof are suggested to persons skilled in the art and are to be included within the spirit and purview of this application and scope of the appended claims.

Examples 1-9 provide examples of assays for evaluating the immunogenicity and antigenicity of multi-epitope constructs.

Example 1

Antigenicity Assays

High-affinity peptide-specific CTL lines can be generated from splenocytes of transgenic mice that have been primed with DNA, peptide/IFA, or lipopeptide. Briefly, splenocytes from transgenic mice are stimulated 0.1 μg/ml peptide and LPS blasts. Ten days after the initial stimulation, and weekly thereafter, cells are restimulated with LPS blasts pulsed for 1 hour with 0.1 μg/ml peptide. CTL lines are assayed 5 days following restimulation in an in situ IFNγ ELISA as described above. Alternatively, CTL lines that are derived from, e.g., patients infected with the targeted pathogen or who have the targeted disease, e.g., cancer, can be used. Specific CTL lines that are not available either from transgenic mice or from patients are generated from PBMC of normal donors, drawing on the expertise in the art.

Target cells to be used in these assays are Jurkat or 0.221 cells transfected with A2.1/$K^b$, A11/$K^b$, A1/$K^b$, or B7/$K^b$ for CTL lines derived from transgenic mice. All these cell lines are currently available to us (Epimmune Inc., San Diego, Calif.). In the case of human CTL lines, 0.221 cells transfected with the appropriate human HLA allele are utilized. We currently have 0.221 cells transfected with A2 and A1, and are generating A11, A24 and B7 transfectants. In an alternative embodiment, if unforeseen problems arise in respect to target cells, LPS blasts and EBV-transformed lines are utilized for murine and human CTL lines, respectively.

To assay for antigenicity, serially diluted CTLs are incubated with $10^5$ target cells and multiple peptide concentrations ranging from 1 to $10^{-6}$ μg/ml. In addition, CTLs are also incubated with target cells transfected with an episomal vector containing a minigene of interest. Episomal vectors are known in the art.

The relative amount of peptide generated by natural processing within the minigene-transfected APCs is quantitated as follows. The amount of IFNγ generated by the CTL lines upon recognition of the transfected target cells are recorded. The amount of synthetic peptide necessary to yield the same amount of IFNγ are interpolated from a standard curve generated when the same CTL line is incubated in parallel with known concentrations of peptide.

Example 2

Mice, Immunizations and Cell Cultures

The derivation of the HLA-A2.1/K$^b$ (Vitiello et al., *J Exp Med*, Vol. 173(4):1007-15 (1991)) and A11/K$^b$ (Alexander et al., *J Immunol*, Vol. 159(10):4753-61 (1997)) transgenic mice used in this study has been described. HLA B7 K$^b$ transgenic mice are available in house (Epimmune Inc., San Diego, Calif.). HLA DR2, DR3 and DR4 transgenic mice are obtained from C. David (Mayo Clinic). Non-transgenic H-2$^b$ mice are purchased from Charles River Laboratories or other commercial vendors. Immunizations are performed as described in (Ishioka et al., *J Immunol*, Vol. 162(7):3915-25 (1999)). All cells are grown in culture medium consisting of RPMI 1640 medium with HEPES (Gibco Life Technologies) supplemented with 10% FBS, 4 mM L-glutamine, 50 μM 2-ME, 0.5 mM sodium pyruvate, 100 μg/ml streptomycin and 100 U/ml penicillin.

HLA transgenic mice and antigenicity assays are used for the purpose of testing and optimization CTL responses. The natural crossreactivity between HLA-DR and IA$^b$ can also be exploited to test HTL responses. This evaluation provides an assessment of the antigenicity and immunogenicity of multi-epitope constructs.

Example 3

Proliferation Assays

To assess the ability of HTL epitopes to induce an immune response, assays such as proliferation assays are often performed. For example, mouse CD4 T lymphocytes are immunomagnetically isolated from splenic single cell suspensions using DynaBeads Mouse CD4 (L3T4) (Dynal). Briefly, $2 \times 10^7$ spleen cells are incubated with $5.6 \times 10^7$ magnetic beads for 40 minutes at 4° C., and then washed 3 times. Magnetic beads are detached using DetachaBead Mouse CD4 (Dynal). Isolated CD4 T lymphocytes ($2 \times 10^5$ cells/well) are cultured with $5 \times 10^5$ irradiated (3500 rad) syngeneic spleen cells in triplicate in flat-bottom 96-well microtiter plates. Purified peptides are added to wells at a final concentration of 20, 1, 0.05 and 0 μg/ml and cells are cultured for a total of 4 days. Approximately 14 hour before harvesting, 1 ,μCi of $^3$H-thymidine (ICN) is added to each well. The wells are harvested onto Unifilter GF/B plates (Packard) using the Filtermate Harvester (Packard). $^3$H-Thymidine incorporation is determined by liquid scintillation counting using the TopCount™ microplate scintillation counter (Packard).

Example 4

$^{51}$Chromium Release Assay

This assay to measure CTL activity is well known in the art. The assay quantifies the lytic activity of the T cell population by measuring the percent $^{51}$Cr released from a $^{51}$Cr-labeled target population (Brunner et al., *Immunology*, Vol. 14(2): 181-96 (1968)). Data derived from the chromium release assay is usually expressed either as a CTL frequency/$10^6$ cell (limiting dilution analysis, LDA; (*Current Protocols in Immunology*, Vol 1, John Wiley & Sons, Inc., USA 1991 Chapter 3; *Manual of Clinical Laboratory Immunology*, Fifth edition, ASM Press, 1997 Section R), or by a less cumbersome quantitative assessment of bulk CTL activity (lytic Units; LU assay). In a LU assay, the standard E:T ratio versus percent cytotoxicity data curves generated in a $^{51}$Cr-release assay are converted into lytic units (LU) per $10^6$ effector cells, with 1 LU defined as the lytic activity required to achieve 30% lysis of target cells (Wunderlick, J., Shearer, G., and Livingston, A. In: J. Coligan, A. Kruisbeek, D. Margulies, E. Shevach, and W. Strober (Eds.), *Current Protocols in Immunology*, Vol 1, "Assays for T cell function: induction and measurement of cytotoxic T lymphocyte activity." John Wiley & Sons, Inc., USA, p. 3.11.18). The LU calculation allows quantifying responses and thus readily comparing different experimental values.

Example 5

In Situ IFNγ ELISA

An in situ IFNγ ELISA assay has been developed and optimized for both freshly isolated and peptide-restimulated splenocytes (see, e.g., McKinney et al., *J. Immunol. Meth.* 237 (1-2):105-117 (2000))IFN. This assay is based on the ELISPOT assay, but utilizes a soluble chromagen, making it readily adaptable to high-throughput analysis. In both the primary and restimulation assays, this technique is more sensitive than either a traditional supernatant ELISA or the $^{51}$Cr-release assay, in that responses are observed in the in situ ELISA that are not detectable in these other assays. On a per cell basis, the sensitivity of the in situ ELISA is approximately one IFNγ secreting cell/$10^4$ plated cells.

96-well ELISA plates are coated with anti-IFNα (rat anti-mouse IFNα MAb, Clone R4-6A2, Pharmingen) overnight at 4° C., and then blocked for 2 hours at room temperature with 10% FBS in PBS. Serially diluted primary splenocytes or CTLs are cultured for 20 hours with peptide and $10^5$ Jurkat A2.1/K$^b$ cells/well at 37° C. with 5% $CO_2$. The following day, the cells are washed out and the amount of IFNγ that had been secreted into the wells is detected in a sandwich ELISA, using biotinylated α-IFNγ (rat anti-mouse IFNγ mAb, Clone XMG1.2, Pharningen) to detect the secreted IFNγ. HRP-coupled strepavidin (Zymed) and TMB (Immunopure® TMB Substrate Kit, Pierce) are used according to the manufacturer's directions for color development. The absorbance is read at 450 nm on a Labsystems Multiskan RC ELISA plate reader. In situ IFNγ ELISA data is evaluated in secretory units (SU), based on the number of cells that secrete 100 pg of IFNγ in response to a particular peptide, corrected for the background amount of IFN in the absence of peptide.

Example 6

ELISPOT Assay

The ELISPOT assay quantifies the frequency of T cells specific for a given peptide by measuring the capacity of individual cells to be induced to produce and release specific lymphokines, usually IFNγ. The increased sensitivity of the ELISPOT assay has allowed investigators to detect responses from cells freshly isolated from infected humans or experimental animals (Murali-Krishna et al., *Immunity*, Vol. 8(2): 177-87 (1998); Ogg et al., *Science*, Vol. 279(5359):2103-6 (1998)). The ELISPOT assays are conducted as described above for the IFNγ ELISA until the final steps, where ExtrAvidin-AP (Sigma, 1:500 dilution) is used in place HRP-strepavidin. Color is developed using the substrate 5-BCIP (Bio-Rad) according to the manufacturer's directions. Spots are counted using a phase contrast microscope. Alternatively, spots are counted utilizing the Zeiss KS ELISPOT reader. In this case the BCIP/NBT substrate is used.

The ELISPOT assay is routinely utilized to quantitate immune responses. The spots can be manually counted, however, in a preferred mode, a KS ELISPOT reader from Zeiss, a microscope-based system with software specifically designed to recognize and count spots is used.

Example 7

Tetramer Staining

Tetramer staining is a flow cytometric technique that detects epitope-specific human CD8+ T-lymphocytes based on the interaction between the peptide epitope, class I antigen and the T-cell receptor specific for the epitope. This assay allows for the rapid quantitation of epitope specific human CD8+ T-lymphocytes in freshly isolated blood samples. MHC tetramers for various HIV peptide/HLA combinations, obtained, e.g., from the NIH repository (Tetramer Core Facility: http://www.miaid.nih.gov/reposit/tetramer/index.html). To label epitope-specific cells, $1 \times 10^6$ PBMC in a 100 μl volume are incubated in the dark for 40 minutes with 5 μg/ml of the appropriate tetramer plus monoclonal antibodies that recognize human CD3 and CD8 (available in different fluorochrome-conjugated forms from commercial sources including PharMingen, San Diego, Calif. or BioSource, Camarillo, Calif.). The cells are washed and paraformaldehyde fixed prior to analysis using a FACsan or FACSCalibur flow cytometer (Becton Dickinson Immunocytometry Systems, San Jose, Calif.). Sample data are analyzed using CellQuest software.

Example 8

Assays from Clinical Samples

Various assays to evaluate the specific CD8+ CTL activity in frozen PBMC samples from patients or volunteers can be used. ELISPOT, chromium release, in situ IFNγ release, proliferation and tetramer assays are all useful to evaluate responses from various experimental models, e.g., those of murine and/or primate origin.

Experimental methods for the murine version of these assays are described above, and these are adapted to human systems as described (Livingston et al, *J Immunol*, Vol. 159 (3):1383-92 (1997); Heathcote et al., *Hepatology*, Vol. 30(2): 531-6 (1999); Livingston et al., *J Immunol*, Vol. 162(5):3088-95 (1999)) and can be further adapted a recognized by one of ordinary skill in the art. Calculations on the amounts of frozen PBMC samples necessary to complete the assays are also described greater detail in Example 14.

Example 9

Transgenic Animals

Transgenic mice (HLA-A2.1/$K^b$ H2$^b$; HLA-A11/$K^b$; HLA-B7/$K^b$) are immunized intramuscularly in the anterior tibialis muscle or subcutaneously in the base of the tail with doses up to 100 μg of DNA or peptide in 10-100 μl volumes. DNA is formulated in saline, and peptides in IFA. 11-21 days later, the animals are sacrificed using $CO_2$ asphyxiation, their spleens removed and used as the source of cells for in vitro determination of CTL function. Typically, 3-6 mice per experimental group are used. In addition, spleens from non-immunized mice are used as a source of APC for restimulation of CTL cultures. Both males and females of 8-12 weeks of age are used.

Example 10

Demonstration of Simultaneous Induction of Responses Against Multiple CTL and HTL Epitopes Construction and testing of CTL epitope strings:

This example provides an example of testing multiple CTL and HTL epitopes. For example, epitope strings encompassing 10-12 different CTL epitopes under the control of a single promoter are synthesized and incorporated in a standard plasmid, pcDNA 3.1 (Invitrogen, San Diego). These constructs include a standard signal sequence and a universal HTL epitope, PADRE®. Each set of epitopes is chosen to allow balanced population coverage. To facilitate testing and optimization, a balanced representation of epitopes that have been shown to be immunogenic in transgenic mice, and/or antigenic in humans are included.

The specific order of these CTL epitopes is chosen to minimize Class I junctional motifs by the use of the computer program, as described herein. If, despite best efforts regarding order optimization, potential junctional epitopes are still present in a construct in accordance with the invention, corresponding peptides are synthesized to monitor for CTL responses against such epitopes in HLA transgenic mice. Generally, minimization of junctional motifs is successful and adequate. However, if responses against any junctional epitopes are detected, these junctional epitopes are disrupted by the use of short one to two residue spacers, such as K, AK, KA, KK, or A, compatible with expected proteolytic cleavage preferences discussed in the previous sections.

Since the ultimate use of optimized constructs is a human vaccine, optimized human codons are utilized. However, to facilitate the optimization process in HLA transgenic mice, care are applied to select, whenever possible, human codons that are also optimal for mice. Human and murine codon usage is very similar. See, for example, Codon usage database at http://www.kazusa.or.jp/codon/.

Human cells transfected with the various minigene vaccine constructs can be used in antigenicity assays, conducted in parallel with in vivo testing in HLA transgenic mice. Any potential discrepancy between minigene vaccine efficacy, due to the differential codon usage, is addressed by the availability of these two different assay systems.

Typically, antigenicity and immunogenicity testing of plasmid constructs is conducted in parallel. In vivo testing in transgenic mice are performed for A2, A11, and B7 HLA transgenic mice. Following a protocol well established in our laboratory, cardiotoxin pretreated mice are injected i.m. with 100 μg of each plasmid and responses evaluated eleven days later (Ishioka et al., *J Immunol*, Vol. 162(7):3915-25 (1999)). Assays will include ELISPOT from freshly isolated cells, as well as interferon gamma release and cytotoxicity chromium release assays from restimulated cell cultures. All of the above mentioned techniques are well established in the art. The simultaneous measurement of responses against epitopes is not problematic, as large colonies of transgenic mice are already established "in house" for these HLA types. Groups of four to six mice are adequate to measure responses against six to ten different epitopes, in multiple readout assays. Testing of HLA A2-restricted, HIV-derived epitopes in HLA A2 transgenic mice is typically employed. However, should problems be encountered, antigenicity testing using human APC can be used as an alternative strategy, or, can be used to complement the transgenic mice studies.

For the purpose of extending the correlation between immunogenicity in transgenic animals and antigenicity, as noted in the studies reported herein, antigenicity testing is utilized to evaluate responses against epitopes such as Pol 498, Env 134, Nef 221, Gag 271, for which high affinity CTL lines are already available in house. For the purpose of generating additional suitable CTL lines, direct immunization of HLA transgenic mice with peptides emulsified in adjuvant, or lipopeptides are utilized, as described herein, and routinely applied in our laboratory, to generate lines for use in antigenicity assays.

Antigenicity assays are also used, as a primary readout for epitopes for which in vivo optimization experiments are not feasible. These epitopes include A24 and possibly A1 restricted epitopes, as well as any epitope which is non-immunogenic in HLA transgenic mice. In any such cases, we use human CTL lines, generated from pathogen exposed individuals. Alternatively, we generate CTL lines for in vitro CTL induction, using GMCSF/IL4-induced dendritic cells and peripheral blood lymphocytes (Celis et al., *Proc Natl Acad Sci* USA, Vol. 91(6):2105-9 (1994)).

Episomal vectors encoding the minigenes are generated and transfected into appropriate human cell lines to generate target cells. For example, the human T cell line Jurkat can be used, but lymphoblastoid cell lines have also been successfully utilized. For experiments utilizing CTL lines of human origin, well-characterized HLA-matched, homozygous, EBV cell lines are commonly used as a source of purified-MHC and as target cells and are used as recipients of the minigene transfections. For experiments utilizing CTL lines derived from HLA transgenic mice, a collection of Class I negative, EBV-transformed, mutant cell lines 0.221 (Shimizu Y, DeMars R., *J Immunol*, Vol. 142(9):3320-8 (1989)) transfected with matching HLA/$K^b$ chimeric constructs are used as the recipient of the minigene transfections. Such cells effectively present peptide antigens to CTL lines (Celis et al., *Proc Natl Acad Sci USA*, Vol. 91(6):2105-9 (1994)).

Construction and Testing of HTL Epitope Strings:

Epitope strings encompassing 3-20 different HTL epitopes under the control of a single promoter are synthesized and incorporated into a standard plasmid, pcDNA 3.1 (Invitrogen, San Diego). To facilitate testing and optimization, each set of epitopes for a given minigene is chosen to provide a balanced representation of epitopes which are already known to be immunogenic in $IA^b$ mice. In addition, all the peptides corresponding to junctions are synthesized and tested for binding to $IA^b$ and, most importantly, for binding to a panel of fourteen different DR molecules, representative of the most common DR alleles worldwide (Southwood et al., *J Immunol*, Vol. 160(7):3363-73 (1998)). Thus, HTL epitopes that are not directed to an antigen of interest are not created within these plasmids. However, should junctional regions with good DR binding potential (and hence, potential DR restricted immunogenicity in vivo) be detected, a spacer such as GPGPG (SEQ ID NO: 369) is introduced to eliminate them. In all constructs, the number of Class I junctional motifs will also be minimized, as described herein.

Experimental vaccine plasmids are tested for immunogenicity using HLA DR transgenic mice and/or mice of the H2b haplotype. Proliferation and/or cytokine production are measured (IL5, IFNγ). In a typical protocol, cardiotoxin treated mice are injected i.m. with 100 μg of each plasmid and responses evaluated eleven days later (Ishioka et al., *J Immunol*, Vol. 162(7):3915-25 (1999)).

Testing for Interactions between CTL and HTL Epitopes

The activities described above yield small, functional blocks of epitopes, which are utilized to demonstrate simultaneous responses/antigenicity against all epitopes analyzable. These blocks are the subject to further optimization, as described in the next example. Using these same minigenes, immunodominance is assessed. Specifically, all the CTL plasmids are mixed together, or all the HTL plasmids are mixed together. The results obtained with the minigene pool are then compared with the results obtained with the same minigene, injected separately.

These minigene plasmids are also used to determine the effects of HTL epitopes on responses to CTL epitopes. Specifically, HTL and CTL containing plasmids are pooled and injected in mice, and CTL and HTL responses to selected epitopes are measured as described herein. Often, it is determined whether the presence, e.g., of HTL epitopes derived from the target antigen enhances CTL responses beyond the level of response attained using a plasmid-containing a pan DR binding epitope, e.g., PADRE® or a PADRE® family molecule, in the CTL minigene. Typically, it is also determined whether PADRE® inhibits or augments responses to target antigen-derived HTL epitopes or conversely, if HTL epitopes derived from the antigen of interest inhibit or augment responses to PADRE® .

Responses to a large number of epitopes is attainable using this methodology. It is possible that the pooling of constructs may inhibit responses against some of the weaker epitopes. In this case, the pooling experiments are repeated after optimization.

Example 11

Optimization of CTL and HTL Minigene Constructs

This example describes the optimization the CTL and HTL constructs described in Example 10. The potential influence of flanking residues on antigenicity and immunogenicity is also assessed in optimizing minigen constructs. These studies involve the inclusion of flanking residues, a synonym for which is "spacers," which have been designed to facilitate effective processing.

Such an analysis can be performed as follows. First, the results of testing of the CTL multi-epitope constructs described in Example 10 are analyzed for trends and correlations between activity and the presence of specific residues at the 3 residues flanking the epitope's N— and C-termini. Epitopes for which suboptimal CTL priming is noted, that are suboptimal with respect to magnitude of response, are the targets for flanking region optimization. For each of the CTL minigene vaccines, encoding 10-12 different CTL epitopes, 'second generation' minigene vaccines, with optimized configuration, are produced.

In one embodiment, the first optimization design is to introduce either an Alanine (A) or Lysine (K) residue at position C+1 for all epitopes associated with suboptimal performance. A second optimization design is to introduce in the C+1 position, the residue naturally occurring in the target antigen, e.g., HIV, that are associated with antigenicity.

For selected epitopes, additional modifications are also introduced. Specifically, the effect of introducing other residue spacers at the epitope C– and N– termini are also investigated. Depending on the results of the analysis of the minigene vaccines described in Example 10, residues investigated may further include, for example, G, Q, W, S and T. If junctional epitopes are created by these modifications, alternative epitope orders eliminating the junctional epitopes, are rationally designed, as described herein. All second generation constructs are tested for antigenicity and immunogenicity, as described herein.

As a result of these modifications, variations in activity that correspond to specific modifications of the minigenes are identified. Certain modifications are found that have general, beneficial effects. To confirm this, generation and testing of additional minigene vaccines in which all epitopes (also the ones which displayed acceptable antigenicity and immunogenicity) are subject to the same modification are conducted. In some instances, increased activity is noted for some epitopes but not others, or less desirably that certain modifications increase the activity of some, but decrease the activity of other epitopes. In such cases, additional minigene vaccines are designed and tested, to retain the beneficial modifications, while excluding those alterations that proved to be detrimental or have no effect.

These minigene vaccines are designated so that: a) a minimum of predicted junctional epitopes are present; and, b) the epitopes which were not functional in the previous minigene vaccines are now in a new more efficacious context.

For HTL minigene vaccines, the data obtained from the "first generation" minigene vaccines are inspected for trends, in terms of junctional epitopes, and epitope position within the minigene, and proximity to spacers, e.g. GPGPG (SEQ ID NO: 369) spacers. If specific trends are detected, second generation minigene vaccines are designed based on these trends. Alternatively, in case of minigenes yielding suboptimal activity, the potential effectiveness of other targeting strategies, such as the ones based on Ii and LAMP are reevaluated, and compared to no targeting and simple, leader sequence targeting.

When large variations in activity of either the CTL or HTL minigene vaccines described in this section are detected, the results are consistent with influences such as conformational or "long-range" effects impacting minigene activity. These variables can be analyzed by means of current molecular and cellular biology techniques. For example, cell lines transfected with the various minigenes could be analyzed for mRNA expression levels, and stability by Northern analysis or primer extension assays (*Current Protocols in Molecular Biology*, Vol 3, John Wiley & Sons, Inc. USA 1999).

In all minigene vaccines, an antibody tag such as MYC/his can also be included. This tag allows for testing of protein expression levels. The inclusion of MYC/his tag (Manstein et al., *Gene*, Vol. 162(l):129-34 (1995)) also allows determination of the stability of the expressed products, by pulse-chase experiments. The results of these assays can then be compared with the results of the antigenicity and immunogenicity experiments. The results are inspected for the presence of trends and general rules, and correlation between the different variables examined.

Example 12

Determination of the Simplest Plasmid Configuration Capable of Effective Delivery of Selected Epitopes The experiments described in Examples 11 and 12 are designed to address variables concerning minigene vaccine design. Ideally, a vector that can be used in humans is used through the entire program, but one DNA vaccine plasmid for the vaccine epitope optimization studies can be used and then switched to a vector suitable for human use. Actual vector selection is dependent on several variables. For example, the availability of vectors, suitable for human use, through a reliable source, such as the National Gene Vector Laboratory (University of Michigan) is a factor.

In this example, the optimized minigenes are also ligated to form larger blocks of epitopes. All constructs are preferably designed to incorporate PADRE and leader sequence targeting in the case of CTL minigenes. Specifically, two pairs of the 10-12 CTL epitope minigenes are ligated to generate two 20-24 CTL epitope minigenes. In a situation where ligation of epitopes yields suboptimal (decreased) activity compared to the smaller minigenes, alternative combinations and orders of ligation are investigated. The specific pair of 20-24 CTL epitope minigenes yielding optimal activity are then ligated and the resulting minigene encompassing all CTL epitopes evaluated for activity. Once again up to two alternative orientations are investigated. Because of the relatively large size of this construct, the specific effect of targeting sequences are confirmed, since it is possible that leader sequence targeting are more effective on small size minigenes, while larger size constructs may be most effectively targeted by ubiquitin signals. Specifically, one construct without any specific targeting sequences is generated and compared to a construct that is targeted for degradation by the addition of a ubiquitin molecule.

A similar strategy is used for HTL. Two pairs of the 3-5 HTL epitope minigenes are ligated to generate two 7-9 HTL epitope minigenes. Once again, in a situation where ligation of these epitopes yields suboptimal (decreased) activity, alternative combinations and order of ligation are investigated. The specific pair of 7-9 CTL epitope minigenes yielding optimal activity are ligated and the resulting minigene, encompassing all HTL epitopes, is evaluated for activity. Once again, up to two alternative orientations are investigated.

Based on these results an optimized plasmid configuration capable of effective delivery of a panel, e.g., of HIV epitopes, are selected for clinical trial evaluation. Of course, epitopes from any antigen of interest (infectious or disease-associated) can be used alone or in combination. This configuration will entail one or more HTL epitope minigene(s) and one or more CTL epitope minigene(s). A combination of one long CTL and one long HTL minigene capable of effectively delivering all epitopes, is most preferable, as it simplifies further clinical development of the vaccine. In case undesirable interactions between the two minigenes are observed when co-injected, injection of the different plasmids in the same animals, but in different injection sites, or at different points in time are examined. Alternatively, if a single CTL minigene and HTL minigene encoding all the desired epitopes is not identified, pools of minigenes are considered for further development.

Example 13

Evaluation and Characterization of CD8+ Lymphocyte Responses Induce Following Immunization with Multi-Epitope Vaccine CD8+ lymphocyte responses were measured mostly relying on the ELISPOT technique. The ELISPOT assay is known in the art, and is regularly used in our laboratory. An automated Zeiss ELISPOT reader is also used as set forth herein. The assays utilized to measure CD8+ responses are primarily the IFNγ ELISPOT assay on freshly isolated cells as well as cells restimulated in vitro with peptide. In addition, in selected instances, chromium release assays are utilized. The results were correlated with the ones observed in the case of the ELISPOT assays. Tetramer staining on selected peptide/MHC combinations was also performed.

The clinical assay was developed and validated. The timing of this activity coincides with the period of time that follows selection of a clinical vaccine minigene, and precedes the availability of actual samples from individuals enrolled in the clinical trial. Assays for CTL evaluation can be established based on experience in the art, for example, experience in establishing assays for CTL evaluations in the Phase I and II trials of the experimental HBV vaccine, Theradigm (Livingston et al, *J Immunol*, Vol. 159(3):1383-92 (1997); Heathcote et al., *Hepatology*, Vol. 30(2):531-6 (1999); Livingston et al., *J Immunol*, Vol. 162(5):3088-95 (1999)). Specifically, Ficoll-purified PBMC derived from normal subjects, as well from, e.g., unvaccinated volunteers can be used. As noted previously, other antigenic target(s) can be used in accordance with the invention.

Example 14

Design of Optimized Multi-Epitope DNA-Based Vaccine Constructs

Optimized constructs were designed with the aid of the computer-assisted methods described above which simultaneously minimize the formation of junctional epitopes and optimize C+1 processing efficiency. The following motifs were utilized for junctional minimization: murine $K^b$ [XXXX(FY)X$_{2-3}$(LIMV)] (SEQ ID NOS: 370 and 371 ); $D^b$[XXXXNX$_{2-3}$LIMV)] (SEQ ID NOS:372 and 373); human A2 [X(LM)X$_{6-7}$V] (SEQ ID NOS: 374 and 375); human A3/A11 [X(LIMV)X$_{6-7}$(KRY)] (SEQ ID NOS: 376 and 377); and human B7 [XPX$_{6-7}$(LIMVF)] (SEQ ID NOS: 378 and 379). The C+1 propensity values were calculated from the data presented in FIG. 6 and are as follows: K=2.2; N=2; G=1.8; T=1.5; A,F,S=1.33; W,Q=1.2; R=1.7; M,Y=1; I=0.86; L=0.76; V,D,H,E,P=0. Insertion of up to four amino acids was permitted. Examples of constructs designed by this procedure and other procedures set forth herein are depicted in FIG. 19. A number of these constructs were characterized in vitro and in vivo immunogenicity studies, which are set forth hereafter. FIG. 20 lists amino acid epitope sequences encoded by certain nucleic acid sequences in the multi-epitope constructs.

Example 15

Figure 14A:
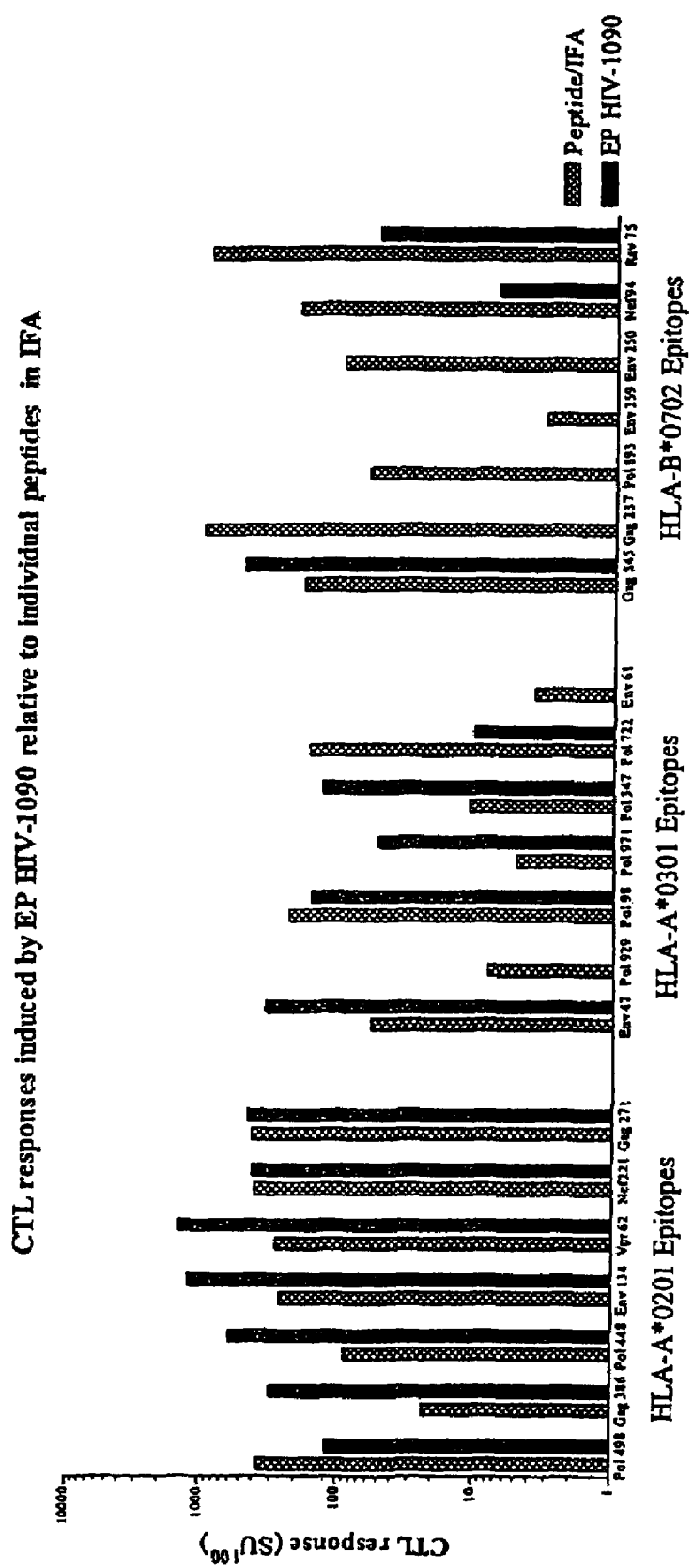
FIG. 14A depicts CTL responses induced by EP-HIV-90 relative to individual peptides in IFA.
Figure 14B:
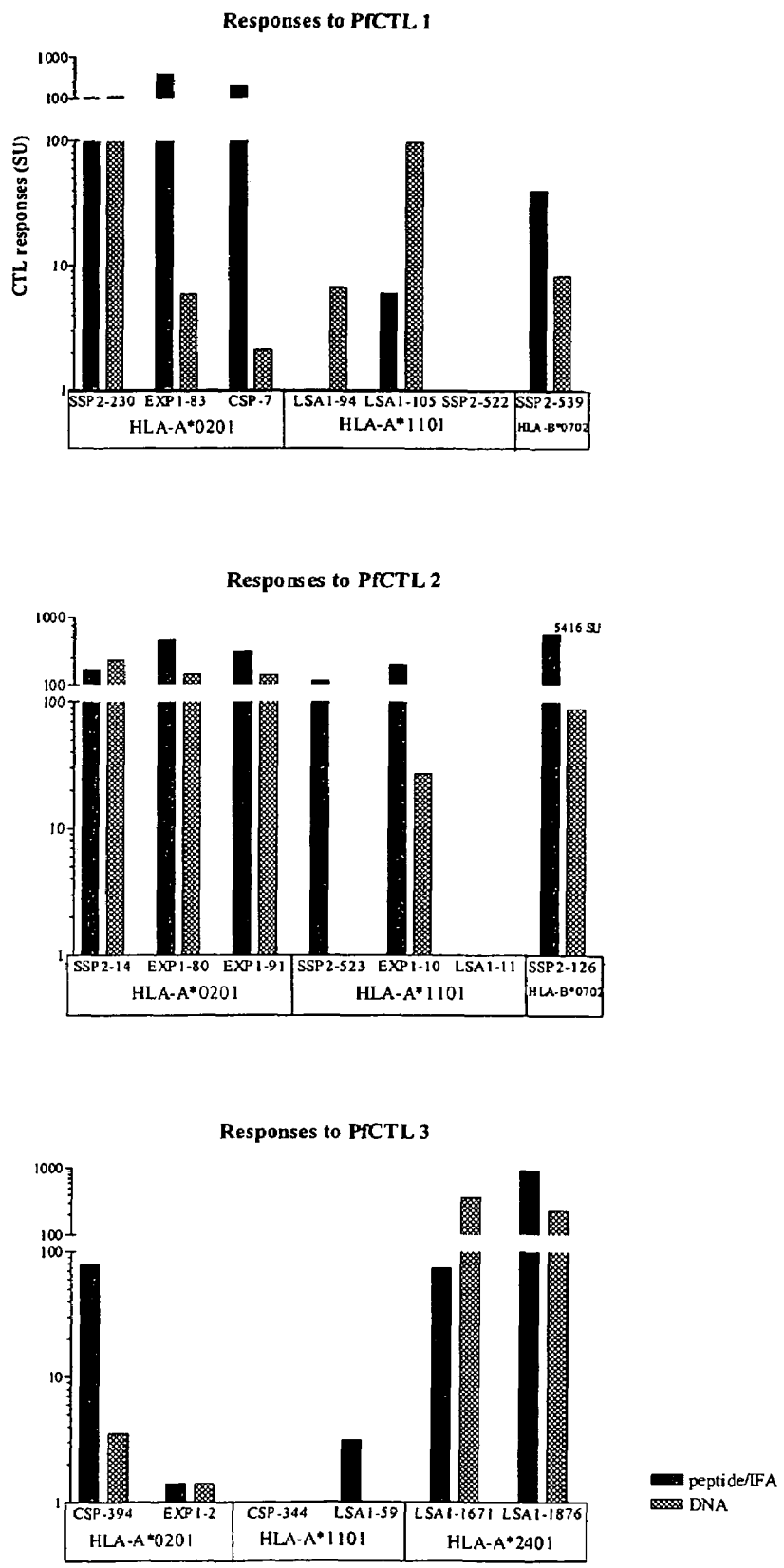
FIG. 14B depicts CTL responses induced by PfCTL.1, PfCTL.2, and PfCTL.3 relative to individual peptides.

Immunogenicity Testing of Multi-epitope CTL Constructs and Influence of Flanking Amino Acids HLA transgenic mice were used for immunogenicity testing of different multi-epitope constructs. One group of mice were pretreated by injecting 50 μl of 10 μM cardiotoxin bilaterally into the tibialis anterior muscle, and then four or five days later, 100 μg of a DNA construct diluted in PBS was administered to the same muscle. In another group, each mouse was injected with a peptide emulsified in CFA, wherein the peptide corresponds to an epitope within the DNA construct administered to mice in the DNA injection group. Eleven to fourteen days after immunization, splenocytes from DNA vaccinated animals and peptide vaccinated animals were recovered and CTL activity was measured in one of several assays, including a standard $^{51}$Cr-release assay, an ELISPOT assay that measured γ-IFN production by purified CD8+ T-lymphocytes without peptide epitope-specific restimulation, and an in situ ELISA, which included an in vitro epitope-specific restimulation step with a peptide epitope. Examples of CTL activity induced by the EP-HIV-1090 construct upon stimulation with peptide epitopes are shown in FIG. 14A, and CTL activity induced by the PfCTL.1, PfCTL.2, and PFCTL.3 constructs upon stimulation with peptide epitopes are shown in FIG. 14B.

The effect of different amino acids in the C+1 flanking position was directly evaluated by inserting different amino acids at the C+1 position relative to the Core 18 epitope in the HBV.1 construct. The immunogenicity data clearly demonstrate reduced immunogenicity of the Core 18 epitope when it was flanked at the C+1 position by W, Y, or L (FIG. 6b). In contrast, insertion of a single K residue dramatically increased the CTL response to Core 18. Enhancement of CTL responses was also observed using R, C, N, or G at the C+1 position. These data clearly demonstrate that C+1 processing optimization can improve minigene design.

Example 16

Figure 15:
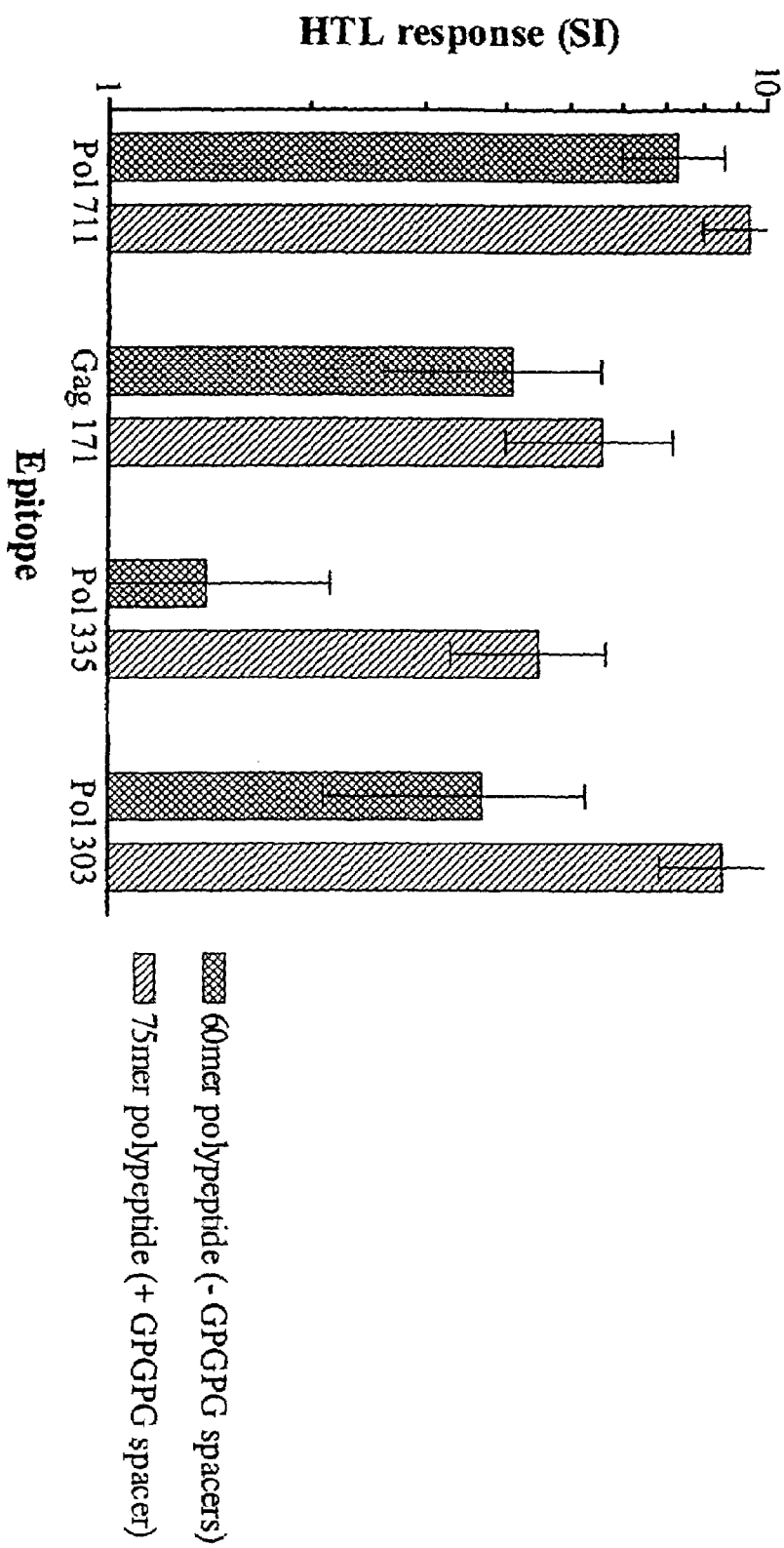
FIG. 15 shows the effect of GPGPG (SEQ ID NO: 369) spacers in class II epitope constructs HIV 75mer and HIV 60mer on HTL responses to particular epitopes.
Figure 16:
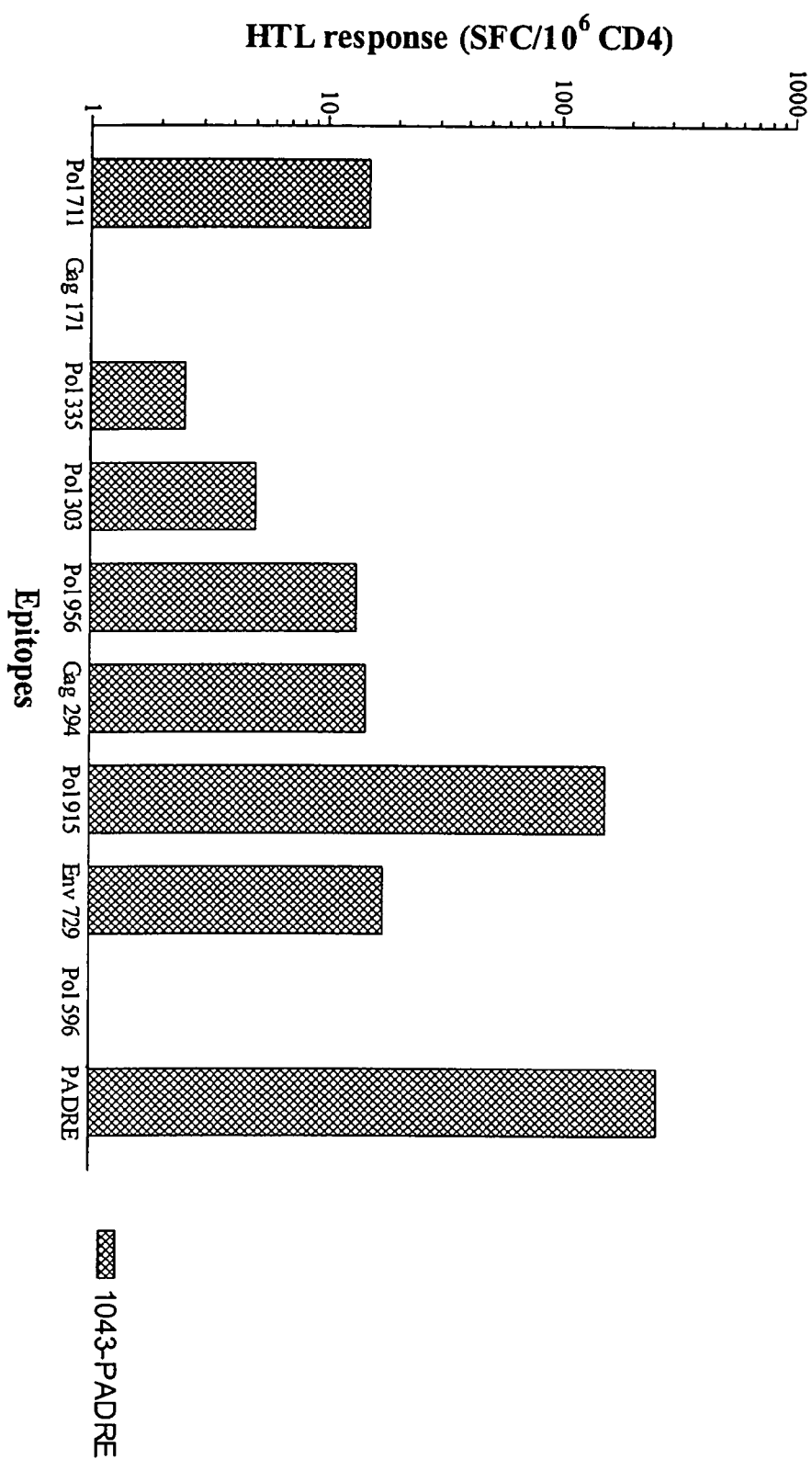
FIG. 16 depicts HTL responses to particular epitopes present in the EP-HIV-1043-PADRE® construct.

Immunogenicity Testing of Multi-epitope HTL Constructs and Influence of Spacer Sequences A universal spacer consisting of GPGPG (SEQ ID NO: 369) was developed to separate HTL epitopes, thus disrupting junctional epitopes. The logic behind the design of this spacer is that neither G nor P are used as primary anchors, positions 1 and 6 in the core region of an HTL peptide epitope, by any known murine or human MHC Class I or MHC Class II molecule. The gap of five amino acids introduced by this spacer separates adjacent epitopes so the amino acids of two epitopes cannot physically serve as anchors in the 1 and 6 positions. The utility of the GPGPG (SEQ ID NO: 369) spacer was tested using synthetic peptides composed of four HIV-1 epitopes, one having three spacers and the other lacking spacers, known to bind mouse IA$^b$. HIV 75mer was the construct having three GPGPG (SEQ ID NO: 369) spacers and HIV 60mer was the construct lacking the three spacers. Immunization of CB6F1 mice with the peptide in CFA induced HTL responses against 3 of 4 of the epitopes in the absence of the spacer but all epitopes were immunogenic when the spacer was present (FIG. 15). This evidence demonstrates that spacers can improve the performance of multi-epitope constructs.

The ability of multi-epitope HTL DNA-based constructs to induce an HTL response in vivo was evaluated by intramuscular immunization of H2$^{bxd}$ mice with an HIV-1043-PA-DRE® construct. The HIV-1043-PADRE® construct is set forth in FIG. 19, and the difference between HIV-1043-PA-DRE® and HIV-1043 is that the former includes a C-terminal GPGPG (SEQ ID NO:369) spacer followed by the PADRE® sequence AKFVAAWTLKAAA (SEQ ID NO:69). Eleven days after immunization, no booster immunizations were administered, CD4 T cells were purified from the spleen, and peptide specific HTL responses were measured in a primary γ-IFN ELISPOT assay. Examples of HTL activity induced by constructs encoding HIV epitopes are shown in FIG. 17. Overall, the HTL responses induced by DNA immunization with the multi-epitope HIV HTL construct were generally of equal or greater magnitude than the responses induced by peptide immunization.

Thus, as described above, the invention provides a novel method and system for automatically analyzing polypeptide junctions, eliminating or reducing the number of junctional epitopes, and identifying spacer combinations to optimize the efficacy of multi-epitope minigenes. Those skilled in the art will know, or be able to ascertain using no more than routine experimentation, many equivalents to the specific embodiments of the invention described herein. These equivalents are intended to be encompassed by the following claims.

What is claimed is:

1. A method for designing an optimized multi-epitope polypeptide comprising:
   (i) selecting ten or more epitopes that contain human leukocyte antigen (HLA) allele-specific motifs or supermotifs, wherein said epitopes are HLA class I cytotoxic T lymphocyte (CTL) epitopes;
   (ii) sorting said ten or more epitopes to minimize the number of junctional epitopes, and
   (iii) incorporating said ten or more CTL epitopes into a multi-epitope polypeptide, wherein, during the incorporation step (iii):
   at least one flanking or spacer amino acid residue is introduced at the C-terminus of one or more of said ten or more CTL epitopes; wherein said flanking or spacer amino acid residue is selected from the group consisting of lysine (K), arginine (R), asparagine (N), glutamine (Q), glycine (G), alanine (A), serine (S), cysteine (C), and threonine (T); and
   wherein said flanking or spacer amino acid residue prevents the occurrence of a CTL junctional epitope.

2. The method of claim 1, wherein said flanking or spacer amino acid residues comprise 1, 2, 3, 4, 5, 6, 7, or 8 amino acid residues selected from the group consisting of alanine (A) and glycine (G).

3. The method of claim 1, wherein said flanking or spacer amino acid residues are selected from the group consisting of lysine (K), arginine (R), asparagine (N), glycine (G) and alanine (A).

4. The method of claim 1, further comprising substituting an N-terminal residue of an HLA epitope that is adjacent to a C-terminus of an HLA epitope comprised by the multi-epitope polypeptide with a residue selected from the group consisting of lysine (K), arginine (R), asparagine (N), glycine (G) and alanine (A).

5. The method of claim 1, wherein said multi-epitope polypeptide contains 20 or more CTL epitopes.

6. The method of claim 5, wherein said multi-epitope polypeptide contains 30 or more CTL epitopes.

7. The method of claim 6, wherein said multi-epitope polypeptide contains 40 or more CTL epitopes.

8. A method for designing an optimized multi-epitope polypeptide comprising:
   (i) selecting five or more epitopes that contain human leukocyte antigen (HLA) allele-specific motifs or supermotifs, wherein said epitopes are HLA class II helper T lymphocyte (HTL) epitopes;
   (ii) sorting said five or more epitopes to minimize the number of junctional epitopes, and
   (iii) incorporating said five or more HTL epitopes into a multi-epitope polypeptide, wherein, during the incorporation step (iii):
   at least one flanking or spacer amino acid residue is introduced at the C-terminus of one or more of said five or more HTL epitopes; wherein said flanking or spacer amino acid residue is selected from the group consisting of glycine (G), proline (P), asparagine (N) or alanine (A); and
   wherein said flanking or spacer amino acid residue prevents the occurrence of an HTL junctional epitope.

9. The method of claim 8, wherein said flanking or spacer amino acid residues are independently selected from residues that are not known human leukocyte antigen (HLA) Class II primary anchor residues.

10. The method of claim 8, wherein said flanking or spacer amino acid residues comprise at least 5 amino acid residues independently selected from the group consisting of glycine (G), proline (P) and asparagine (N).

11. The method of claim 10, wherein said flanking or spacer amino acid residues are glycine-proline-glycine-proline-glycine (GPGPG) (SEQ ID NO: 369).

12. The method of claim 8, wherein said multi-epitope polypeptide contains 10 or more HTL epitopes.

13. The method of claim 12, wherein said multi-epitope polypeptide contains 20 or more HTL epitopes.

14. The method of claim 13, wherein said multi-epitope polypeptide contains 30 or more HTL epitopes.

15. The method of claim 14, wherein said multi-epitope polypeptide contains 40 or more HTL epitopes.

16. A method for designing a polynucleotide encoding an optimized multi-epitope polypeptide comprising:
   (i) selecting five or more nucleic acid sequences which encode epitopes that contain human leukocyte antigen (HLA) allele-specific motifs or supermotifs, wherein said epitopes are HLA class I cytotoxic T lymphocyte (CTL) epitopes;
   (ii) sorting said five or more nucleic acid sequences to minimize the number of encoded junctional epitopes, and
   (iii) incorporating said five or more CTL epitope-encoding nucleic acid sequences into a multi-epitope polynucleotide, wherein, during the incorporation step (iii):
   a polynucleotide encoding at least one flanking or spacer amino acid residue is introduced at the C-terminus of one or more of said five or more CTL epitope-encoding nucleic acid sequences; wherein said flanking or spacer amino acid residue is selected from the group consisting of lysine (K), arginine (R), asparagine (N), glutamine (Q), glycine (G), alanine (A), seine (S), cysteine (C) and threonine (T); and
   wherein said flanking or spacer amino acid residue prevents the occurrence of a CTL junctional epitope.

17. The method of claim 16, wherein said flanking or spacer amino acid residues are selected from the group consisting of lysine (K), arginine (R), asparagine (N), glycine (G) and alanine (A).

18. A method for designing a polynucleotide encoding an optimized multi-epitope polypeptide comprising:
   (i) selecting five or more nucleic acid sequences which encode epitopes that contain human leukocyte antigen (HLA) allele-specific motifs or supermotifs, wherein said epitopes are HLA class II helper T lymphocyte (HTL) epitopes;
   (ii) sorting said five or more nucleic acid sequences to minimize the number of encoded junctional epitopes, and
   (iii) incorporating said five or more HTL epitope-encoding nucleic acid sequences into a multi-epitope polynucleotide, wherein, during the incorporation step (iii):
   polynucleotide encoding at least one flanking or spacer amino acid residue is introduced at the C-terminus of one or more of said five or more HTL epitope-encoding nucleic acid sequences; wherein said flanking or spacer amino acid residue is selected from the group consisting of glycine (G), proline (P), asparagine (N) or alanine (A); and
   wherein said flanking or spacer amino acid residue prevents the occurrence of a HTL junctional epitope.

19. The method of claim 18, wherein said flanking or spacer amino acid residues comprise at least 5 amino acid residues independently selected from the group consisting of glycine (G), proline (P) and asparagine (N).

20. The method of claim 18, wherein said flanking or spacer amino acid residues are glycine-proline-glycine-proline-glycine (GPGPG) (SEQ ID NO: 369).

* * * * *